(12) United States Patent
Purushottam et al.

(10) Patent No.: US 11,263,749 B1
(45) Date of Patent: Mar. 1, 2022

(54) PREDICTIVE PROGNOSIS BASED ON MULTIMODAL ANALYSIS

(71) Applicant: In-Med Prognostics Inc., Lewes, DE (US)

(72) Inventors: Rajesh Kumar Purushottam, Pune (IN); Allen Richard Curran, Lewes, DE (US); Latha Chandrasekaran Poonamallee, Lewes, DE (US); Viyan Sathya Poonamallee, Lewes, DE (US); Juhi Rajesh Desai, Pune (IN); Praful Ramachandra Naik, Pune (IN); Preeti Kabra, Pune (IN); Sonia Joy, Lewes, DE (US); Shubham Rajesh Halyal, Pune (IN); Udit Goswami, Pune (IN); Apeksha Sakegaonkar, Pune (IN); Hussain Murtuza Ghadiyali, Pune (IN); Shivalika Goyal, Pune (IN)

(73) Assignee: In-Med Prognostics Inc., Lewes, DE (US)

( * ) Notice: Subject to any disclaimer, the term of this patent is extended or adjusted under 35 U.S.C. 154(b) by 0 days.

(21) Appl. No.: 17/339,151

(22) Filed: Jun. 4, 2021

(51) Int. Cl.
| | |
|---|---|
| *G06K 9/00* | (2006.01) |
| *G06T 7/00* | (2017.01) |
| *G16H 30/20* | (2018.01) |
| *G16H 30/40* | (2018.01) |
| *G16H 10/60* | (2018.01) |

(Continued)

(52) U.S. Cl.
CPC ............ *G06T 7/0012* (2013.01); *G06F 16/55* (2019.01); *G06N 3/08* (2013.01); *G06T 7/12* (2017.01); *G16H 10/60* (2018.01); *G16H 15/00* (2018.01); *G16H 30/20* (2018.01); *G16H 30/40* (2018.01); *G16H 50/20* (2018.01); *G16H 50/30* (2018.01); *G16H 50/50* (2018.01); *G16H 50/70* (2018.01); *G06T 2200/24* (2013.01); *G06T 2207/20081* (2013.01); *G06T 2207/20084* (2013.01);

(Continued)

(58) Field of Classification Search
CPC ......... G16H 50/20; G16H 50/30; G16H 30/40
See application file for complete search history.

(56) References Cited

U.S. PATENT DOCUMENTS

| 4,201,224 A | 5/1980 | John |
| 6,901,280 B2 | 5/2005 | Pelletier et al. |

(Continued)

FOREIGN PATENT DOCUMENTS

| CN | 101593345 A | 12/2009 |
| EP | 3714467 A2 | 9/2020 |

*Primary Examiner* — Hadi Akhavannik
(74) *Attorney, Agent, or Firm* — Dave Law Group LLC; Raj S. Dave

(57) ABSTRACT

The present disclosure describes a method comprising: obtaining one or more first images of a region of interest of an anatomy from an image source; obtaining at least one of a text input, and one or more physiological signals of a patient; automatically segmenting one or more second images of at least one structure that resides within the one or more first images; extracting one or more volumes of the at least one structure from the one or more first images of the region of interest; determining a feature associated with the at least one structure based on the one or more volumes and one or more inputs, and rendering the feature in at least one of a two-dimensional (2D) format, a three-dimensional (3D) format, and at least one anatomical plane.

20 Claims, 74 Drawing Sheets
(60 of 74 Drawing Sheet(s) Filed in Color)

(51) Int. Cl.
  *G16H 50/20* (2018.01)
  *G16H 50/50* (2018.01)
  *G16H 50/30* (2018.01)
  *G16H 50/70* (2018.01)
  *G16H 15/00* (2018.01)
  *G06N 3/08* (2006.01)
  *G06F 16/55* (2019.01)
  *G06T 7/12* (2017.01)

(52) U.S. Cl.
  CPC ............ *G06T 2207/20104* (2013.01); *G06T 2207/30016* (2013.01); *G06T 2207/30168* (2013.01)

(56) References Cited

U.S. PATENT DOCUMENTS

| | | | |
|---|---|---|---|
| 7,283,652 B2 | 10/2007 | Mendonca et al. | |
| 7,672,497 B2 | 3/2010 | Nicponski | |
| 8,634,614 B2 | 1/2014 | Madsen et al. | |
| 9,002,081 B2 | 4/2015 | Brown | |
| 9,588,204 B2 | 3/2017 | Zagorchev et al. | |
| 2004/0082846 A1* | 4/2004 | Johnson | A61B 6/507 600/410 |
| 2005/0119534 A1 | 6/2005 | Trost et al. | |
| 2008/0249396 A1 | 10/2008 | Biglieri et al. | |
| 2010/0080432 A1 | 4/2010 | Lilja et al. | |
| 2010/0266173 A1 | 10/2010 | Lorenz et al. | |
| 2010/0292545 A1* | 11/2010 | Berka | A61B 5/168 600/301 |
| 2013/0267827 A1 | 10/2013 | Grodzki et al. | |
| 2015/0248470 A1* | 9/2015 | Coleman | G16H 10/20 707/740 |
| 2017/0032485 A1* | 2/2017 | Vemury | G06Q 50/265 |
| 2017/0055926 A1* | 3/2017 | Takahashi | A61B 6/5217 |
| 2017/0330336 A1* | 11/2017 | Roblek | G06T 7/90 |
| 2018/0018767 A1* | 1/2018 | Shih | A61B 6/501 |
| 2018/0061054 A1* | 3/2018 | Abraham | A61B 6/5217 |
| 2018/0181593 A1* | 6/2018 | Ranzinger | G06F 16/5838 |
| 2019/0109830 A1 | 4/2019 | McFarland et al. | |
| 2019/0139223 A1 | 5/2019 | Nie et al. | |
| 2020/0315455 A1 | 10/2020 | Lee et al. | |

* cited by examiner

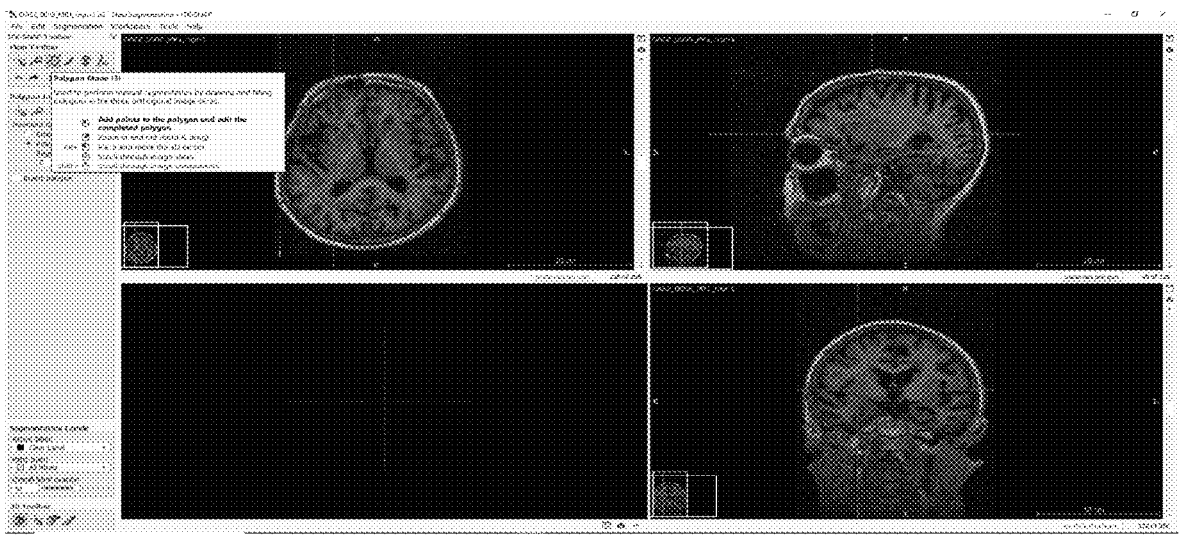
FIG. 21b
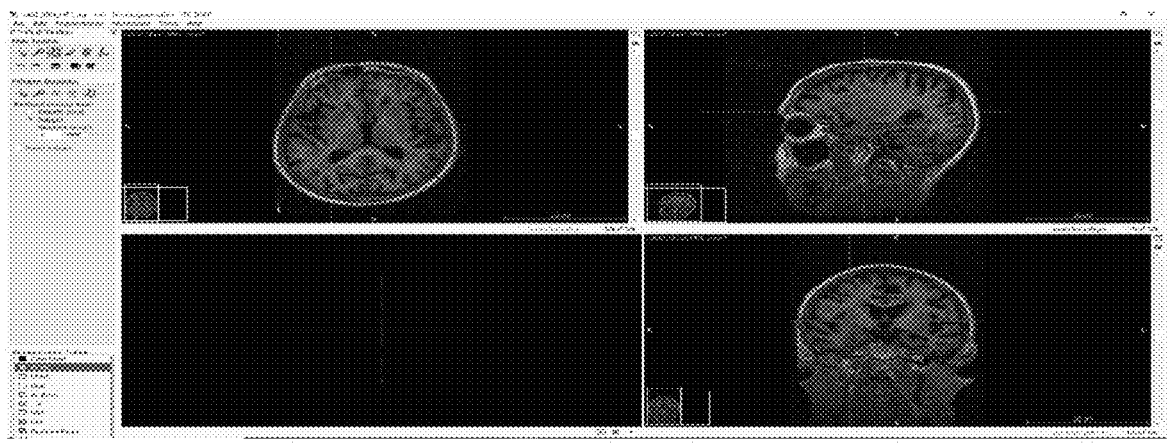
FIG. 21c
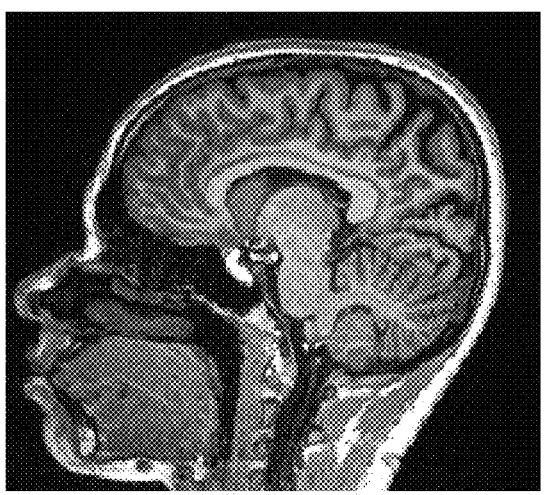   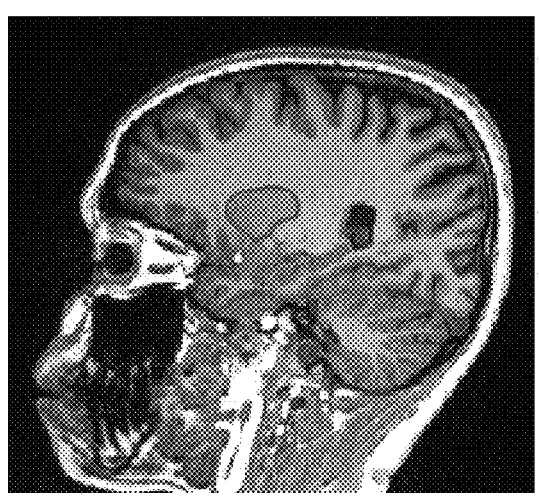
FIG. 21d                FIG. 21e

| *Integrated Analysis* | | |
|---|---|---|
| PATIENT NAME: MR. xyz | PATIENT ID:000XX | SITE ID:xxxx |
| PATIENT CONTACT: | AGE: 25 | SEX: M |
| REFERRING PHYSICIAN: DR. abc | EXAM DATE: 11/10/2020 | |
| Output | | |
| Clinical Information | | |
| Symptoms | Fits, Weakness, Mood swings | |
| Existing conditions | B12 Deficiency | |
| Additional info (applicable history/family history etc) | | |
| Cognitive Function Test | CCTE (10/10/2020) | |

Cognitive Test

MRI Volumetric Analysis
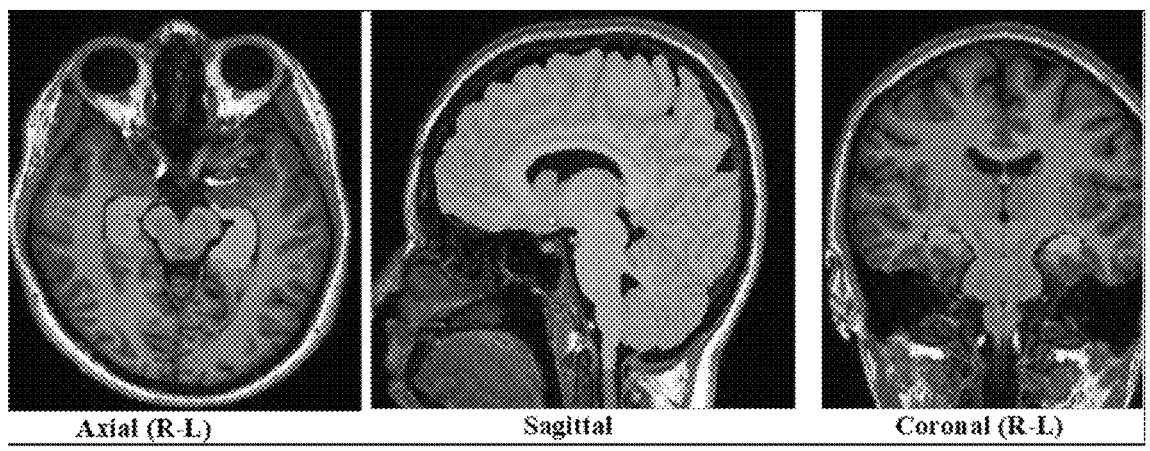
Segmented Image
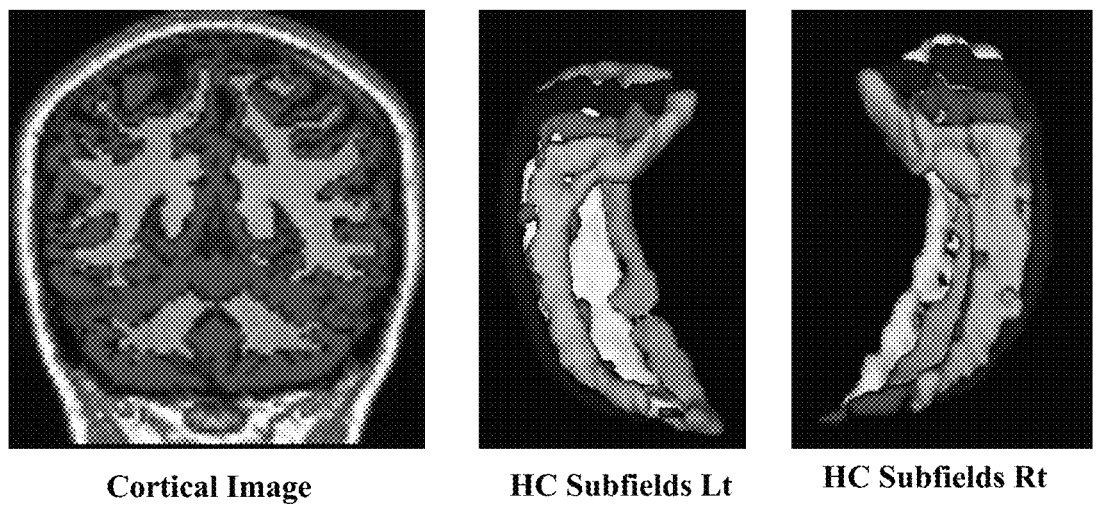
FIG. 28b

| Cortical Analysis | | |
|---|---|---|
| Structure | Absolute Volume (cm3) | Relative Volume (%) |
| CSF | 295 | 20.4 |
| Grey Matter | 727 | 50.2 |
| White Matter | 427 | 29.4 |
| Cortical Thickness | 2.84/0.82 mm | - |
| Structural Volumetric Analysis | | |
| STRUCTURE | VOLUME (ML) | VOLUME AS % ICV | REFERENCE RANGE* |
| ICV Volume | 1280 | - | - |
| Whole Brain | 1109 | 86.83 | 1100-1400 |
| Temporal Lobe | 208.79 | 16.32 | 200 - 250 |
| Frontal Lobe | 307.81 | 24.05 | 300 - 400 |
| Parietal Lobe | 212.38 | 16.59 | 200 - 300 |
| Occipital Lobe | 109.89 | 8.58 | 100 - 150 |
| Ventricles | 27.04 | 2.11 | 15 - 40 |
| Lateral Ventricles | 20.32 | 1.58 | 15 - 30 |
| Temporal Horn | 5.24 | 0.41 | 2 - 8 |
| Left Hippocampus | 3.47 | 0.27 | 3.2 – 4.2 |
| Right Hippocampus | 3.45 | 0.27 | 3.2 – 4.5 |
| Basal Ganglia | 177.14 | 13.84 | 150 - 250 |
| Thalamus | 105.59 | 8.25 | 6 - 20 |

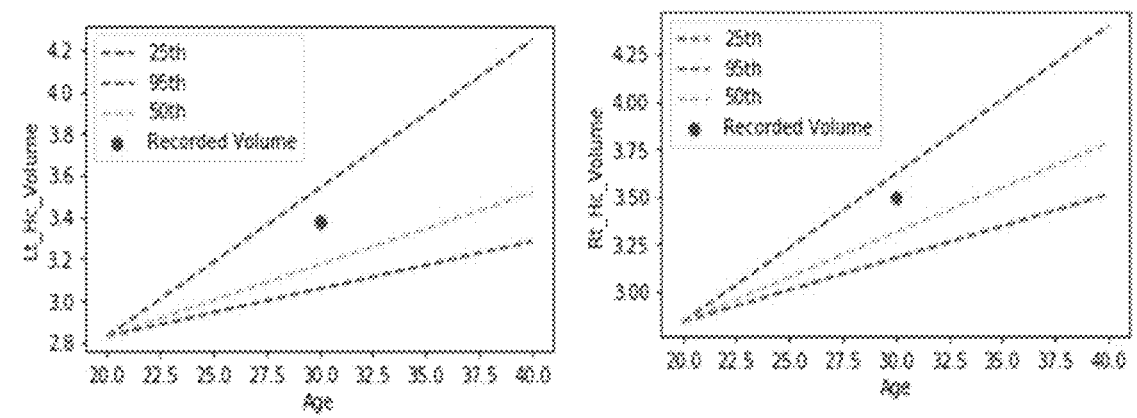

FIG. 29a

| Volumetric Derived Analysis | | |
|---|---|---|
| Analysis | Output | Reference |
| Hippocampus Asymmetry Index** | 0.57 | ~ -2.4 |
| Temporal Lobe Asymmetry Index** | -2.41 | ~ - 3.25 |
| Annual Volume Changes | 0.16 | 0 - 0.20 |
Time Series Volumetric Changes
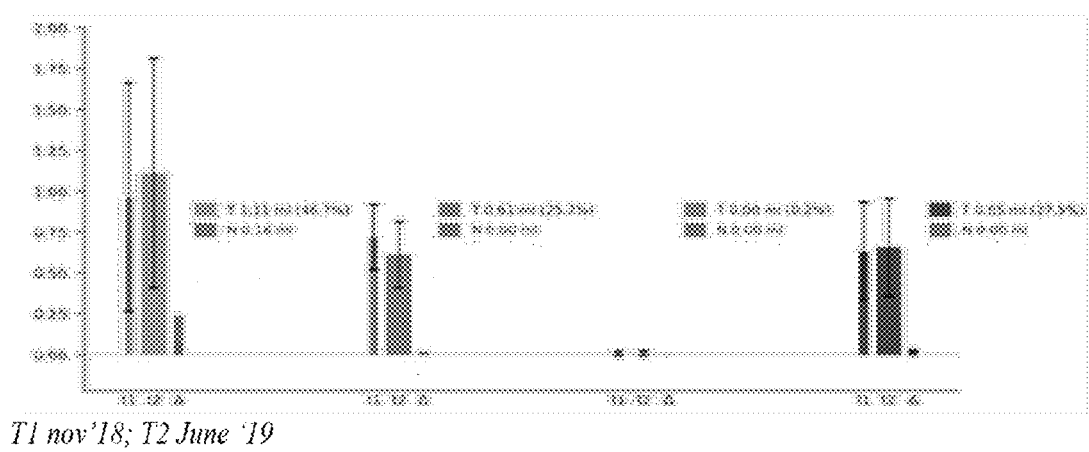
*T1 nov'18; T2 June '19*
DTI & Functional Output
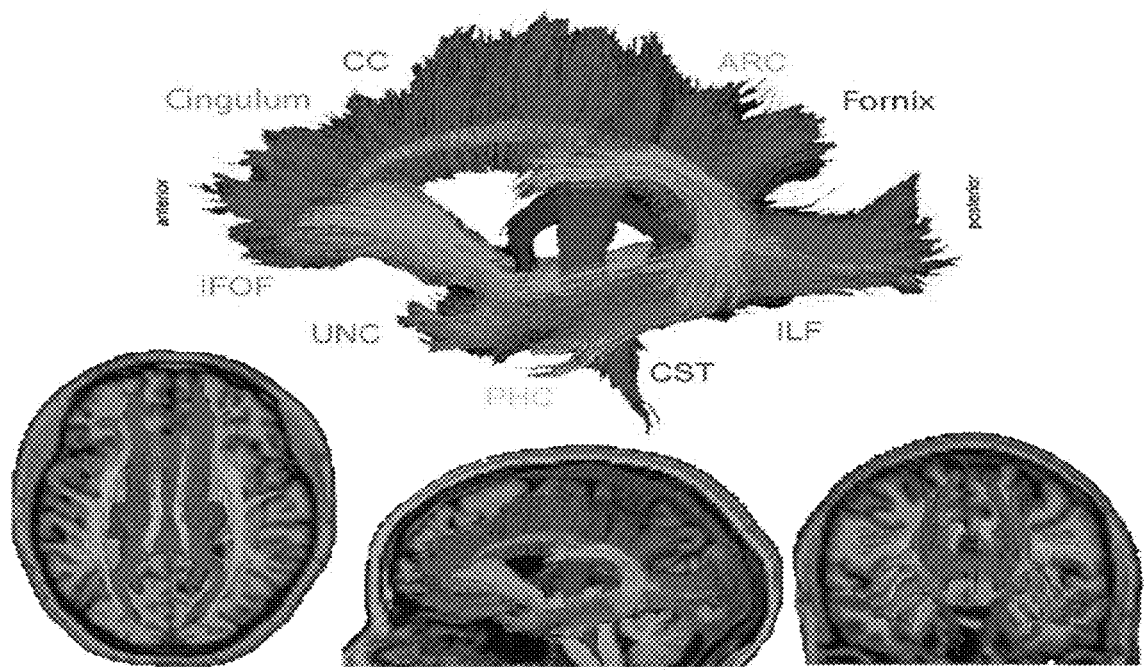
FIG. 29b

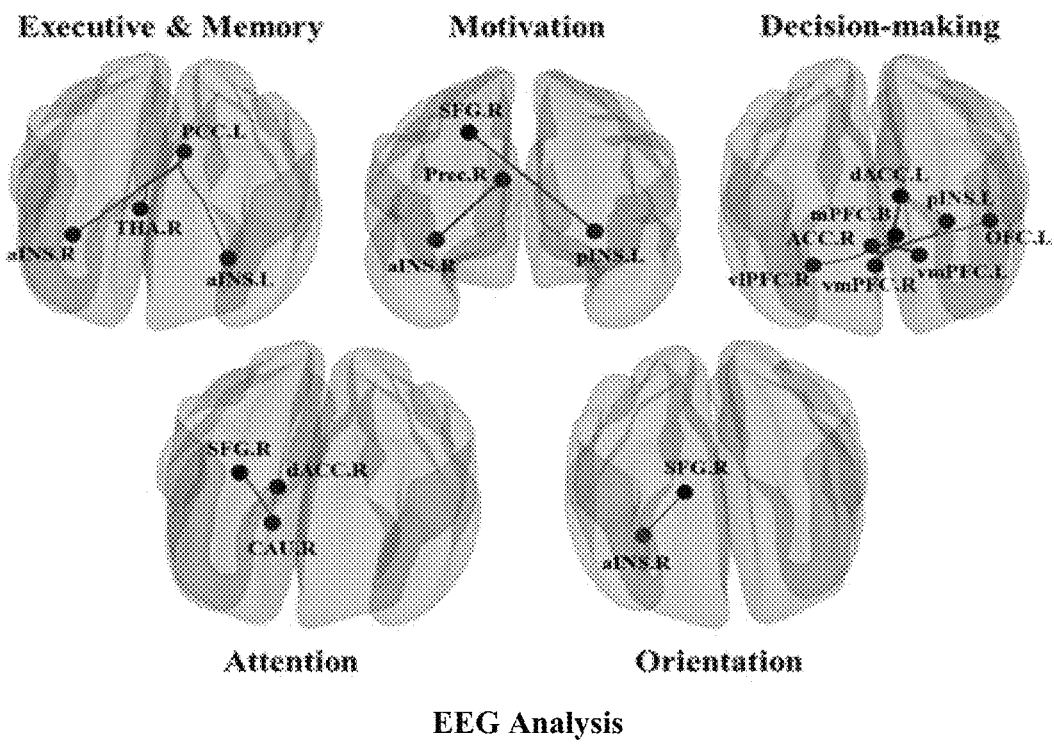
EEG Analysis
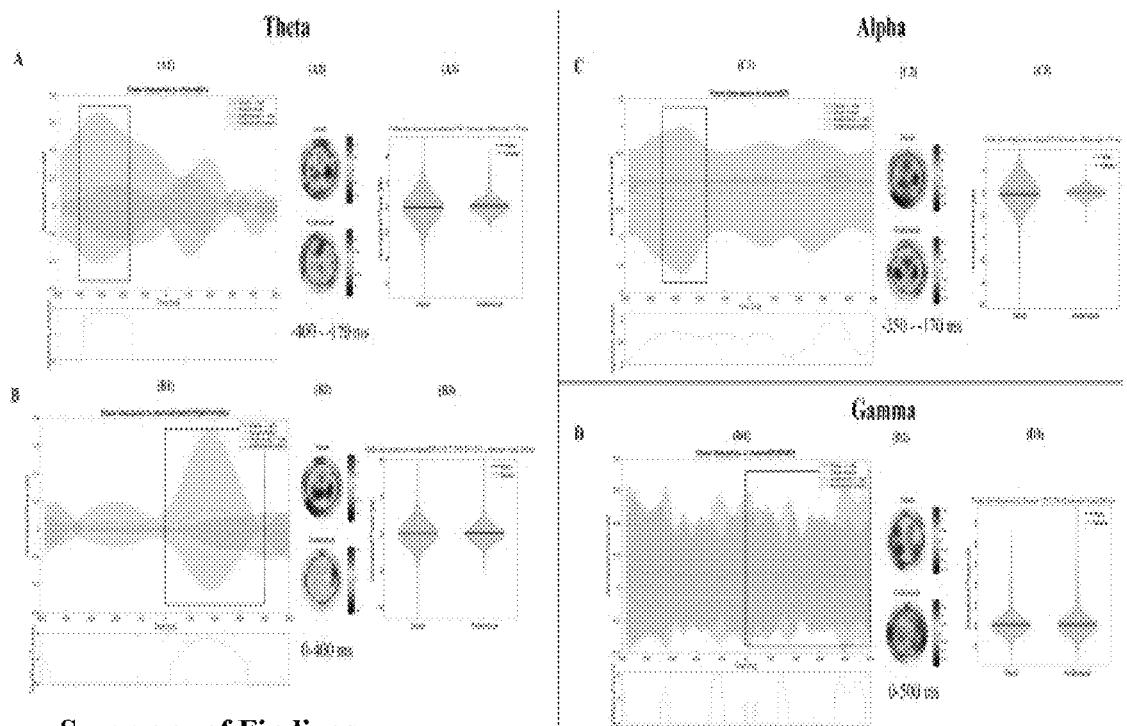
Summary of Findings:
Bilateral asynchronous, 4-5 Hz spike, Focal somatosensory, Auditory jerks with EEG correlates (Polyspikes)
FIG. 29c

EEG Detailed Report

Information/ Recording conditions

Study Id - 555555098
Date: 9/5/2020
Time period of recording: Start- 11:31 AM, Stop - 11:51 AM
Recorded 20 min
EEG type: Sleep deprived EEG
Indication: Suspicion of epilepsy
Alertness (Sleep state): Drowsy, Asleep
Sensor focus: inferior row, 10/20 system
Extra Recording Electrodes: 2 ECG

Modulators/Procedures eye-closure sensitivity: yes
photo paroxysmal response: posterior stimulus-dependent response

Findings

Background Activity-
posterior dominant Rhythm
Activity- Reduced on the left side (reactivity to eye opening)
Amplitude: 50–100
Frequency: 9-10 Hz

Sleep /Drowsiness -
Sleep stages: graphoelement - sleep spindles/K-complex
Interictal findings:
Epileptiform activity: periodic lateralized epileptiform discharges
Location: Bilateral temporal. Primary bilateral asynchronous activity.
Time features: Rhythmic trains or bursts 4 - 5 Hz.
Duration: 1 seconds - 3 seconds.
Modulators: Increased during sleep, activation of pre-existing epileptogenic areas.

Episodes -
Focal somatosensory seizure
Localized temporal. Evolving to bilateral convulsive seizure
Timing & context: Consciousness not tested.
Is aware of the episode. Simultaneous Clinical and EEG start.
Awake at the start of the episode.
Semiology: Auditory (buzzing, humming, ringing sounds)
Sensory modifiers: Ear, Leg

Ictal EEG activity
Morphology: Polyspikes.
Location: Bilateral temporal, parietal.
Symmetrical amplitude. Primary bilateral asynchronous activity.

Artifacts: Low voltage, Lack of compliance
Rhythmic/ periodic patterns in critically ill patients: Periodic epileptiform discharges
Pattern with uncertain significance if any: NIL

FIG. 30a

Polygraphic Channels

ECG: Sinus Rhythm

Summary of Findings

Bilateral asynchronous, 4-5 Hz spike, Focal somatosensory, Auditory jerks with EEG correlates (Polyspikes)
Conclusion
Boy 20 years; 470 AER; Focal epilepsy Diagnostic significance
Headache, Sound related symptoms and Abnormal recording supporting: Autosomal Clinical components
Considering the patient's medical history, the electroclinical findings in this recording support the diagnosis of Autosomal dominant partial epilepsy Screen Shots

FIG. 30b

| Integrated Analysis |||
|---|---|---|
| PATIENT NAME: MR. xyz | PATIENT ID: 000XX | SITE ID: xxxx |
| PATIENT CONTACT: | AGE: 25 | SEX: M |
| REFERRING PHYSICIAN: DR. abc | EXAM DATE: 11/10/2020 ||
| Output |||
| CCTE- Incidental memory at standard deviation of - 1.0 from normal, EEG: Bilateral asynchronous, 4-5 Hz spike, Focal somatosensory, MRI- left sided hippocampal asymmetry with left temporal lobe volume at 25th percentile. |||
| Clinical Information |||
| Symptoms | Fits, Weakness, Mood swings ||
| Existing conditions | B12 Deficiency ||
| Additional info (applicable history/family history etc) |  ||
| Cognitive Function Test | CCTE (10/10/2020) ||
| MRI Volumetric Analysis |||
|  |  | 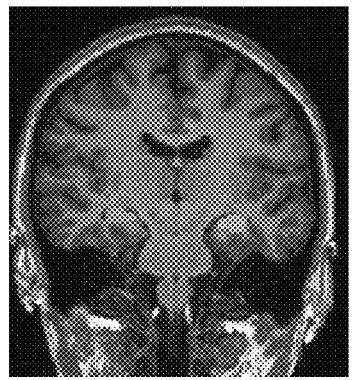 |
| Axial (R-L) | Sagittal | Coronal (R-L) |
| Segmented Image |||
|  | 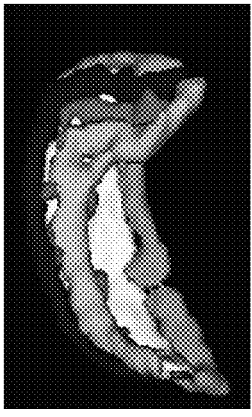 | 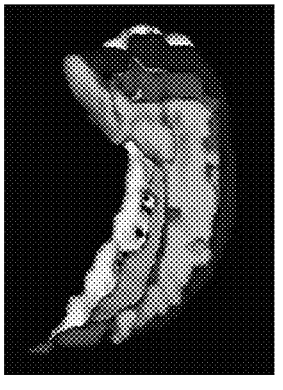 |
| Cortical image | HC Subfields lt | HC Subfields Rt |

Cortical Analysis

FIG. 38a

| Structure | Absolute Volume (cm3) | Relative Volume (%) |
|---|---|---|
| CSF | 295 | 20.4 |
| Grey Matter | 727 | 50.2 |
| White Matter | 427 | 29.4 |
| Cortical Thickness | 2.84/0.82 mm | - |
| Structural Volumetric Analysis | | |
| STRUCTURE | VOLUME (ML) | VOLUME AS % ICV | REFERENCE RANGE* |
| ICV Volume | 1280 | - | - |
| Whole Brain | 1109 | 86.83 | 1100-1400 |
| Temporal Lobe | 208.79 | 16.32 | 200 - 250 |
| Frontal Lobe | 307.81 | 24.05 | 300 - 400 |
| Parietal Lobe | 212.38 | 16.59 | 200 - 300 |
| Occipital Lobe | 109.89 | 8.58 | 100 - 150 |
| Ventricles | 27.04 | 2.11 | 15 - 40 |
| Lateral Ventricles | 20.32 | 1.58 | 15 - 30 |
| Temporal Horn | 5.24 | 0.41 | 2 - 8 |
| Left Hippocampus | 2.47 | 0.17 | 3.2 – 4.2 |
| Right Hippocampus | 3.05 | 0.18 | 3.2 – 4.5 |
| Basal Ganglia | 177.14 | 13.84 | 150 - 250 |
| Thalamus | 10.59 | 8.25 | 6 - 20 |
| Epilepsy Population Comparison | | | |

FIG. 38b

PREDICTIVE PROGNOSIS BASED ON MULTIMODAL ANALYSIS

FIELD OF THE INVENTION

The present disclosure relates broadly to computer aided prognosis, and more particularly to predictive prognosis based on multimodal and multivariate pattern analysis of image, text, and signal inputs.

BACKGROUND

"In the past, 2D models were the main models for medical image processing applications, whereas the wide adoption of 3D models has appeared only in recent years. The 2D Fuzzy C-Means (FCM) algorithm has been extensively used for segmenting medical images due to its effectiveness. Various extensions of it were proposed throughout the years. In this work, we propose a modified version of FCM for segmenting 3D medical volumes, which has been rarely implemented for 3D medical image segmentation. We present a parallel implementation of the proposed algorithm using Graphics Processing Unit (GPU). Researchers state that efficiency is one of the main problems of using FCM for medical imaging when dealing with 3D models. Thus, a hybrid parallel implementation of FCM for extracting volume objects from medical files is proposed. The proposed algorithm has been validated using real medical data and simulated phantom data. Segmentation accuracy of predefined datasets and real patient datasets were the key factors for the system validation. The processing times of both the sequential and the parallel implementations are measured to illustrate the efficiency of each implementation. The acquired results conclude that the parallel implementation is 5× faster than the sequential version of the same operation." [Source: Parallel Implementation for 3D Medical Volume Fuzzy Segmentation; Shadi AlZfdesu'bi; Mohammed A. Shehab; Mahmoud Al-Ayyoub; Yaser Jararweh; Brij Gupta; published in July 2018].

"Neuroimaging has been playing pivotal roles in clinical diagnosis and basic biomedical research in the past decades. As described in the following section, the most widely used imaging modalities are magnetic resonance imaging (MRI), computerized tomography (CT), positron emission tomography (PET), and single-photon emission computed tomography (SPECT). Among them, MRI itself is a non-radioactive, non-invasive, and versatile technique that has derived many unique imaging modalities, such as diffusion-weighted imaging, diffusion tensor imaging, susceptibility-weighted imaging, and spectroscopic imaging. PET is also versatile, as it may use different radiotracers to target different molecules or to trace different biologic pathways of the receptors in the body." [Source: Advances in multimodal data fusion in neuroimaging: Overview, challenges, and novel orientation; Yu-Dong Zhang; Zhengchao Dong; Shui-Hua Wang; Xiang Yu; Xujing Yao; Qinghua Zhou; Hua Hu, Min Li; Carmen Jiménez-Mesa; Javier Ramirez; Francisco J. Martinez; and Juan Manuel Gorriz; published on Jul. 17, 2020]

"Therefore, these individual imaging modalities (the use of one imaging modality), with their characteristics in signal sources, energy levels, spatial resolutions, and temporal resolutions, provide complementary information on anatomical structure, pathophysiology, metabolism, structural connectivity, functional connectivity, etc. Over the past decades, everlasting efforts have been made in developing individual modalities and improving their technical performance. Directions of improvements include data acquisition and data processing aspects to increase spatial and/or temporal resolutions, improve signal-to-noise ratio and contrast to noise ratio, and reduce scan time. On application aspects, individual modalities have been widely used to meet clinical and scientific challenges. At the same time, technical developments and biomedical applications of the concert, integrated use of multiple neuroimaging modalities is trending up in both research and clinical institutions. The driving force of this trend is twofold. First, all individual modalities have their limitations. For example, some lesions in MS can appear normal in T1-weighted or T2-weighted MR images but show pathological changes in DWI or SWI images[1]. Second, a disease, disorder, or lesion may manifest itself in different forms, symptoms, or etiology; or on the other hand, different diseases may share some common symptoms or appearances[2, 3]. Therefore, an individual image modality may not be able to reveal a complete picture of the disease; and multimodal imaging modality (the use of multiple imaging modalities) may lead to a more comprehensive understanding, identify factors, and develop biomarkers of the disease." [Source: Advances in multimodal data fusion in neuroimaging: Overview, challenges, and novel orientation; Yu-Dong Zhang; Zhengchao Dong; Shui-Hua Wang; Xiang Yu; Xujing Yao; Qinghua Zhou; Hua Hu, Min Li; Carmen Jiménez-Mesa; Javier Ramirez; Francisco J. Martinez; and Juan Manuel Gorriz; published on Jul. 17, 2020].

Considering the knowledge of the persons skilled in the art, there is a long-felt need for a structural analysis and integrated multimodal analysis of image, signal, and text inputs for ensuring accuracy in atrophy determination, clinical prognosis, and diagnosis.

SUMMARY

The present disclosure describes one or more aspects of image segmentation, volumetric extraction and volumetric analysis for performing at least one of predictive prognosis, diagnosis, and atrophy determination.

In an aspect, a method is described herein. The method comprises: obtaining one or more first images of a region of interest of an anatomy from an image source; obtaining at least one of a text input, and one or more physiological signals of a patient; automatically segmenting, through a neural network, one or more second images of at least one structure that resides within the one or more first images; extracting one or more volumes of the at least one structure from the one or more first images of the region of interest; determining a feature associated with the at least one structure based on the one or more volumes and one or more inputs; and rendering the feature in at least one of a two-dimensional (2D) format, a three-dimensional (3D) format, and at least one anatomical plane. The text input comprises information of at least one of micro-ethnicity information, an age, a race, a gender, a medical condition, a symptom, clinical history, a patient history, a medical test, medication information, and a cognitive analysis report. The feature comprises at least one of the one or more volumes of the region of interest (ROI), a cortical thickness, an atrophy percentage, an asymmetry index score, a subfield volumetry of the region of interest, annular volume changes, a progressive supranuclear palsy (psp) index score, a magnetic resonance perfusion imaging (MRPI) score, a frontal horn width to intercaudate distance ratio (FH/CC), a medial temporal lobe atrophy (MTA) score, a global cortical atrophy (GCA) scale, identification of Intracranial bleeds, hemorrhage, microbleeds and their volume analysis, a fracture detection, a midline shift identification, a measurement of the midline shift identification and the at least one structure with respect to the midline shift identification, identifying a pathology associated with the at least one structure, classifying the pathology identified, a tissue density identification, an infarct identification, a Penumbra-core-viable tissue identification, classification and volume calculation, diffusion-weighted imaging (DWI) maps and apparent diffusion coefficient (ADC) maps of the at least one structure, perfusion maps comprising resting state functional magnetic resonance imaging (rsfMRI), an alberta stroke programme early CT score (ASPECTS) calculation, a collateral detection, a mismatch ratio calculation, an angiography labeling and/or annotation, a large vessel occlusion (LVO) detection, an Hypoperfusion index calculation, Diffusion tensor imaging (DTI) fiber tracks, neural pathway connectivity maps, correlation between a signal input, an image input and the text input, classifying the signal input, identifying a normal signal, identifying an abnormal signal, identifying a pre-ictal signal, identifying an ictal signal, extracting symptoms, and grading of condition specific effects.

In an embodiment, the method further comprises performing a first quality analysis on the one or more first images of the region of interest prior to automatically segmenting the at least one structure.

In another embodiment, performing the first quality analysis on the one or more first images of the region of interest prior to automatically segmenting the one or more second images of the at least one structure comprises: determining whether the one or more first images of the region of interest are obtained from one of computed tomography (CT), positron emission tomography (PET), structural magnetic resonance imaging (sMRT), functional magnetic resonance imaging (fMRI), Diffusion-weighted imaging (DWI), Diffusion Tensor Imaging (DTI), and magnetic resonance imaging (MRI) with a predefined magnetic strength value.

In yet another embodiment, the predefined magnetic strength value comprises a value more than 1.5 Tesla.

In yet another embodiment, automatically segmenting, through the neural network, the one or more second images of the at least one structure that resides within the one or more first images comprise: performing a second quality analysis manually on the one or more second images that are segmented; and determining whether the one or more second images, that are segmented, passes the second quality analysis.

In yet another embodiment, determining whether the one or more second images, that are segmented, passes the second quality analysis comprises: providing a user interface when the one or more second images, that are segmented, fails the second quality analysis; manually editing and correcting at least one of boundaries and the one or more volumes of the at least one structure based on one or more inputs received from the user; and creating a mask for the at least one structure.

In yet another embodiment, the image source comprises one of (a) a magnetic resonance imaging (MRI) machine, (b) a computed tomography (CT) machine, and (c) a computing unit.

In yet another embodiment, the anatomy belongs to an organism.

In yet another embodiment, the organism comprises one of (a) a human being, (b) an animal, (c) a mammal, and (d) a bird.

In yet another embodiment, the computing unit comprises a personal digital assistant.

In yet another embodiment, automatically segmenting, through the neural network, the one or more second images of the at least one structure that resides within the one or more first images comprises: training the neural network using at least one of (a) the one or more first images, (b) the information of at least one of the micro-ethnicity information, the age, the race, the gender, the medical condition, the symptom, the clinical history, the patient history, the medical test, the medication information, and the cognitive analysis report, (c) the one or more physiological signals, (d) the one or more volumes of the at least one structure, (e) one or more reference volumes, and (f) one or more reference segmented second images.

In yet another embodiment, manually editing and correcting at least one of the boundaries and the one or more volumes of the at least one structure based on the one or more inputs received from the user comprises: creating a log for the mask using the one or more inputs received from the user; retraining the neural network based on the log created; and automatically segmenting, through the neural network, the one or more second images of the at least one structure in future based on the retraining provided to the neural network.

In yet another embodiment, extracting the one or more volumes of the at least one structure from the one or more first images of the region of interest comprises: assigning a voxel of a mask of the one or more second images, that are segmented, as a unit; tabulating a plurality of units in the mask; and estimating one or more quantitative volumes of the at least one structure from the plurality of units.

In yet another embodiment, the method further comprises: recording the one or more volumes of the at least one structure in a database; and categorizing the one or more volumes of the at least one structure in the database with respect to one or more categories of at least one of the micro-ethnicity information, an intracranial volume (ICV), the age, the race, the gender, a family history, the clinical history, the patient history, the symptom, psych analysis information, brain dominance information, food habitat information, stress information, and the medical condition.

In yet another embodiment, extracting the one or more volumes of the at least one structure from the one or more first images of the region of interest: extracting one or more boundaries of the at least one structure from the one or more first images; and populating one or more voxels within the one or more boundaries of the at least one structure using one or more identifiers.

In yet another embodiment, obtaining the one or more first images of the region of interest of the anatomy from the image source comprises: obtaining the one or more first images of the region of interest in a Digital Imaging and Communications in Medicine (DICOM) format.

In yet another embodiment, the method further comprises anonymizing the one or more first images by discarding metadata from the one or more first images. The metadata comprises user identifying information.

In yet another embodiment, the method further comprises discarding the metadata from the one or more first images by converting the one or more first images from a Digital Imaging and Communications in Medicine (DICOM) format to a Neuroimaging Informatics Technology Initiative (NIfTI) format.

In yet another embodiment, the one or more physiological signals comprises at least one of an event related potential (ERP), electrocardiography (ECG) signal, an electroencephalogram (EEG) signal, an Electromyography (EMG), a galvanic skin response (GSR), a blood pressure, and a pulse rate.

In yet another embodiment, the one or more first images comprise one of a three-dimensional (3D) magnetic resonance imaging (MRI), a three-dimensional (3D) computed tomography (CT), a three-dimensional (3D) Functional magnetic resonance imaging (fMRI), and a three-dimensional (3D) positron emission tomography (PET).

In yet another embodiment, the method further comprises: assigning a user identification data to the patient upon obtaining at least one of the one or more first images, the text input, and the one or more physiological signals. The text input comprises at least one of the patient history, and a cognitive test.

In yet another embodiment, assigning the user identification data to the patient upon obtaining at least one of the one or more first images, the text input, and the one or more physiological signals comprises: assigning a first user identification data to the patient upon obtaining at least one of the one or more first images, the text input, and the one or more physiological signals at a first station; and assigning a second user identification data to the patient upon obtaining at least one of the one or more first images, the text input, and the one or more physiological signals at a second station.

In yet another embodiment, the method further comprises linking information of the patient associated with the first user identification data and the second user identification data upon receiving a linking request from the user.

In yet another embodiment, manually editing and correcting at least one of the boundaries, and the one or more volumes of the at least one structure based on the one or more inputs received from the user comprises: performing at least one of adding, and deleting one or more voxels within the boundaries of the at least one structure based on the one or more inputs received from the user.

In yet another embodiment, the at least one structure comprises at least one organ.

In yet another embodiment, the at least one organ comprises a body part of at least one of one of a circulatory system, a nervous system, a muscular system, an endocrine system, a respiratory system, a digestive system, a urinary system, a reproductive system, an integumentary system, an immune system, and a skeletal system.

In yet another embodiment, the at least one anatomical plane comprises a sagittal plane, an axial plane, a parasagittal plane, and a coronal plane.

In another aspect, a method is described herein. The method comprises: obtaining one or more first images of a region of interest of an anatomy from an image source; obtaining at least one of a text input, and one or more physiological signals of a patient; automatically segmenting one or more second images of at least one structure that resides within the one or more first images; estimating one or more quantitative volumes of the at least one structure; and predicting a prognosis based on comparison of the one or more quantitative volumes of the at least one structure with one or more reference volumes, at least one of the text input, and the one or more physiological signals. The text input comprises information of at least one of micro-ethnicity information, an age, a race, a gender, a medical condition, a symptom, clinical history, a patient history, a medical test, medication information, and a cognitive analysis report.

In an embodiment, the method further comprises generating a structure-based analysis report comprising at least one of the one or more quantitative volumes of the at least one structure, a snippet of output, a graphical representation of the prognosis, and the one or more second images in at least one anatomical plane.

In another embodiment, the one or more reference volumes range between 25th and 95th percentile. The 25th and the 95th percentile are calculated by matching at least one of an age, a gender, a micro-ethnicity information, and an intracranial volume (ICV) of the patient with a normative population of individuals and then deriving the 25th and the 95th percentile references.

In yet another embodiment, the 25th and the 95th percentile is calculated by matching a medical condition of the patient with a population of individuals having the medical condition and then deriving the 25th and the 95th percentile.

In yet another embodiment, the method comprises: predicting a first prognosis state of the patient based at least one of the medical condition, and a first medication information of the patient at a first point of time and generating a first analysis report; and predicting a second prognosis state of the patient based on at least one of the medical condition, and a second medication information of the patient at a second point of time and generating a second analysis report.

In yet another embodiment, the method comprises: comparing the first prognosis state and the second prognosis state; and determining a percentage of one of a deterioration and an improvement in at least one of one or more volumes, and the one or more quantitative volumes based on the comparison of the first prognosis state and the second prognosis state.

In yet another embodiment, the method comprises: training, a neural network, using at least one of medical condition, the first medication information, the second medication information, and the percentage of the deterioration or the improvement in at least one of one or more volumes, and the one or more quantitative volumes at a plurality of different point of times.

In yet another embodiment, the method further comprises: detecting a diagnosis of the patient at a third point of time; performing a predictive prognosis and predicting a third prognosis state of the patient at the third point of time; and generating a third analysis report comprising a clinical analytical outcome at the third point of time.

In yet another embodiment, the method further comprises: rendering the third analysis report to a physician, the third analysis report comprises brief summary that assist the physician in determining whether a first medical regime prescribed to a patient is effective, and prescribing a second medication regime with respect to the third prognosis state of the patient.

In yet another embodiment, obtaining the one or more first images of the region of interest of the anatomy from the image source comprises: obtaining the one or more first images of the region of interest at a first instance; and obtaining the one or more first images of the region of interest at a second instance.

In yet another embodiment, the method further comprises generating a first structure-based analysis report based on the one or more first images obtained at the first instance; and generating a second structure-based analysis report based on the one or more first images obtained at the second instance.

In yet another embodiment, the method further comprises predicting the prognosis based on comparison of the first structure-based analysis report and the second structure-based analysis report, and the one or more first images of the region of interest that are obtained at a third instance; estimating one of a progression and a regression of the prognosis associated with the at least one structure between the first instance and the second instance; and generating a third structure-based analysis report comprising at least one of the one or more quantitative volumes of the at least one structure, a snippet, a graphical representation of the prognosis, and the one or more second images in at least one anatomical plane.

In yet another aspect, a method is described herein. The method comprises: obtaining one or more first images of a region of interest of an anatomy from an image source; obtaining a text input; automatically segmenting, through a neural network, one or more second images of at least one structure that resides within the one or more first images; extracting one or more volumes of the at least one structure from the one or more first images of the region of interest; determining a feature associated with the at least one structure based on the one or more volumes and one or more inputs; and rendering the feature in at least one of a two-dimensional (2D) format, a three-dimensional (3D) format, and at least one anatomical plane. The text input comprises micro-ethnicity information of a patient. The feature comprises at least one of the one or more volumes of the region of interest (ROI), a cortical thickness, an atrophy percentage, an asymmetry index score, a subfield volumetry of the region of interest, annular volume changes, a progressive supranuclear palsy (psp) index score, a magnetic resonance perfusion imaging (MRPI) score, a frontal horn width to intercaudate distance ratio (FH/CC), a medial temporal lobe atrophy (MTA) score, a global cortical atrophy (GCA) scale, identification of Intracranial bleeds, hemorrhage, microbleeds and their volume analysis, a fracture detection, a midline shift identification, a measurement of the midline shift identification and the at least one structure with respect to the midline shift identification, identifying a pathology associated with the at least one structure, classifying the pathology identified, a tissue density identification, an infarct identification, a Penumbra-core-viable tissue identification, classification and volume calculation, diffusion-weighted imaging (DWI) maps and apparent diffusion coefficient (ADC) maps of the at least one structure, perfusion maps comprising resting state functional magnetic resonance imaging (rsfMRI), an alberta stroke programme early CT score (ASPECTS) calculation, a collateral detection, a mismatch ratio calculation, an angiography labeling and/or annotation, a large vessel occlusion (LVO) detection, an Hypoperfusion index calculation, Diffusion tensor imaging (DTI) fiber tracks, neural pathway connectivity maps, correlation between a signal input, an image input and the text input, classifying the signal input, identifying a normal signal, identifying an abnormal signal, identifying a pre-ictal signal, identifying an ictal signal, extracting symptoms, and grading of condition specific effects.

In yet another embodiment, automatically segmenting, through the neural network, the one or more second images of the at least one structure that resides within the one or more first images comprises: training the neural network using at least one of (a) the one or more first images, (b) the information of at least one of the micro-ethnicity information, a cognitive score, and a patient history, (c) the one or more volumes, (d) one or more reference volumes, and (e) one or more reference segmented second images.

In yet another embodiment, obtaining the text input of the patient comprises: obtaining the micro-ethnicity information of the patient through a global positioning system (GPS).

In yet another embodiment, obtaining the text input of the patient comprises: extracting at least one of the text inputs of the patient, a cognitive score, and detailed history of the patient from one or more patient records available in one or more databases.

In yet another embodiment, the text input further comprises an age, a race, and a gender.

In yet another aspect, a database is described herein. The database comprises one or more first images of a region of interest of an anatomy obtained from an image source; a text input comprising information of at least one of micro-ethnicity information, an age, a race, a gender, a medical condition, a symptom, clinical history, a patient history, a medical test, medication information, and a cognitive analysis report; one or more physiological signals acquired from a patient; one or more volumes of at least one structure that resides within the one or more first images with respect to micro-ethnicity information in at least one of a three-dimensional (3d) format, and at least one anatomical plane; one or more quantitative volumes of the at least one structure of the region of interest that are categorized with respect to the micro-ethnicity information; one or more structure-based analysis report generated based on at least one of the one or more first images, the text input, the one or more quantitative volumes of the at least one structure, and the one or more physiological signals; one or more reference volumes; and an index for the one or more volumes, and the one or more quantitative volumes. The one or more volumes, the one or more quantitative volumes, and the one or more reference volumes are stored in a data structure on a computer readable storage medium that is associated with a computer executable program code.

In an embodiment the database comprises: user identification data assigned to the patient; a progression and a regression state of prognosis; and a health condition of the patient.

In yet another aspect, a system is described herein. The system comprises a server comprising a memory, and a processor communicatively coupled to the memory. The processor is operable to obtain one or more first images of a region of interest of an anatomy from an image source; obtain at least one of a text input, and one or more physiological signals of a patient; automatically segment, through a neural network, one or more second images of at least one structure that resides within the one or more first images; extract one or more volumes of the at least one structure from the one or more first images of the region of interest; determine a feature associated with the at least one structure based on the one or more volumes and one or more inputs; and render the feature in at least one of a two-dimensional (2D) format, a three-dimensional (3D) format, and at least one anatomical plane. The text input comprises information of at least one of micro-ethnicity information, an age, a race, a gender, a medical condition, a symptom, clinical history, a patient history, a medical test, medication information, and a cognitive analysis report. The feature comprises at least one of the one or more volumes of the region of interest (ROI), a cortical thickness, an atrophy percentage, an asymmetry index score, a subfield volumetry of the region of interest, annular volume changes, a progressive supranuclear palsy (psp) index score, a magnetic resonance perfusion imaging (MRPI) score, a frontal horn width to intercaudate distance ratio (FH/CC), a medial temporal lobe atrophy (MTA) score, a global cortical atrophy (GCA) scale, identification of Intracranial bleeds, hemorrhage, microbleeds and their volume analysis, a fracture detection, a midline shift identification, a measurement of the midline shift identification and the at least one structure with respect to the midline shift identification, identifying a pathology associated with the at least one structure, classifying the pathology identified, a tissue density identification, an infarct identification, a Penumbra-core-viable tissue identification, classification and volume calculation, diffusion-weighted imaging (DWI) maps and apparent diffusion coefficient (ADC) maps of the at least one structure, perfusion maps comprising resting state functional magnetic resonance imaging (rsfMRI), an alberta stroke programme early CT score (ASPECTS) calculation, a collateral detection, a mismatch ratio calculation, an angiography labeling and/or annotation, a large vessel occlusion (LVO) detection, an Hypoperfusion index calculation, Diffusion tensor imaging (DTI) fiber tracks, neural pathway connectivity maps, correlation between a signal input, an image input and the text input, classifying the signal input, identifying a normal signal, identifying an abnormal signal, identifying a pre-ictal signal, identifying an ictal signal, extracting symptoms, and grading of condition specific effects.

In yet another aspect, a system is described herein. The system comprises a server comprising a memory, and a processor communicatively coupled to the memory. The processor is operable to obtain one or more first images of a region of interest of an anatomy from an image source; obtain at least one of a text input, and one or more physiological signals of a patient; automatically segment one or more second images of at least one structure that resides within the one or more first images; estimate one or more quantitative volumes of the at least one structure; and predict a prognosis based on comparison of the one or more quantitative volumes of the at least one structure with one or more reference volumes, the text input, and the one or more physiological signals. The text input comprises information of at least one of micro-ethnicity information, an age, a race, a gender, a medical condition, a symptom, clinical history, a patient history, a medical test, medication information, and a cognitive analysis report.

In yet another aspect, a system is described herein. The system comprises a server comprising a memory, and a processor communicatively coupled to the memory. The processor is operable to obtain one or more first images of a region of interest of an anatomy from an image source; obtain a text input; automatically segment, through a neural network, one or more second images of at least one structure that resides within the one or more first images; extract one or more volumes of the at least one structure from the one or more first images of the region of interest; determine a feature associated with the at least one structure based on the one or more volumes and one or more inputs; and render the feature in at least one of a two-dimensional (2D) format, a three-dimensional (3D) format, and at least one anatomical plane. The text input comprises micro-ethnicity information of a patient. The feature comprises at least one of the one or more volumes of the region of interest (ROI), a cortical thickness, an atrophy percentage, an asymmetry index score, a subfield volumetry of the region of interest, annular volume changes, a progressive supranuclear palsy (psp) index score, a magnetic resonance perfusion imaging (MRPI) score, a frontal horn width to intercaudate distance ratio (FH/CC), a medial temporal lobe atrophy (MTA) score, a global cortical atrophy (GCA) scale, identification of Intracranial bleeds, hemorrhage, microbleeds and their volume analysis, a fracture detection, a midline shift identification, a measurement of the midline shift identification and the at least one structure with respect to the midline shift identification, identifying a pathology associated with the at least one structure, classifying the pathology identified, a tissue density identification, an infarct identification, a Penumbra-core-viable tissue identification, classification and volume calculation, diffusion-weighted imaging (DWI) maps and apparent diffusion coefficient (ADC) maps of the at least one structure, perfusion maps comprising resting state functional magnetic resonance imaging (rsfMRI), an alberta stroke programme early CT score (ASPECTS) calculation, a collateral detection, a mismatch ratio calculation, an angiography labeling and/or annotation, a large vessel occlusion (LVO) detection, an Hypoperfusion index calculation, Diffusion tensor imaging (DTI) fiber tracks, neural pathway connectivity maps, correlation between a signal input, an image input and the text input, classifying the signal input, identifying a normal signal, identifying an abnormal signal, identifying a pre-ictal signal, identifying an ictal signal, extracting symptoms, and grading of condition specific effects.

In yet another embodiment, the processor comprises a graphical processing unit (GPU).

In yet another aspect, a non-transitory computer storage medium storing a sequence of instructions, which when executed by a processor, causes: obtaining one or more first images of a region of interest of an anatomy from an image source, obtaining at least one of a text input, and one or more physiological signals of a patient, automatically segmenting, through a neural network, one or more second images of at least one structure that resides within the one or more first images, extracting one or more volumes of the at least one structure from the one or more first images of the region of interest, determining a feature associated with the at least one structure based on the one or more volumes and one or more inputs; and rendering the feature in at least one of a two-dimensional (2D) format, a three-dimensional (3D) format, and at least one anatomical plane. The text input comprises information of at least one of micro-ethnicity information, an age, a race, a gender, a medical condition, a symptom, clinical history, a patient history, a medical test, medication information, and a cognitive analysis report. The feature comprises at least one of the one or more volumes of the region of interest (ROI), a cortical thickness, an atrophy percentage, an asymmetry index score, a subfield volumetry of the region of interest, annular volume changes, a progressive supranuclear palsy (psp) index score, a magnetic resonance perfusion imaging (MRPI) score, a frontal horn width to intercaudate distance ratio (FH/CC), a medial temporal lobe atrophy (MTA) score, a global cortical atrophy (GCA) scale, identification of Intracranial bleeds, hemorrhage, microbleeds and their volume analysis, a fracture detection, a midline shift identification, a measurement of the midline shift identification and the at least one structure with respect to the midline shift identification, identifying a pathology associated with the at least one structure, classifying the pathology identified, a tissue density identification, an infarct identification, a Penumbra-core-viable tissue identification, classification and volume calculation, diffusion-weighted imaging (DWI) maps and apparent diffusion coefficient (ADC) maps of the at least one structure, perfusion maps comprising resting state functional magnetic resonance imaging (rsfMRI), an alberta stroke programme early CT score (ASPECTS) calculation, a collateral detection, a mismatch ratio calculation, an angiography labeling and/or annotation, a large vessel occlusion (LVO) detection, an Hypoperfusion index calculation, Diffusion tensor imaging (DTI) fiber tracks, neural pathway connectivity maps, correlation between a signal input, an image input and the text input, classifying the signal input, identifying a normal signal, identifying an abnormal signal, identifying a pre-ictal signal, identifying an ictal signal, extracting symptoms, and grading of condition specific effects.

In yet another aspect, a non-transitory computer storage medium storing a sequence of instructions, which when executed by a processor, causes: obtaining one or more first images of a region of interest of an anatomy from an image source, obtaining at least one of a text input, and one or more physiological signals of a patient, automatically segmenting one or more second images of at least one structure that resides within the one or more first images, estimating one or more quantitative volumes of the at least one structure, and predicting a prognosis based on comparison of the one or more quantitative volumes of the at least one structure with one or more reference volumes, the text input, and the one or more physiological signals. The text input comprises information of at least one of micro-ethnicity information, an age, a race, a gender, a medical condition, a symptom, clinical history, a patient history, a medical test, medication information, and a cognitive analysis report.

In yet another aspect, a non-transitory computer storage medium storing a sequence of instructions, which when executed by a processor, causes: obtaining one or more first images of a region of interest of an anatomy from an image source, obtaining a text input, automatically segmenting, through a neural network, one or more second images of at least one structure that resides within the one or more first images, extracting one or more volumes of the at least one structure from the one or more first images of the region of interest, determining a feature associated with the at least one structure based on the one or more volumes and one or more inputs; and rendering the feature in at least one of a two-dimensional (2D) format, a three-dimensional (3D) format, and at least one anatomical plane. The text input comprises micro-ethnicity information of a patient.

In one embodiment, the method further comprises: obtaining one or more physiological signals of the patient from a signal source.

In another embodiment, the method further comprises detecting at least one spike within the one or more physiological signals that indicates abnormality, and predicting a prognosis based on correlation and integrated analysis of the at least one spike detected and the one or more volumes.

In yet another embodiment, the method further comprises detecting an abnormal region, using the neural network, in the one or more volumes based on the at least one spike detected, and indicating the abnormal region using a different identifier.

In yet another embodiment, the method further comprises detecting an abnormal region, using the neural network, in the one or more physiological signals based on volumetric analysis, and indicating the abnormal region comprising the at least one spike, using a different identifier.

In yet another embodiment, the method further comprises automatically transforming the one or more physiological signals from a sinusoidal wave format to a quantitative format, and predicting a prognosis based on correlation and integrated analysis of at least one spike detected and the numerical representation of the one or more physiological signals. The quantitative format comprises a numerical representation of the one or more physiological signals.

In yet another aspect, a method is described herein. The method comprises: obtaining one or more physiological signals of a patient from a signal source, obtaining a text input of the patient, automatically detecting, using artificial intelligence, at least one spike within the one or more physiological signals that indicates abnormality, and predicting a prognosis based on the at least one spike detected from the one or more physiological signals, and the micro-ethnicity information. The text input comprises micro-ethnicity information.

In one embodiment, the method further comprises: generating an analysis report, based on the prognosis, comprising a snippet, and a graphical representation of the prognosis.

In another embodiment, the method further comprises indicating a portion of the one or more physiological signals where the at least one spike, indicating the abnormality, is located.

In yet another embodiment, the signal source comprises one of (a) a physiological signal acquisition unit, and (b) a computing unit.

In yet another embodiment, the method further comprises pre-processing the one or more physiological signals. The pre-processing comprises at least one of: filtering one or more noises associated with the one or more physiological signals, and removing artifacts associated with the one or more physiological signals.

In yet another embodiment, filtering the one or more noises associated with the one or more physiological signals comprises: passing the one or more physiological signals through at least one of a notch filter, and a bandpass filter.

In yet another embodiment, the method further comprises post-processing the one or more physiological signals using artificial intelligence. The post-processing comprises: comparing one or more first physiological signals obtained at a first instance and one or more second physiological signals obtained at a second instance, predicting the prognosis based on comparison of the one or more first physiological signals and the one or more second physiological signals, estimating one of a progression and a regression of the prognosis associated with the patient between the first instance and the second instance, and generating an analysis report, based on the prognosis, comprising a snippet, and a graphical representation of the prognosis.

In yet another embodiment, the method further comprises: obtaining one or more first images of an anatomy of the patient from an image source, automatically segmenting, through a neural network, one or more second images of at least one structure that resides within the one or more first images, extracting one or more volumes of the at least one structure from the one or more first images, determining a feature associated with the at least one structure based on the one or more volumes and one or more inputs; and rendering the feature in at least one of a two-dimensional (2D) format, a three-dimensional (3D) format, and at least one anatomical plane.

In yet another embodiment, the method further comprises overlaying the one or more physiological signals as a heat map on the one or more volumes of the at least one structure, and predicting an orientation, a position, a shape, and a source of at least one abnormality within the at least one structure.

In yet another embodiment, the text input further comprises at least one of a cognitive score, a patient history, and clinical information.

In yet another embodiment, the method comprises: predicting the prognosis based on the at least one spike detected from the one or more physiological signals, the micro-ethnicity information and at least one of the cognitive score, the patient history, and the clinical information.

In yet another aspect, a method is described herein. The method comprises: obtaining one or more physiological signals of a patient from a signal source, obtaining a text input of the patient, automatically transforming the one or more physiological signals from a sinusoidal wave format to a quantitative format, predicting a prognosis, using an artificial intelligence, based on the numerical representation of the one or more physiological signals, and generating an analysis report, based on the prognosis, comprising a snippet, and a graphical representation of the prognosis. The quantitative format comprises a numerical representation of the one or more physiological signals. The text input comprises micro-ethnicity information.

In yet another aspect, a method is described herein. The method comprises: obtaining at least one of one or more physiological signals of a patient in response to at least one stimulus applied to the patient, obtaining a text input of the patient, predicting at least one of cognitive performance and cognitive deficits, using an artificial intelligence, of the patient based on the one or more physiological signals, and the micro-ethnicity information, and generating an analysis report, based on at least one of the cognitive performance, and the cognitive deficits, comprising a snippet, and a graphical representation of a prognosis. The at least one stimulus comprises at least one of a tangible stimulus, and an intangible stimulus. The text input comprises micro-ethnicity information.

In an embodiment, the at least one stimulus comprises an auditory stimulus, a visual stimulus, an olfactory stimulus, and a palpable stimulus.

In yet another aspect, a system is described herein. The system comprises a server. The server comprises a memory, and a processor communicatively coupled to the memory. The processor is operable to: obtain one or more physiological signals of a patient from a signal source, obtain a text input of the patient, automatically detect, using artificial intelligence, at least one spike within the one or more physiological signals that indicates abnormality, and predict a prognosis based on the at least one spike detected from the one or more physiological signals, and the micro-ethnicity information. The text input comprises micro-ethnicity information.

In another embodiment, a system is described herein. The server comprises a memory, and a processor communicatively coupled to the memory. The processor operable is to obtain one or more physiological signals of a patient from a signal source, obtain a text input of the patient, automatically transform the one or more physiological signals from a sinusoidal wave format to a quantitative format, predict a prognosis, using an artificial intelligence, based on the numerical representation of the one or more physiological signals, and generate an analysis report, based on the prognosis, comprising a snippet, and a graphical representation of the prognosis. The text input comprises micro-ethnicity information. The quantitative format comprises a numerical representation of the one or more physiological signals.

In yet another aspect, a system is described herein. The system comprises a server comprising a memory, and a processor communicatively coupled to the memory. The processor is operable to: obtain one or more physiological signals of a patient in response to at least one stimulus applied to the patient, obtain a text input of the patient, predict at least one of cognitive performance and cognitive deficits, using an artificial intelligence, of the patient based on the one or more physiological signals, and the micro-ethnicity information, and generate an analysis report, based on at least one of the cognitive performance, and the cognitive deficits, comprising a snippet, and a graphical representation of a prognosis. The at least one stimulus comprises at least one of a tangible stimulus, and an intangible stimulus. The text input comprises micro-ethnicity information.

In yet another aspect, a non-transitory computer storage medium is described herein. The non-transitory computer storage medium stores a sequence of instructions, which when executed by a processor, causes: obtaining one or more physiological signals of a patient from a signal source, obtaining a text input of the patient, automatically detecting, using artificial intelligence, at least one spike within the one or more physiological signals that indicates abnormality, and predicting a prognosis based on the at least one spike detected from the one or more physiological signals, and the micro-ethnicity information. The text input comprises micro-ethnicity information.

In yet another aspect, a non-transitory computer storage medium is described herein. The non-transitory computer storage medium storing a sequence of instructions, which when executed by a processor, causes: obtaining one or more physiological signals of a patient from a signal source, obtaining a text input of the patient, automatically transforming the one or more physiological signals from a sinusoidal wave format to a quantitative format, predicting a prognosis, using an artificial intelligence, based on the numerical representation of the one or more physiological signals, and generating an analysis report based on the prognosis. The analysis report comprising at least one of a snippet, and a graphical representation of the prognosis. The quantitative format comprises a numerical representation of the one or more physiological signals. The text input comprises micro-ethnicity information.

In yet another aspect, a non-transitory computer storage medium is described herein. The non-transitory computer storage medium storing a sequence of instructions, which when executed by a processor, causes: obtaining at least one of one or more physiological signals of a patient in response to at least one stimulus applied to the patient, obtaining a text input of the patient, predicting at least one of cognitive performance and cognitive deficits, using an artificial intelligence, of the patient based on the one or more physiological signals, and the micro-ethnicity information, and generating an analysis report based on at least one of the cognitive performance, and the cognitive deficits. The analysis report comprising at least one of a snippet, and a graphical representation of a prognosis. The text input comprises micro-ethnicity information. The at least one stimulus comprises at least one of a tangible stimulus, and an intangible stimulus.

In yet another aspect, a method is described. The method comprises: obtaining one or more first images of a region of interest of an anatomy from an image source; obtaining at least one of a text input, and one or more physiological signals of a patient, wherein the text input comprises information of at least one of micro-ethnicity information, an age, a race, a gender, a medical condition, a symptom, clinical history, a patient history, a medical test, medication information, and a cognitive analysis report; automatically segmenting, through a neural network, one or more second images of at least one structure that resides within the one or more first images; extracting one or more volumes of the at least one structure from the one or more first images of the region of interest; determining a feature associated with the at least one structure based on the one or more volumes and one or more inputs; and rendering the feature in at least one of a two-dimensional (2D) format, a three-dimensional (3D) format, and at least one anatomical plane.

In an embodiment, the method further comprises: performing a second quality analysis manually on the one or more second images that are segmented; and determining whether the one or more second images, that are segmented, passes the second quality analysis.

In another embodiment, the method further comprises: providing a user interface to the user when the one or more second images that are segmented fails the second quality analysis; manually editing and correcting at least one of boundaries and the one or more volumes of the at least one structure based on one or more inputs received from the user; and creating a mask for the at least one structure.

In yet another embodiment, the method further comprises: training the neural network using at least one of (a) the one or more first images, (b) the information of at least one of the micro-ethnicity information, the age, the race, the gender, the medical condition, the symptom, the clinical history, the patient history, the medical test, the medication information, and the cognitive analysis report, (c) the one or more physiological signals, (d) the one or more volumes of the at least one structure, (e) one or more reference volumes, and (f) one or more reference segmented second images.

In yet another embodiment, the method further comprises: creating a log for the mask using the one or more inputs received from the user; retraining the neural network based on the log created; and automatically segmenting, through the neural network, the one or more images of the at least one structure in future based on the retraining provided to the neural network.

In yet another embodiment, the method further comprises: assigning a voxel of a mask of the one or more second images, that are segmented, as a unit; tabulating a plurality of units in the mask; and estimating one or more quantitative volumes of the at least one structure from the plurality of units.

In yet another embodiment, the method further comprises: recording the one or more volumes of the at least one structure in a database; and categorizing the one or more volumes of the at least one structure in the database with respect to one or more categories of at least one of the micro-ethnicity information, an intracranial volume (ICV), the age, the race, the gender, a family history, the clinical history, the patient history, the symptom, psych analysis information, brain dominance information, food habitat information, stress information, and the medical condition.

In yet another embodiment, the method further comprises: extracting one or more boundaries of the at least one structure from the one or more first images; and populating one or more voxels within the one or more boundaries of the at least one structure using one or more identifiers.

In yet another embodiment, the method further comprises: performing at least one of adding, and deleting one or more voxels within the boundaries of the at least one structure based on the one or more inputs received from the user.

In yet another embodiment, the method further comprises: detecting at least one spike within the one or more physiological signals that indicates abnormality; and predicting a prognosis based on correlation and integrated analysis of the at least one spike detected, the text input, and the one or more volumes.

In yet another embodiment, the method further comprises: correlating with at least one of temporal resolution and spatial resolution of an image input and detecting an abnormal region, using the neural network, in the one or more volumes based on the at least one spike detected; and indicating the abnormal region using a different identifier.

In yet another embodiment, the method further comprises transforming automatically the one or more physiological signals from a sinusoidal wave format to a quantitative format; predicting a prognosis based on correlation with an image input and integrated analysis of at least one spike detected and the numerical representation of the one or more physiological signals; and generating an analysis report based on the prognosis. The analysis report comprising at least one of a feature, a snippet describing the prognosis, one or more volumes of the at least one structure, one or more quantitative volumes, and a graphical representation of the prognosis. The quantitative format comprises a numerical representation of the one or more physiological signals.

In yet another embodiment, the one or more reference volumes range between 25th and 95th percentile. The 25th and the 95th percentile are calculated by matching at least one of the age, the gender, the micro-ethnicity information, and an intracranial volume (ICV) of the patient with a normative population of individuals and then deriving the 25th and the 95th percentile references.

In yet another embodiment, the 25th and the 95th percentile is calculated by matching the medical condition of the patient with a population of individuals having the medical condition and then deriving the 25th and the 95th percentile.

In yet another embodiment, the method further comprises: predicting a first prognosis state of the patient based at least one of the medical condition, and first medication information of the patient at a first point of time and generating a first analysis report; and predicting a second prognosis state of the patient based on at least one of the medical condition, and second medication information of the patient at a second point of time and generating a second analysis report.

In yet another embodiment, the method further comprises: comparing the first prognosis state and the second prognosis state; determining a percentage of one of a deterioration and an improvement in at least one of one or more volumes, and the one or more quantitative volumes based on the comparison of the first prognosis state and the second prognosis state; and training, a neural network, using at least one of medical condition, the first medication information, the second medication information, and the percentage of the deterioration or the improvement in at least one of one or more volumes, and the one or more quantitative volumes at a plurality of different point of times.

In yet another embodiment, the method further comprises: detecting a diagnosis, via the neural network, at a third point of time by comparing the first prognosis state and the second prognosis state based on the training; performing a predictive prognosis, via the neural network, and predicting a third prognosis state of the patient at the third point of time based on the training; and performing a predictive prognosis, via the neural network, and predicting a third prognosis state of the patient at the third point of time based on the training; and generating a third analysis report comprising a clinical analytical outcome at the third point of time.

The server described herein provides clinicians objective analysis to aid in their assessment of a patient's prognosis. The server further supports a physician's clinical impression with quantitative numbers. The server further performs on-going multi time point evaluation to track structural volumetric changes over time. The server presents earlier insights about accelerated neurodegeneration which assists physicians in identifying, treating and lifestyle planning for such patients. The server helps as a Neuro-Imaging Tool in conduct of Clinical Trials to determine eligibility/monitor progress and as a Clinical End Point for multi centric Neurology Clinical Trials. The server assists in clinical research in studying population and disease characteristics. The server provides services such as a Neuro-Imaging tool for Medical Devices Companies developing products for Imaging. The server further assists in acute cases like stroke and traumatic brain injury (TBI) can be escalated as fast as possible. The server further assists in performing volumetric analysis remotely. The server further assists in early prognosis for Neurodegeneration. The server further assists in Development of reference ranges for the Indian Population. The server further assists in connecting hospitals and diagnostic centers to doctors in the urban areas. The structure-based analysis report adds objectivity to the physician's report. The server is useful in determining the physiological age of the brain, allowing to know the state of his/her general brain health.

In an embodiment, the server can detect stroke, haemorrhage region, haemorrhage types (intraparenchymal, sub dural, extradural, subarachnoid, intraventricular), Segmentation of haemorrhage, Total haemorrhage volume, measurement of oedema/oedematous tissue using HU values, Measurement of midline shift and Lobe herniation; Detection of Skull and cervical fractures; and Spinal cord evaluation (Atlanto-axial). The server is also capable of performing Segmentation of bleed, Fracture detection, Measurement of midline shift, Region of bleed, Differentiation between bleed, calcification and bone and measurement of HU (Hounsfield unit) value, differentiation between normal tissue density and oedematous, extracting Intra and Extra-ventricular volume; and extracting Superior and Inferior tentorium CSF volume. The server is also capable of epilepsy, memory dementia, pre-Alzheimer's diagnostics, etc.

The server provides the following aspects on various MRI sequences. Conventional MR images may not show positive findings in cases of ischemic infarction for 8 to 12 hours after onset, a time period beyond that when neuroprotective drugs are most likely to be given and more likely to be effective. Diffusion weighted MR images, on the other hand, can show regions of ischemic injury within minutes after stroke onset. The server performs comparison between ADC and perfusion imaging to understand blood flows. The server is also capable of overlaying the diffusion map onto a T1 map for better understanding of structural mapping. The server also easily interprets magnetic resonance angiography (MRA) maps and identifies brain regions with reduced blood vessel density. The server then performs comparison between Apparent diffusion coefficient (ADC) and perfusion imaging and overlay diffusion map onto the T1 map (e.g., Diffusion-weighted imaging (DWI)) for better understanding of structural mapping.

The methods and systems disclosed herein may be implemented in any means for achieving various aspects and may be executed in a form of a non-transitory machine-readable medium embodying a set of instructions that, when executed by a machine, causes the machine to perform any of the operations disclosed herein. Other aspects will be apparent from the accompanying drawings and from the detailed description that follows.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Color drawings have been submitted in this application because in figures such as FIG. 11*d*, FIG. 11*e*, FIG. 12*e*, FIG. 12*f*, FIG. 12*g*, FIG. 12*h*, FIG. 12*i*, FIG. 12*j*, FIG. 12*k*, FIG. 13*d*, FIG. 13*e*, FIG. 13*f*, FIG. 13*g*, FIG. 13*h*, FIG. 14*c*, FIG. 15*a*, FIG. 15*b*, FIG. 15*c*, FIG. 15*d*, FIG. 16*a*, FIG. 16*b*, FIG. 16*c*, FIG. 17*a*, FIG. 17*c*, FIG. 17*d*, FIG. 17*e*, FIG. 17*f*, FIG. 17*g*, FIG. 17*h*, FIG. 18, FIG. 19, FIG. 20*d*, FIG. 20*e*, FIG. 21*d*, FIG. 21*e*, FIG. 21*f*, FIG. 21*g*, FIG. 22*c*, FIG. 22*d*, FIG. 22*e*, FIG. 22*f*, FIG. 23*c*, FIG. 24*c*, FIG. 24*d*, FIG. 24*e*, FIG. 24*f*, FIG. 24*g*, FIG. 24*h*, FIG. 24*i*, FIG. 24*j*, FIG. 25*e*, FIG. 25*f*, FIG. 25*g*, FIG. 25*h*, FIG. 25*i*, FIG. 26*c*, FIG. 26*d*, FIG. 26*e*, FIG. 26*f*, FIG. 26*g*, FIG. 26*h*, FIG. 27*c*, FIG. 27*d*, FIG. 27*e*, FIG. 27*f*, FIG. 27*g*, FIG. 28*b*, FIG. 29*a*, FIG. 29*b*, FIG. 29*c*, FIG. 32*c*, FIG. 38*a*, FIG. 38*b*, FIG. 38*c*, FIG. 38*d*, and FIG. 38*e*, different colors represent different structures, different boundaries, different volumes, and variations in different graphical representations. The variation in color gives obvious visual cues about how the phenomenon is clustered or varies. The colors in the abovementioned figures have specific meaning and denote specific structures in the region of interest in a standardized way. For example, in FIG. 11*e*, the blue color indicates the region of interest in a left side, and the pink color indicates the region of interest in a right side. Further, the colors in the abovementioned drawings are used for easy interpretation of output to the users in a standardized way. The usage of colors is the only way to distinguish and delineate the structures within the region of interest exactly. If shadings are used to distinguish and delineate the structures, the structures cannot be exactly portrayed or displayed for the user's assessment. The corners or edges of the region of interest may be hidden due to shading, and therefore, might result in possibility of a medical error. Thus, the color drawing is the only practical medium by which aspects of the claimed subject matter may be accurately conveyed.

Figure 1:
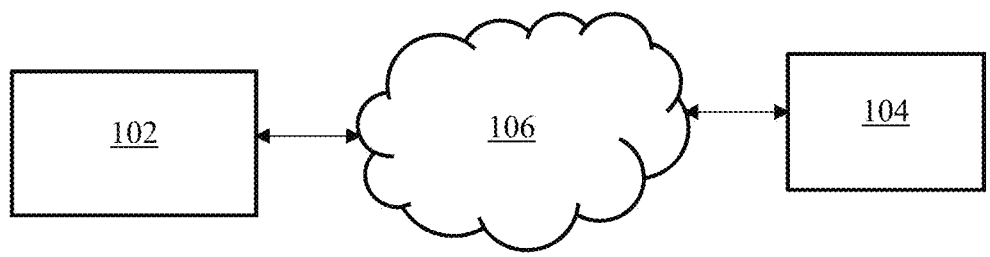

In the present disclosure, reference is made to the accompanying drawings, which form a part hereof. In the drawings, similar symbols typically identify similar components, unless context dictates otherwise. Various embodiments described in the detailed description, and drawings, are illustrative and not meant to be limiting. Other embodiments may be used, and other changes may be made, without departing from the spirit or scope of the subject matter presented herein. It will be understood that the aspects of the present disclosure, as generally described herein, and illustrated in the Figures, can be arranged, substituted, combined, separated, and designed in a wide variety of different configurations, all of which are contemplated herein. The embodiments are illustrated by way of example and not limitation in the figures of the accompanying drawings, in which like references indicate similar elements and in which:

FIG. 1 illustrates a schematic view of a system, according to one or more embodiments.

Figure 2:
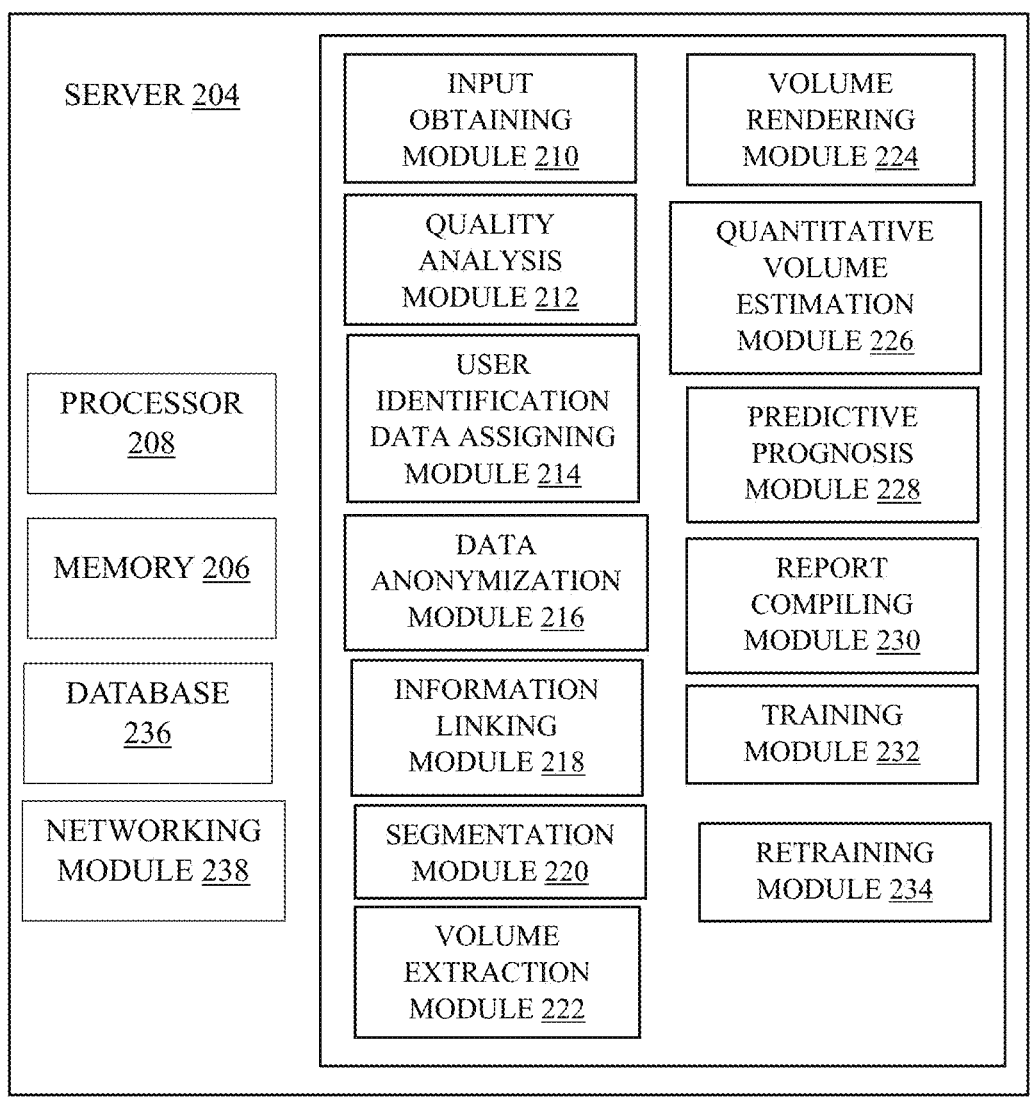

FIG. 2 illustrates an exploded view of a server, according to one or more embodiments.

Figure 3:
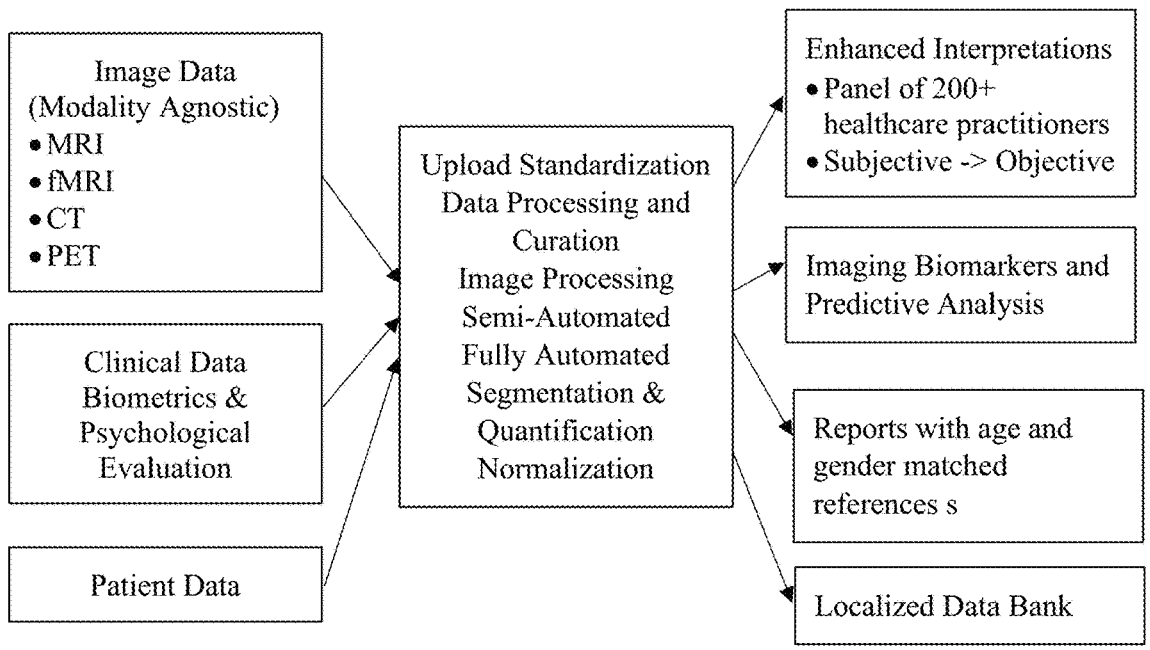

FIG. 3 illustrates an overview of a system, according to one or more embodiments.

Figure 4:
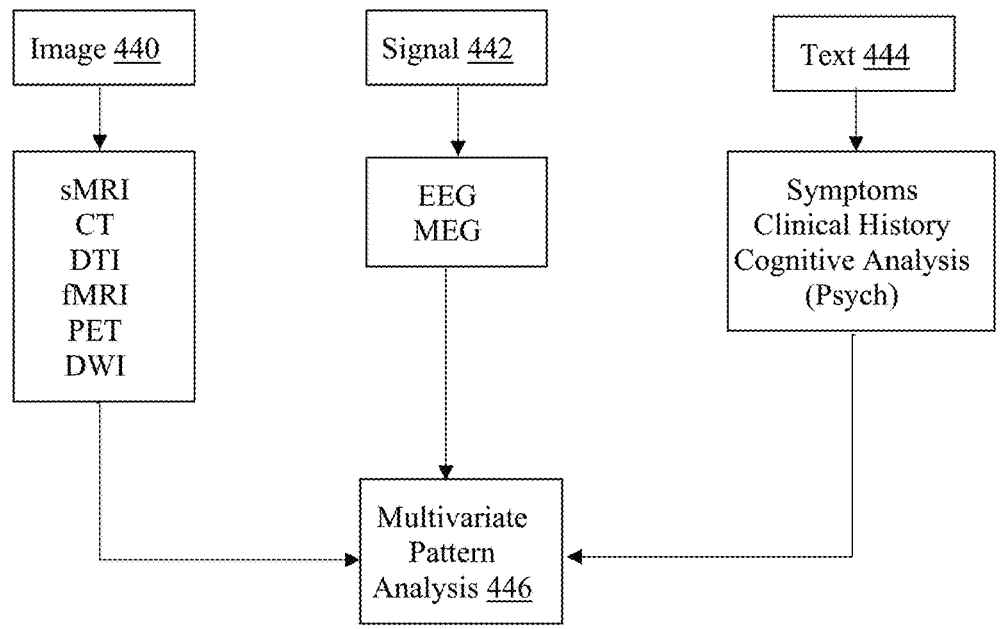

FIG. 4 illustrates a multivariate pattern analysis performed by a system, according to one or more embodiments.

Figure 5:
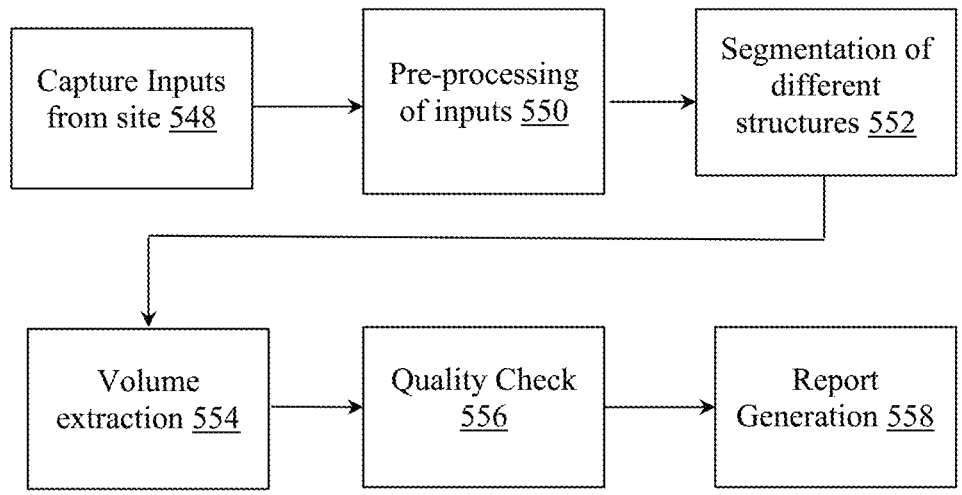

FIG. 5 illustrates a method of structure-based analysis report generation, according to one or more embodiments.

Figure 6:
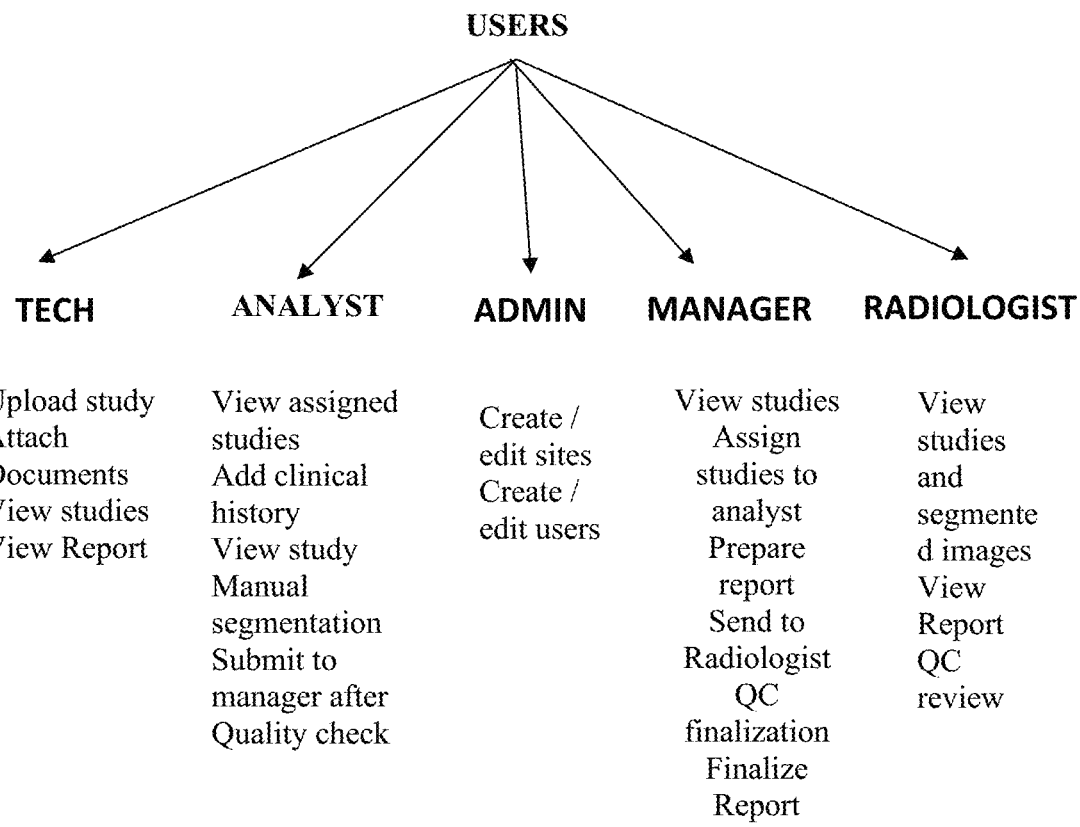

FIG. 6 illustrates users of a system, according to one or more embodiments.

Figure 7:
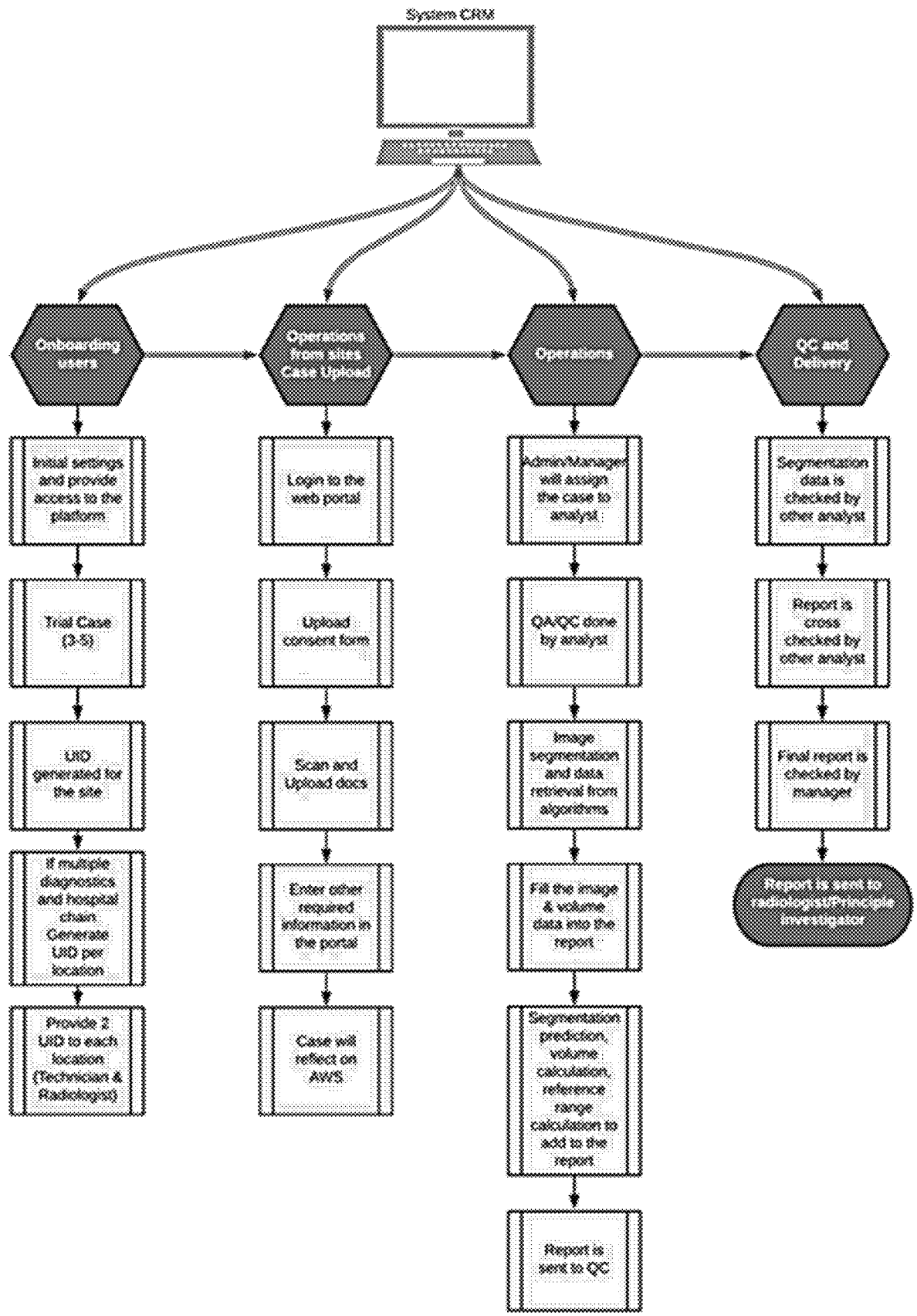

FIG. 7 illustrates a process flow of a system, according to one or more embodiments.

Figure 8:
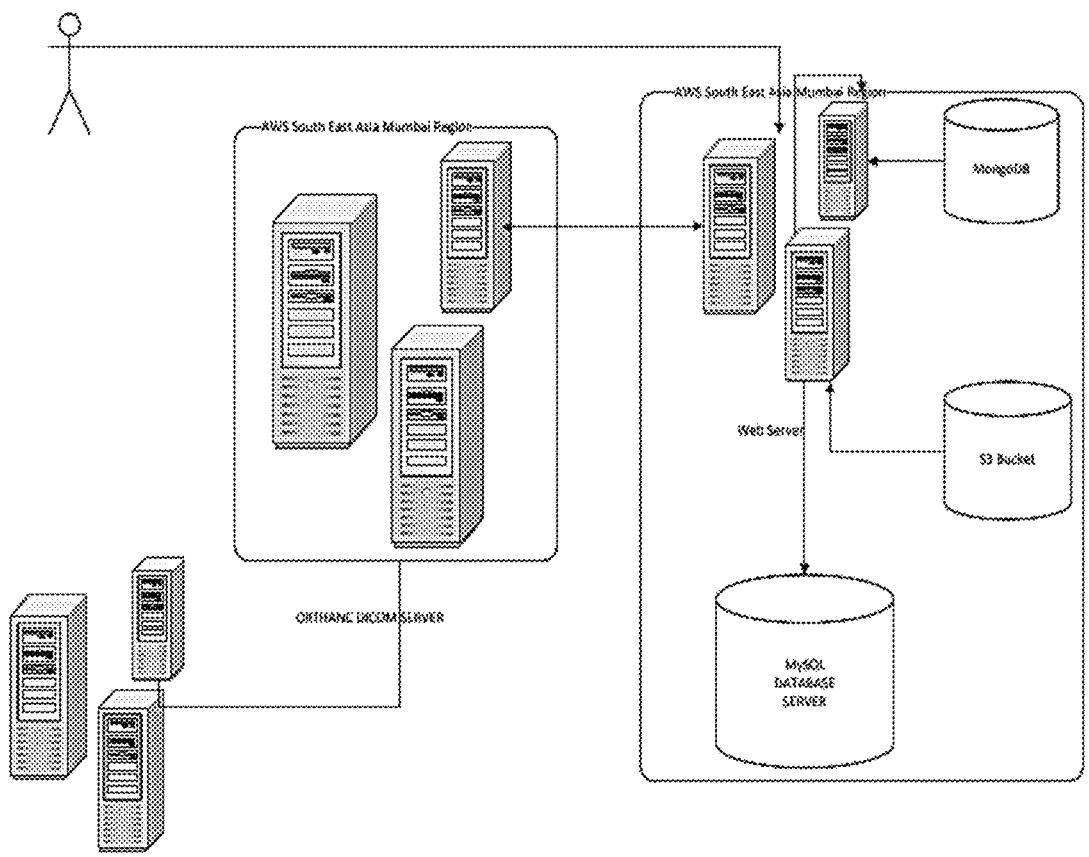
Figure 9:
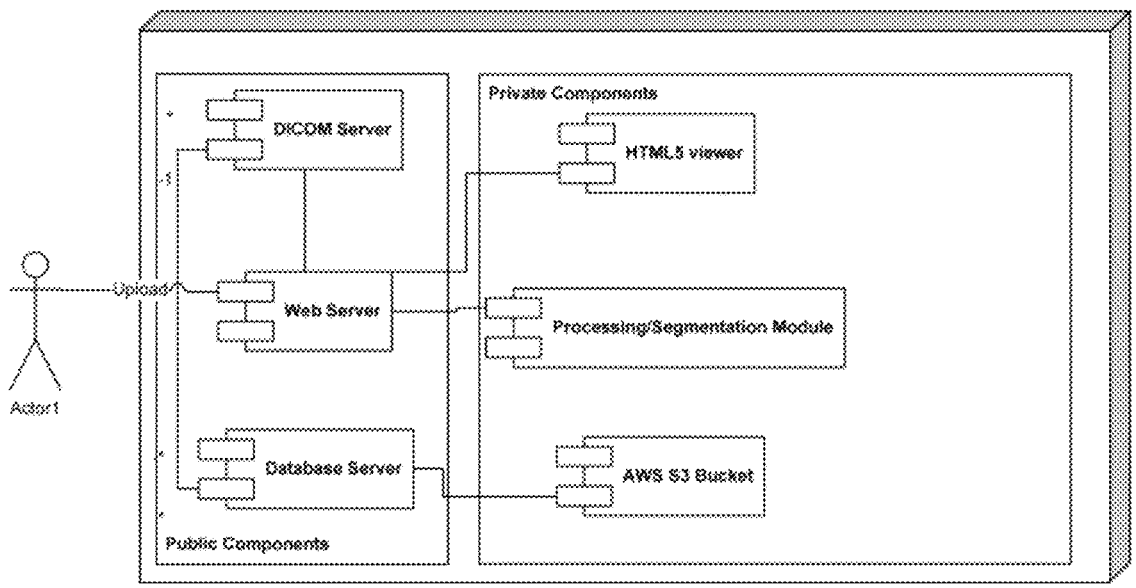

FIGS. 8 and 9 illustrate a system architecture, according to one or more embodiments.

Figure 10:
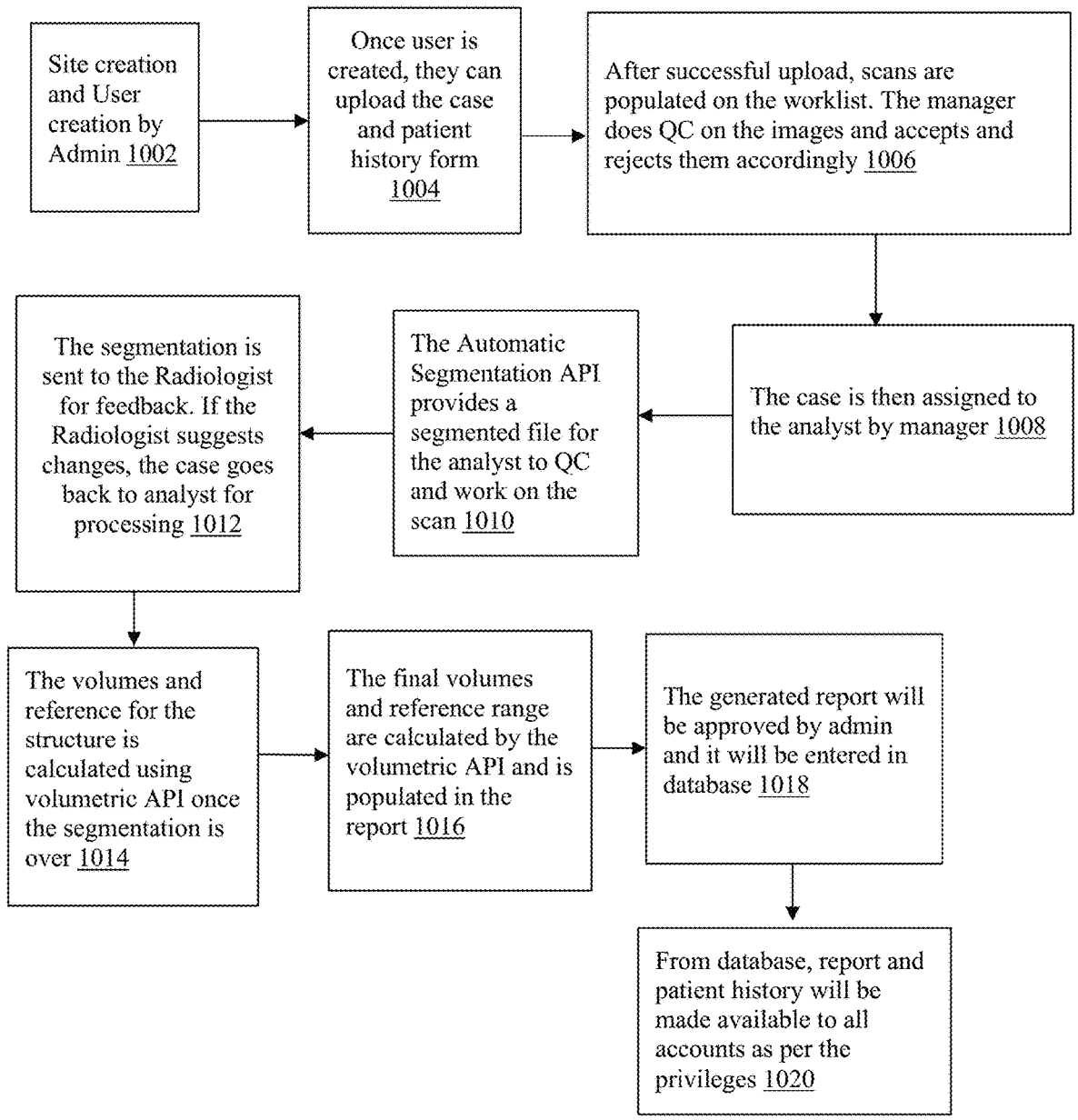

FIG. 10 illustrates a workflow, according to one or more embodiments.

FIG. 11*a*-11*e* illustrate a process of segmentation of Hippocampus, according to one or more embodiments.

FIG. 12a-12k illustrate a process of segmentation of Ventricles, according to one or more embodiments.

FIG. 13a-13h illustrate a process of segmentation of a Whole Brain, according to one or more embodiments.

Figure 14A:
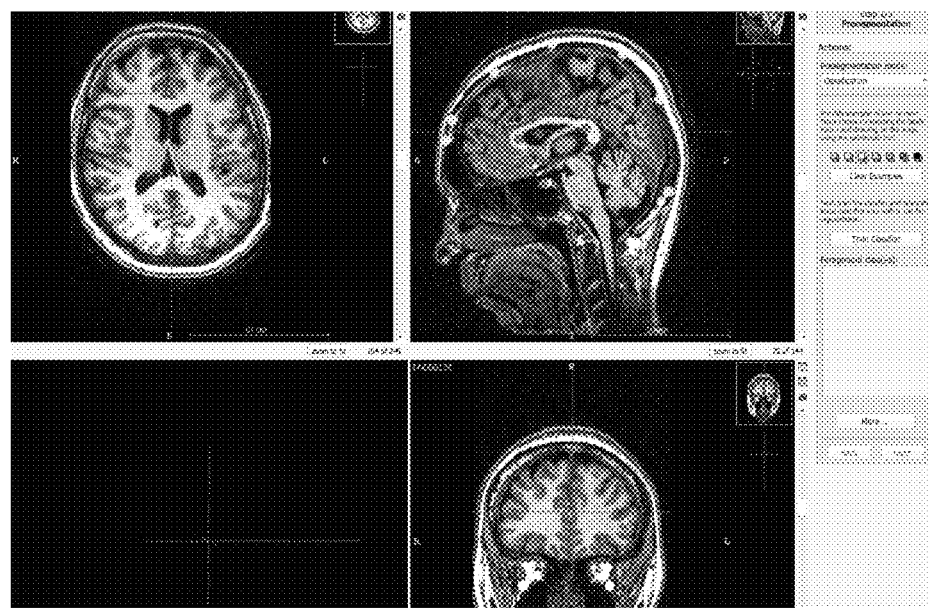
Figure 14B:
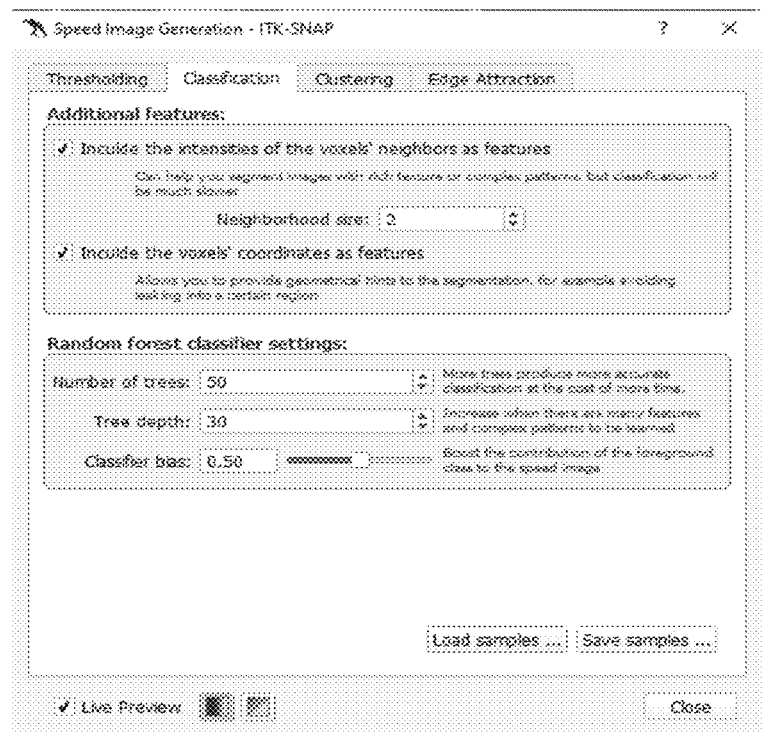
Figure 14C:
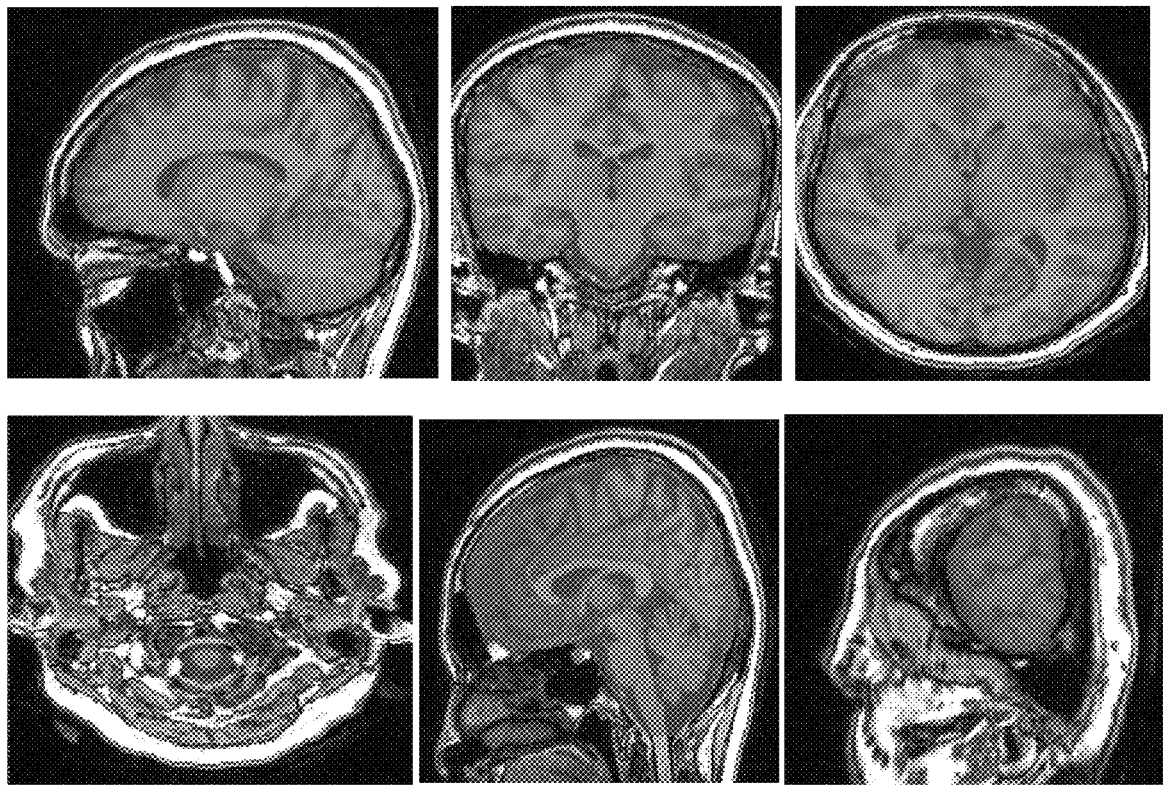

FIG. 14a-14c illustrate a process of segmentation of an intracranial volume (ICV), according to one or more embodiments.

FIG. 15a-15d illustrate a process of segmentation of Cerebrum, according to one or more embodiments.

Figure 16A:
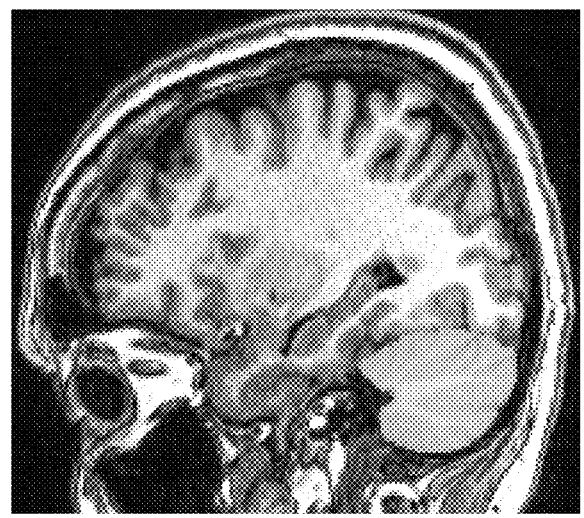
Figure 16B:
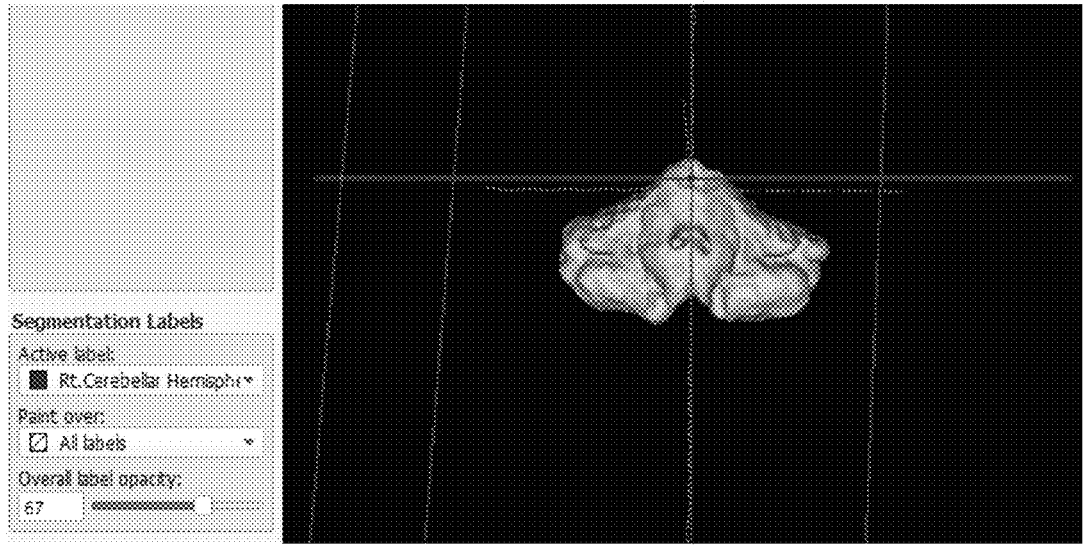
Figure 16C:
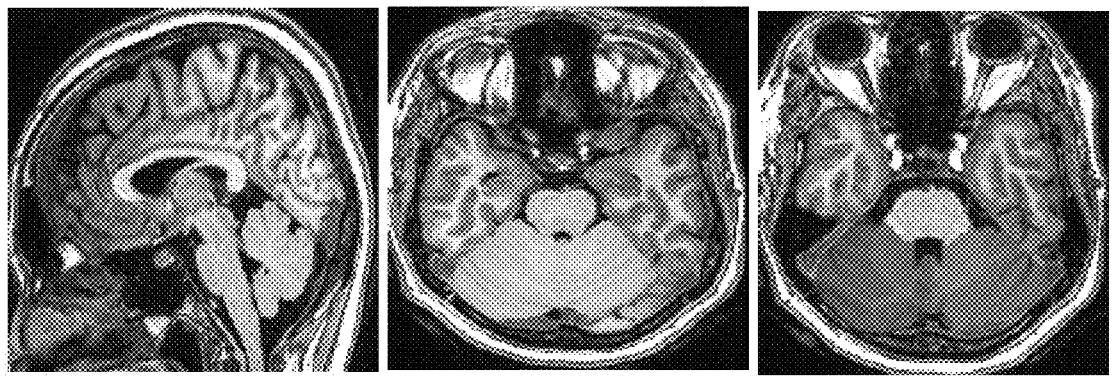

FIG. 16a-16c illustrate a process of segmentation of Cerebellum, according to one or more embodiments.

FIG. 17a-17h illustrate a process of segmentation of Brainstem, according to one or more embodiments.

Figure 18:
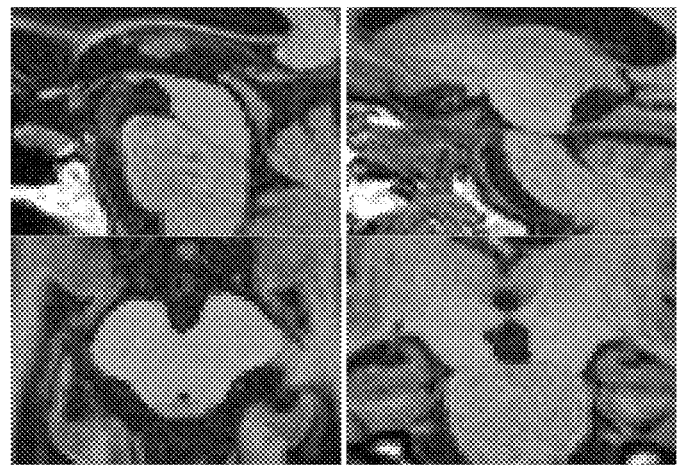

FIG. 18 illustrates a process of segmentation of Midbrain, according to one or more embodiments.

Figure 19:
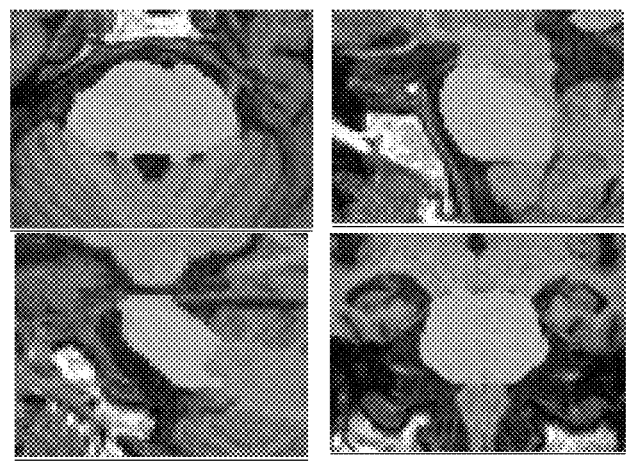

FIG. 19 illustrates a process of segmentation of Pons, according to one or more embodiments.

FIG. 20a-20e illustrate a process of segmentation of Amygdala, according to one or more embodiments.

FIG. 21a-21g illustrate a process of segmentation of Basal Ganglia, according to one or more embodiments.

FIG. 22a-22f illustrate a process of segmentation of Thalamus, according to one or more embodiments.

Figure 23A:
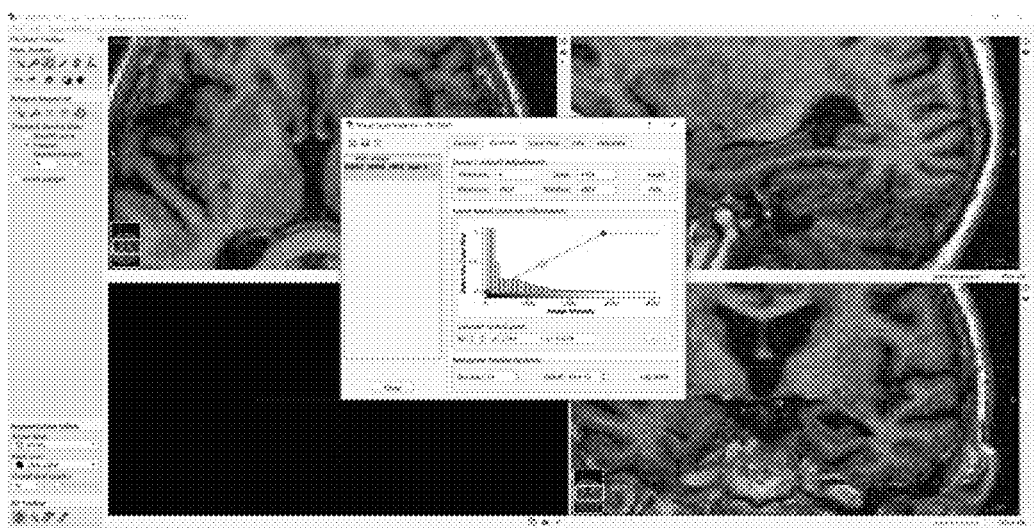
Figure 23B:
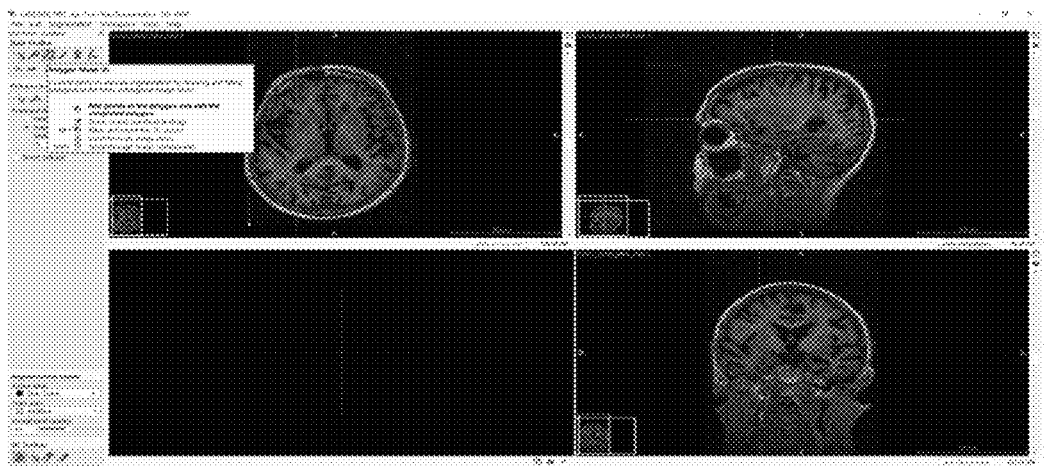
Figure 23C:
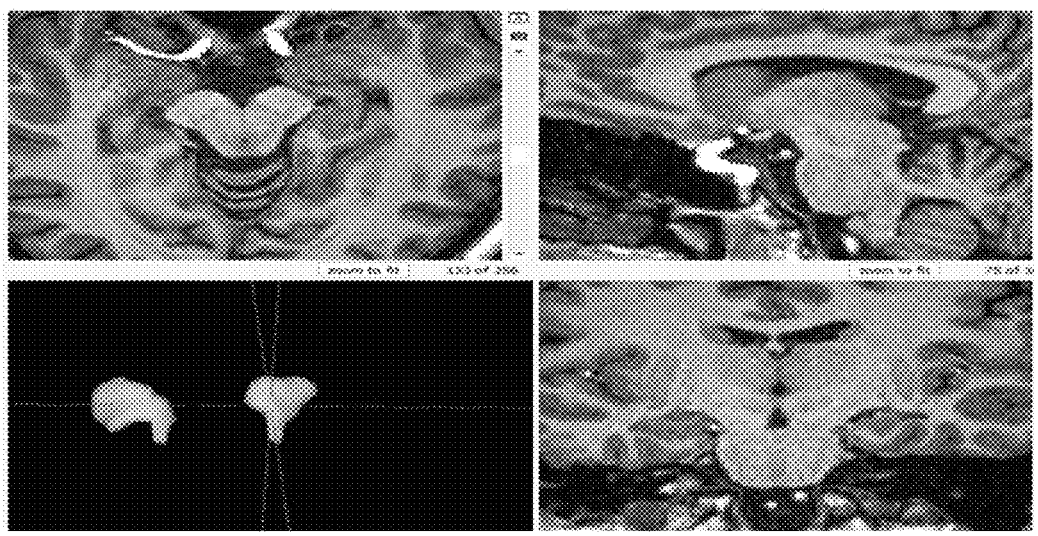

FIG. 23a-23c illustrate a process of segmentation of Substantia Nigra, according to one or more embodiments.

FIG. 24a-24j illustrate a process of segmentation of Frontal Lobes, according to one or more embodiments.

FIG. 25a-25i illustrate a process of segmentation of Parietal Lobes, according to one or more embodiments.

FIG. 26a-26h illustrate a process of segmentation of Occipital Lobes, according to one or more embodiments.

FIG. 27a-27g illustrate a process of segmentation of Temporal Lobes, according to one or more embodiments.

Figure 28A:
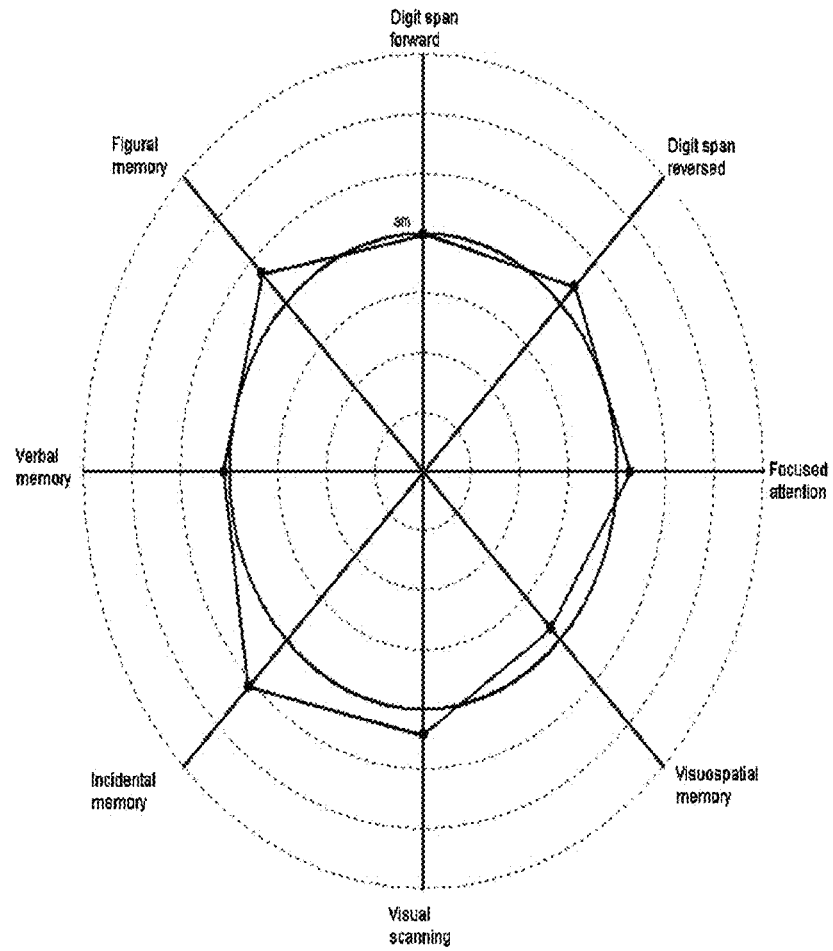

FIG. 28a and 28b illustrate a structure-based analysis report, according to one or more embodiments.

FIG. 29a-29c illustrate an integrated analysis report showing an integrated multimodal analysis of an image input, a text input, and a signal input, according to one or more embodiments.

FIG. 30a-30b illustrate an EEG detailed report, according to one or more embodiments.

Figure 31:

FIG. 31 illustrates monitoring of one or more physiological signals, according to one or more embodiments.

Figure 32A:
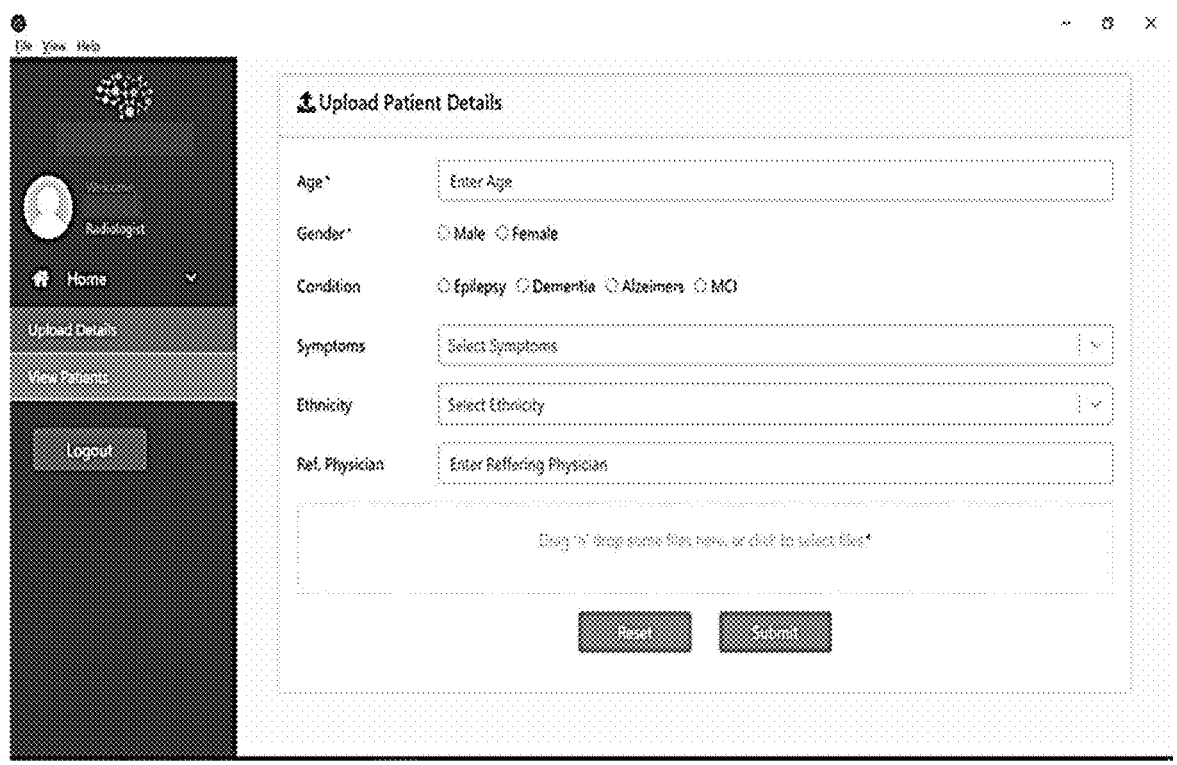

FIG. 32a illustrates a screenshot of a user interface that allows a user to upload patient details, according to one or more embodiments.

Figure 32B:
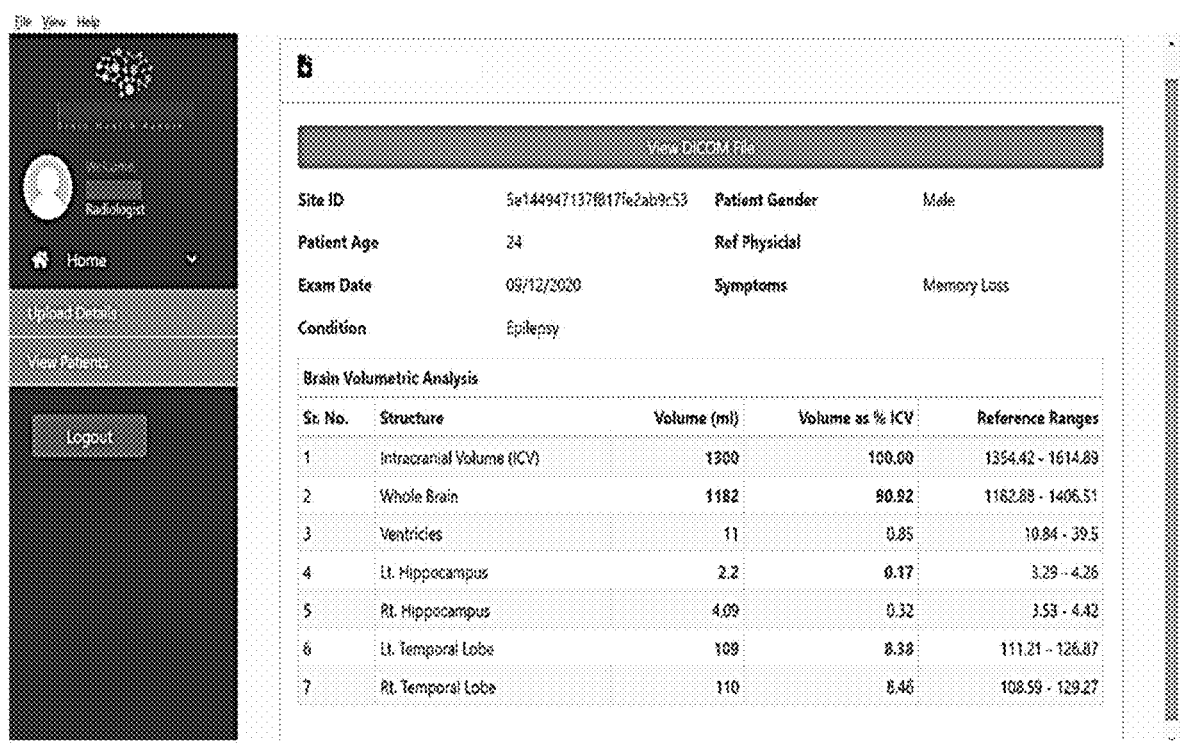

FIG. 32b illustrates a screenshot of a user interface that allows a user to view patient details, according to one or more embodiments.

Figure 32C:
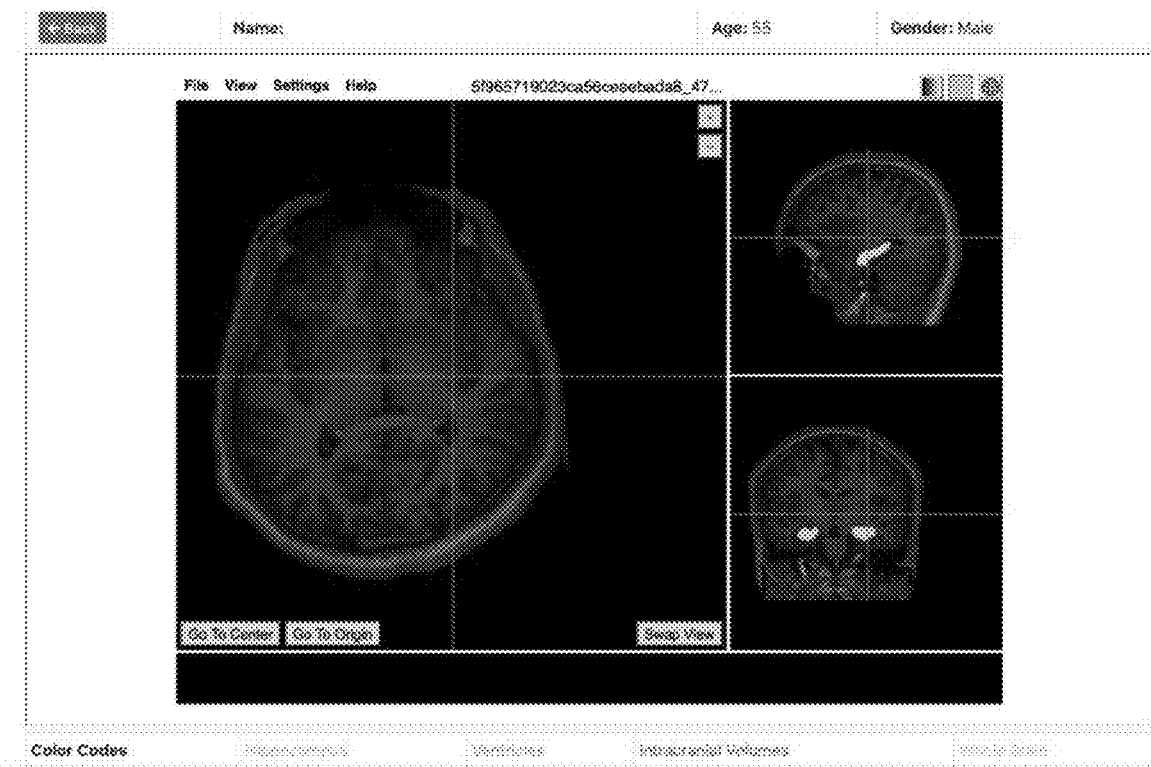

FIG. 32c illustrates a screenshot of a user interface rendering a segmented image, according to one or more embodiments.

Figure 32D:
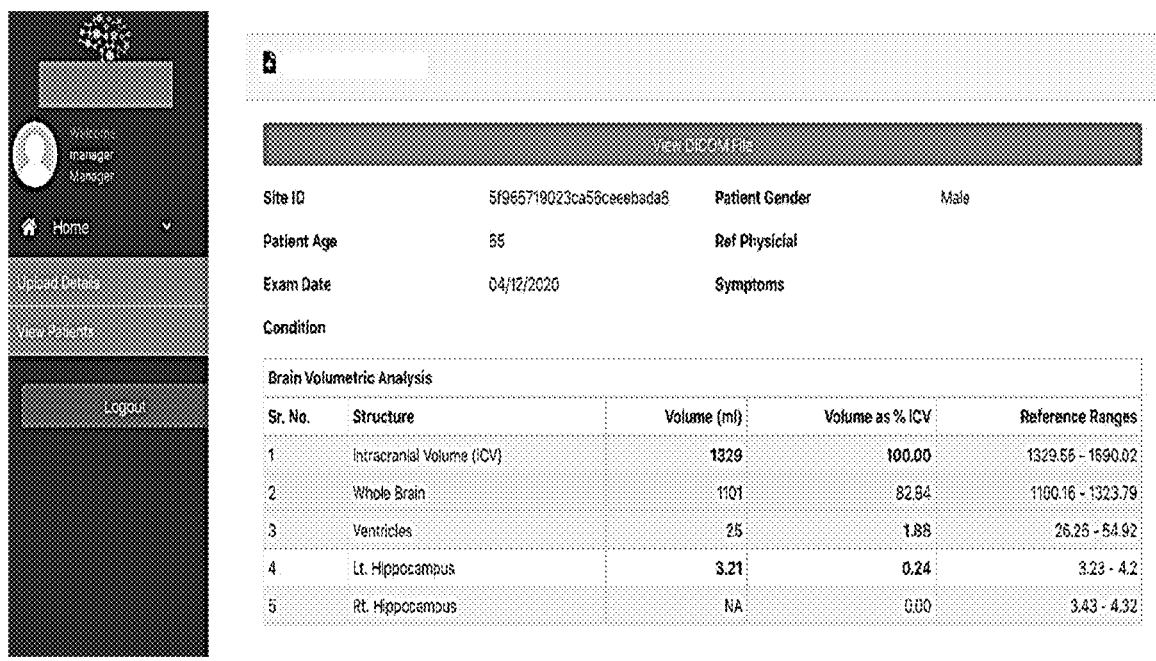

FIG. 32d illustrates a screenshot of a user interface that allows a user to view patient details, according to one or more embodiments.

Figure 33:
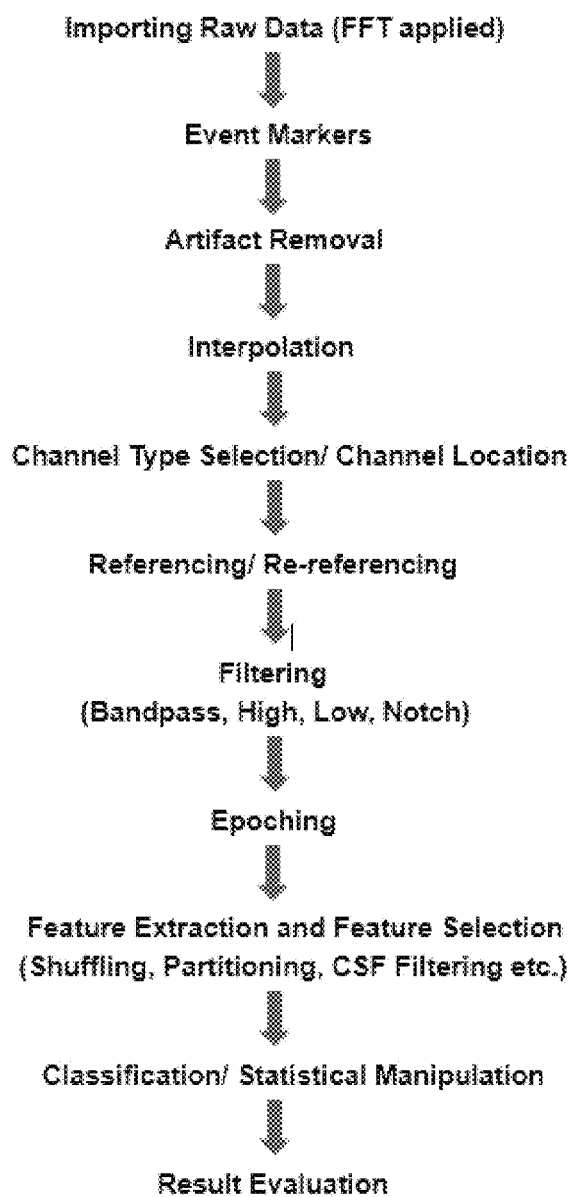

FIG. 33 illustrates the processing of EEG signals, according to one or more embodiments.

Figure 34:
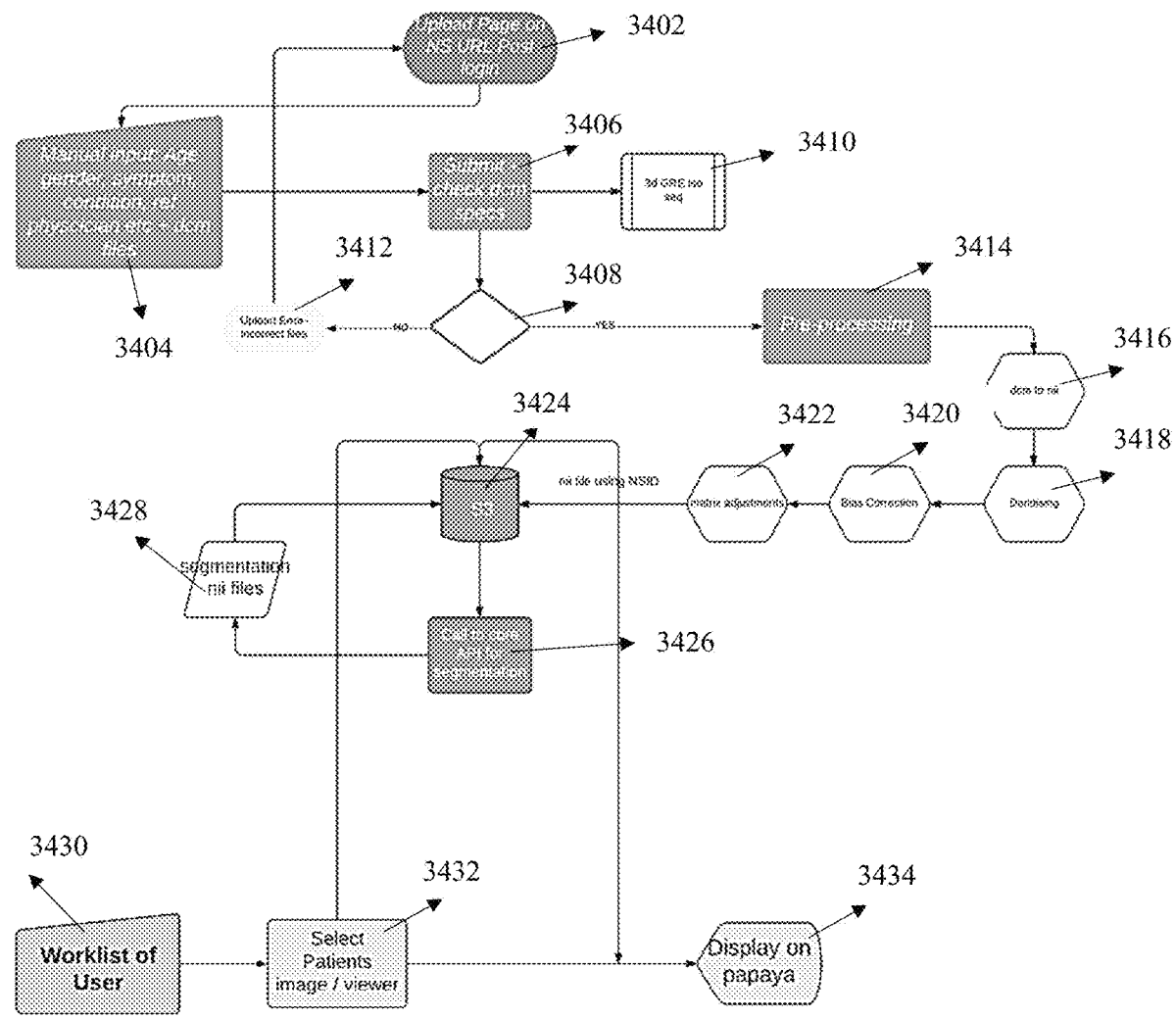

FIG. 34 illustrates a data flow of a system, according to one or more embodiments.

Figure 35:
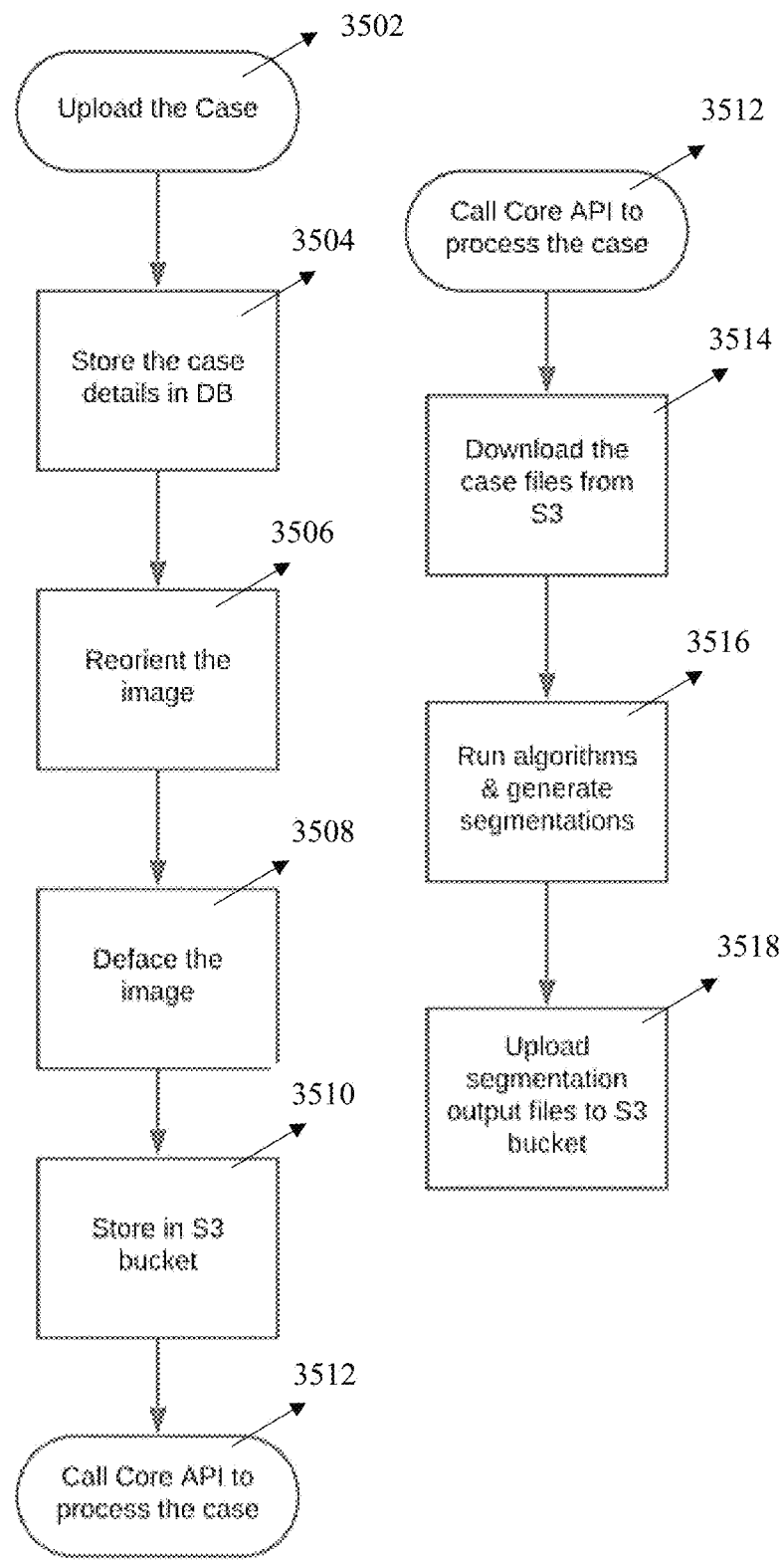

FIG. 35 illustrates a workflow of a system, according to one or more embodiments.

Figure 36:
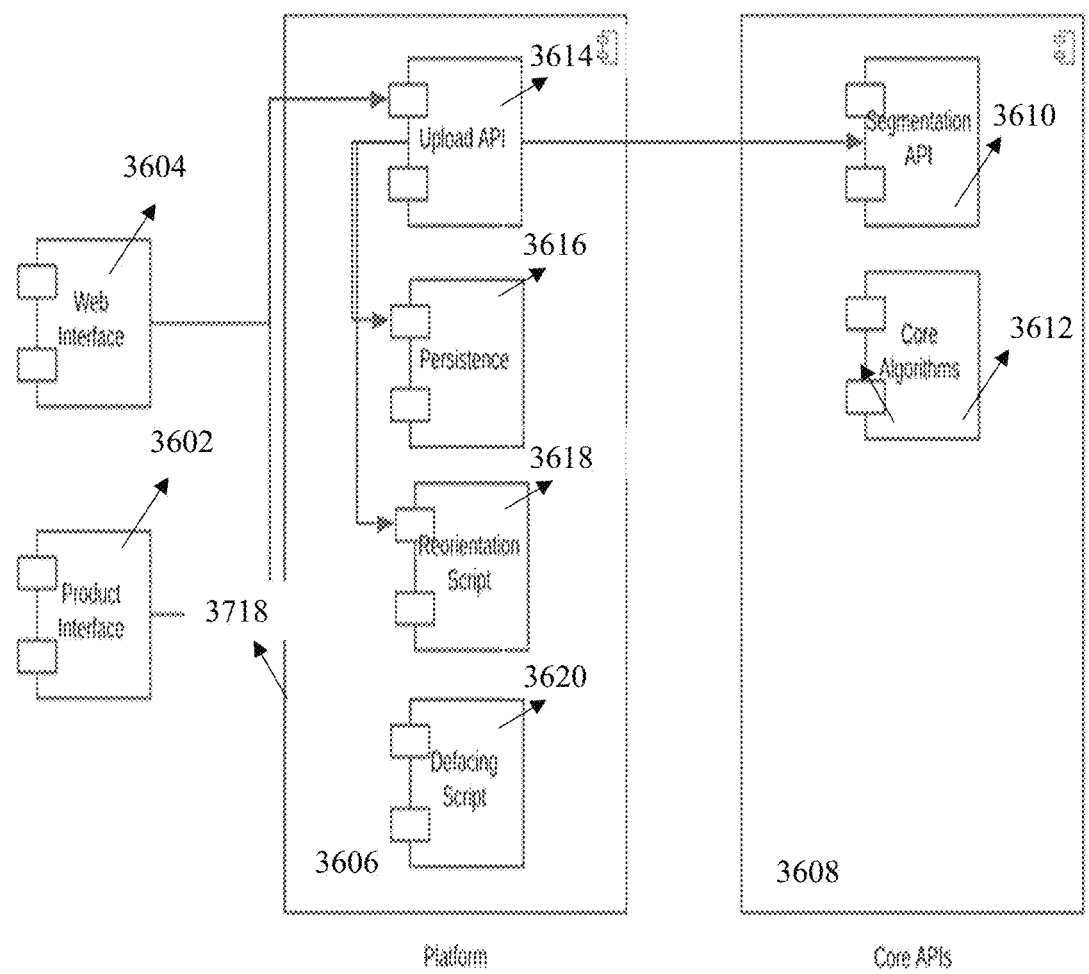

FIG. 36 further illustrates an architecture of a system, according to one or more embodiments.

Figure 37:
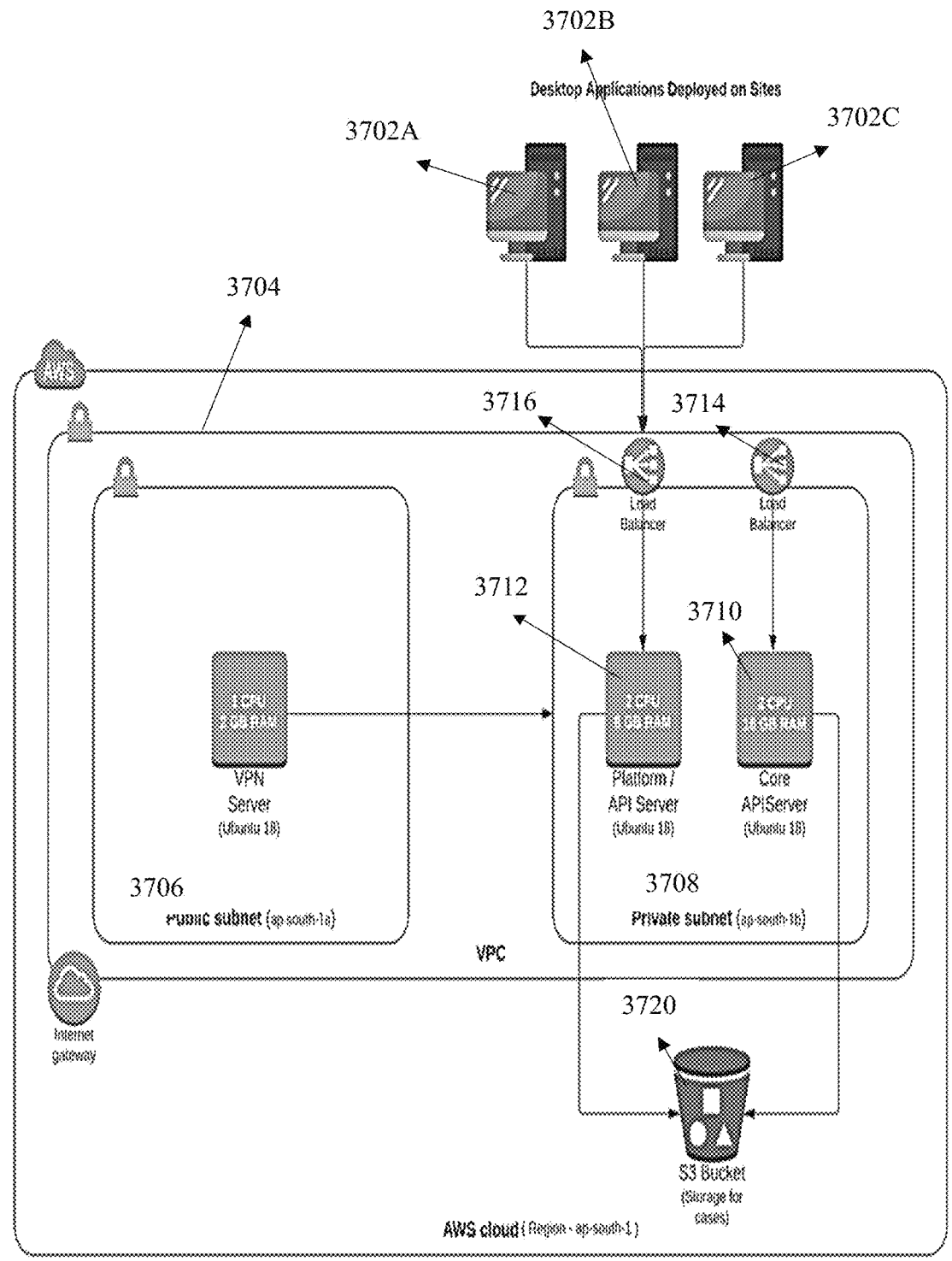
Figure 38C:
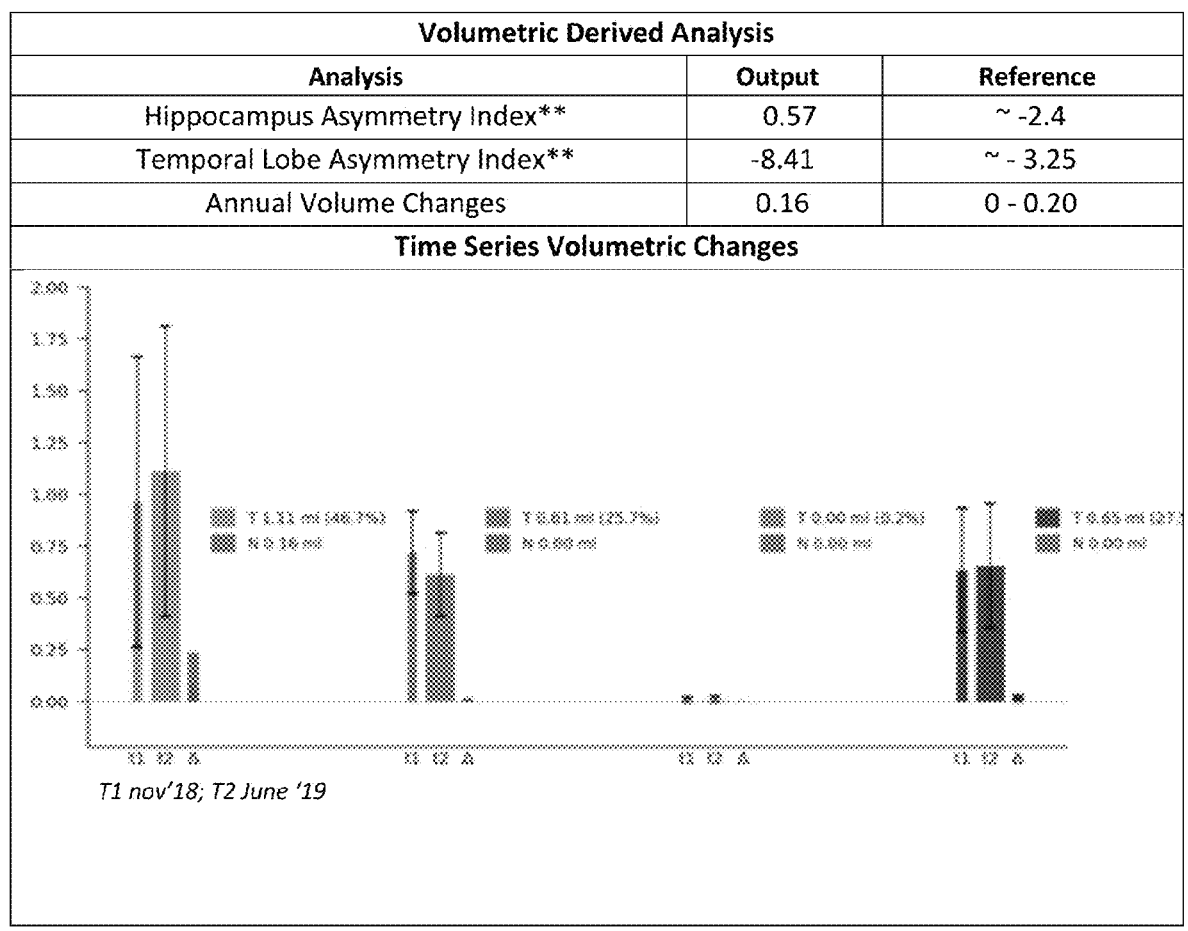
Figure 38D:
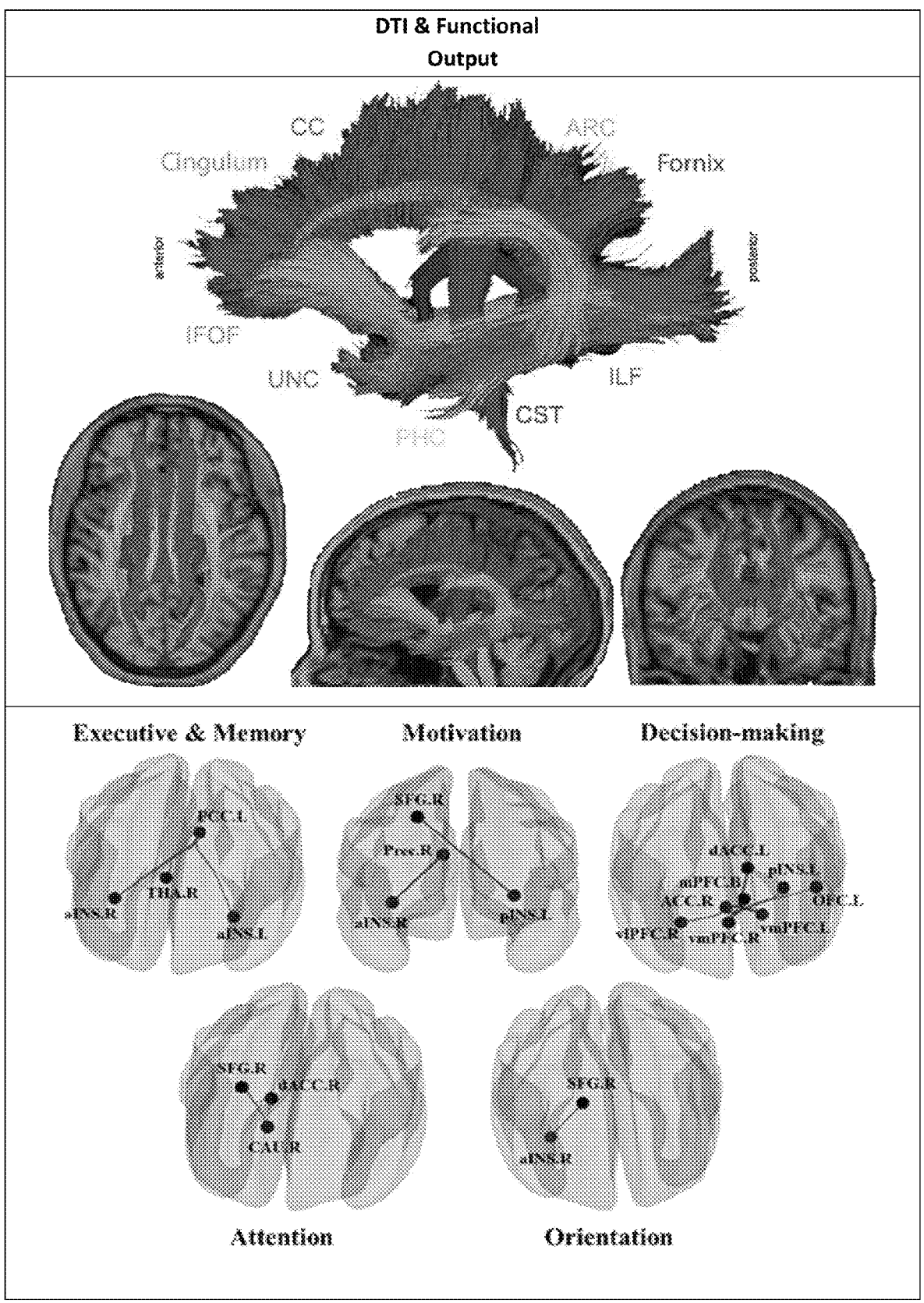
Figure 38E:
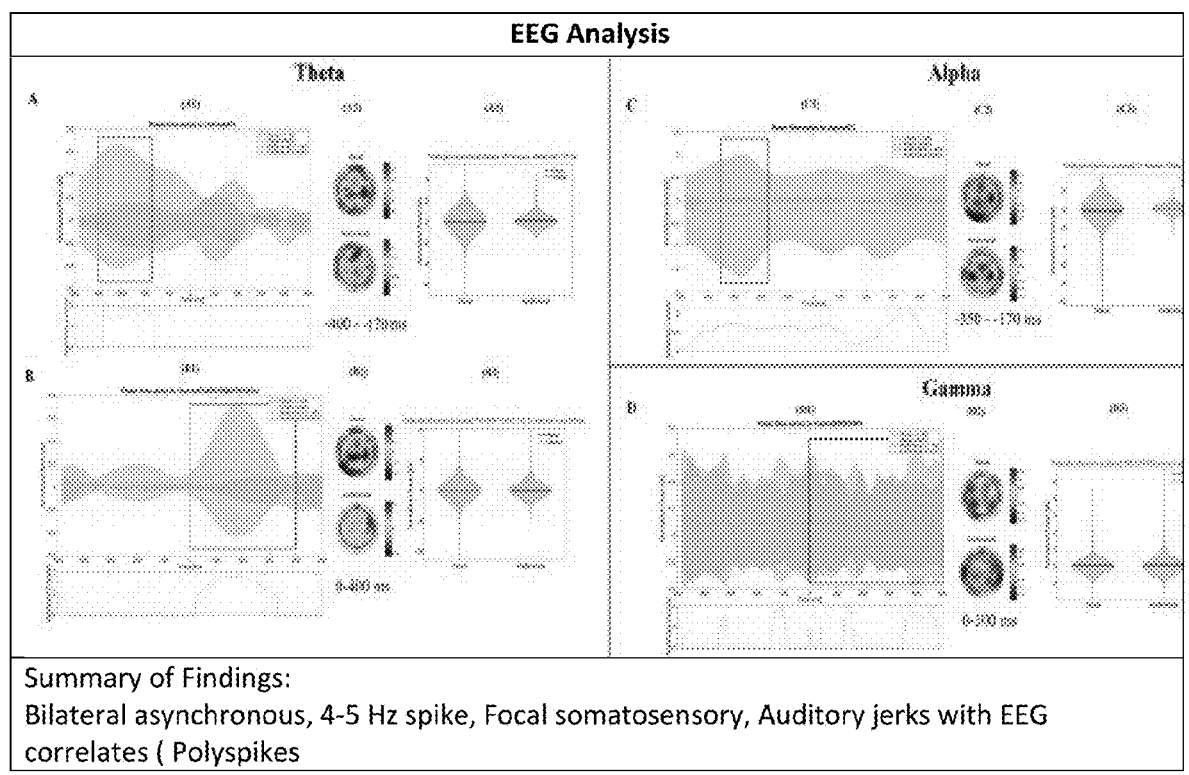

FIG. 37 illustrates an architecture of a system, according to one or more embodiments.

FIG. 38a-38e illustrate an analysis report generated based on condition specific analysis, according to one or more embodiments.

Other aspects of the present embodiments will be apparent from the accompanying drawings and from the detailed description that follows.

DETAILED DESCRIPTION

Although the following detailed description contains many specifics for the purpose of illustration, a person of ordinary skill in the art will appreciate that many variations and alterations to the following details can be made and are considered to be included herein.

Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

The articles "a" and "an" are used herein refers to one or to more than one (i.e., to at least one) of the grammatical object of the article. By way of example, "an element" means one element or more than one element.

No element, act, or instruction used herein should be construed as critical or essential unless explicitly described as such. Also, as used herein, the articles "a" and "an" are intended to include items, and may be used interchangeably with "one or more." Furthermore, as used herein, the term "set" is intended to include items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open-ended term in this written description, like "comprising" or "including," it is understood that direct support should also be afforded to "consisting essentially of" language as well as "consisting of" language as if stated explicitly and vice versa.

As used herein, the term "about" is used to provide flexibility to a numerical range endpoint by providing that a given value may be "a little above" or "a little below" the endpoint. However, it is to be understood that even when the term "about" is used in the present specification in connection with a specific numerical value, that support for the exact numerical value recited apart from the "about" terminology is also provided.

Reference throughout this specification to "an example", "an instance", "for example" means that a particular aspect, structure, or characteristic described in connection with the example is included in at least one embodiment. Thus, appearances of the phrases "in an example" in various places throughout this specification are not necessarily all referring to the same embodiment.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products, i.e., one or more modules of computer program instructions encoded on a computer readable medium for execution by, or to control the operation of, data processing apparatus. The computer readable medium may be a machine-readable storage device, a machine-readable storage substrate, a memory device, a composition of matter affecting a machine-readable propagated signal, or a combination of one or more of them. The term "computing system" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

The actual specialized control hardware or software code used to implement these systems and/or methods is not limited to the implementations. Thus, the operation and behavior of the systems and/or methods were described herein without reference to specific software code—it being understood that software and hardware can be designed to implement the systems and/or methods based on the description herein.

A computer program (also known as a program, software, software application, script, or code) may be written in any appropriate form of programming language, including compiled or interpreted languages, and it may be deployed in any appropriate form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, for example without limitation, a PLC (Programmable Logic Controller), an FPGA (field programmable gate array), an ASIC (application specific integrated circuit), Application-specific Standard Products (ASSPs), System-on-a-chip systems (SOCs), Complex Programmable Logic Devices (CPLDs), etc.

Processors suitable for the execution of a computer program include, by way of example, both general and special purpose microprocessors, and any one or more processors of any appropriate kind of digital computer. Generally, a processor will receive instructions and data from a read only memory or a random-access memory or both. Elements of a computer can include a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., Erasable Programmable Read Only Memory (EPROM), Electrically Erasable Programmable Read Only Memory (EEPROM), and flash memory devices; magnetic disks, e.g., internal hard disks or removable disks; magneto optical disks; and compact disk Read-only memory (CD ROM) and Digital Versatile Disk-Read-only memory (DVD-ROM) disks. The processor and the memory may be supplemented by, or incorporated in, special purpose logic circuitry.

To provide for interaction with a user, implementations may be realized on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any appropriate form of sensory feedback, e.g., visual feedback, auditory feedback, or tactile feedback; and input from the user may be received in any appropriate form, including acoustic, speech, or tactile input.

Implementations may be realized in a computing system that includes a back-end component, e.g., as a data server, or that includes a middleware component, e.g., an application server, or that includes a front-end component, e.g., a client computer having a graphical user interface or a Web browser through which a user may interact with an implementation, or any appropriate combination of one or more such back end, middleware, or front-end components. The components of the system may be interconnected by any appropriate form or medium of digital data communication, e.g., a communication network. Examples of communication networks include a local area network ("LAN") and a wide area network ("WAN"), e.g., the Internet.

The computing system may include clients and servers. A client and server are generally remote from each other and typically interact through a communication network. The relationship of client and server arises by virtue of computer programs running on the respective computers and having a client-server relationship to each other.

Embodiments of the present disclosure may comprise or utilize a special purpose or general-purpose computer including computer hardware. Embodiments within the scope of the present disclosure also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the disclosure can comprise at least two distinctly different kinds of computer-readable media: physical computer-readable storage media and transmission computer-readable media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural aspects and/or methodological acts, it is to be understood that the subject matter defined in the appended claims is not necessarily limited to the described aspects or acts described. Rather, the described aspects and acts are disclosed as example forms of implementing the claims.

Physical computer-readable storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network, such as a 5G network, or another communications connection (either hardwired, wireless, or a combination of hardwired or wireless) to a computer, the computer properly views the connection as a transmission medium. Transmission media can include a network and/or data links which can be used to carry data or desired program code means in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural aspects and/or methodological acts, it is to be understood that the subject is not necessarily limited to the described aspects or acts described above. Rather, the described aspects and acts are disclosed as example forms of implementing subject matter.

While this specification contains many specifics, these should not be construed as limitations on the scope of the disclosure or of what may be claimed, but rather as descriptions of aspects specific to particular implementations. Certain aspects that are described in this specification in the context of separate implementations may also be implemented in combination in a single implementation. Conversely, various aspects that are described in the context of a single implementation may also be implemented in multiple implementations separately or in any suitable subcombination. Moreover, although aspects may be described above as acting in certain combinations and even initially claimed as such, one or more aspects from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

Even though particular combinations of aspects are disclosed in the specification, these combinations are not intended to limit the disclosure of possible implementations.

Further, the methods may be practiced by a computer system including one or more processors and computer-readable media such as computer memory. In particular, the computer memory may store computer-executable instructions that when executed by one or more processors cause various functions to be performed, such as the acts recited in the embodiments.

An initial overview of technology embodiments is provided below, and specific technology embodiments are then described in further detail. This initial summary is intended to aid readers in understanding the technology more quickly but is not intended to identify key or essential technological aspects, nor is it intended to limit the scope of the claimed subject matter.

The embodiments herein and the various aspects and advantageous details thereof are explained more fully with reference to the non-limiting embodiments that are illustrated in the accompanying drawings and detailed in the following description.

In order to fully understand the scope of the invention, the following terms used herein are hereby defined.

As used herein, "Image source" refers to any medical assessment device including but not limited to electroencephalogram (EEG), computed tomography (CT) Scan, magnetic resonance imaging (MRI), Magnetoencephalography (MEG), Functional magnetic resonance imaging (fMRI), positron emission tomography (PET), X Rays, ultrasound, 2D Fluid-attenuated inversion recovery (FLAIR), 3D Magnetic resonance angiography (MRA) and psychological assessment (PA) or any computing device used to obtain and/or store images of an organ of an organism.

In an embodiment, "image source" refers to different sources including, but not limited to one or more of the following: medical centers, large pharmaceutical companies (e.g., in association with pre-clinical evaluations or during clinical trials), contract research organizations (CRO) (for both pre-clinical and clinical analysis), medical laboratories and practices (e.g., scanning centers), hospitals, clinics, medical centers, small biotechnology companies (e.g., in association with pre-clinical evaluations or during clinical trials), and bio-medical research organizations.

As used herein "Anatomy" refers to structure and internal workings of an organism.

As used herein "Anatomically meaningful region" refers to a region or a structure within an organism, functions individually and/or in combination, that has an influence in predicting prognosis, diagnosis, volumetric extraction, volumetric analysis, and atrophy information. Anatomically meaningful region may also refer to a region or a structure, individually and/or in combination, that comprises distinct or unique functional characteristics.

In an embodiment, the term "anatomically meaningful region" refers to a region formed as a result of analysing image data obtained via photographing or scanning, and dividing it into spatial regions that are anatomically and physiologically meaningful.

As used herein, the term "based on" is defined as dependent on.

As used herein, the term "a plurality of" is defined as multiple.

As used herein, the term "memory" is defined as any device in which information can be stored.

As used herein, the term "execute" is defined as run or launch.

As used herein, the term "instructions" is defined as software program or machine executable code.

As used herein, "neural network" refers to a computational learning system that uses a network of functions to understand and translate a data input of one form into a desired output, usually in another form.

In an embodiment, the term "neural network" refers to a computational model implemented in software or hardware that mimics the computational ability of a biological system using a large number of interconnected artificial neurons. The neural network, in the present disclosure, is trained to predict a prognosis, atrophy and diagnosis based on structural analysis. The neural network is also capable of predicting prognosis based on multimodal analysis such as by receiving at least one of an image input, a text input, and a signal input.

As used herein "Physiological signals" refers to signals that are acquired from an organism such as at least one of but not limited to an electrocardiography (ECG) signal, an electroencephalogram (EEG) signal, an Electromyography (EMG), a galvanic skin response (GSR), a blood pressure, event related potential (ERP), a pulse rate, etc.

In an embodiment, the term signal "Physiological signals" refers to signals acquired from an organism for measuring or detection of a physiological parameter or change of such a parameter.

As used herein "Demographic information" refers to a collection of data comprising age, race, gender, genotype and micro-ethnicity. Further demographic information, used herein, refers to information that is used to recognize, identify, classify, group, and/or categorize an organism.

In an embodiment, the "Demographic information" refers to demographic details of the patient which include, but are not restricted to, name, age, gender, and bed location. The demographic details refer to personal details that contribute to recognizing the identity of a patient.

As used herein "image input" refers to inputs that are in pictorial representation. The image inputs may be obtained by scanning at least one organ or capturing images of at least one organ of an organism. The organ may be an internal organ or an external organ. The image input may be acquired or obtained or received from an image source.

In an embodiment, the term "image input" refers to the medical images that are received as an input to perform image segmentation and predict a prognosis. In another embodiment, the "image input" refers to digital data capable of producing a visual representation. For instance, the term "image input" includes digital images and digital video.

As used herein "text input" refers to inputs that are in written format in any language. The text input comprises inputs in text format that are entered into a machine and extracted from one or more records. The text input may be obtained by a natural language processing (NLP) technique. The NLP technique may be used to read, decipher, understand, and make sense of the human languages in a manner that is valuable and can assist in predictive prognosis and diagnosis. The text input may also be converted from a first language to a second language that is understandable by a system.

In an embodiment, the term "text input" refers to an input obtained by the server in a text format. The text inputs may comprise details such as a medical condition, a gender, an age, a micro-ethnicity, symptoms, physician details.

As used herein "signal input" refers to inputs that are in graphical format. The signal input comprises physiological signals that are acquired from an organism usually in a sinusoidal wave format. The signal input may comprise at least one spike that may represent abnormal functioning or normal functioning of an organism. The signal input may comprise a recorded physiological signal. The signal input may also be a physiological signal that is acquired from the organism in real-time.

In an embodiment, the term "signal input" refers to input in the form of signals. The signals may be any physiological signals that are adapted for measuring or detection of a physiological parameter or change of such a parameter.

As used herein "Metadata" refers to patient metadata, or descriptive information about the patient (including demographics, pharmaceuticals, diagnosis, etc.), that needs to be recorded in a way that is interoperable. Additionally, Metadata also refers to administrative metadata that needs to be included for the records to be understandable outside of the context in which they were created. Administrative metadata is data describing the electronic medical records; Metadata can include information about the controlled vocabularies and standards used, necessary information to ensure patient privacy, and specifics of the electronic health records' authenticity and creation.

In an embodiment, the term "metadata" refers to data that represents information about user or system data and describes attributes of actual user or system data. Further, metadata is data that describes other data stored in the downloadable medical files that may provide the functionality needed to manage and access the data in medical files. The metadata may be protected from manipulation and/or access using one or more methods of encryption As used herein "Intracranial volume (ICV)" refers to volume within the cranium including the brain, meninges, and CSF. The ICV also refers to an estimated volume of cranial cavity as outlined by supratentorial dura mater or cerebral contour when dura is not clearly detectable. The Intracranial volume sometimes refers to the total intracranial volume (TIV).

In an embodiment, the term "Intracranial Volume (ICV)" is a standard measure to correct for head size in different brain studies and in AD related literature. The ICV measure, sometimes referred to as total intracranial volume (TIV), refers to the estimated volume of the cranial cavity as outlined by the supratentorial dura mater or cerebral contour when dura is not clearly detectable. ICV is often used in studies involved with analysis of the cerebral structure under different imaging modalities, such as Magnetic Resonance (MR), MR and Diffusion Tensor Imaging (DTI), MR and Single-photon Emission Computed Tomography (SPECT), Ultrasound and Computed Tomography (CT). ICV consistency during aging makes it a reliable tool for correction of head size variation across subjects in studies that rely on morphological characteristics of the brain. ICV, along with age and gender are reported as covariates to adjust for regression analysis in investigating progressive neurodegenerative brain disorders, such as Alzheimer's disease, aging and cognitive impairment.

As used herein "Quantitative volumes" refers to voxel-based analysis of tissue characteristics such as volume, T2 and diffusion density/concentration in an organ. Quantitative volumes further refer to numerical representation of structure or volume, density of the at least one organ in the organism.

As used herein "progression" refers to the forecast of the probable outcome or course of a disease; the patient's chance of recovery. Progression further to increase in severity and/or size of diseased area at a later point.

In an embodiment, the term "progression" refers to evolution of the disease over time. Further progression implies that a patient is initially diagnosed with an early stage of the disease with worsening at the current examination.

As used herein "regression" refers to a characteristic of diseases such as decrease in severity and/or size without completely disappearing. At a later point, symptoms may return.

In an embodiment, the term "regression" implies the presence of the disease at the preceding examination with an improvement at the current examination.

As used herein "diagnosis" refers to a process of identifying a disease, condition, or injury from its signs and symptoms. A health history, physical exam, and tests, such as blood tests, imaging tests, and biopsies, may be used to perform a diagnosis.

In an embodiment, the term "diagnosis" refers to methods by which the person skilled in the art can estimate and/or measure the probability ("likelihood") whether a patient suffers from a given disease or condition. In the present disclosure, "diagnosis" refers to the use of the system to analyze the structural changes in at least one organ and estimate the medical condition of a patient based on structure. The term diagnosis also refers to an estimation of detection of disease or medical condition of the patient based on multimodal analysis using at least one of image input, text input and signal input.

As used herein "prognosis" refers to a forecast, a prospect, a prediction of what the future stage of disease will be, regarding a single case. It also refers to the probability that an applied treatment will be effective equals the probability that the treatment will, in a beneficent way, alter the course and eventual outcome of the disease.

In an embodiment, the term "prognosis" refers to a prediction of the probable course and outcome of a clinical condition, a state, or a disease of a patient. A prognosis of the patient is usually made by evaluating factors or symptoms of a disease that are indicative of an outcome of the disease. The skilled artisan will understand that the term "prognosis" refers to an increased probability that a certain course or outcome will occur; that is, that a course or outcome is more likely to occur in a patient exhibiting a given condition, when compared to those individuals not exhibiting the condition. A prognosis may be expressed as the amount of time a patient can be expected to survive. Alternatively, a prognosis may refer to the likelihood that the disease goes into remission or to the amount of time the disease can be expected to remain in remission. A prognosis is often determined by examining one or more prognostic factors or indicators or change in structural volumes of at least one organ. The progression may also refer to progression or regression status of the disease.

As used herein "biomarkers" refers to any substance, structure, or process that can be measured in the body or its products and influence or predict the incidence of outcome or disease.

In an embodiment, the term "biomarkers" is a clinical or biological characteristic that provides information on the likely patient health outcome. The biomarkers may be at least one of a prognostic biomarker, and a predictive biomarker. A prognostic biomarker provides information about the patient's overall disease outcome and progression or regression of the disease, regardless of therapy, whereas a predictive biomarker gives information about the effect of a treatment.

As used herein "anonymization" refers to the process of turning data into a form that does not identify and recognize individuals. Anonymization breaks the link between data and a given participant so that the participant cannot be identified, directly or indirectly (e.g., through cross-referencing), from their data.

In an embodiment, the term "anonymization" refers to a process of concealing patient identity before transferring data and images outside the confidential confines of the patient care facility. Medical images are commonly encoded and stored in a DICOM (digital imaging and communications in medicine) format. DICOM images have a header section that includes several fields, such as patient name, patient identification, birth date, hospital name, date of acquisition, techniques used for acquisition, etc. Key patient identifiable fields, such as, but not limited to patient name and patient ID, need to be anonymized before the images can be shared with research facilities. Once the data is anonymized, the patient identity is concealed such that one cannot trace or track the source (e.g., patient identity, site identity, etc.) of the medical data.

As used herein "reference volume" refers to volume of an organ or body part within the organism that are empirically defined based on known clinical cases. Reference volumes may be used to compare with current estimated volumes of a patient based on at least age, gender, micro-ethnicity and ICV to predict a prognosis and to perform a diagnosis.

In an embodiment, the term "reference volume" refers to a volume of at least one organ which is obtained by averaging one or more volumes that are manually segmented. In one embodiment, the reference volume serves as the basis to train the system in automatic image segmentation.

As used herein "reference quantitative volume" refers to quantitative volumes of an organ or body part within the organism that are empirically defined based on known clinical cases. Reference quantitative volumes may be used to compare with current estimated quantitative volumes of a patient based on at least age, gender, micro-ethnicity and ICV to predict a prognosis and to perform diagnosis.

In an embodiment "reference quantitative volume" refers to quantitative volumes of an organ or body part within the organism that are used as a reference to make any decisions or actions in further processing of image segmentation, volumetric analysis or prognosis prediction.

As used herein "users" refers to a person who has privileges or has permission to access the system.

In an embodiment "user" comprises one of a Radiologist, a Doctor, a technical specialist, a manager, an administrator, an analyst, etc.

As used herein "computing unit" refers to any personal digital assistant unit comprising but not limited to a desktop, a Laptop, a mobile phone, a handheld PC, a smart phone, etc.

In an embodiment, the term "computing unit" refers to a group of physical components having close physical relationship with each other and can be used as a basic unit for executing a task As used herein "Segmented image" refers to the structures in the image that have been "gathered" into anatomically meaningful regions. The segmented image also refers to the image (i.e., anatomically meaningful region) that has been segmented from the image of the region of interest of an anatomy. The segmented image may be useful in volumetric extraction, volumetric analysis which in turn may be helpful in predicting prognosis, diagnosis and atrophy information.

In an embodiment, the term "Segmented image" refers to a collection of pixels that is segmented from a medical image. The segmented image may be an anatomically meaningful portion of the medical image.

As used herein "image quality analysis" refers to the method of determining whether the images of the region of interest meets current industry standard of volumetric extraction. In an embodiment, the image quality analysis refers to determining whether the images obtained comprise a predefined magnetic strength value more than 1.5 Tesla.

In an embodiment, the term "image quality analysis" refers to analysing quality of the image and determining whether the image captured is appropriate for image segmentation, volumetric analysis, and volumetric extraction and other processing.

As used herein "database" refers to a set of computer readable storage mediums associated with a set of computer executable programs. The database stores the information related to the user details, one or more first images of a region of interest of an anatomy obtained from an image source, demographic information, and one or more physiological signals acquired from a patient, one or more volumes of at least one structure that resides within the one or more first images with respect to micro-ethnicity information in at least one of a three-dimensional (3d) format, and at least one medical plane, one or more quantitative volumes of the at least one structure of the region of interest categorized with respect to the micro-ethnicity information, one or more structure-based analysis report, one or more reference volumes, an index for the one or more volumes, and the one or more quantitative volumes, user identification data assigned to the patient, progression and a regression state of prognosis and a health condition of the patient. The database stores population-based volume/structure standardization and big data gathering. The database in one aspect, stores a neuroimaging data bank. The database in another aspect, stores orthoimage data repository. The one or more volumes, the one or more quantitative volumes, and the one or more reference volumes are stored in a data structure.

In an embodiment, the "database" refers to an organized collection of data, generally stored and recorded such that the data can be accessed and updated electronically from a computing unit. Database also refers to a systematic collection of data. Database further supports electronic storage and manipulation of data.

As used herein "organ" refers to a body part of an organism. The organ comprises at least one of one of a circulatory system, a nervous system, a muscular system, an endocrine system, a respiratory system, a digestive system, a urinary system, a reproductive system, an integumentary system, an immune system, and a skeletal system.

As used herein "Anatomical plane" refers to a hypothetical plane used to transect the body, in order to describe the location, position and orientation of structures. It includes but is not limited to horizontal plane, coronal plane, sagittal plane, parasagittal plane, transverse plane, anterior axillary line, mid axillary line, midclavicular line, posterior axillary line and the like.

In an embodiment "anatomical planes" refers to imaginary flat surfaces or planes that pass through the body in the anatomical position and are used to divide the body. These planes are imaginary lines and can be vertical or horizontal and drawn through an upright body.

As used herein "Segmentation" refers to a process that allows to mainly define subsets of pixels or voxels of images, based on at least one of structure, volume and density, of the region of interest of an anatomy and define boundaries to form at least one anatomically meaningful region. Once said subsets and boundaries have been defined it is possible to transform each subset into a virtual object therefore having its functional or semantic unit. Segmentation can be done through at least one of automatically, semi-automatically or manually.

In an embodiment, "Segmentation" refers to the detection of boundaries of structures of at least one body part such as organs, vessels, different types of tissue, pathologies, medical devices, etc., in medical images of a patient. Segmentation also involves marking the boundaries and determining the quantitative volumes of Automatic segmentation of anatomical objects is a prerequisite/mandatory for many medical image analysis tasks, such as prognosis, disease diagnosis, atrophy determination, and quantification. Segmentation is a computer aided process which automatically segments anatomical meaningful regions (e.g., organs) once training is provided to the system.

As used herein "Micro-ethnicity information" refers to the information related to groups of peoples belonging to a particular geographical area (e.g., a sub region, a sub zone, a region, a zone, a district, a city, a state, a country, a continent etc.) who have certain racial, cultural, religious, or other traits in common. Patients belonging to a particular micro-ethnicity may have unique anatomical characteristics such as volume, weight, cross sectional area and dimensions of the internal organs (e.g. cardiovascular organs, neural organs, orthopaedic organs, etc.), an intracranial volume (ICV), information about previous and present diseases, psych analysis information, brain dominance information, cognitive measures, stress information, food habits and physical activity habits, blood type, cholesterol level, handedness, and comorbidity conditions, etc.

In an embodiment, the term "micro-ethnicity information" refers to the information related to small groups and localized ethnic communities-cum-sociological groups ('micro-ethnic groups'), or sets of neighboring or previously neighboring groups or not neighboring sharing common identity, and sometimes, but not always, common origins.

As used herein "atrophy" refers to progressive degeneration or shrinkage of at least one organ. Atrophy may help to perform patient-specific predictive prognosis and diagnosis.

In an embodiment, the term "atrophy" refers to progressive loss of muscle mass and/or progressive weakening and degeneration of muscles, including skeletal and voluntary muscles, cardiac muscles that control the heart (cardiomyopathies), and smooth muscles. Atrophy also refers to a decrease in size of a body part, cell, organ, or other tissue. The term "atrophy" implies that the atrophied part was of a size normal for the individual, considering age and circumstance, prior to the diminution.

As used herein "site" refers to a place where image segmentation, volumetric analysis, volumetric extraction is performed. The site also refers to a place where predictive prognosis, diagnosis, and atrophy information is needed. The site comprises one of a diagnostic center, a hospital, a clinic, a healthcare unit, an organization where at least one of research, analysis, and generating three-dimensional models of structure of organs is performed, and the like. The site also refers to a place where accuracy, quality of the segmented image is verified and enhanced in terms of boundaries, volumes, shape, density, orientation, intensity and the like.

In an embodiment, the term "site" refers to but not limited to one or more of the following: medical centers, large pharmaceutical companies (e.g., in association with pre-clinical evaluations or during clinical trials), contract research organizations (CRO) (for both pre-clinical and clinical analyzes), medical laboratories and practices (e.g., scanning centers), hospitals, clinics, medical centers, medical image processing organizations, Research Centers, small biotechnology companies (e.g., in association with pre-clinical evaluations or during clinical trials), and bio-medical research organizations.

As used herein "volumetric extraction" refers to a process of segmenting and extracting one or more volumes of at least one structure in a two-dimensional and a three-dimensional format. The process of the volumetric extraction renders the one or more volumes of the at least one structure in a three-dimensional format that enables a user to study, investigate and analyze the volumes of at least one structure.

As used herein "volumetric analysis" refers to a process of analyzing, researching, investigating, and studying the one or more volumes, shape, orientation, location, and boundaries of the at least one structure. The volumetric analysis also refers to analyzing the one or more volumes of the at least one structure and identifying the cause of the prognosis, diagnosis, atrophy, and progression and regression of the prognosis.

In an embodiment, the term "volumetric analysis" refers to dealing with cross-sectional data and seeking measurement of part of or the total volume of a structure or region of interest. In another embodiment, the term "volumetric analysis" is any method of quantitative chemical analysis in which the amount of a substance is determined by measuring the volume that it occupies or, in broader usage, the volume of a second substance that combines with the first in known proportions.

As used herein "family history" refers to the history of medical events, medical condition, food habitat, brain dominance information, stress information, micro-ethnicity information, psych analysis information, symptoms, immunity level, treatments undergone, medication information, diseases, etc. and the like that are acquired from family members (e.g., blood relation) of a patient.

In an embodiment, the term "family history" refers to family structure and relationships within family, including information about diseases in family members. Family history provides a ready view of problems or illnesses within the family and facilitates analysis of inheritance or familial patterns. In another embodiment, the term "family history" refers to past occurrences (of a medical or mental health condition) in family members or past incidences (of a type of behavior) by family members. Further "family history" also refers to a record of one's ancestors.

As used herein "patient history" refers to the history of medical events such as treatments, surgeries, medication that the patient is undergoing/has undergone till date. The patient history also refers to medical conditions, food habitat, brain dominance information, stress information, micro-ethnicity information, psych analysis information, symptoms, immunity level, treatments undergone, medication information, diseases, etc. and the like that are acquired from the patient.

In an embodiment, the term "patient history" refers to case history of a patient, especially treating the history with correlated results. Patient history can provide valuable information for the response, resistance and operative risk of the patient. In another embodiment, the term "patient history" refers to having relevant information bearing on their health past, present, and future. The patient history also comprises medical history, being an account of all medical events and problems a patient has experienced is an important tool in the management of the patient.

As used herein "event related potentials (ERP)" refers to one or more physiological signals that are acquired in response to an event such as applying at least one stimulus to a patient. The stimulus may be a tangible stimulus, and a non-tangible stimulus.

In an embodiment, the term "event related potentials (ERP)" is the measured brain response that is the direct result of a specific sensory, cognitive, or motor event. Further, ERP is any stereotyped electrophysiological response to a stimulus, and includes event-related spectral changes, event-related network dynamics, and the like. The stimulus can be a visual stimulus, palpable stimulus, etc.

In an embodiment, the system comprises a computing unit and a server communicatively coupled to the computing unit via a communication network.

In another embodiment, a server may be located in one of a client's site and a remote place.

In yet another embodiment, the system comprises a dongle associated with a computing unit to perform at least one of image segmentation, volumetric extraction, volumetric analysis, determining atrophy and performing predictive prognosis and diagnosis.

FIG. 1 illustrates a schematic view of a system, according to one or more embodiments. The system described herein comprises a computing unit 102, and a server 104. The computing unit 102 is communicatively coupled to the server 104 via a communication network 106. The communication network 106 may be a wired communication network or a wireless communication network. In an embodiment, the computing unit 102 is located at a site and the server 104 is located at a remote place. In another embodiment, the server 104 and the computing unit 102 is located at the site. The site may be a hospital, a diagnostic center, a pharmacy, a health care unit, etc. In an embodiment, the server 104 comprises a black box. The black box is located locally at the site itself for securely processing an input and rendering an output (e.g., volumes, quantitative volumes, structure-based analysis reports) in the site itself. In an embodiment, the black box is located locally at the site to minimize or restrict data anonymization. The server 104 may receive inputs in any combination.

The system may comprise a plug-in device. The plug-in device may comprise a dongle. The dongle may be associated with the computing unit 102. In an embodiment, the dongle is communicatively coupled with the computing unit 102 to perform at least one of volumetric extraction, volumetric measurements, volumetric analysis, predicting prognosis, diagnosis, atrophy determination, and generating a structure-based analysis report. In another embodiment, the dongle is communicatively coupled with the computing unit 102 to securely communicate with the server 104 and perform at least one of the volumetric extraction, the volumetric measurements, the volumetric analysis, predicting prognosis, diagnosis, and generating the structure-based analysis report. The dongle is a key to enable the computing unit 102 to perform at least one of volumetric extraction, volumetric measurements, volumetric analysis, atrophy determination, predicting prognosis, diagnosis, and generating a structure-based analysis report.

The server 104 receives inputs as at least one of an image input, a text input, and a signal input. The server 104 receives and analyzes the inputs in any combination (i.e., multivariate pattern analysis). The server 104 is also capable of receiving different inputs and performing a multimodal analysis. The image input comprises one or more first images of a region of interest of an anatomy. The anatomy may belong to an organism. The organism comprises one of a human being, an animal, a bird, a mammal and the like. The one or more first images may comprise one of (a) one or more computed tomography (CT) scan images, and (b) one or more magnetic resonance imaging (MRI) scan images, (c) positron emitted tomography (PET) scan images. The text input comprises demographic information. The demographic information comprises at least one of an age, a gender, a race, a micro-ethnicity information and the like. The text input further comprises a symptom, a medical condition, etc.

The server 104 may comprise a natural language processing (NLP) module. The NLP module is configured to check and capture current clinical symptoms from the text stored on a hospital information system (HIS). The NLP module may also identify pre indicators like vitamin deficiency, family history, genetic history, trauma, etc. The NLP may also extract cognitive analysis from relevant test analysis like Computerized Cognitive Testing in Epilepsy (CCTE), Montreal Score, Cambridge Neuro-psychological Test Automated Battery (CANTAB), Mini Mental State Examination (MMSE), Mini-Cog, etc.

The signal input comprises one or more physiological signals of a patient. The one or more physiological signals comprise an electrocardiography (ECG) signal, an electroencephalogram (EEG) signal, an Electromyography (EMG), a galvanic skin response (GSR), a blood pressure, and a heart rate, etc. In an embodiment, the server 104 can integrate with existing EEG hardware. In another embodiment, server 104 provides an independent and cloud EEG service and is available on one-click. The server 104 is also capable of monitoring the signal input for a predefined period of time as set by the user and detect for an anomaly (e.g., abnormal spike, pre-ictal issue, etc.). The signal input may be a prestored signal or a live signal that is acquired real-time.

FIG. 2 illustrates an exploded view of a server 204, according to one or more embodiments. The server 204 comprises a memory 206, and a processor 208. The server 204 also comprises a database 236, and a networking module 238. The database 236 records and stores a data repository of segmented images, volumes of the segmented images, quantitative volumes, categorized with respect to demographic information (e.g., age, gender, micro-ethnicity information, etc.). The networking module 238 is configured to communicate with a computing unit and other hardware or components that the server 204 interacts with. The processor 208 comprises a graphical processing unit (GPU). The graphical processing unit (GPU) is configured to support in segmenting images, volumetric analysis, volumetric extraction, and rendering the one or more volumes in a three-dimensional format, and at least one anatomical plane. The server 204 further comprises an input obtaining module 210, a quality analysis module 212, a user identification data assigning module 214, a data anonymization module 216, an information linking module 218, a segmentation module 220, a volume extraction module 222, a volume rendering module 224, a quantitative volume estimation module 226, a predictive prognosis module 228, a report compiling module 230, a training module 232, and a retraining module 234. The processor 208, in association with the above-mentioned modules, is configured to perform at least one of image segmentation, volumetric extraction, volumetric measurements, volumetric analysis, predicting prognosis, diagnosis, atrophy determination, and generating a structure-based analysis report.

The input obtaining module 210 obtains inputs as at least one of an image input, a text input, and a signal input. In an embodiment, the input obtaining module 210 obtains the inputs as the image input, the signal input, and the text input (e.g., micro-ethnicity information). The input obtaining module 210 obtains the inputs in any combination. The image input comprises one or more first images of a region of interest of an anatomy. The anatomy may belong to an organism. The organism comprises one of a human being, an animal, a bird, and a mammal. The one or more first images may comprise one of computed tomography (CT), positron emission tomography (PET), structural magnetic resonance imaging (sMRI), functional magnetic resonance imaging (fMRI), Diffusion-weighted imaging (DWI), Diffusion Tensor Imaging (DTI), and magnetic resonance imaging (MRI) and the like. The text input comprises demographic information. The demographic information comprises details that describe characteristics of a patient. The demographic information comprises at least one of an age, a gender, a race, and a micro-ethnicity information. The text input comprises at least one of an age, a race, a gender, a medical condition, a symptom, clinical history, a patient history, a medical test, medication information, a physician detail, and a cognitive analysis report, and the like. The signal input comprises one or more physiological signals of a patient. The one or more physiological signals comprise an electrocardiography (ECG) signal, an electroencephalogram (EEG) signal, an Electromyography (EMG), a galvanic skin response (GSR), an event related potential (ERP), a blood pressure, and a pulse rate, etc. In an embodiment, the ERP is acquired by the server 204 to derive clinical endpoints in at least one of but not limited to mild cognitive impairment (MCI), Dementia, Alzheimer, Neurodegeneration, depression, migraines, stress, concussion, and the like.

The input obtaining module 210 obtains the inputs from at least one of a computing unit, a Magnetic Resonance Imaging (MRI) scanning machine, a positron emission tomography (PET) scan machine, a Computed Tomography (CT) scanning machine and the like. In an embodiment, the input obtaining module 210 obtains the inputs from the Magnetic Resonance Imaging (MRI) scanning machine, and the Computed Tomography (CT) scanning machine directly while scanning the region of interest of the anatomy (i.e., the server is integrated with existing scanning machine). In another embodiment, the input obtaining module 210 obtains the inputs that are obtained and prestored in the computing unit 202.

The quality analysis module 212 analyzes and determines whether the quality of the inputs (e.g., the image input, the signal input, the text input etc.) meets a predefined quality at least one of qualitatively, and quantitatively. In case of the image input, the quality analysis module 212 analyzes and determines, in a quantitative manner, whether a magnetic strength value of the one or more first images is equivalent to a predefined magnetic strength value. The predefined magnetic strength value comprises greater than 1.5 Tesla. In an embodiment, the quality analysis module 212 performs bias correction on the one or more first images by compensating bias present in the one or more first images due to variation in magnetic field and gradient strength of different (MRI) scanning machines that are currently available in the market. In another embodiment, the quality analysis module 212 performs intensity normalization by normalizing the difference in signal intensities of the one or more first images. The one or more first images comprise difference in signal intensities due to variation in acquisition protocol at different sites. In an embodiment, the quality analysis module 212 enables a user (e.g., radiologist, technician, etc.) to determine, in a qualitative manner, whether the one or more first images have the predefined quality (e.g., without blur or distortion of pixels, etc.) and can be utilized for further processing.

In case of the signal input, the quality analysis module 212 analyzes and determines, in a qualitative manner, whether an amplitude of the one or more physiological signals is equivalent to a predefined amplitude. In an embodiment, the quality analysis module 212 performs amplitude normalization by normalizing the difference in amplitude of the one or more physiological signals. The one or more physiological signals comprises differences in amplitudes due to variation in acquisition protocol at different sites. In an embodiment, the quality analysis module 212 enables the user to determine, in a qualitative manner, whether the one or more physiological signals have the predefined amplitude that can be utilized for further processing.

In case of the signal input, the signal inputs are pre-processed (such as running through a set of protocol to make it suitable to the server 204) to filter noises (e.g., bad channel removal) and artifacts by passing through at least one of a notch filter, a high pass filter, and a bandpass filter. The signal inputs are then pre-processed to perform event marking and channel locating within the inputs. The pre-processing of the signal inputs may include re-reference and resample of the inputs. The pre-processing of the signal inputs also includes independent component analysis (component rejection, if required). The post-processing of the signal inputs comprises characteristic extraction and characteristic selection to identify statistically significant characteristics from the signal inputs using techniques such as Multivariate time series, Time-frequency (Wavelet transform), Frequency Domain (Fourier), Time Domain (Principal component analysis), Independent component analysis (ICA), etc. The post-processing of the signal inputs further comprises optimal parameter and characteristic set identification (e.g.— characteristics shuffle analysis, ranking characteristics, etc.). The post-processing of the signal inputs further comprises Classification/Statistical Manipulation (ML) (e.g.—Linear discriminant analysis (LDA), Multi-layer perceptron (MLP), Support vector machine (SVM), etc.). The post-processing of the signal inputs further comprises generating electroencephalogram (EEG) patterns.

The user identification data assigning module 214 assigns a user identification data (UID) upon receipt of the inputs. In an embodiment, the user identification data assigning module 214 assigns a first user identification data (UID) and a second user identification data (UID) upon receipt of the inputs at a first site and a second site, respectively. In an embodiment, the user identification data assigning module 214 assigns a third user identification data (UID) upon receipt of the inputs at the first site at a second time. The third user identification data may be derived from the first user identification data since the inputs are received at the first site at two different instances.

The data anonymization module 216 anonymizes the inputs received by discarding the metadata associated with the inputs. The data anonymization module 216 anonymizes the inputs to remove patient details from the inputs. The patient details may contribute to determining the identity or recognizing the patient. Without the patient details, it would be impossible to detect from whom (e.g., which patient, which user, etc.) the inputs are received. In an embodiment, the data anonymization module 216 anonymizes the inputs by removing facial detection information and biometrics information from the inputs. For instance, when the one or more first images of the same patient received at different instances are combined, it may contribute to detect/recognize facial information or personal information of the user. In such a case, the data anonymization module 216 discards one or more first portions of the one or more first images. The one or more first portions are the portions that may assist in recognizing or identifying the user (e.g., patient).

The information linking module 218 links information associated with the first user identification data and the second user identification data, upon receiving a linking request from the user. The user, through a user interface, may generate a linking request to the server 204. For instance, the inputs of the user may be received by the server 204 at different instances and at different sites. In such a case, the information linking module 218 links and consolidates the information, associated with the first user identification data and the second user identification data, that are obtained at the different sites and the different instances to give an overall history of the patient to a medical practitioner.

The segmentation module 220 segments at least one second image of a structure that resides within the one or more first images. In an embodiment, the segmentation module 220 segments the at least one second image using an artificial neural network. The segmentation module 220 segments the at least one second image of the structure through one of automatically, semi-automatically, and manually. The segmentation module 220 segments the at least one second image from the one or more first images based on structure of the at least one object (e.g., organ) within the at least one second image. The segmentation module 220 segments the at least one second image from the one or more first images through an atlas independent method. In an embodiment, the segmentation module 220 segments the at least one second image based on the structure and not by comparing or aligning with reference image i.e., atlas independent. In an embodiment, the segmentation module 220 segments the at least one second image based on the pixels in the structure. In another embodiment, the segmentation module 220 segments the at least one second image based on at least one of density/intensity within the structure. The volume extraction module 222 extracts one or more volumes of at least one structure from the one or more first images. The volume extraction module 222 extracts the one or more volumes by extracting one or more boundaries of the at least one structure from the one or more first images, and populating one or more voxels within the one or more boundaries of the at least one structure using one or more identifiers.

The volume extraction module 222 analyzes the one or more volumes of the at least one structure and allows the user to determine the quality of the one or more volumes extracted. The volume extraction module 222 communicates a signal to the segmentation module 220 when the quality of the one or more volumes extracted is not up to expected. The segmentation module 220 provides a user interface, in response to the signal, that allows the user to manually edit and correct at least one of boundaries, shape, and the one or more volumes of the structure. The segmentation module 220 then creates a mask for the structure and allows to populate one or more identifiers within the structure to correct the one or more volumes manually. In an embodiment, the mask is created based on the training provided to the server 204.

The volume rendering module 224 renders the one or more volumes of the structure in at least one of a two-dimensional format, and the three-dimensional format. The segmentation module 220 further renders the one or more volumes of the structure in the at least one anatomical plane. The anatomical plane comprises at least one of a horizontal plane, a coronal plane, a sagittal plane, a parasagittal plane, a transverse plane, an anterior axillary line, a mid-axillary line, a midclavicular line, a posterior axillary line and the like. The quantitative volume estimation module 226 estimates one or more quantitative volumes of the at least one structure based on the pixels/voxels within the structure. The quantitative volume estimation module 226 provides a numerical representation of the one or more volumes of the at least one structure that supports and aids the physician's clinical impression with quantitative numbers. The numerical representation i.e., quantitative numbers make the physicians convenient in making their decisions when compared to the graphical representation or visual representation of the at least one structure. The quantitative numbers readily enable the physicians to assess the at least on structure and predict a prognosis and perform a diagnosis.

The server 204 creates the data repository (e.g., neuroimaging, orthopaedic, etc.) using age and gender other than micro-ethnicity information to create an array of the volumes of different structures. The server 204 records the volumes of each structure that comes across and creates the data repository for normal and abnormal brains for detecting seizures and dementia, MS, schizophrenia and other anomalies. The server 204 can remove the effect of age on the volume using a Linear Regression model and calculating coefficient (e.g., skewness coefficient). The predictive prognosis module 228 calculates the standard deviation of the volume of the structures across the cohort. The predictive prognosis module 228 calculates 25th and 95th percentile of the standard deviation. The predictive prognosis module 228 calculates the 25th and the 95th percentile by matching age, gender, micro-ethnicity information, a medical condition (e.g., epilepsy), and intracranial volume (ICV) of a patient in the population of individuals and then deriving the 25th and the 95th percentile based on matching the age, gender, micro-ethnicity information, medical condition (e.g., epilepsy), and ICV. The 25th and the 95th percentile are personalized percentile references in detecting the predictive prognosis.

The predictive prognosis module 228 determines a feature associated with the at least one structure based on the one or more volumes and one or more inputs. The feature comprises at least one of the one or more volumes of the region of interest (ROI), a cortical thickness, an atrophy percentage, an asymmetry index score, a subfield volumetry of the region of interest, annular volume changes, a progressive supranuclear palsy (psp) index score, a magnetic resonance perfusion imaging (MRPI) score, a frontal horn width to intercaudate distance ratio (FH/CC), a medial temporal lobe atrophy (MTA) score, a global cortical atrophy (GCA) scale, identification of Intracranial bleeds, hemorrhage, microbleeds and their volume analysis, a fracture detection, a midline shift identification, a measurement of the midline shift identification and the at least one structure with respect to the midline shift identification, identifying a pathology associated with the at least one structure, classifying the pathology identified, a tissue density identification, an infarct identification, a Penumbra-core-viable tissue identification, classification and volume calculation, diffusion-weighted imaging (DWI) maps and apparent diffusion coefficient (ADC) maps of the at least one structure, perfusion maps comprising resting state functional magnetic resonance imaging (rsfMRI), an alberta stroke programme early CT score (ASPECTS) calculation, a collateral detection, a mismatch ratio calculation, an angiography labeling and/or annotation, a large vessel occlusion (LVO) detection, an Hypoperfusion index calculation, Diffusion tensor imaging (DTI) fiber tracks, neural pathway connectivity maps, correlation between a signal input, an image input and the text input, classifying the signal input, identifying a normal signal, identifying an abnormal signal, identifying a pre-ictal signal, identifying an ictal signal, extracting symptoms, and grading of condition specific effects.

The predictive prognosis module 228 also enables to perform condition specific analysis. The condition specific analysis is performed by matching a patient's medical condition (e.g., epilepsy) with epilepsy population among the population of individuals and then deriving the 25th and the 95th percentile to perform proficient predictive prognosis, accurate diagnosis and comprehensive management. The predictive prognosis module 228 predicts prognosis by analyzing the one or more quantitative volumes and comparing the one or more quantitative volumes with one or more reference quantitative volumes (i.e., 25th and 95th percentile) predominantly based on micro-ethnicity information. The predictive prognosis module 228 determines and concludes that the one or more volumes of the patient is normal, when the one or more volumes of the patient falls between the 25th and the 95th percentile. The predictive prognosis module 228 also predicts prognosis and diagnosis by comparing the one or more quantitative volumes with one or more reference quantitative volumes based on at least one of an intracranial volume, an age, a gender, a symptom, and a medical condition. The predictive prognosis module 228 also predicts prognosis and diagnosis by finding biomarker findings within the one or more volumes and relating to prestored clinical observations. Based on the comparison, the predictive prognosis module 228 predicts the prognosis. The predictive prognosis module 228 is also configured to determine the progression and the regression of the prognosis over time.

The predictive prognosis module 228 also performs predictive prognosis by performing volumetric derived analysis such as at least one of structural analysis, physiological analysis, functional analysis, and cognitive analysis. For instance, the structural analysis is performed in case of magnetic resonance imaging (MRI) inputs. For another instance, the physiological analysis is performed in case of PET and electroencephalogram (EEG) inputs. For yet another instance, the functional analysis is performed in case of Magnetoencephalography (MEG) and fMRI inputs. For yet another instance, cognitive analysis (i.e., cognitive performance, cognitive effects, cognitive deficits) is performed in case of physiological assessment (PA). In view of the above, the predictive prognosis module 228 may socialize preventive brain health. The predictive prognosis module 228 identifies biomarkers from the one or more volumes and relates biomarkers to clinical presentations and tracks disease progression longitudinally. In one embodiment, the predictive prognosis module 228 performs structural volumetric analysis based on 3D MRI correlated with normative population (specific to micro-ethnicity) when the inputs received are sMRI. In another embodiment, the predictive prognosis module 228 performs functional mapping of the brain based on an imaging technique to map different connectivity maps that helps in understanding disease affected areas and related cognitive/functional deficits, when the inputs received are fMRI. In another embodiment, the predictive prognosis module 228 performs structural as well as perfusion-based analysis of the CT images to derive a first look into the disease pattern when the inputs received are CT inputs. In yet another embodiment, the predictive prognosis module 228 performs white matter tract analysis when the inputs received are Diffusion tensor imaging (DTI) inputs. The predictive prognosis module 228 performs predictive prognosis, diagnosis, and atrophy determination through an atlas independent method.

The report compiling module 230 generates and compiles a structure-based analysis report. The structure-based analysis report comprises at least one of the feature, the one or more quantitative volumes of the structure, one or more volumes of the structure, a snippet, volumetric derived analysis, a graphical representation of prognosis, and the segmented image of the structure in the at least one anatomical plane. The at least one feature is rendered in at least one of a two-dimensional (2D) format, and a three-dimensional (3D) format. The snippet comprises a brief written description about the medical condition of the patient. The report compiling module 230 generates and compiles a first structure-based analysis report and a second structure-based analysis report for the inputs obtained at a first instance and a second instance, respectively. The predictive prognosis module 228 predicts the prognosis based on comparison of the first structure-based analysis report and the second structure-based analysis report, and the inputs that are obtained at a third instance. The predictive prognosis module 228 further estimates one of a progression and a regression of the prognosis associated with the structure between the first instance and the second instance. The report compiling module 230 generates and compiles a third structure-based analysis report based on one of the progression, and the regression estimated.

In an embodiment, the report compiling module 230 calculates volumetric derived analysis by using one or more equations. Few of the sample equations are provided below:

$$ICV = (\text{Volume of structure}/ICV) * 100 \qquad 1)$$

$$\text{Hippocampal asymmetry} = \left( \frac{LTHC - RTHC}{\frac{LTHC + RTHC}{2}} \right) * 100 \qquad 2)$$

where LTHC is left Hippocampus and RTHC is right Hippocampus $$\text{Atrophy percentage} = \qquad 3)$$
$$\frac{(\text{reference lower limit} - \text{volume of structure})}{(\text{reference lower limit})} * 100$$

$$\text{Volume loss} = \text{reference lower limit} - \text{volume of structure} \qquad 4)$$

$$\text{Total Hippocampus percentage} = ((LTHC - RTHC)/ICV) * 100 \qquad 5)$$

$$\text{Parkinson's index} = \left( \frac{\text{area of Pons in midsagittal plane}}{\text{area of Midbrain in midsagittal plane}} \right) * \qquad 6)$$
$$\left( \frac{\text{width of middle cerebellar peduncle}}{\text{width of superior cerebellar peduncle}} \right)$$

The training module 232 trains artificial intelligence based neural network using at least one of the inputs (i.e., the image input, the text input, and the signal input), the one or more volumes, the one or more quantitative volumes, the one or more reference volumes and the one or more reference segmented images. The training module 232 enables the artificial intelligence based neural network to segment the one or more second images of the at least one structure from the one or more first images. The training module 232 further enables the artificial intelligence based neural network to perform at least one of volumetric extraction, volumetric analysis, atrophy determination, performing predictive prognosis and diagnosis. In an embodiment, the training module 232 creates a log using one or more inputs received from the user while performing manual segmentation on the one or more first images.

The retraining module 234 retrains the artificial intelligence based neural network using the log created. The retraining module 234 enables the artificial intelligence based neural network to automatically segment the one or more second images of the at least one structure from next time optimized based on the retraining provided. The retraining module 234 is configured to learn and perform at least one of the image segmentation, volumetric extraction, volumetric analysis, atrophy determination, performing predictive prognosis and accurate diagnosis automatically for any type of patient belonging to any micro-ethnicity having any type of medical condition/symptoms in future without any manual intervention. The predictive prognosis and accurate diagnosis enable the server to perform a comprehensive management of the patient's health. The comprehensive management of the patient's health is performed by performing a predictive prognosis over time.

For instance, consider the server has predicted a first prognosis for a condition specific analysis for a first point of time. The first prognosis is predicted for the first point of time considering the medication information (e.g., medication that the patient has intake during the first point of time) of the patient and other relevant information. The server has also predicted a second prognosis for a condition specific analysis for a second point of time. The second prognosis is predicted for the second point of time considering the medication information (e.g., medication that the patient has intake during the second point of time) of the patient and other relevant information. The server is also capable of determining deterioration or improvement in at least one volumetric changes and quantitative volumes by comparing the first prognosis and the second prognosis. The server determines the deterioration or the improvement, in terms of percentage, between the first prognosis and the second prognosis. The server is then trained with different values of the deterioration or the improvement for different points of time. The server is then capable of determining the deterioration or improvement in the volumetric changes and quantitative volumes for a third point of time (in future) based on the training provided. The server determines the deterioration or the improvement for the third point of time in quantitative values. The quantitative values of the deterioration or the improvement in the future enables and assists the physicians to treat/change the medication regime for the patient accordingly.

The training module 232 and the retraining module 234 enables the artificial intelligence based neural network to learn and evolve based on the training and retraining provided. In an embodiment, the training module 232 and the retraining module 234 enables creating a data repository for an Indian ethnicity. In another embodiment, the server 204 records the data repository for a micro-ethnicity (e.g., a sub region, a sub zone, a city, a state, etc.). In another embodiment, the server 204 records the data repository for a macro-ethnicity (e.g., a country, a continent etc.). As the average volumes for Indian ethnicity were 1122.48 ml (whole brain) and 1339.75 ml (ICV) as compared to 1222.68 ml (whole brain) and 1482.87 ml (ICV) in Caucasian's ethnicity; and the age and gender matched comparison of Indian (group 1) and Caucasian (group 2) brain and intracranial volumes (ICV) showed significant difference. The process/method of creating the data repository of volumes for the Indian ethnicity and its micro-ethnicity seems significant to implement Artificial intelligence, predict prognosis, atrophy determination, volumetric extraction, volumetric analysis, diagnosis and treat patients of the Indian ethnicity.

FIG. 3 illustrates an overview of a system, according to one or more embodiments. The system obtains inputs as at least one of an image input, a text input, and a signal input at one or more instances, and at one or more sites. The image input, the text input, and the signal input has been described above. The signal input further comprises clinical data biometrics, and psychological evaluation. The text input comprises patient data such as demographic information. Once the inputs are obtained, the system standardizes the inputs as per the current industry standards by performing bias correction and normalization.

The system then performs data processing, curation and image processing to perform segmentation. The segmentation has been described above. The segmentation can be performed through automatically, semi-automatically, and manually. The system then extracts one or more volumes of at least one structure that resides within one or more first images. The system calculates a feature associated with the at least one structure. The feature comprises at least one of the one or more volumes of the region of interest (ROI), a cortical thickness, an atrophy percentage, an asymmetry index score, a subfield volumetry of the region of interest, annular volume changes, a progressive supranuclear palsy (psp) index score, a magnetic resonance perfusion imaging (MRPI) score, a frontal horn width to intercaudate distance ratio (FH/CC), a medial temporal lobe atrophy (MTA) score, a global cortical atrophy (GCA) scale, identification of Intracranial bleeds, hemorrhage, microbleeds and their volume analysis, a fracture detection, a midline shift identification, a measurement of the midline shift identification and the at least one structure with respect to the midline shift identification, identifying a pathology associated with the at least one structure, classifying the pathology identified, a tissue density identification, an infarct identification, a Penumbra-core-viable tissue identification, classification and volume calculation, diffusion-weighted imaging (DWI) maps and apparent diffusion coefficient (ADC) maps of the at least one structure, perfusion maps comprising resting state functional magnetic resonance imaging (rsfMRI), an alberta stroke programme early CT score (ASPECTS) calculation, a collateral detection, a mismatch ratio calculation, an angiography labeling and/or annotation, a large vessel occlusion (LVO) detection, an Hypoperfusion index calculation, Diffusion tensor imaging (DTI) fiber tracks, neural pathway connectivity maps, correlation between a signal input, an image input and the text input, classifying the signal input, identifying a normal signal, identifying an abnormal signal, identifying a pre-ictal signal, identifying an ictal signal, extracting symptoms, and grading of condition specific effects.

The system then quantifies the one or more volumes and provides a numerical representation of the one or more volumes. The system then normalizes the one or more quantitative volumes so that the one or more quantitative volumes can be used for prognosis, diagnosis, atrophy determination, and treatment purposes. Based on the quantitative numbers, the physician can determine the percentage of atrophy over time.

The one or more volumes, the one or more quantitative volumes, etc. are recorded as a data repository. The data repository is provided to a wide range of healthcare practitioners to aid in their assessment of a patient's prognosis. The one or more volumes and the one or more quantitative volumes also assists the wide range of healthcare practitioners for performing at least one of an objective analysis, and a subjective analysis. The objective analysis helps in analyzing and studying characteristics of the least one object (i.e., structure). The subjective analysis helps in analyzing and studying characteristics of the least one subject (e.g., patient). The system also provides services such as imaging biomarkers and predictive analytics (i.e., predictive prognosis, diagnosis and atrophy). The system also generates a structure-based analysis report comprising at least one of the feature, the one or more volumes of the at least one structure represented in a three-dimensional format and an anatomical plane which aids to perform subjective and/or objective analysis. The system also creates a localized data repository comprising one or more volumes and one or more quantitative volumes of at least one organ categorized with respect to micro-ethnicity, age, gender, race, ICV, and the like. The appropriate users may be structure-based analysis report consumers, software and enhanced service consumers, and data insights consumers. The system comprises a layer having at least one of neural networks, deep learning and artificial intelligence algorithms and data analytics. The system further comprises a layer of data integrity, cyber security and compliance. The system further comprises a layer of cloud-based user interface platform for anonymization and clinical and medical imaging data management.

FIG. 4 illustrates a multivariate pattern analysis performed by a system, according to one or more embodiments. The server receives inputs as at least one of an image input 440, a text input 444, and a signal input 442. The image input 440 comprises one or more first images of a region of interest of an anatomy. The anatomy may belong to an organism. The organism comprises one of a human being, an animal, a bird, a mammal, and the like. The one or more first images may comprise one of (a) one or more computed tomography (CT) scan images, (b) one or more magnetic resonance imaging (MRI) scan images, (c) one or more positron emitted tomography scan images (PET), (d) one or more functional magnetic resonance imaging (fMRI) scan images, (e) one or more structural magnetic resonance imaging (fMRI) scan images, (f) Diffusion Tensor Imaging (DTI), and (g) Diffusion-weighted imaging (DWI). The text input 444 predominantly comprises demographic micro-ethnicity information. The text input 444 further comprises information of at least one of an age, a gender, a race, an intracranial volume (ICV), a symptom, a medical condition, clinical history, psych analysis information, stress information, brain dominance information, food habitat information, family history, clinical history, etc. The signal input 442 comprises one or more physiological signals such as at least one of but not limited to electrocardiography (ECG) signal, an electroencephalogram (EEG) signal, an Electromyography (EMG), a galvanic skin response (GSR), a blood pressure, and a heart rate, etc. The signal input 442 may be one or more physiological signals that are recorded and/or pre-stored. In an embodiment, the signal input may be one or more physiological signals that are acquired in real-time.

The server receives the inputs in any combination to perform multivariate pattern analysis 446. The server receives the inputs in any combination such as (i) combination comprising the image input and the text input, (ii) combination comprising the signal input and the text input, (iii), combination comprising the image input, the signal input, and the text input. Since the micro-ethnicity information serves as a major distinguishing factor between groups of peoples to perform structure-based analysis, volumetric extraction, volumetric analysis, atrophy determination, quantification, and perform predictive prognosis and diagnosis, the text input comprises predominantly the micro-ethnicity information. The text input further comprises intracranial volume (ICV), age, gender, race, medical symptoms, and the like. The text input such as the micro-ethnicity information, age, gender, ICV and the like may have an impact in the volumes of the at least one structure in the one or more first images.

FIG. 5 illustrates a method of structure-based analysis report generation, according to one or more embodiments. The method of structure-based analysis report generation comprises steps of capturing and/or obtaining inputs from a site (step 548), pre-processing of the inputs (step 550), segmentation (step 552), volume extraction (step 554), quality check (step 556), and reporting (step 558). The pre-processing step 550 further comprises discarding metadata associated with the inputs by converting the inputs from a first format (e.g., Digital Imaging and Communications in Medicine (DICOM) format) to a second format (e.g., Neuroimaging Informatics Technology Initiative (NIfTI) format). The inputs are verified for meeting industry standards and quality. In case of an image input, one or more first images are then verified for magnetic strength value having more than 1.5 Tesla associated with the one or more first images. One or more second images of at least one structure resided within the one or more first images are then segmented at step 552. One or more volumes of the at least one structure is extracted and rendered to a user to perform structure-based analysis (i.e., volumetric analysis) at step 554. At least one feature is also determined at step 554 based on the one or more volumes extracted and the one or more inputs received.

The feature comprises at least one of the one or more volumes of the region of interest (ROI), a cortical thickness, an atrophy percentage, an asymmetry index score, a subfield volumetry of the region of interest, annular volume changes, a progressive supranuclear palsy (psp) index score, a magnetic resonance perfusion imaging (MRPI) score, a frontal horn width to intercaudate distance ratio (FH/CC), a medial temporal lobe atrophy (MTA) score, a global cortical atrophy (GCA) scale, identification of Intracranial bleeds, hemorrhage, microbleeds and their volume analysis, a fracture detection, a midline shift identification, a measurement of the midline shift identification and the at least one structure with respect to the midline shift identification, identifying a pathology associated with the at least one structure, classifying the pathology identified, a tissue density identification, an infarct identification, a Penumbra-core-viable tissue identification, classification and volume calculation, diffusion-weighted imaging (DWI) maps and apparent diffusion coefficient (ADC) maps of the at least one structure, perfusion maps comprising resting state functional magnetic resonance imaging (rsfMRI), an alberta stroke programme early CT score (ASPECTS) calculation, a collateral detection, a mismatch ratio calculation, an angiography labeling and/or annotation, a large vessel occlusion (LVO) detection, an Hypoperfusion index calculation, Diffusion tensor imaging (DTI) fiber tracks, neural pathway connectivity maps, correlation between a signal input, an image input and the text input, classifying the signal input, identifying a normal signal, identifying an abnormal signal, identifying a pre-ictal signal, identifying an ictal signal, extracting symptoms, and grading of condition specific effects.

The at least one feature is rendered. The one or more volumes are also rendered in at least one of a three-dimensional format, and a two-dimensional format. The one or more volumes are also rendered in at least one anatomical plane. The one or more volumes are then sent for quality control, at step 556, to provide an optimum quality and optimum shape of pictorial representation of the one or more volumes, prior to compiling a structure-based analysis report. At step 558, the server generates a structure-based analysis report that gives insights to the physicians, caregivers, radiologists, researchers, etc. The system also performs integrated analysis by using at least one of the text input, and the signal input with the image input acquired from the same patient to provide optimum accuracy in predictive prognosis, diagnosis, and atrophy determination. The structure-based analysis report aids physicians, doctors, and medical practitioners in their assessment of a patient's prognosis.

FIG. 6 illustrates users of a system, according to one or more embodiments. The system extracts and renders one or more volumes of at least one structure in at least one of a three-dimensional (3D) format, and an anatomical plane. Since the rendered volumes are utilized for research and study purposes, the one or more volumes rendered should be rendered in optimized quality. Further the one or more rendered volumes are utilized for treatment purposes, the system may be utilized and accessed by the users at a site. The site may comprise a hospital, a diagnostic center, a health care unit, etc. The system is also utilized in creating a database with respect to a micro-ethnicity (e.g., an Indian micro-ethnicity) comprising one or more features, one or more volumes, one or more quantitative volumes, age, gender, micro-ethnicity information, etc. At least for the above use cases, the system may be utilized by the users such as radiologist, technician, manager, analyst, doctors, students, researchers, physicians, etc.

The technicians may upload, study, attach documents, view studies, view reports, etc., to finalize and pass on to the next stage. The analyst may view assigned studies, add clinical story, view study, perform manual segmentation, submit to the manager after quality check, etc. The admin may create/edit sites, and create/edit users. The manager may view studies, assign studies to an analyst, prepare reports, send to a radiologist, quality check finalization, and finalize reports. The radiologist may view studies and segmented images, view reports, and perform QC review.

FIG. 7 illustrates a process flow of a system, according to one or more embodiments. The process flow shown here splits the flow under different sections for illustrative purposes. The process flow is split under different sections such as onboarding users, operations from sites, operations, and quality control and delivery. Under the onboarding users' section, the user is enabled to perform initial settings (e.g., register, sign-up, etc.) and provide access to a server. Performing Initial settings comprise providing user information and logging in. Once the access has been given, the server depicts demos such as trial cases (3-5). The trial cases enable the server in understanding variations associated with each user and knowing what should not be changed at that point. User ID is then generated for a site at which the user is operating. In an embodiment, User ID is generated for each user, in addition to the user ID generated for the site. When there are multiple diagnostic and hospital chains, the user ID is generated per location as described above. The server also provides two user IDs for each location. For example, the server provides a first user IDs for a technician and a second user ID for a radiologist at the same location.

Once the user IDs have been generated, the server enables the user to perform the operations, such as case uploads, from sites. The server enables the user to login to a web portal using the user ID generated. The user must upload a consent form. The user can then scan and upload inputs (e.g., one or more first images, one or more physiological signals, text inputs). The user is enabled to enter or provide other information to the server (portal or platform). Once the requisite and mandatory information has been uploaded, the uploaded case will reflect online in a cloud (such as Amazon Web Services (AWS®)) to all users who have access as per privileges given. For instance, when the case is uploaded the doctor can access his patient's case and perform the assessment. The doctor cannot access the case history of other doctor patients.

Once the case has been uploaded from the sites, the server enables the user to perform operations such as management operations. Under the operations, the user such as manager may assign the case to an analyst. Upon assigning the case to the analyst, the analyst gets access to it. The analyst then performs quality assurance/quality control. Once the quality assurance has been complied, an image segmentation is performed (e.g., automatically, semi-automatically, or manually) to segment at least one structure that resides within the one or more first images. Data retrieval (e.g., logs) from algorithms is then performed to train the neural networks.

An analysis report is then generated and compiled. The analysis report comprises at least one of the feature, volumetric analysis such as one or more segmented images in at least one anatomical plane and the one or more quantitative volumes of the at least one structure. The analysis report further comprises volumetric derived analysis such as segmentation prediction, volume calculation, reference range calculation, atrophy, ICV volume, Volume loss, etc. The analysis report is then passed on to the quality control.

Under the quality control and delivery, the server enables a second analyst to check the one or more segmented images and make appropriate changes, as necessary. The compiled report is then cross checked by a third analyst to ensure quality and make appropriate changes, as necessary. The final report is then checked by a manager. The final report is then sent to the radiologist/principal investigator. The final report readily provides quantitative numbers, volumes of at least one organ, reference quantitative volumes, a snippet regarding prognosis, etc. to the physicians. The final report aids the physicians in predictive prognosis and diagnosis.

FIGS. 8 and 9 illustrate a system architecture, according to one or more embodiments. The system architecture depicts a user interacting with at least one DICOM server (e.g., ORTHANC) through a web server. The DICOM server is communicatively coupled to other database servers. DICOM studies are uploaded directly to the DICOM servers by DICOM users or through the web server by non-DICOM users. The high-level design shown in FIG. 8 illustrates that both the DICOM and non-DICOM users interact with the system. The DICOM server provides the one or more first images, the one or more second images, and the segmented structures to a web portal for all purposes including investigation, study, treatment and other two dimensional or three-dimensional model creation purposes. The DICOM servers let the users focus on content of the DICOM files, hiding the complexity of the DICOM format and of the DICOM protocol. The DICOM server provides imaging contents to the web server for all purposes and will be the primary source for the study list.

Once the DICOM studies are populated, the documents are uploaded to S3 bucket (e.g., AWS® S3 bucket) based on user ID. The S3 bucket is configured to store physical image files for the application. Other metadata about clinical history and other demographic information will be uploaded in a second database (e.g., MYSQL database) which will be the portal main database and not accessible outside. The subsequent workflows about study management will be handled in the second database. In an embodiment, the system uses a viewer (e.g., papaya viewer) to view and edit the one or more first images.

FIG. 10 illustrates a workflow, according to one or more embodiments. The process flow describes a sequential process. A server allows the user (e.g., admin) to create an account for a site and an account for the user, at step 1002. Once the account for the user is created, the user is enabled to upload a case and a patient history form through the account created, at step 1004. The user is also enabled to upload inputs such as at least one of an image input, a text input, and a signal input. At step 1006, upon successful uploads, the inputs are populated on a worklist of a responsible user by the server. A manager does quality control by verifying the quality of the inputs and accepts and rejects the inputs accordingly. At step 1008, the server enables the manager to assign the case to an analyst for quality assurance/quality control. Once the quality assurance is performed, the inputs are passed on for processing. At step 1010, in case of the image input, one or more second images of at least one structure that resides within one or more first images are segmented by an automatic segmentation application programming interface (API).

The segmented images are then sent to the analyst to quality control and work on the image input. In case of the signal input, one or more physiological signals are then sent to the analyst to quality control and work on the signal input. At step 1012, the segmented images are sent to the radiologist for feedback. If the Radiologist suggests changes, the case goes back to the analyst for processing (e.g., manual segmentation, volumetric extraction, volumetric analysis, atrophy, and quantification). The process is repeated until there is no negative feedback from the radiologist. At step 1014, one or more features associated with the at least one structure, one or more volumes of the at least one structure, one or more quantitative volumes, and reference ranges (e.g., 25th percentile and 95th percentile) for the at least one structure is then calculated using the volumetric API by the server once the segmentation is over. At step 1016, the final volumes and the reference ranges are calculated by the volumetric API and are populated in a structure-based analysis report by the server. At step 1018, the generated report will be approved by an admin and it will be entered in a database. At step 1020, the structure-based analysis report and a patient history will be made available to all user accounts by the server as per privileges assigned.

FIG. 11a-11e illustrate a process of segmentation of Hippocampus, according to one or more embodiments. The process of segmentation of the Hippocampus comprises the following technical steps to be executed. A server enables a user to upload one or more first images of a region of interest (i.e., skull) to an ITK snap layer of the server. The ITK snap layer of the server allows the user to navigate three-dimensional medical images, manually delineate anatomical regions of interest, and perform automatic image segmentation. The server enables the user to import a label file for the Hippocampus. Hippocampus label file comprises predefined RGB values. In an embodiment, the predefined RGB values of the Hippocampus label file assigned are R-255, G-182, B-139.

Figure 11A:
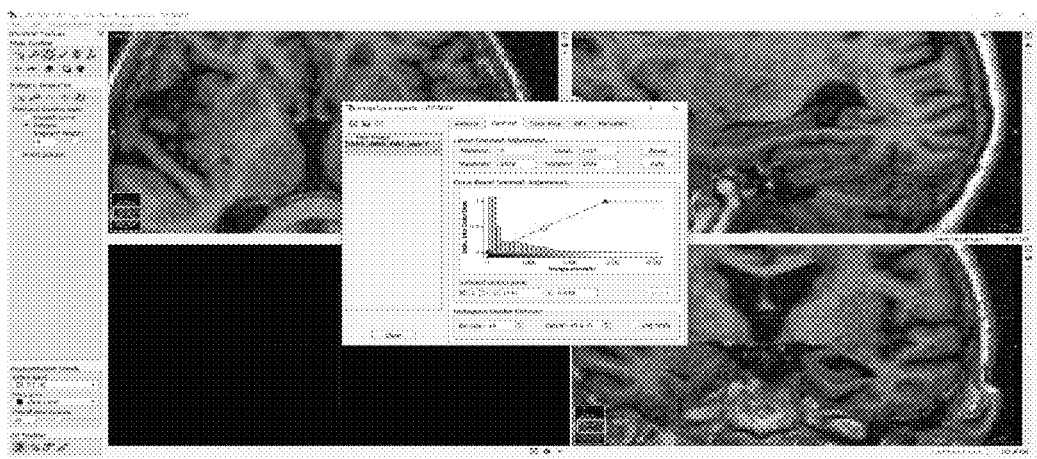

Once the Hippocampus label file is imported, the Hippocampus structure is segmented automatically, using artificial intelligence, from the one or more first images. Then a contrast inspector drop-down tab is accessed as shown in FIG. 11a via a user interface, rendered by the server, to adjust the contrast so that grey matter (GM) and white matter (WM) differentiation is optimum. The one or more segmented images are then rendered in at least one anatomical plane such as a sagittal plane, an axial plane, and a coronal plane to readily enable a user to visualize the Hippocampus in the at least one anatomical plane and identify a location, position and shape of the Hippocampus. The Hippocampus comprises a right Hippocampus and a left Hippocampus. Upon determining, when the one or more segmented images do not comprise optimized quality in terms of shape, boundary and volume of at least one structure, the segmented images can be further manually edited by performing manual segmentation.

Figure 11B:
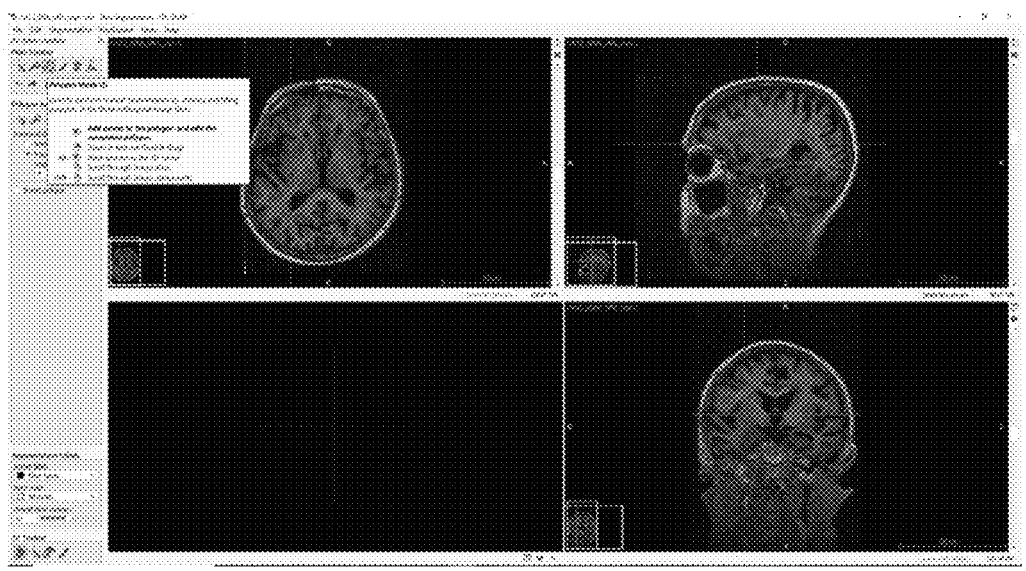
Figure 11C:
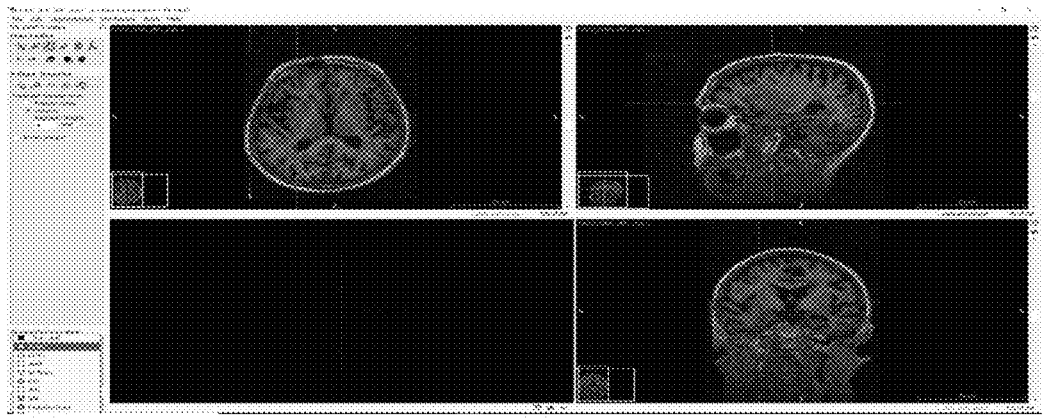

The server, via the user interface, enables the user to move to an image slice using a sagittal plane when the right Hippocampus disappears. The server enables the user to use a "polygon" tool on a main toolbar as shown in FIG. 11b. The "polygon" tool, upon selecting, enables the user to perform the manual segmentation by drawing and filling polygons in orthogonal image slices. In an embodiment, the manual segmentation can be done individually in the anatomical plane. The manual segmentation, via the polygon tool, enables the user to add points to the polygon and edit the completed polygon. The "polygon" tool enables the user to zoom in and out (hold and drag) to view any specific portion of the Hippocampus. The "polygon" tool further enables the user to place and move 3D cursor, scroll through image slices and scroll through image components to view, edit and correct the volume, shape and structure of the Hippocampus. The server further provides an "active label" tool under "segmentation label". Under the "active label" drop-down tool, the user is enabled to select an appropriate label (i.e., right Hippocampus in this instance) as shown in FIG. 11c. The server further enables the user to select the "paint over" tool as all labels.

Figure 11D:
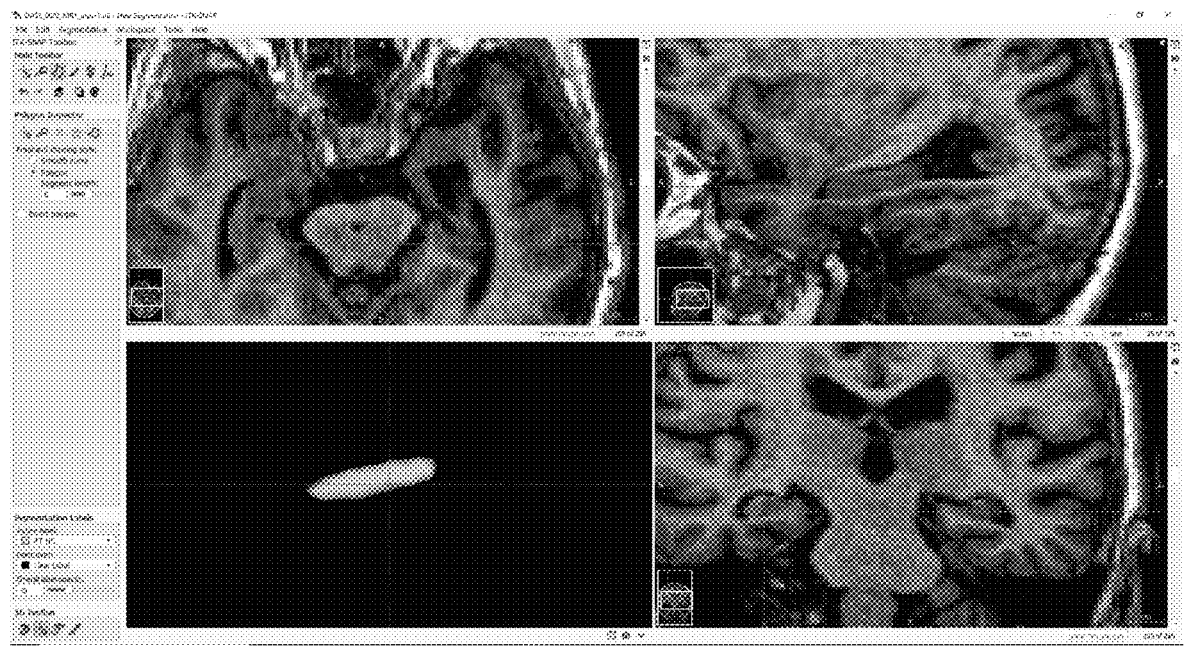

The server enables the user to choose opacity so as not to obscure/hide tissue boundaries. In an embodiment, the opacity ranges between 15-30. The server enables the user to outline the outermost border of the Hippocampus using the image slice chosen as shown in FIG. 11d. In an embodiment, a first color (e.g., pink) is used for an active polygon and a second color (e.g., red) stands for completed polygon. The server further enables the user to retrace borders of the Hippocampus and detect any missing pixels or voxels by zooming in. The server provides a "brush" tool. The "brush" tool enables the user to edit and add the missing pixels/voxels by selecting an appropriate brush (e.g., round brush, square brush) and appropriate bush size. If the edits have been done more than the actual voxels/pixels (i.e., in case of over estimation), the server enables the user to select the "active label" as "clear label" and edit the voxels/pixels.

In an embodiment, the Hippocampus was defined to comprise subiculum, Ammon's horn (CA1-CA4), dentate gyrus, and associated white matter tracts (alveus, fimbria). Ammon's horn within the posterior uncus was also included. In an embodiment, disarticulation of the Hippocampal head from the amygdala and uncinate gyms on the most anterior sections was aided by recognizing the undulating contour of the pes digitations and by the fact that the alveus provides a high signal intensity (white matter) marker defining superior border of the head of the Hippocampus where it directly abuts the overlying.

Figure 11E:
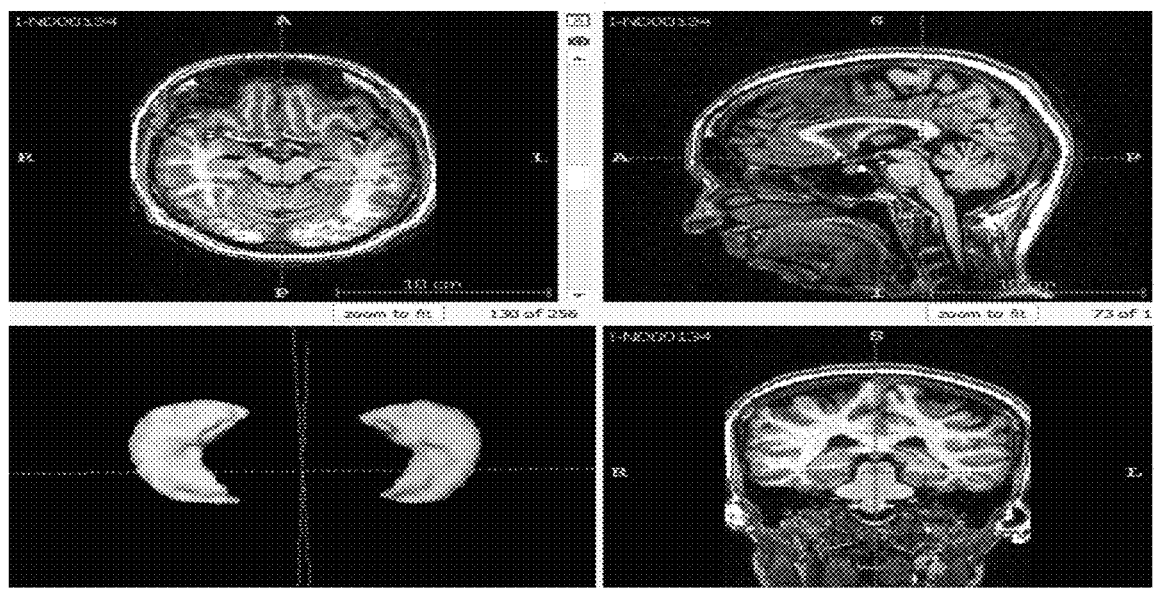

The server also enables the user to segment the left Hippocampus and extract volumes of the left Hippocampus. Once the right Hippocampus is completed repeat the above steps for the left Hippocampus. To proceed with the left Hippocampus, the server enables the user to change the "active label" as left Hippocampus (Lt HC) before starting left HC. The segmented image and extracted volumes of both the left Hippocampus (Lt HC) and the right Hippocampus (Lt HC) are shown in FIG. 11e.

Once both the segmentation and volume extraction of the right HC and left HC are complete, the server enables the user to save the one or more first images, workspace, mesh and the one or more segmented images with a patient id name. The server enables the user to place the directory location for the image files in the patient ID folder. The server enables the user to capture screenshots/save the segmented images at all anatomical planes in such a way that both the Lt HC and Rt HC are displayed well with labels. The server further allows the user to capture screenshots of the segmented image in a three-dimensional image format with both the left HC and right HC zoomed well.

The server enables the user to check for errors, starting from the tail of the hippocampus in the axial plane. It is to be noted that Hippocampus do not include the Gyms. The server enables the user to check the boundary using the cursor and check in all three anatomical planes shown. Since the tail of the Hippocampus is close to Thalamus, check the voxels/pixels in the sagittal plane and the coronal plane for better visualization for separation between the Thalamus and the Hippocampal tail. Fimbria is to be included with the Hippocampus. Fimbria is visualized as a hyperintense layer on the surface of the Hippocampus. Fimbria is also visualized in the sagittal plane and the axial plane attaching the head of the Hippocampus to the Amygdala. Further the head of the Hippocampus and the Amygdala is distinguished by a slight hyperintense boundary of the Hippocampal head. The slight hyperintense boundary of the Hippocampal head is visualized in the anatomical planes. The server allows the user to trace the slight hyperintense boundary of the Hippocampal head using the "cursor chase" option and add the slight hyperintense boundary in the image segmentation.

Figure 12A:
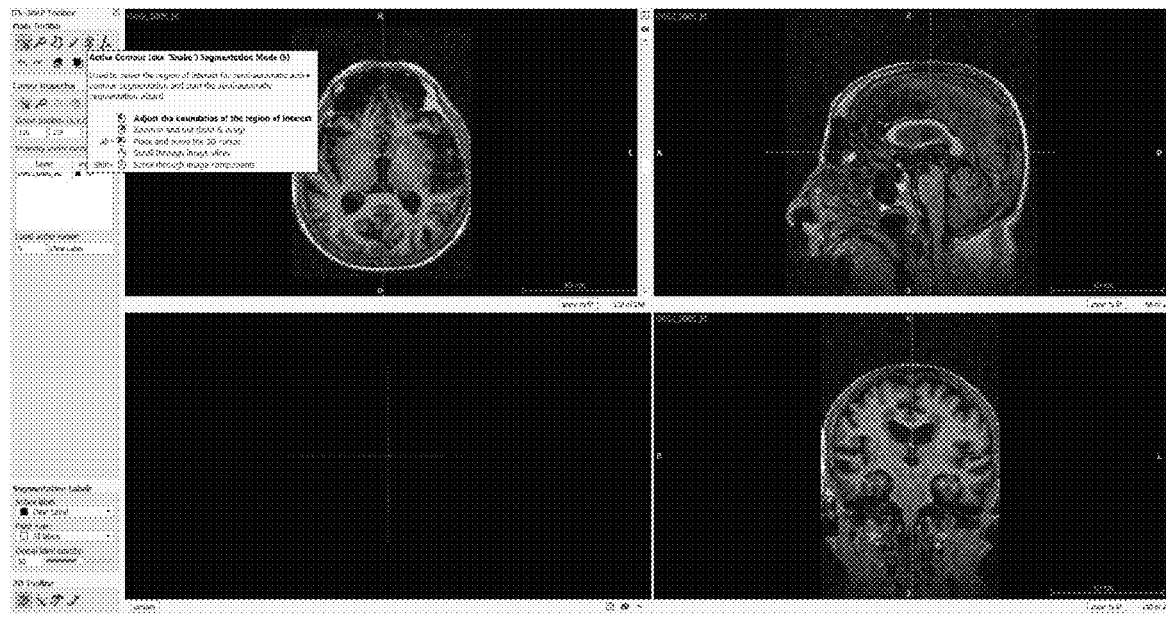

FIG. 12a-12k illustrate a process of segmentation of Ventricles, according to one or more embodiments. The process of segmentation of the Ventricles comprises the following technical steps to be executed. While performing the segmentation, a server enables a user to select the "active label" as "Ventricles". In an embodiment, RGB values assigned for the Ventricles are: R-181, G-176, and B-22. The server further enables the user to segment the Ventricles in at least one of Automatic segmentation, Semi-automatic segmentation, and Manual segmentation. As the Ventricles are bounded by complex tissue matters, the Ventricles is mostly segmented using Contour Segmentation i.e., Semi-automatic segmentation. The contour segmentation allows the user to select a region of interest from uploaded one or more first images (e.g., skull) for semi-automatic active contour segmentation and start the semi-automatic segmentation as shown in FIG. 12a. The contour segmentation enables the user to adjust the boundaries of the region of interest. Once the 'active label' is assigned as 'Ventricles', the server renders the one or more first images in at least one anatomical plane and a three-dimensional format. The server enables the user to identify the Ventricles in the at least one anatomical plane rendered by the server.

The Ventricles can be identified by understanding the structure of the Ventricles. Cerebral ventricular system is made up of four ventricles that comprises two lateral ventricles (one in each cerebral hemisphere), a third ventricle in a diencephalon, and a fourth ventricle in a hindbrain. The lateral ventricle is a C-shaped cavity situated within each cerebral hemisphere. The two lateral ventricles are separated from each other by a thin vertical sheet of nervous tissue called septum pellucidum covered on either side by ependyma. The two lateral ventricles communicate with the third ventricle through the interventricular foramen of Monro. Each of the lateral ventricles is made up of a central part (body) and three horns (cornua) namely the anterior horn, posterior horn, and inferior horn. Anterior wall is formed by the posterior surface of the genu of corpus callosum and the rostrum. The roof is formed by an inferior surface or anterior part of the body of the corpus callosum. Medial wall is formed by the septum pellucidum. The floor is formed majorly by the head of the caudate nucleus, while a small portion on the medial side is formed by the upper surface of the rostrum of the corpus callosum. The roof and lateral wall of the posterior horn are formed by the sheet of fibers of corpus callosum known as tapetum. This separates the posteriorly sweeping optic radiation from the cavity of the posterior horn. The medial wall has 2 bulges. In the upper part, it is formed by the fibers of the occipital lobe sweeping backward known as forceps major and is referred to as the bulb of the posterior horn. The second elevation below this is called calcar avis and corresponds to the in-folding of the anterior part of calcarine sulcus.

The inferior horn forms a curve around the posterior end of the thalamus, descending posterior laterally and then anteriorly into the temporal lobe. The area where inferior horn and posterior horn diverge is called collateral trigone or atrium. Laterally, the roof is covered by the inferior surface of the tapetum of the corpus callosum and medially by the tail of the caudate nucleus and stria terminalis. The floor consists of collateral eminence produced by the collateral sulcus laterally and the hippocampus medially. The fibers of the hippocampus form a thin layer of white matter called alveus that covers the ventricular surface and converge medially to form the fimbria. Most medially on the floor lies the choroid plexus passing through the choroid fissure.

The third ventricle is a median slit-like cavity situated between the two thalami and part of the hypothalamus. In the anterosuperior aspect, the third ventricle communicates with the lateral ventricles while on its posteroinferior aspect the third ventricle communicates with the fourth ventricle through the cerebral aqueduct of Sylvius. The space of the third ventricle is lined by ependyma and is traversed by a mass of grey matter called interthalamic adhesion or Massa intermedia, located posterior to the foramen of Monroe and connects the two thalami. The fourth ventricle is bounded anteriorly by the pons and cranial half of the medulla and posteriorly by the cerebellum. The fourth ventricle appears triangular on the sagittal section and rhomboidal on the horizontal section. Superiorly, the fourth ventricle is continuous with the cerebral aqueduct while inferiorly the fourth ventricle is continuous with the central canal of the spinal cord.

Figure 12B:
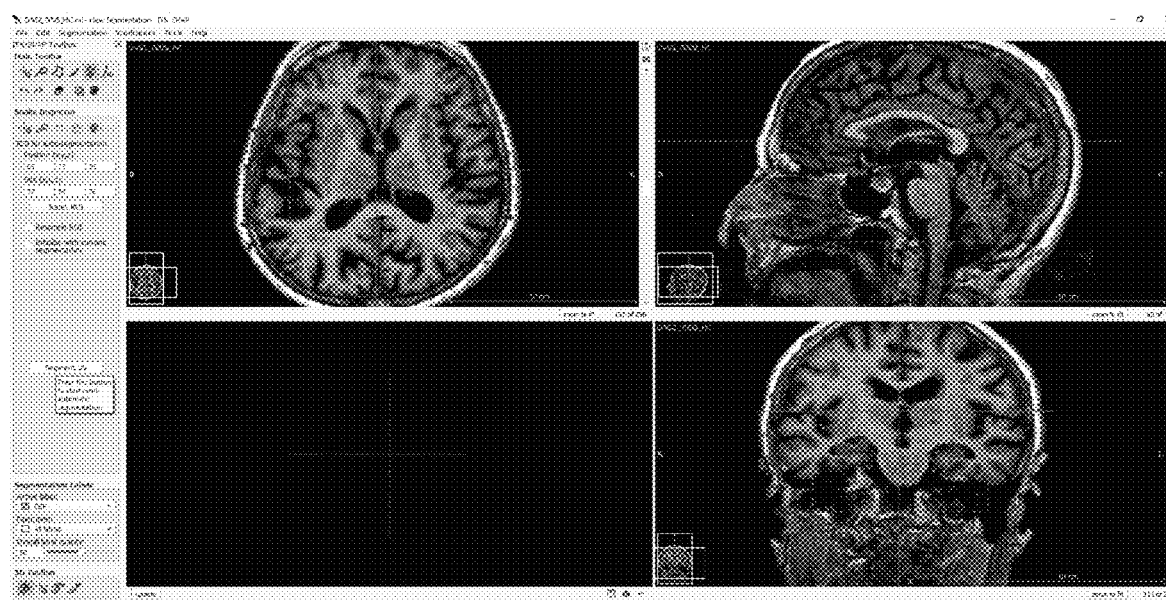
Figure 12C:
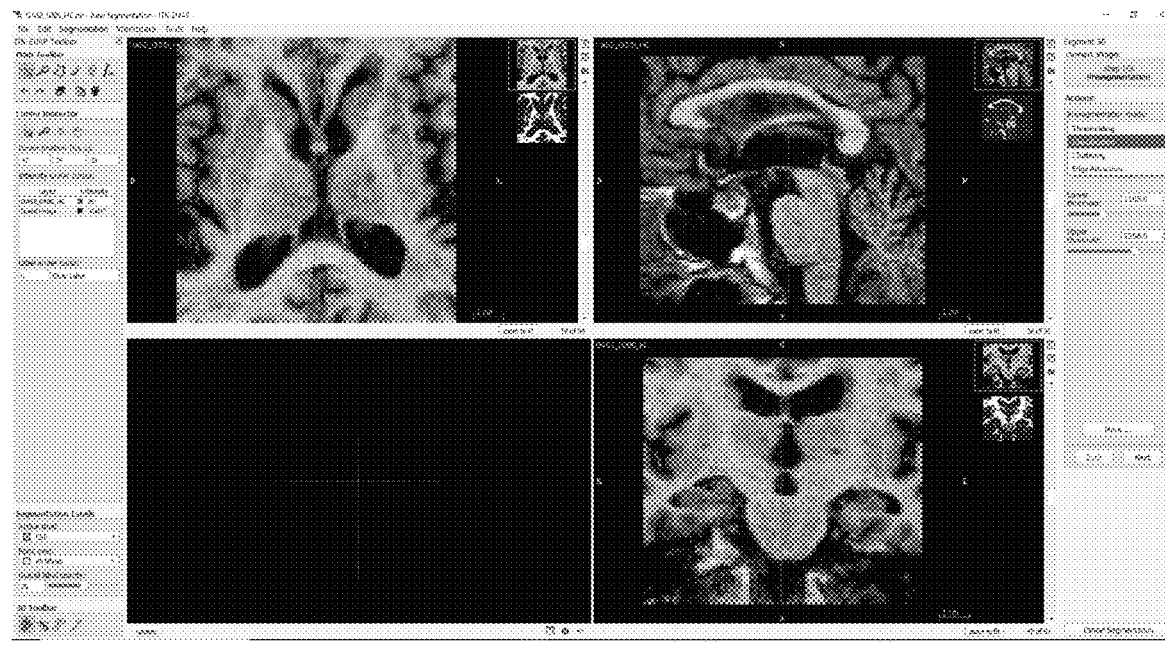
Figure 12D:
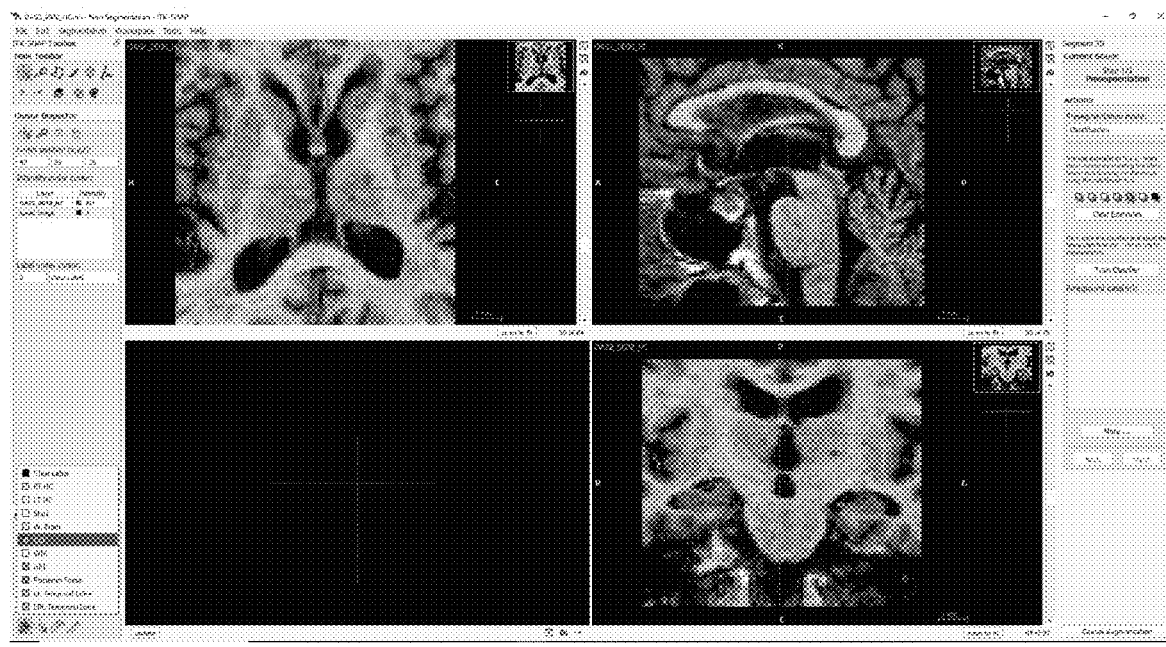

Once the Ventricles are identified, the server enables the user to mark a region of interest covering the Ventricles and check whether the Ventricles is covered in the anatomical planes as shown in FIG. 12b. The server provides a "segment 3D" tool that allows the user to start semi-automatic segmentation. The user upon clicking the "segment 3D" tool a toolbar appears. The toolbar provides a "pre-segmentation" tool. The "pre-segmentation" tool provides at least one of "thresholding", "classification", "clustering", and "edge attraction" as shown in FIG. 12c. The user can select any of the four tools under the "pre-segmentation" tool. For example, the "classification" tool is selected by the user as shown in FIG. 12d.

Before starting the "classification" type segmentation, the server enables the user to choose a label indicating "Ventricles" under the "Segmentation labels" tool. The "Segmentation label" tool is used to record and save information (e.g., volumes, quantitative volumes, boundaries, manual edits performed to the segmentation, etc.) obtained as a result of the segmentation performed on the at least one structure (i.e., the ventricles). The server further provides a "brush" tool that allows the user to select appropriate brush (e.g., round brush, square brush) and appropriate brush size to mark the Ventricles under the "Ventricles" label of the "Segmentation labels". The server further allows the user to differentiate tissue samples and the Ventricles. The different tissue samples comprise white matter (WM) and grey matter (GM). The server allows the user to select the "Segmentation labels" as "Brain" and mark the tissue samples such as the WM and GM.

Figure 12E:
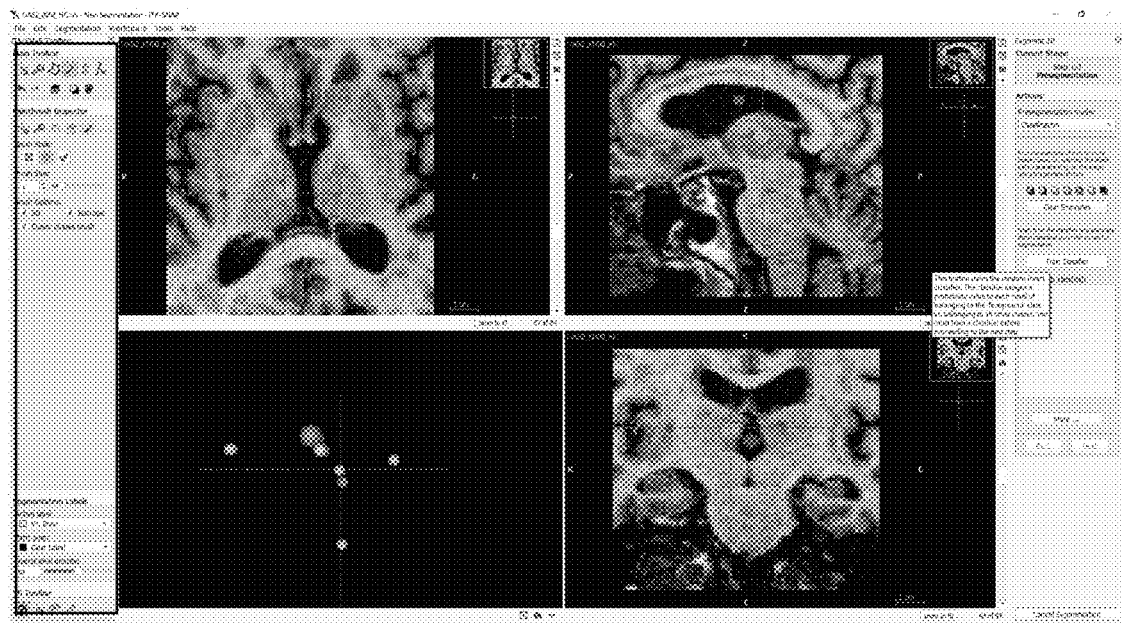
Figure 12F:
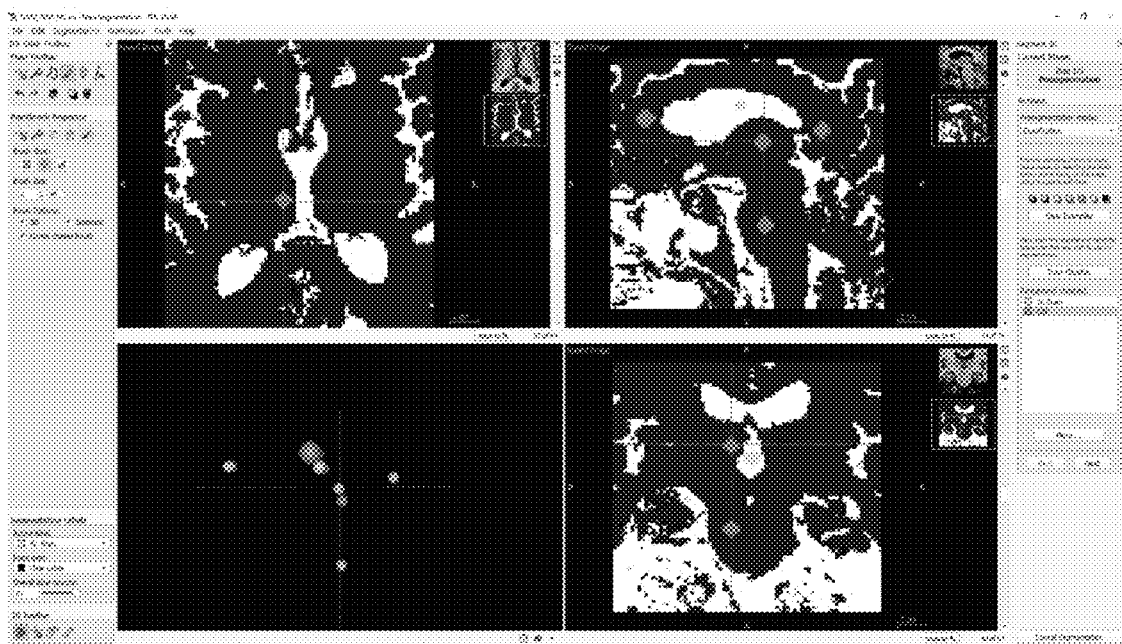

The server further provides a "train classifier" tool that allows the user to train a classifier by clicking on the "train classifier" tool once the tissue samples are marked appropriately. The server further renders a speed image that shows the classification. The "train classifier" assigns a probability value to a voxel belonging to the "foreground" class vs. a voxel belonging to all other classes i.e., the Ventricles and the Brain. Once the classifier is trained using the manual segmentation (i.e., marking and differentiating the tissue samples and the Ventricles) the classifier automatically segments at least one structure within the one or more first images of a different patient in future based on micro-ethnicity information, age, race, gender, patient history, clinical history, medical condition, symptoms, brain dominance information, stress information, food habitat information, psych analysis information, etc. "Foreground class" tab below shows the labels (e.g., Ventricles and Brain) of structures within the region of interest for which the boundaries are marked and differentiated. Upon selecting the "Ventricles" label under the "Foreground class", the server renders the Ventricles in the anatomical planes and in the speed image, as shown in FIG. 12e. Similarly, upon selecting the "Brain" label under the "Foreground class", the server renders the whole brain in the anatomical planes and in the speed image as shown in FIG. 12f. The server provides a "Next" tab to complete and finalize the segmentation process.

Figure 12G:
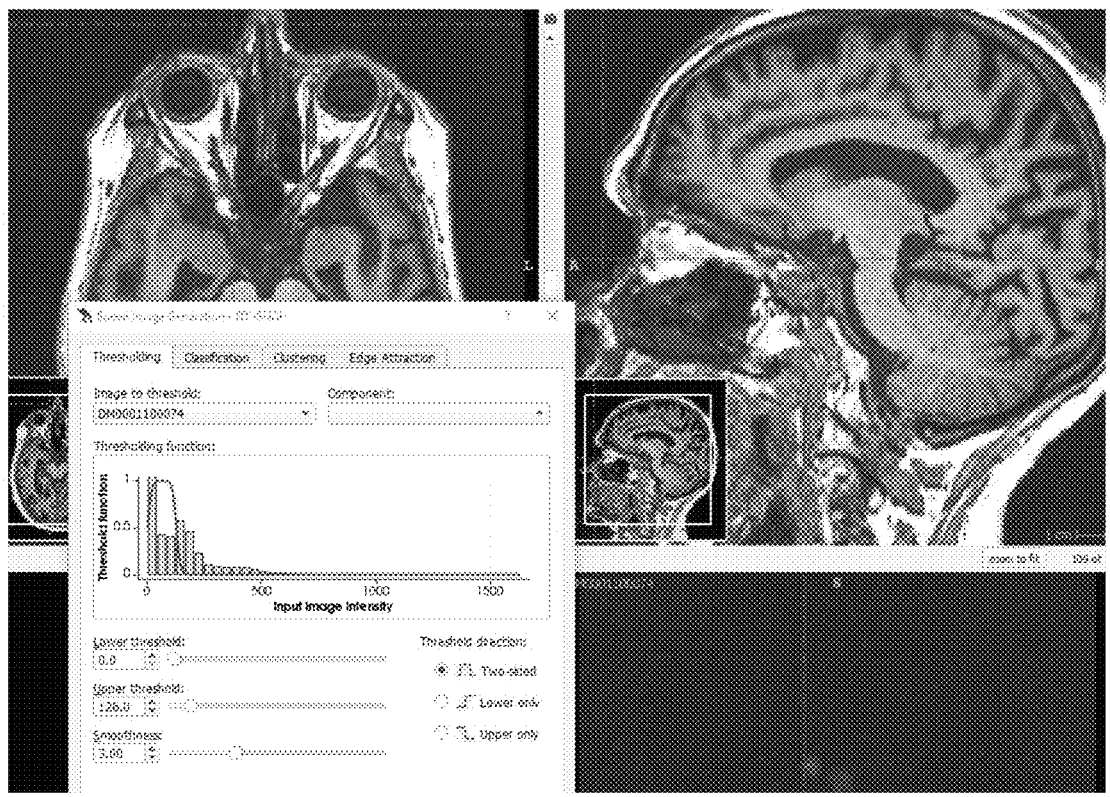

FIG. 12g illustrates the segmentation of the Ventricles performed using a thresholding method. Under the "pre-segmentation" tool select the "thresholding" tool. The server provides a "More" tab that provides a speed image generation window (as shown in FIG. 12c). Speed image generation renders a lower threshold slider, an upper threshold slider, and a smoothness slider that allows the user to adjust an upper threshold value, a lower threshold value and smoothness value. The sliders are adjusted to remove the white matter (WM) from the selection/classification area properly. In an embodiment, the lower threshold value is adjusted to zero while the upper threshold value is adjusted to a minimum value to remove the white matter from the classification/selection area. Once the white matter is removed, the server provides a "Next" tab to finalize and submit the threshold levels.

Figure 12H:
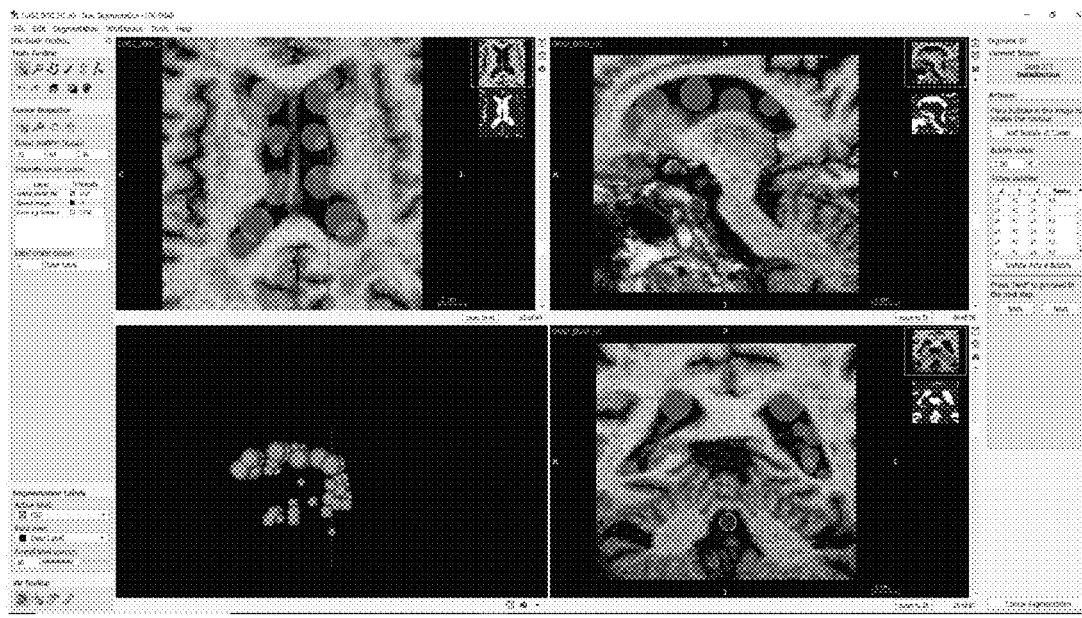

The server then provides an "Add bubble at cursor" tool that allows the user to populate bubbles of appropriate sizes exactly in the ventricles in at least three anatomical planes to exactly extract the volume of the Ventricles as shown in FIG. 12h. The server also provides a "Bubble radius" slider that allows the user to vary the size of the bubbles. The server further provides an "active bubbles" drop down menu that shows the bubbles and its radius that are active. The server allows the user to add a sufficient number of bubbles in the Ventricles. The server also provides a "delete active bubbles" tool that enables the user to delete appropriate bubbles and populate the bubbles exactly only within the boundaries of the Ventricles. The server provides a "Next" tab to finalize the volume extraction.

Figure 12I:
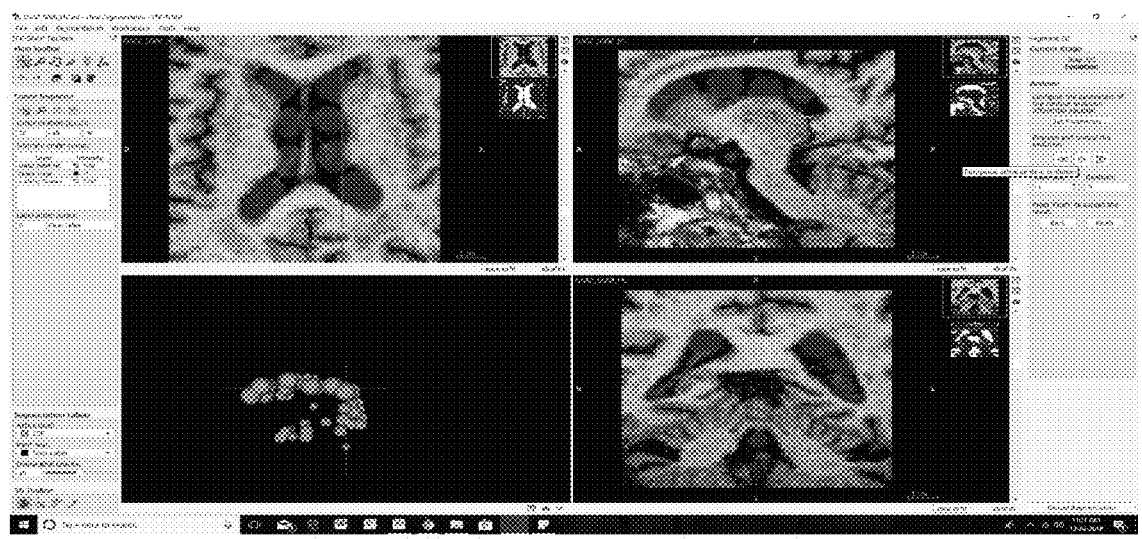
Figure 12J:
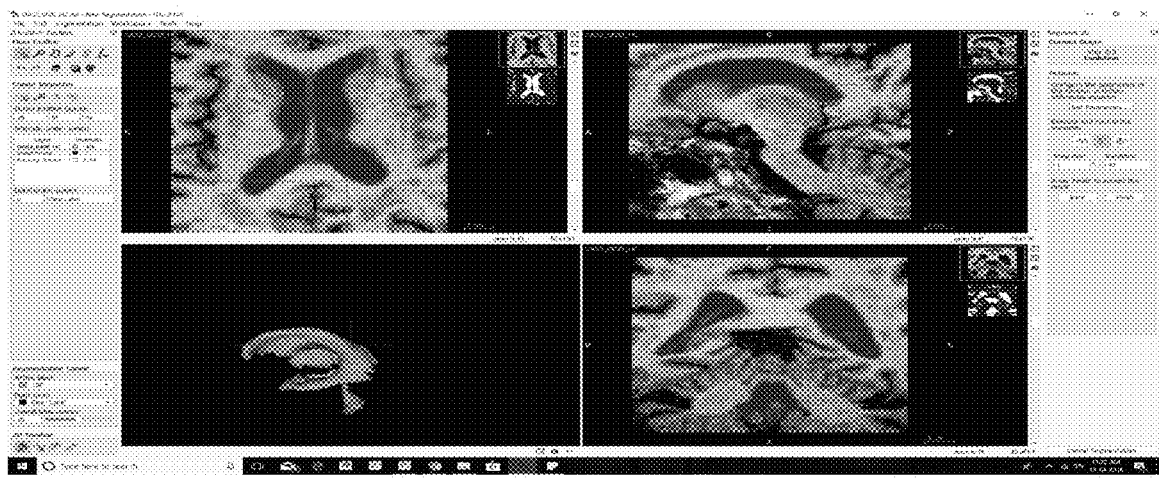

The server provides a "continuous update" tool that enables to continuously update contour evolution. The server further provides a "play" that allows the user to play and pause Active Contour Evolution as shown in FIG. 12i. The server further provides a "finish" tab as shown in FIG. 12j that allows the user to submit when the active contour evolution is done. The server allows the user to change the "active label" to "clear label" and edit the voxels when the active contour evolution goes out of the boundaries of the Ventricles. The server allows the user to edit the voxels by accessing the "brush" tool and selecting appropriate brush and appropriate brush size. The server allows the user to change the "active label" to "Ventricles" and edit the voxels/pixels when the active contour evolution has not reached any part of the Ventricles. The server allows the user to edit the voxels/pixels by accessing the "brush" tool and selecting appropriate brush and appropriate brush size. The server captures and records actions performed by the user under the "active label".

Figure 12K:
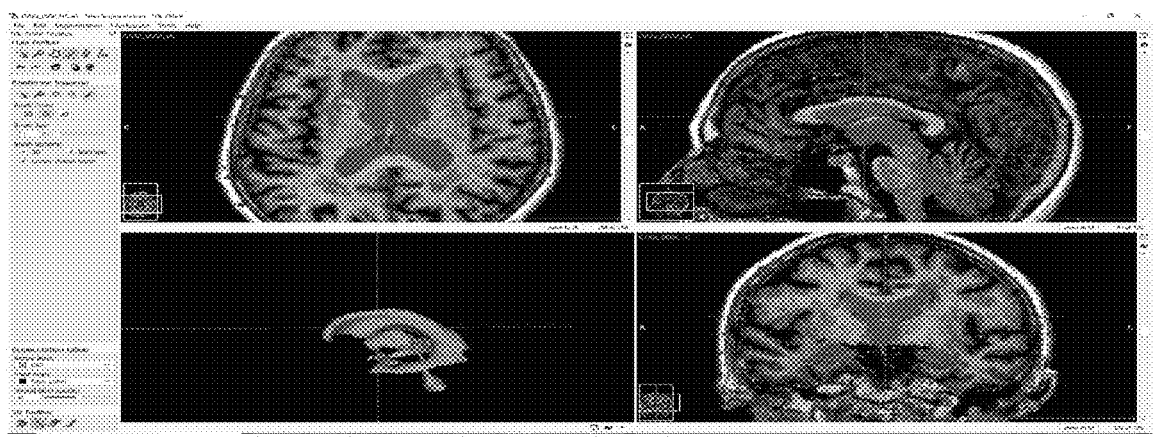

Once both the segmentation and volume extraction of the Ventricles are complete, the Ventricles are rendered in at least one anatomical plane and a three-dimensional format as shown in FIG. 12k. The server enables the user to save the one or more first images, the workspace, the mesh and the one or more segmented images with a patient id name. The server also places directory location for the image files in the patient ID folder. The server enables the user to capture screenshots of the segmented images at all anatomical planes in such a way that Ventricles are displayed well with labels. The server further allows the user to capture screenshots of the segmented image in a three-dimensional image format with the Ventricles zoomed in and displayed well. Boundaries of the Ventricles comprises the following. The lateral ventricles temporal horn is separated by the fimbriae. Segmentation to be done according to separation. The marked area boundaries are the defined anterior and posterior boundaries for the third ventricles.

Figure 13A:
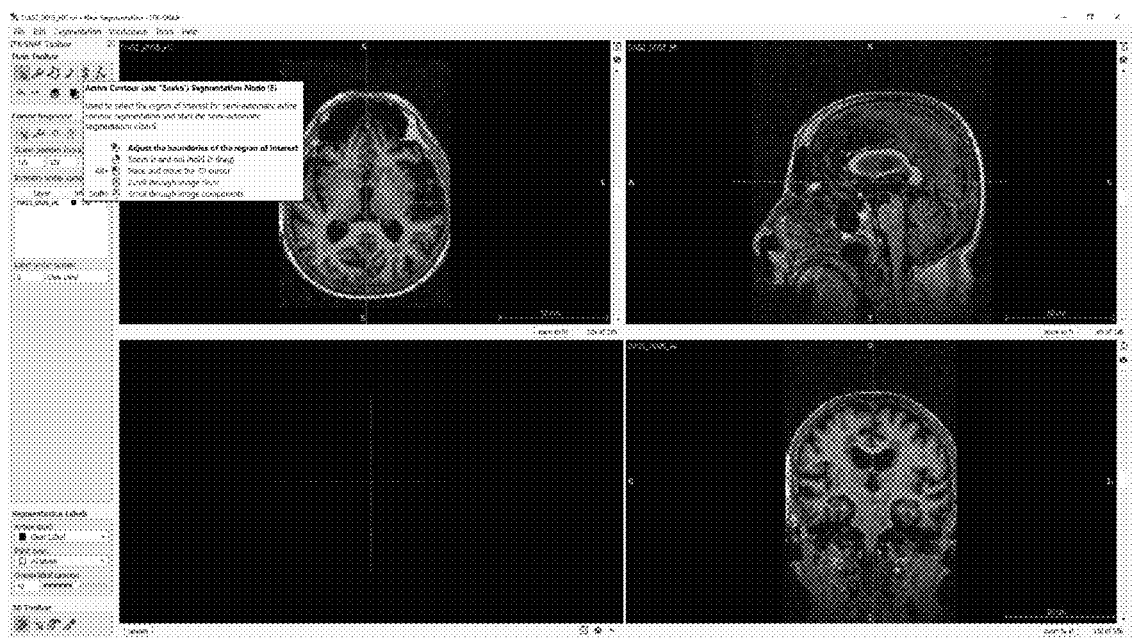

FIG. 13a-13h illustrate a process of segmentation of a Whole Brain, according to one or more embodiments. The process of segmentation of the Whole Brain comprises the following technical steps to be executed. While performing the segmentation, a server enables a user to select the "active label" as "Whole Brain". In an embodiment, RGB Values assigned for the Brain are: R-197, G-239, and B-91. The server further enables the user to segment the Whole Brain in at least one of Automatic segmentation, Semi-automatic segmentation, and Manual segmentation. As the Brain is bounded by complex tissue matters, the Brain is mostly segmented using Contour Segmentation mode i.e., Semi-automatic segmentation. The contour segmentation allows the user to select a semi-automatic "active contour segmentation" tool and start the semi-automatic segmentation as shown in FIG. 13a. The contour segmentation enables the user to adjust the boundaries of the region of interest covering the Whole Brain. Once the 'active label' is assigned as "Whole Brain", one or more first images (e.g., skull) are rendered in at least one anatomical plane and a three-dimensional format. The server enables the user to identify the Whole Brain in the at least one anatomical plane.

Figure 13B:
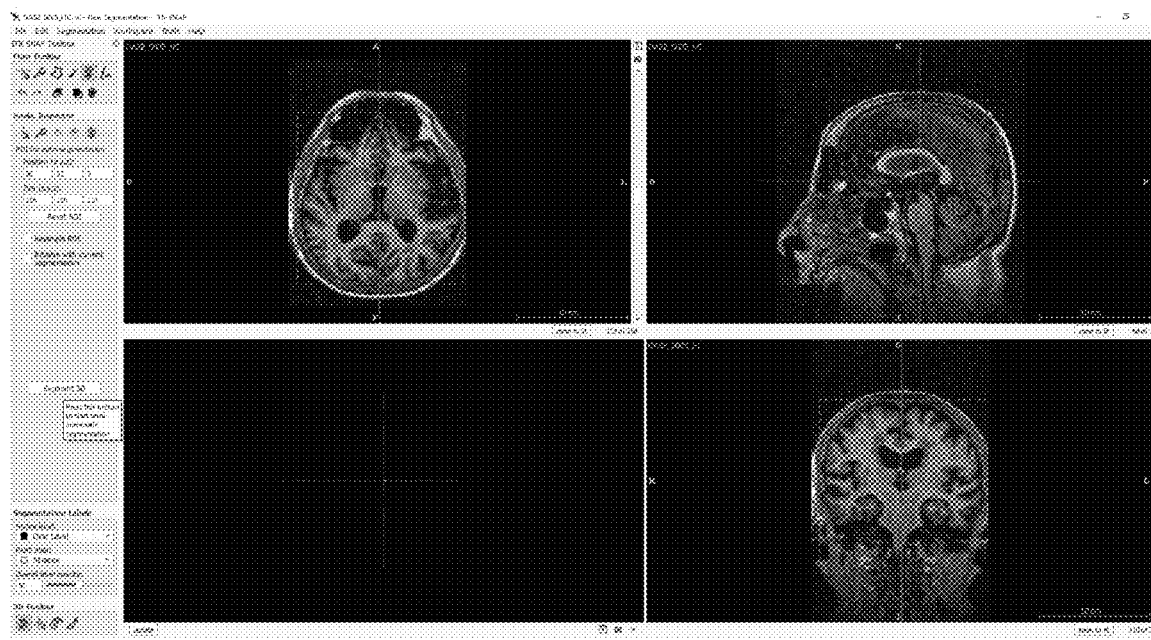

Once the Whole Brain is identified, the server enables the user to mark a region of interest covering the Whole Brain and check whether the Whole Brain is covered in the anatomical planes as shown in FIG. 13b. The server provides a "segment 3D" tool that allows the user to start semi-automatic segmentation. The user upon clicking the "segment 3D" tool a toolbar appears. The toolbar provides a "pre-segmentation" tool. The "pre-segmentation" tool provides a "thresholding", "classification", "clustering", and "edge attraction". The user can select any of the four tools under the "pre-segmentation" tool. For example, the "classification" tool is selected by the user as shown in FIG. 13c.

Before starting the "classification" type segmentation, the server enables the user to choose a label indicating "Whole Brain" under the "Segmentation labels" tool. The "Segmentation label" tool is used to record and save information (e.g., volumes, boundaries, manual edits performed to the segmentation, etc.) obtained as a result of the segmentation performed on the at least one structure i.e., Whole brain. The server further provides a "brush" tool that allows the user to select appropriate brush (e.g., round brush) and appropriate brush size to mark the Whole Brain under the "Whole Brain" label of the "Segmentation labels". The Whole Brain structure marked comprises brain structures (e.g., grey matter (GM), white matter (WM), Midbrain, Pons, Medulla). The "classification" tool allows the user to classify between Brain and Intracranial Volume (ICV) under two labels "Whole Brain" and "ICV". The "Whole Brain" label is used to classify between white matter and grey matter. The "ICV" label is used to classify between dura, skull bone, Ventricles or cerebrospinal fluid (csf). In an embodiment, if there is an error, the "classification" tool further allows the user to add a third label as "Ventricles" to classify the Ventricles separately. The different tissue samples comprise white matter (WM) and grey matter (GM). The server allows the user to mark the tissue samples such as the WM and GM.

Figure 13C:
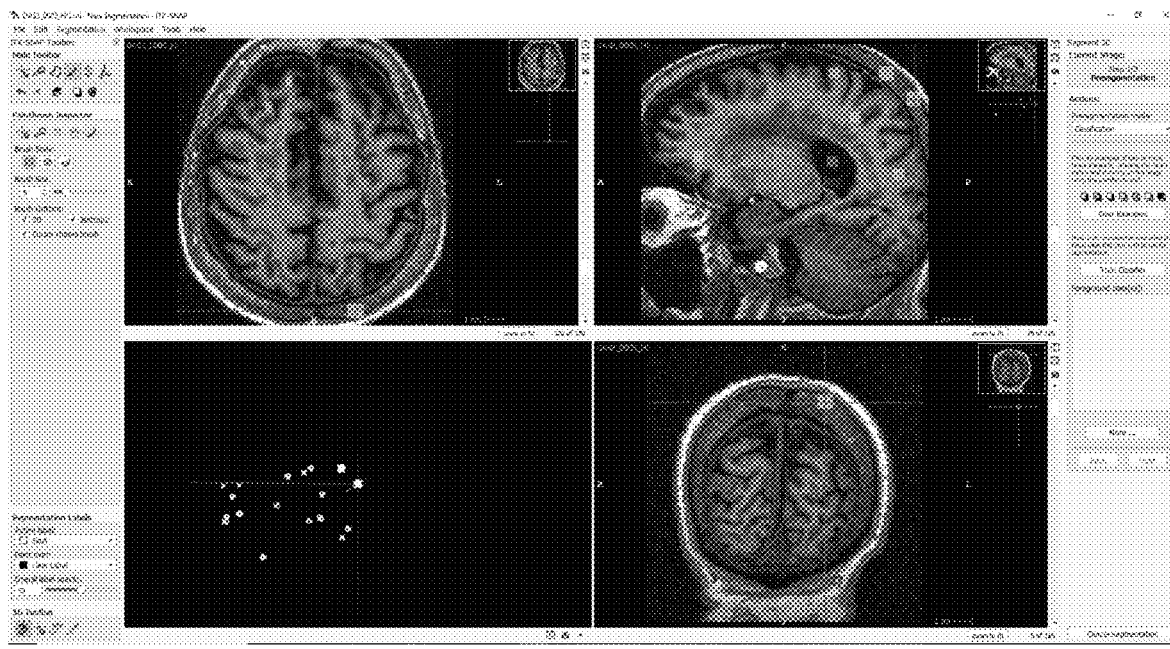
Figure 13D:
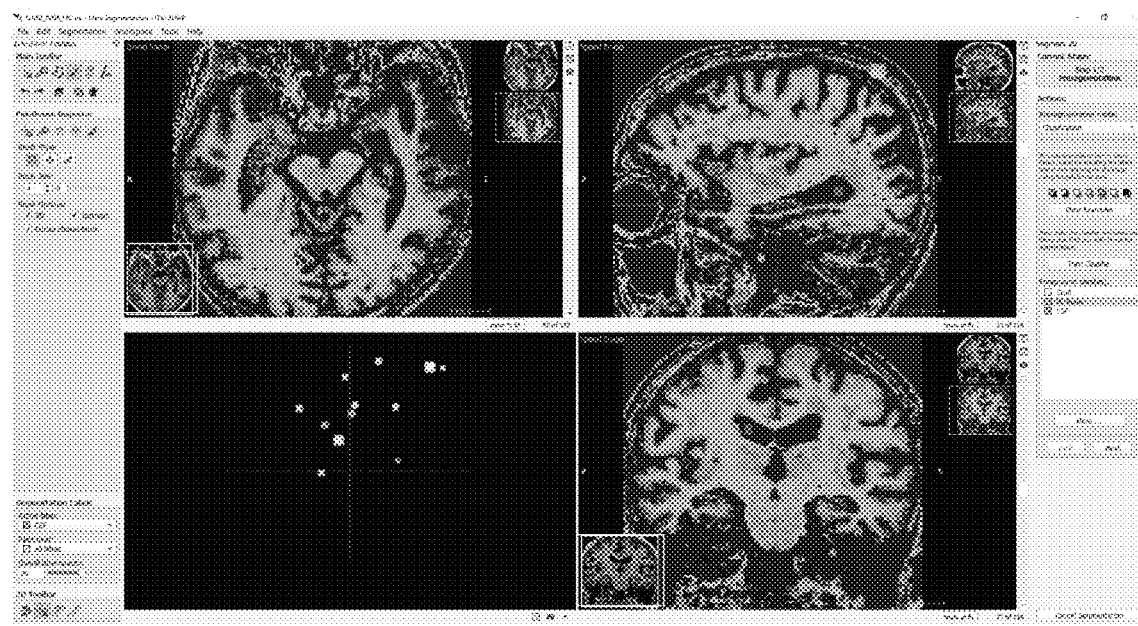

The server further provides a "train classifier" tool that allows the user to train the classifier by clicking on the "train classifier" tool as shown in FIG. 13c. The server further renders a speed image that shows the classification between the whole brain, skull and ICV. The "train classifier" assigns a probability value to a voxel belonging to the "foreground" class vs. belonging to all other classes. Once the classifier is trained using the manual segmentation (i.e., marking and differentiating the tissue samples, Brain, ICV, and the Ventricles) the classifier automatically segments at least one structure within the one or more first images of a different patient in future based on micro-ethnicity information, age and gender. "Foreground class" tool below shows the labels (e.g., Skull, ICV and Brain) of structures within the region of interest for which the boundaries are marked and differentiated. Upon selecting the "Whole Brain" label under the "Foreground class", the server renders the Whole Brain in the speed image, as shown in FIG. 13d. Similarly, upon selecting the "Skull" label under the "Foreground class", the server renders the Skull in the speed image. The server provides a "Next" tool to complete the segmentation process.

Figure 13E:
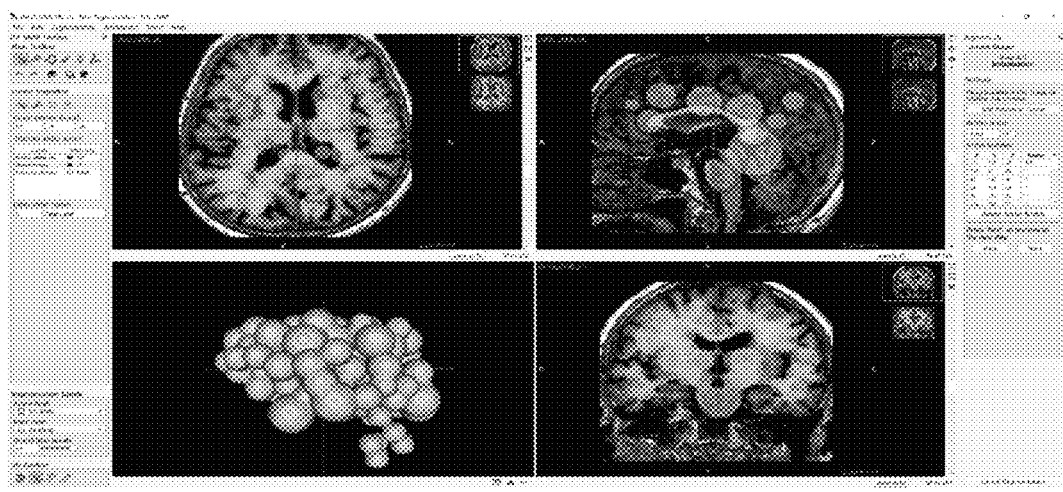
Figure 13F:
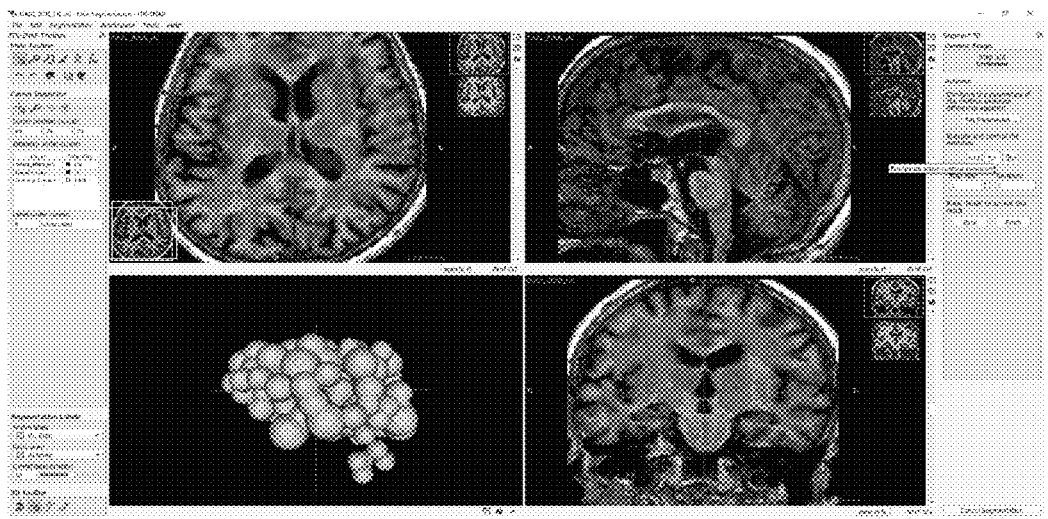

The server provides an "Add bubble at cursor" tool that allows the user to populate bubbles of appropriate sizes exactly in the Whole Brain in at least three anatomical planes to exactly extract the volume of the Whole Brain as shown in FIG. 13e. Further the server provides a "Bubble radius" slider that allows the user to vary the size of the bubbles. The server further provides an "active bubbles" drop down menu that shows the bubbles and its radius that are active. The server allows the user to add a sufficient number of bubbles in the Whole Brain. The server also provides a "Delete active bubbles" tool that enables the user to delete one or more active bubbles within the boundaries of the Brain. The server provides a "Next" tab to finalize the volume extraction as shown in FIG. 13f.

The server provides a "continuous update" tool in a three-dimensional window that enables to continuously update contour evolution. The server further provides a "play" tab that allows the user to play and pause Active Contour Evolution as shown in FIG. 13f. The server further provides a "finish" tab that allows the user to submit when the active contour evolution is done. The server allows the user to change the "active label" to "clear label" and edit the voxels when the active contour evolution goes out of the boundaries of the Brain Parenchyma. The server allows the user to edit the voxels by accessing the "brush" tool and selecting appropriate brush and appropriate brush size. The server allows the user to change the "active label" to "Whole Brain" and add/edit the voxels when the active contour evolution has not reached any part of the Brain Parenchyma. The server allows the user to edit the voxels by accessing the "brush" tool and selecting appropriate brush and appropriate brush size.

Figure 13G:
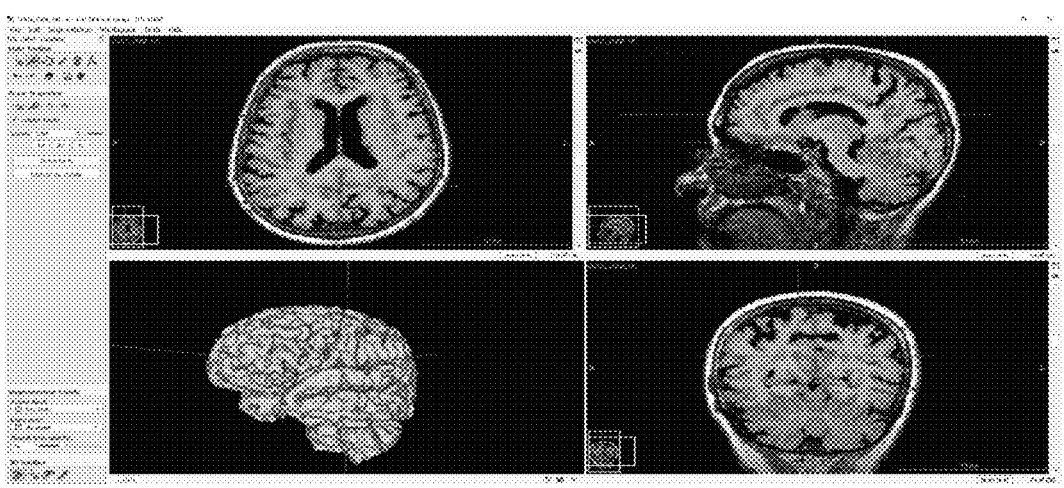
Figure 13H:
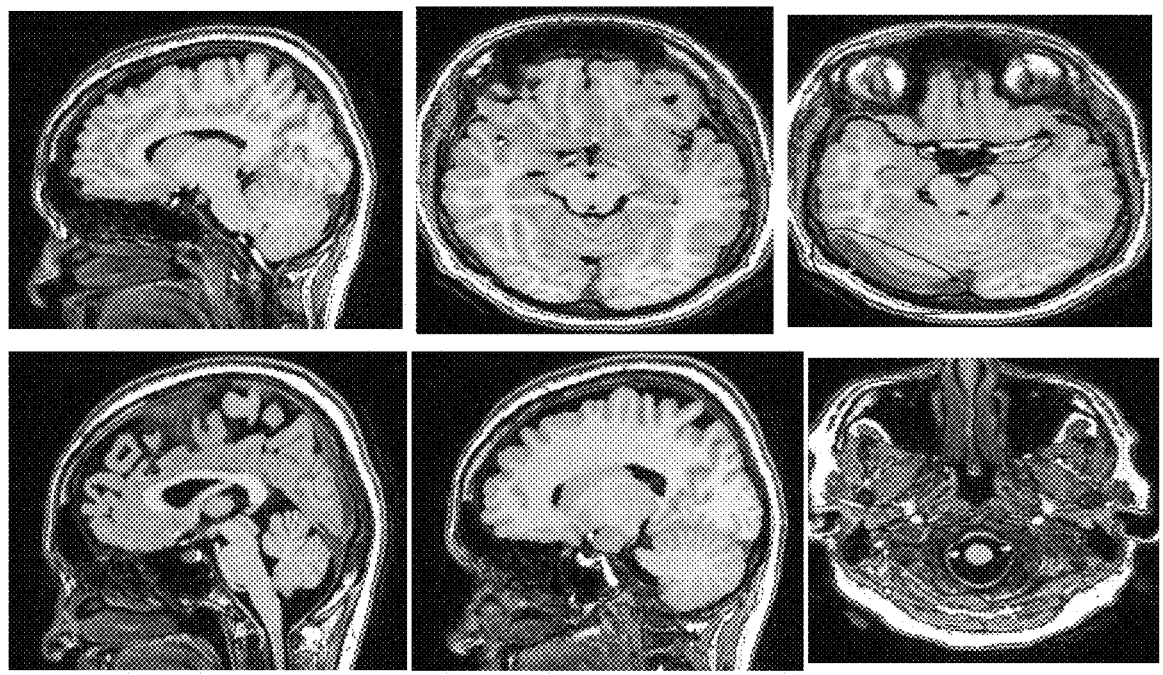

The server may render and save the Brain in at least one anatomical pane and in three-dimensional format under the "Active Label" as "Whole Brain" as shown in FIG. 13g. Once the segmentation and volume extraction of the Whole Brain are complete, the server enables the user to save the one or more first images, the workspace, the mesh and the one or more segmented image with a patient id name. The server enables the user to place the directory location for the image files in the patient ID folder. The server enables the user to capture screenshots of the segmented image at all anatomical planes in such a way that Whole Brain is displayed well with labels. The server further allows the user to capture screenshots of the segmented image in a three-dimensional image format with the Whole Brain zoomed in and displayed well. Boundaries of the Whole Brain are shown in FIG. 13h. FIG. 13h shows reference figures that illustrate the following. While segmenting Whole brain, the arteries and sinuses should be removed from the brain segmentation. The ventricles, (cerebrospinal fluid) csf spaces, dura mater and skull are excluded. Sella turcica is removed properly. The brainstem should include four image slices below the cerebellum ends. The server also enables the user to check that the whole brain parenchyma is included, using the "brush" tool if any area is excluded or included. The server renders the segmented image in the at least one anatomical plane and enables the user to check for errors in the intensity of the image that might lead to ring-like deficits appearing on the image after the bubbles are evolved.

FIG. 14a-14c illustrate a process of segmentation of an intracranial volume (ICV), according to one or more embodiments. The process of segmentation of the ICV comprises the following technical steps to be executed. While performing the segmentation, a server enables a user to select "active label" as "ICV". In an embodiment, RGB values assigned for the ICV are: R-126, G-84, and B-126. The server further enables the user to select the "Classification" tool under "pre-segmentation" tool as shown in FIG. 14a and add a classifier "ICV". The classifier for "ICV" comprises regions covering brain parenchyma, ventricles and csf spaces. The server further enables the user to select the "Classification" tool under the "pre-segmentation" tab and add a classifier "Skull". The server renders a "speed image generation" window and enables the user to check two options as shown in FIG. 14b under the "More" tool (shown in FIG. 14a). The two options comprise (a) Include the intensities of voxels' neighbors as aspects and (b) Include the voxels' coordinates as aspects. The two options are configured to differentiate and train the classifiers. The server provides a "Train Classifier" tool that allows the user to train the classifier. Once the classifier is trained, the server provides a "Next" tab to complete the training.

The server further provides a "Add bubbles at cursor" tool that allows the user to add bubbles of appropriate size throughout the trained area of the segmented image. The server allows the user to evolve the bubbles until the bubbles cover the whole Intra Cranial Cavity (ICV) properly. The server allows the user to change the "active label" to "clear label" and edit the voxels when the active contour evolution goes out of the boundaries of the ICV. The server allows the user to edit the voxels by accessing a "brush" tool and selecting appropriate brush and appropriate brush size. The server allows the user to change the "active label" to "ICV" and edit/add the voxels when the active contour evolution has not reached any part of the ICV. The server allows the user to edit the voxels by accessing the "brush" tool and selecting appropriate brush and appropriate brush size. The server also provides a "three-dimensional (3D) brush" to include the area of the ICV that might have been missed after evolving the bubbles. The server also allows the user to edit the missed area of the ICV in a sagittal plane and to start the editing in mid sagittal slice. The server also allows the user to use a two-dimensional brush instead of the three-dimensional brush when an orbital area of the ICV is not visible in the sagittal plane. The above steps are repeated for the other side of the ICV.

Once the segmentation and volume extraction of the ICV are complete, the server enables the user to save the one or more first images, workspace, mesh and the one or more segmented images with a patient id name. The server places the directory location for the image files in the patient ID folder. Boundaries of the ICV in different anatomical planes are shown in FIG. 14c. In an embodiment, the boundaries of the ICV excludes dura mater, skull and bones (Sella turcica area). The boundaries of the ICV include arteries and sinuses in the segmentation. In an axial plane, the boundaries of the ICV include four image slices below the cerebellar end in the segmentation.

Figure 15A:

FIG. 15a-15d illustrate a process of segmentation of Cerebrum, according to one or more embodiments. The process of segmentation of the Cerebrum comprises the following technical steps. In an embodiment, a server enables a user, via a user interface, to upload the segmented image of a whole brain in Neuroimaging Informatics Technology Initiative (NIfTI) format. The server allows the user to change the "active label" as "clear label" and utilize the "brush" tool to remove structures of Cerebellum and Brain stem from the whole brain as shown in FIG. 15a. The server renders the Cerebrum in at least one anatomical plane and a three-dimensional format. The server enables the user to view the Cerebrum in the three-dimensional format once the removal is done and use a cursor and place it on a longitudinal fissure of the Cerebrum.

Figure 15B:
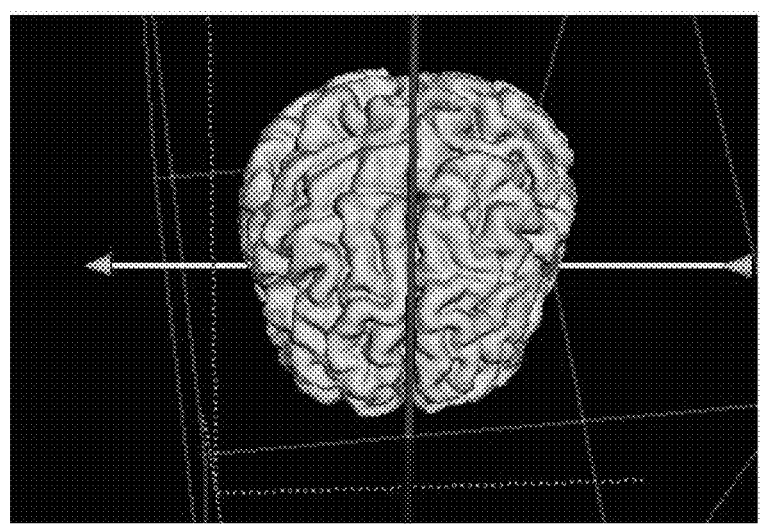

The server provides a "split" tool that enables the user to place a line which traces the longitudinal fissure as shown in FIG. 15b. The server shows the Cerebrum with an arrow pointing at one of the left side and right side. The server allows the user to select the "active label" as "Right Cerebral Hemisphere" when the arrow is pointing at the left side. The RGB values for the Right Cerebral Hemisphere are: R-107, G-101 and B-194. The server provides an "accept" tab that allows the user to accept and update the segmentation of 3D view format. The server further enables the user to check in an axial plane whether the right Cerebral Hemisphere is labelled properly.

Figure 15C:
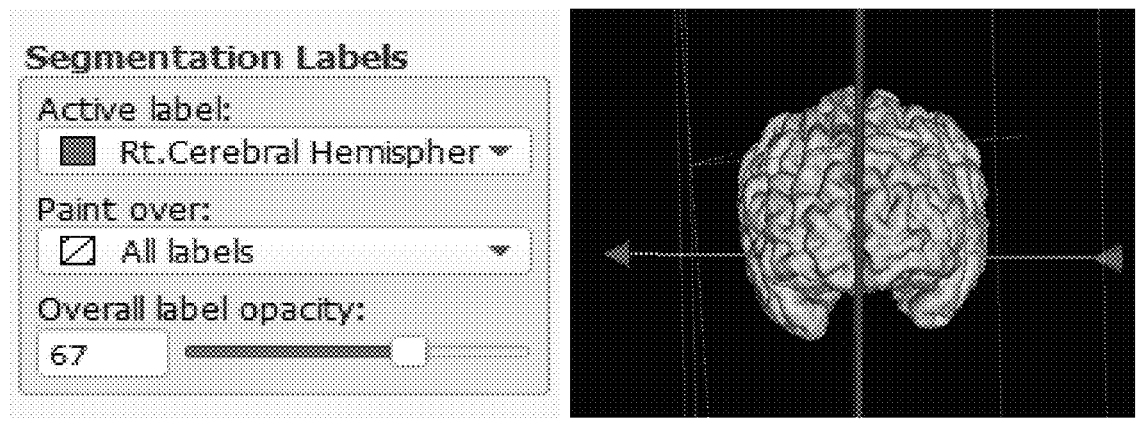
Figure 15D:
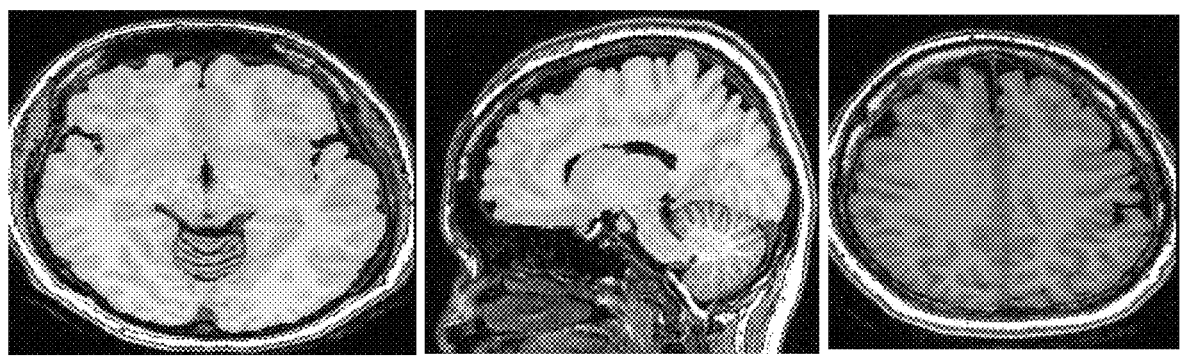

The server allows the user to repeat the above steps starting from utilizing the "split" tool for the left Cerebral Hemisphere. The server enables the user to change the "active label" as "Left Cerebral Hemisphere" as shown in FIG. 15c. The RGB values for the left Cerebral Hemisphere are: R-0 G-181 B-121. The server allows the user to select the "paint over" label as 'whole brain'. The server allows the user to use 3D brush and keep the size to its maximum and use it over the left cerebrum which is present in the whole brain label. Once the segmentation is done, the server allows the user to save the segmented images of the Right Cerebrum and the Left Cerebrum with the patient ID. The server also enables the user to place the directory location for the image files in the patient ID folder. The boundaries of the right cerebrum and the left cerebrum are shown in FIG. 15d. FIG. 15d illustrates the following. The boundaries of the Cerebrum are obtained by removing Brainstem and Cerebellum from the whole brain segmentation. The boundaries of the Cerebrum are further obtained by removing arteries and sinus (if edits are seen). The segmented image rendered uses the longitudinal fissure for separating the left cerebral hemispheres and the right cerebral hemispheres. The Cerebrum includes the lobes properly.

FIG. 16a-16c illustrate a process of segmentation of Cerebellum, according to one or more embodiments. The process of segmentation of the Cerebellum comprises the following technical steps. A server enables a user, via a user interface, to upload a segmented image of a whole brain in Neuroimaging Informatics Technology Initiative (NIfTI) format. The server allows the user to change the "active label" as "clear label" and utilize the "brush" tool to remove structures of Cerebrum and Brain stem from the whole brain. The server renders the Cerebellum in at least one of an anatomical plane, and a three-dimensional format as shown in FIG. 16a. The server enables the user to view the Cerebellum in the three-dimensional format and use a cursor and place it on a Vermis.

The server provides a "split" tool that enables the user to place a line which traces mid of the Vermis. The server depicts the Cerebellum with an arrow pointing at one of the left side and right side. The server allows the user to select the "active label" as "Right Cerebellar Hemisphere" as shown in FIG. 16b when the arrow is pointing at the left side. The RGB values for the Right Cerebral Hemisphere are: R-103, G-5 and B-173. The server provides an "accept" tab that allows the user to accept and update the segmentation of the Right Cerebral Hemisphere's 3D view format. The server further enables the user to check in the axial plane whether the right Cerebellar Hemisphere has been labelled properly.

The server allows the user to repeat the above steps starting from utilizing the "split" tool for left Cerebellar Hemisphere or allows the user to change the "active label"

as "Left Cerebellar Hemisphere". The RGB values are: R-0, G-145, B-16. The server allows the user to select the "paint over" label as 'whole brain'. The server allows the user to use 3D brush and keep the size to its maximum and use the 3d brush over the left cerebellum which is present in the whole brain label. The server allows the user to save the segmented images of the Right Cerebellum and the Left Cerebellum with the patient ID. The server also enables the user to place the directory location for the image files in the patient ID folder. The boundaries of the right cerebellum and the left cerebellum are shown in FIG. 16c. FIG. 16c illustrates the following. The boundaries of the Cerebellum are obtained by removing Brainstem and Cerebrum from the whole brain segmentation. FIG. 16c depicts that in an axial plane, the segmented image uses superior and middle cerebellar peduncle as a point of separation of the Cerebellum from the Brainstem. FIG. 16d depicts that the segmented image uses the transverse fissure for separating the Cerebrum from the Cerebellum. The boundaries of the Cerebellum are exactly obtained by removing transverse sinus, if not removed from the segmented image of the Cerebellum.

Figure 17A:
Figure 17B:
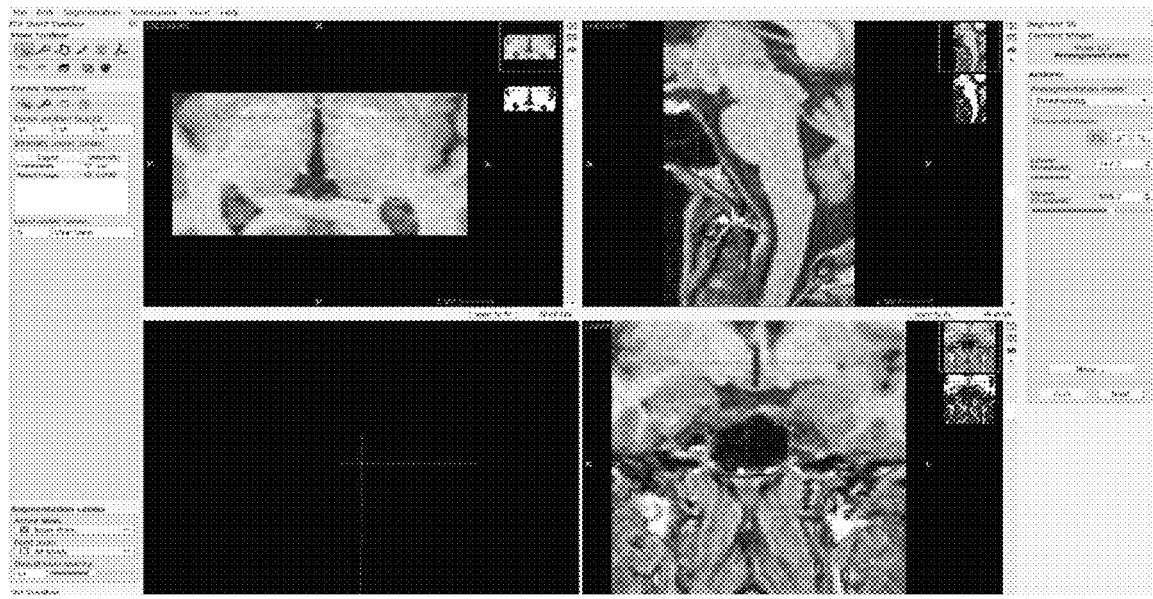

FIG. 17a-17h illustrate a process of segmentation of Brainstem, according to one or more embodiments. The process of segmentation of the Brainstem comprises the following technical steps. A server enables a user, via a user interface, to upload the image of the whole brain in Neuroimaging Informatics Technology Initiative (NIfTI) format. The server allows a user to change the "active label" as "Brainstem". The RGB values are: R-0, G-216, B-249. The server provides a "segmentation" tool that enables the user to set a field of view (FOV) according to a region of interest (ROI) in the anatomical planes as shown in FIG. 17a. The segmentation can be done by any of (a) classification, (b) thresholding, (c) clustering, and (d) edge attraction. The server provides a "speed image generation" window upon selecting the "thresholding" tool as shown in FIG. 17b. The "speed image generation" window provides an "upper threshold" slider and a "lower threshold" slider. The server enables the user to vary an upper threshold value and a lower threshold value using the "upper threshold" slider and the "lower threshold" slider, respectively.

Figure 17C:
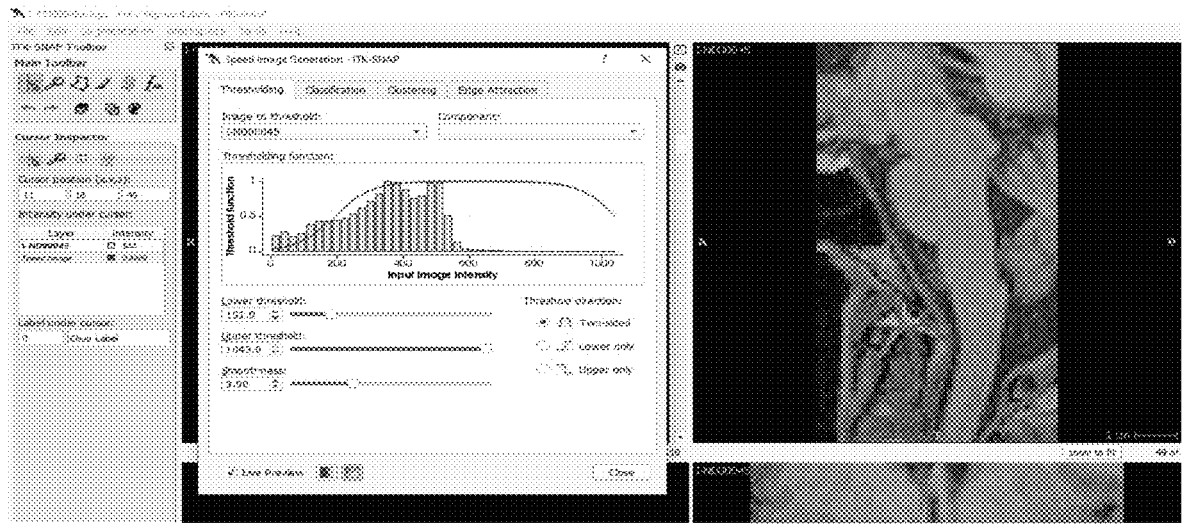
Figure 17D:

In an embodiment, the upper threshold value is varied so that the upper threshold value is moved to the highest value possible and the lower threshold value is varied to increase the lower threshold value slowly till the csf is removed from the classifier or the overlay as shown in FIG. 17c. The server renders volume of the Brainstem as per the threshold values, which enables the user to check that the voxels of the Brainstem are included in the overlay area. The server provides a "Next" tab that is to be clicked when the threshold values are adjusted and finalized. The server further provides a "add bubbles on cursor" tool that allows the user to add bubbles of appropriate size within the boundaries of the brainstem as shown in FIG. 17d.

Figure 17E:
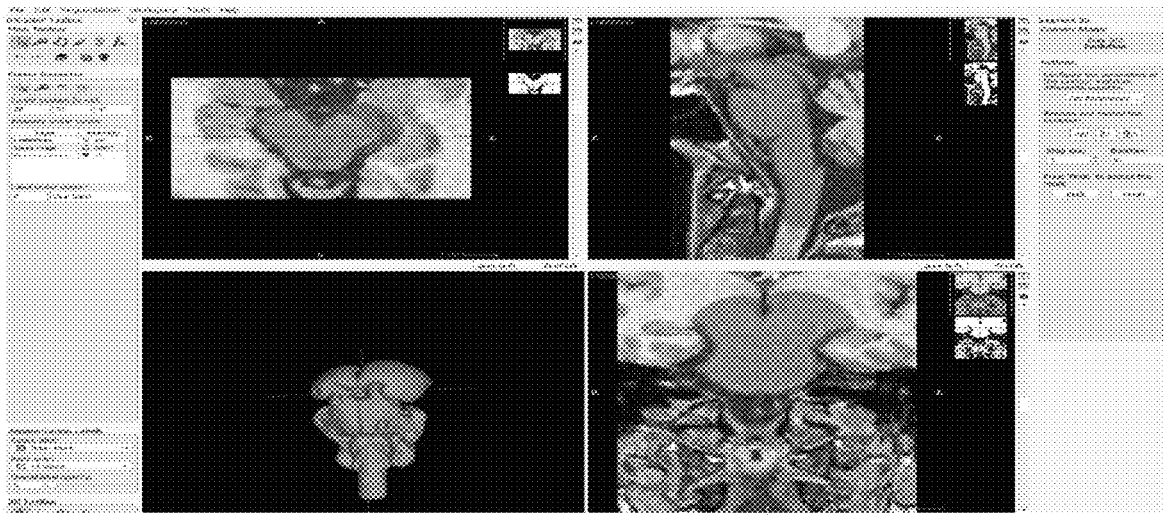
Figure 17F:
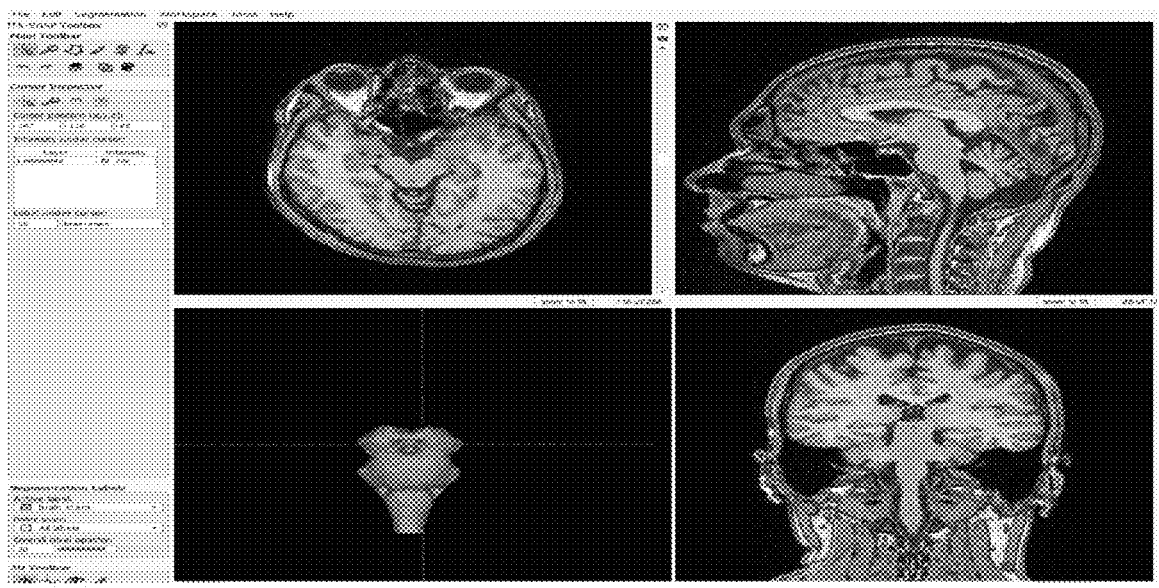

The server allows the user to evolve the bubbles until the bubbles cover the brainstem entirely as shown in FIG. 17e. The server further provides a "Finish" tab that enables the user to click when the bubbles are populated in the Brainstem. The server further provides a "Brush" tool that allows the user to edit/add or delete voxels of the brainstem when the bubbles are overestimated or not reached the entire structure of the Brainstem, respectively. Once the segmentation and volume extraction of the Brainstem are complete, the server renders the Brainstem in at least one anatomical plane and the three-dimensional format as shown in FIG. 17f. The server enables the user to save the one or more first images, the workspace, the mesh and the one or more segmented images with a patient id name. The server enables the user to place the directory location for the image files in the patient ID folder. The final volumes of the Brainstem are rendered in the at least one anatomical plane and in a three-dimensional format view as shown in FIG. 17f.

Figure 17G:
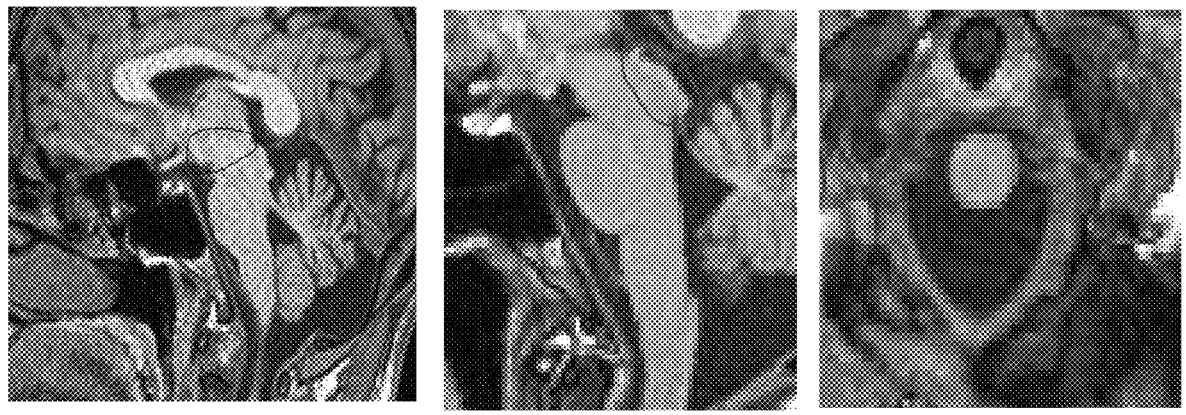
Figure 17H:
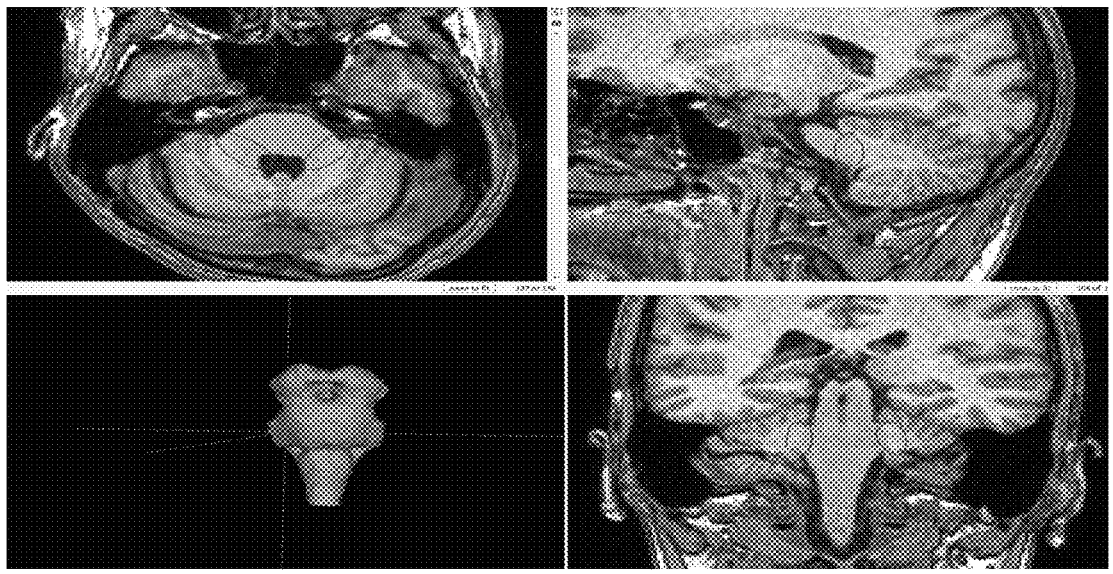

FIGS. 17g, and 17h depict boundaries of the Brainstem. The Brainstem is separated by a thin hyperintense boundary from a Thalamus in a superior aspect. Middle cerebellar peduncle and superior cerebellar peduncle separate the Brainstem from a Cerebellum. The segmented image does not include the tectal plate in the segmentation. The image includes 4 slices below the cerebellum end.

FIG. 18 illustrates a process of segmentation of Midbrain, according to one or more embodiments. The process of segmentation of the Midbrain comprises the following technical steps. A server allows a user to upload the main file on ITK snap. The server provides an "add segmentation file" tool that enables the user to Upload Brainstem segmentation files. The server further provides a "brush" tool and "3D brush" tool under the "brush" tool that enables the user to remove Pons and Medulla oblongata from the segmentation. The server further enables to select "active label" as "clear label" before removing the Pons and the Medulla Oblongata from the Brainstem segmentation file.

The server renders the segmented image of the Midbrain in the at least one anatomical plane and a three-dimensional format and enables the user to check the boundaries of the midbrain in the three anatomical planes. The server allows the user to select the "active label" as "Midbrain" and "paint over" label as "Brainstem". In an embodiment, RGB values are: R-255, G-130, B-153. The server further enables the user to paint the Midbrain region using a "brush" tool as 3D brush and add/edit voxels within the brainstem.

Once the segmentation and volume extraction of the Midbrain are complete, the server enables the user to save the one or more first images, workspace, mesh and the one or more segmented images with a patient id name. The server enables the user to place a directory location for the image files in a patient ID folder. Boundaries of the Midbrain are shown in FIG. 18. FIG. 18 shows that Pons is separated from the Midbrain by Superior Pontine Sulci. FIG. 18 further shows that the midbrain is superiorly separated from Thalamus by a thin hyperintense border.

FIG. 19 illustrates a process of segmentation of Pons, according to one or more embodiments. The process of segmentation of the Pons comprises the following technical steps. A server allows a user to upload the main file on ITK snap. The server provides an "add segmentation file" that enables the user to Upload Brainstem segmentation file. The server further provides a "brush" tool and "3D brush" tool under "brush" tool that enables the user to remove Midbrain and Medulla oblongata from the segmentation. The server further provides an "active label" as "clear label" before removing the Pons and the Medulla Oblongata from the Brainstem segmentation file.

The server renders the segmented image of the Pons in the at least one anatomical plane and a three-dimensional format and enables the user to check the boundaries of the midbrain in the three anatomical planes. The server allows the user to select the "active label" as "Pons" and "paint over" label as "Brainstem". In an embodiment, RGB values are: R-255, G-182, B-193. The server further enables the user to paint the Pons region using a "brush" tool as "3D brush".

Once the segmentation and volume extraction of the Pons are complete, the server enables the user to save the one or more first images, the workspace, the mesh and the one or more segmented images with patient id name. The server enables the user to place the directory location for the image files in the patient ID folder. Boundaries of the Pons are shown in FIG. 19. FIG. 19 shows that Pons is separated from the Midbrain by a Superior Pontine Sulci. FIG. 19 further shows that the Pons is separated from Medulla by an inferior pontine sulcus.

Figure 20A:
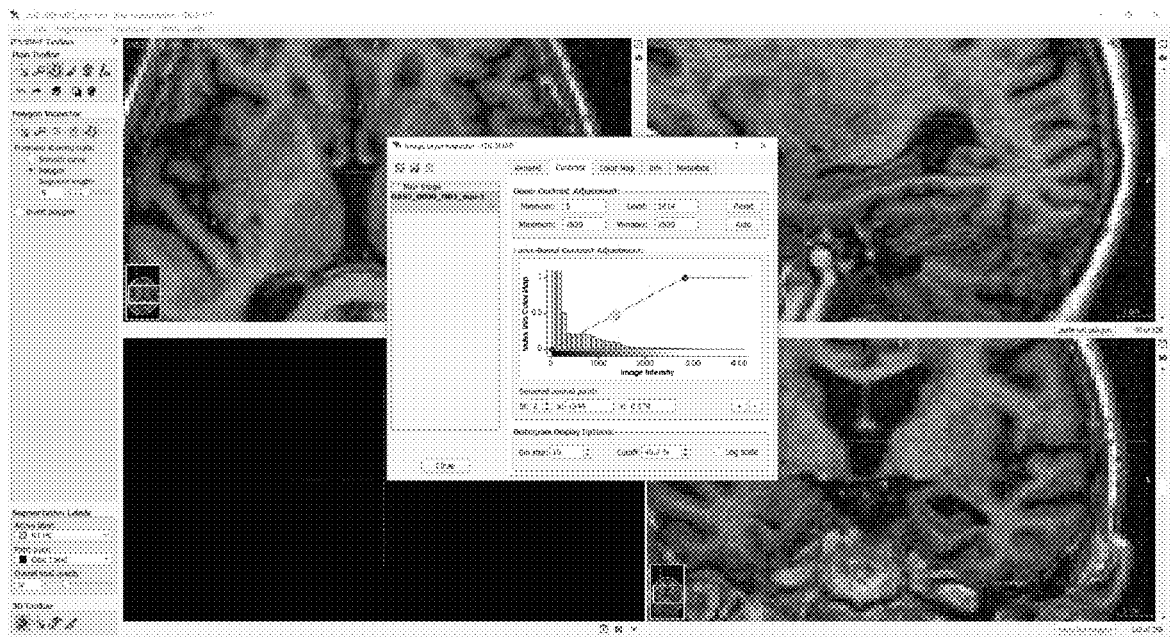

FIGS. 20a-20e illustrate a process of segmentation of Amygdala, according to one or more embodiments. The process of segmentation of the Amygdala comprises the following technical steps. One or more first images of a region of interest (i.e., skull) are uploaded to an ITK snap layer of a server. A label file is imported for the Amygdala. Amygdala label file comprises predefined RGB values. In an embodiment, the predefined RGB values of a right Amygdala assigned are R-255, G-94, B-97. In another embodiment, the predefined RGB values of a left Amygdala assigned are R-253, G-255, B-89. A server enables the user to access a contrast inspector drop-down tab via a user interface to adjust the contrast so that grey matter (GM) and white matter (WM) differentiation is optimum as shown in FIG. 20a. The one or more first images are rendered in at least one anatomical plane such as a sagittal plane, an axial plane, and a coronal plane to readily enable a user to visualize the Amygdala in the at least one anatomical plane and identify a location, position and shape of the Amygdala. The Amygdala comprises a right Amygdala and a left Amygdala. The server enables the user to select "active label" as "right Amygdala" or "left Amygdala" accordingly.

The Amygdala can be identified by the following. The Amygdala is an ovoid mass of gray matter situated in the superomedial portion of the temporal lobe, partly above the tip of the inferior horn of the lateral Ventricle. The Amygdala occupies the superior part of the anterior segment of the uncus and partially overlies the head of the Hippocampus, being separated from that structure by the uncal recess of the inferior horn of the Lateral Ventricle. On the superomedial surface of the uncus, the Amygdala forms a distinct protrusion, the Semilunar Gyms, which corresponds to the Cortical Amygdaloid Nucleus. It is separated from the Ambient Gyms by the Semiannual or Amygdaloid Sulcus, which forms the boundary between the Amygdala and the Entorhinal Cortex.

Figure 20B:
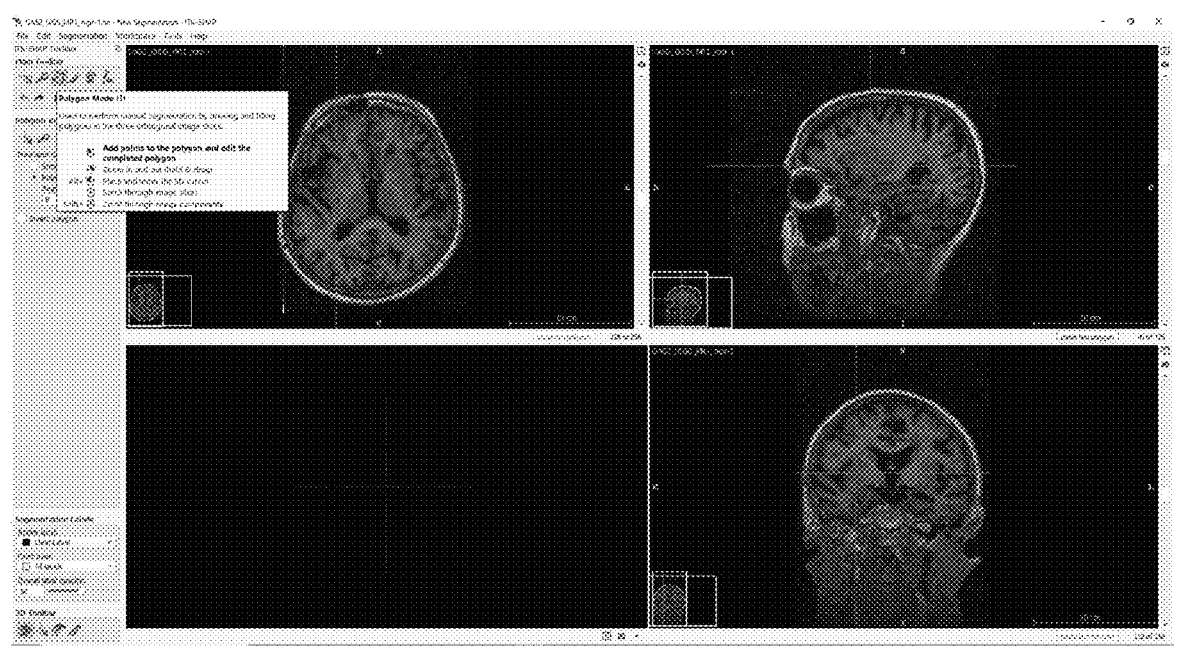

Upon determining, when the one or more first images do not comprise optimized quality in terms of shape, boundary and volume of at least one structure, the images can be further manually edited by performing manual segmentation. The server enables the user to move to an image slice using a sagittal plane when the right Amygdala disappears and scrolls to the next visible image slice. The server provides a "polygon" tool on a main toolbar as shown in FIG. 20b. The "polygon" tool, upon selecting, enables the user to perform the manual segmentation by drawing and filling polygons in orthogonal image slices. In an embodiment, the manual segmentation can be done individually in the at least one anatomical plane. The manual segmentation, via the polygon tool, enables the user to add points to the polygon and edit the completed polygon.

Figure 20C:
Figure 20D:
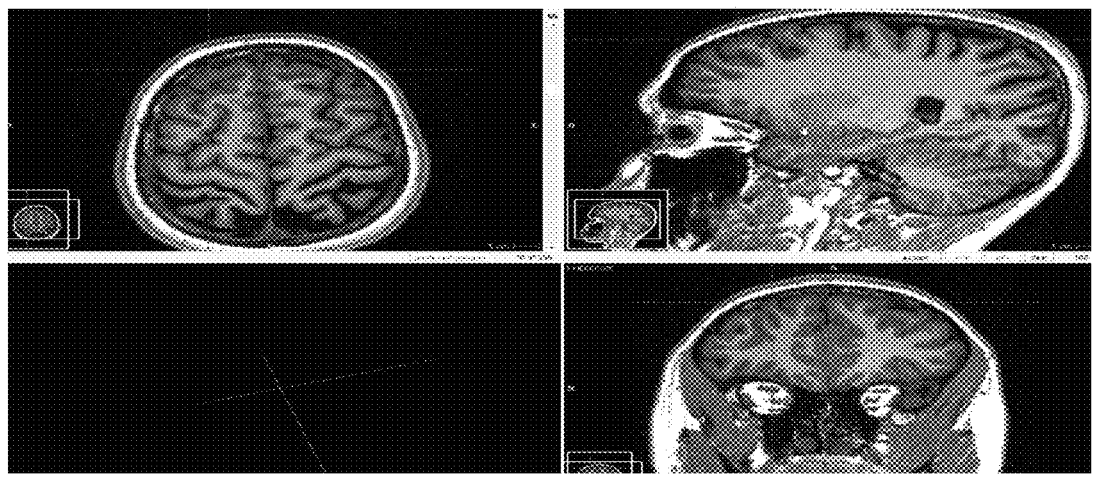

The "polygon" tool enables the user to zoom in and out (hold and drag) to view any specific portion of the Amygdala. The "polygon" tool further enables the user to place and move 3D cursor, scroll through image slices and scroll through image components to view, edit and correct the volume, shape and structure of the Amygdala. The server further provides an "active label" tool under "segmentation label". Under the "active label", the user is enabled to select an appropriate label (i.e., right HC in this instance) as shown in FIG. 20c. The server further enables the user to select the "paint over" tool as all labels. The server rendered enables the user to choose opacity so as not to obscure/hide tissue boundaries. In an embodiment, the opacity ranges between 15-30. The server enables the user to outline the outermost border of the Amygdala using the image slice chosen in the at least one anatomical plane as shown in FIG. 20d. In an embodiment, a first color (e.g., pink) is used for an active polygon and a second color (e.g., red) stands for a completed polygon.

The server further enables the user to retrace borders of the Amygdala and detect any missing pixels or voxels by zooming in. The server further provides a "brush" tool. The "brush" tool further enables the user to edit and add the missing pixels/voxels by selecting an appropriate brush (e.g., round brush) and appropriate bush size. If the edits have been done more than the actual voxels/pixels (i.e., in case of over estimation), the server enables the user to select the "active label" as "clear label" and edit the voxels.

Figure 20E:
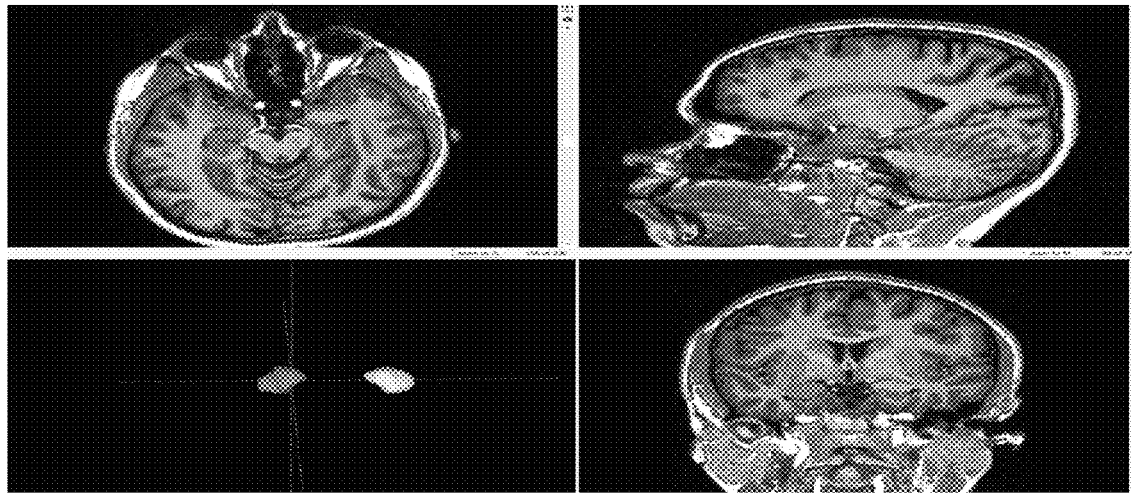

The server also enables the user to segment left Amygdala and extract volumes of the left Amygdala. Once the right Amygdala is completed repeat the above steps for the left Amygdala. To proceed with the left Amygdala, the user should change the "active label" as left Amygdala before starting left Amygdala. The segmented image and extracted volumes of both the left Amygdala and the right Amygdala are shown in FIG. 20e.

Once the segmentation and volume extraction of the right Amygdala and left Amygdala are complete, the server enables the user to save the one or more first images, the workspace, the mesh and the one or more segmented image with patient id name. The server enables the user to place the directory location for the image files in the patient ID folder. The server enables the user to capture screenshots of the segmented image at all anatomical planes in such a way that both the Left Amygdala and Right Amygdala are displayed well with labels. The server further allows the user to capture screenshots of the segmented image in a three-dimensional image format with both the left Amygdala and right Amygdala zoomed well.

Boundaries of the segmented Amygdala illustrates the following: The Amygdala lies in an anterior aspect of the Hippocampus. The Amygdala is best viewed in the sagittal plane and axial plane. Sulci lines and temporal horn of the Ventricle are useful while segmenting the Amygdala. The lateral aspect of the Hippocampus is differentiated from the White matter. The posterior aspect is separated from the Hippocampal head and the Fimbria. However, medially, the Hippocampal head and Amygdala seem to attach or have no space in between. This attachment area should be segmented by viewing the thin Hyperintense border of the Hippocampal head.

Figure 21A:
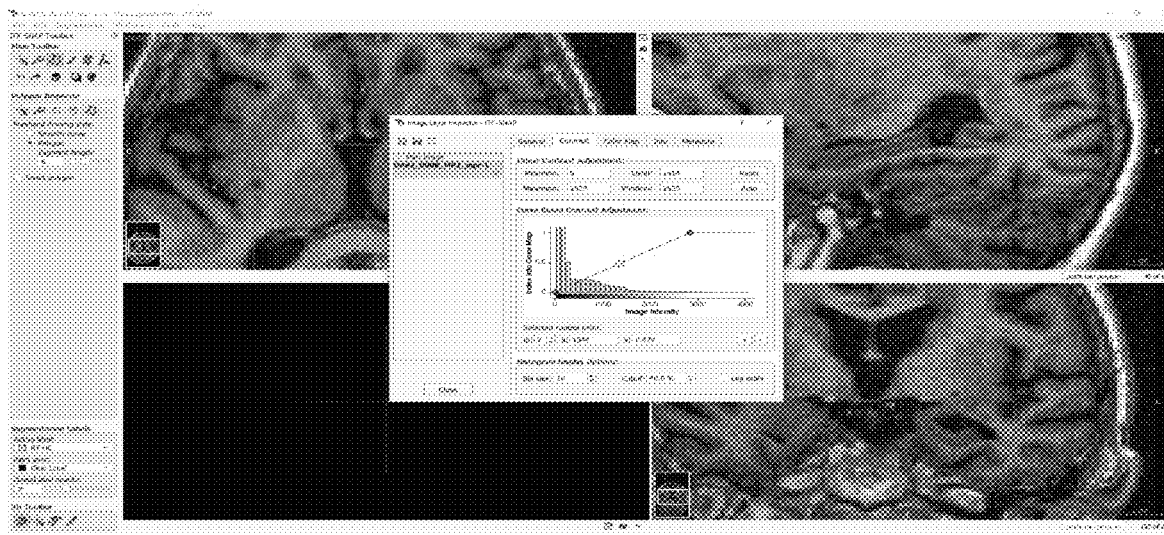

FIG. 21a-21g illustrate a process of segmentation of Basal Ganglia, according to one or more embodiments. The process of segmentation of the Basal Ganglia comprises the following technical steps. One or more first images of a region of interest (i.e., skull) are uploaded to an ITK snap layer of a server. A label file is imported for the Basal Ganglia. Basal Ganglia label file comprises predefined RGB values. In an embodiment, the predefined RGB values of the Basal Ganglia assigned are R-122, G-180, B-181. A server enables the user to access a contrast inspector drop-down tool via a user interface to adjust the contrast so that grey matter (GM) and white matter (WM) differentiation is optimum as shown in FIG. 21a. The one or more first images comprising the Basal Ganglia are rendered in at least one anatomical plane such as a sagittal plane, an axial plane, and a coronal plane to readily enable a user to visualize the Basal Ganglia in the at least one anatomical plane and identify a location, a position and a shape of the Basal Ganglia. The Basal Ganglia comprises a right Basal Ganglia and a left Basal Ganglia.

The boundaries of the Basal Ganglia can be identified considering the following: The tracing of Caudate Nucleus starts at a section where it is first visualized in the Frontal Horn of Lateral Ventricles and ends at the section where it is no longer identifiable; the Nucleus Accumbens is used as Ventral boundary, the Lateral ventricle is used as Medial boundary, and Internal Capsule is used as Lateral Boundary. For the boundary of the Putamen, the medial boundary is the Internal capsule (Anterior Putamen) and the External Pallidum (Posterior Putamen); the lateral boundary is defined by the External Capsule.

Upon determining, when the one or more segmented images do not comprise optimized quality in terms of shape, boundary and volume of at least one structure, the segmented images can be further manually edited by performing manual segmentation. The server enables the user to move to an image slice using a sagittal plane when right Basal Ganglia disappears and moves to the next visible image slice. The server provides a "polygon" tool on a main toolbar as shown in FIG. 21b. The "polygon" tool, upon selecting, enables the user to perform the manual segmentation by drawing and filling polygons in orthogonal image slices. In an embodiment, the manual segmentation can be done individually in each anatomical plane. The manual segmentation, via the polygon tool, enables the user to add points to the polygon and edit the completed polygon.

The "polygon" tool enables the user to zoom in and out (hold and drag) to view any specific portion of the Basal Ganglia. The "polygon" tool further enables the user to place and move 3D cursor, scroll through image slices and scroll through image components to view, edit and correct the volume, shape and structure of the Basal Ganglia. The server further provides an "active label" tool under "segmentation label". Under the "active label", the user is enabled to select an appropriate label (i.e., right HC in this instance) as shown in FIG. 21c. The server further enables the user to select the "paint over" tool as all labels. The server enables the user to choose opacity so as not to obscure/hide tissue boundaries. In an embodiment, the opacity ranges between 15-30. The server enables the user to outline the outermost border of the Basal Ganglia using the image slice chosen as shown in FIGS. 21d and 21e. In an embodiment, a first color (e.g., pink) is used for an active polygon and a second color (e.g., red) stands for completed polygon.

The server further enables the user to retrace borders of the Basal Ganglia and detect any missing pixels or voxels by zooming in. The server further provides a "brush" tool. The "brush" tool further enables the user to edit and add the missing pixels by selecting an appropriate brush (e.g., round brush) and appropriate bush size. If the edits have been done more than the actual voxels (i.e., in case of over estimation), the server enables the user to select the "active label" as "clear label" and edit the voxels.

Figure 21F:
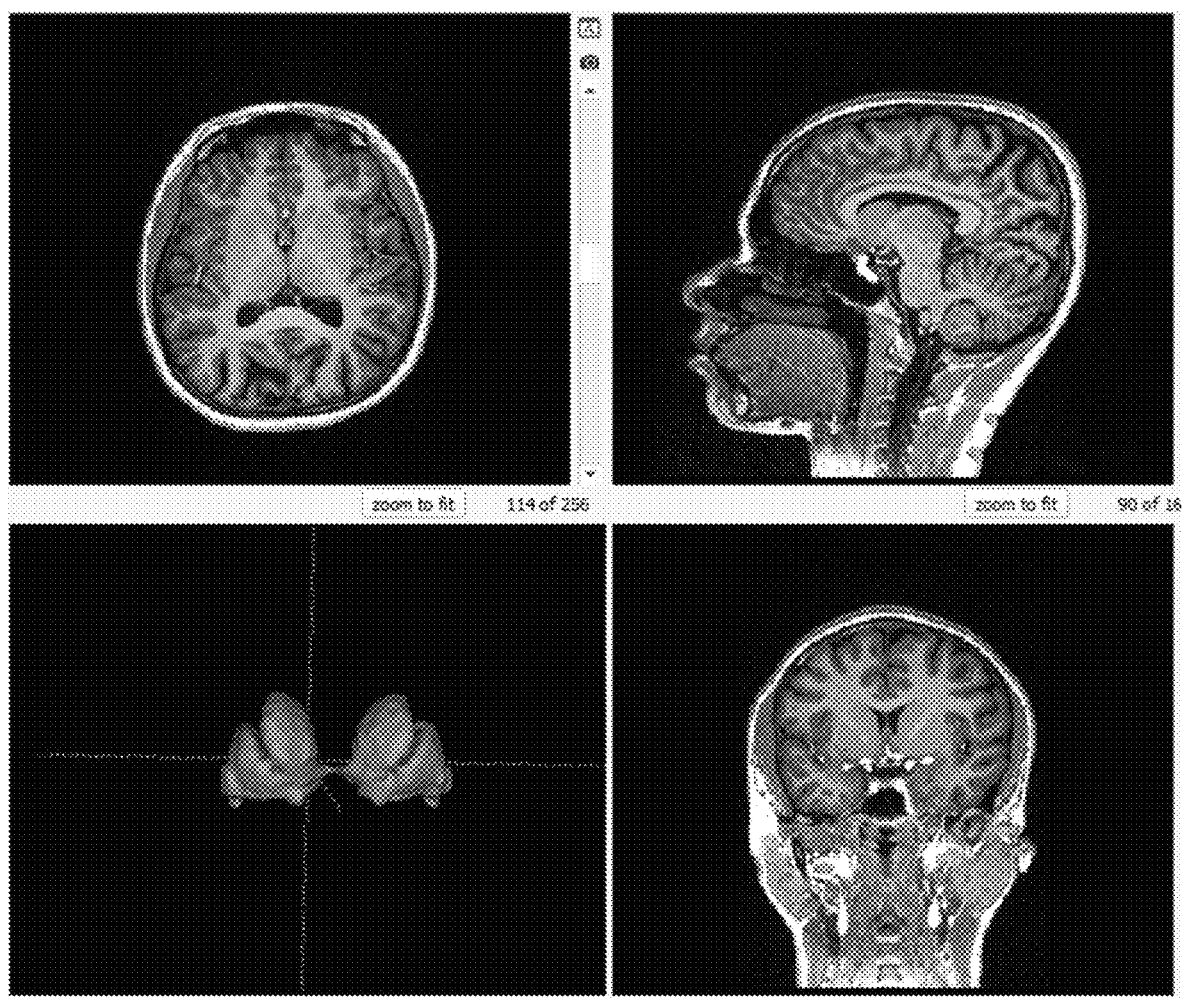

The server also enables the user to segment left Basal Ganglia and extract volumes of the left Basal Ganglia. Once the right Basal Ganglia is completed repeat the above steps for the left Basal Ganglia. To proceed with the left Basal Ganglia, the user should change the "active label" as "left HC" before starting the left Basal Ganglia. The segmented image and extracted volumes of both the left Basal Ganglia and the right Basal Ganglia are shown in FIG. 21f.

Figure 21G:
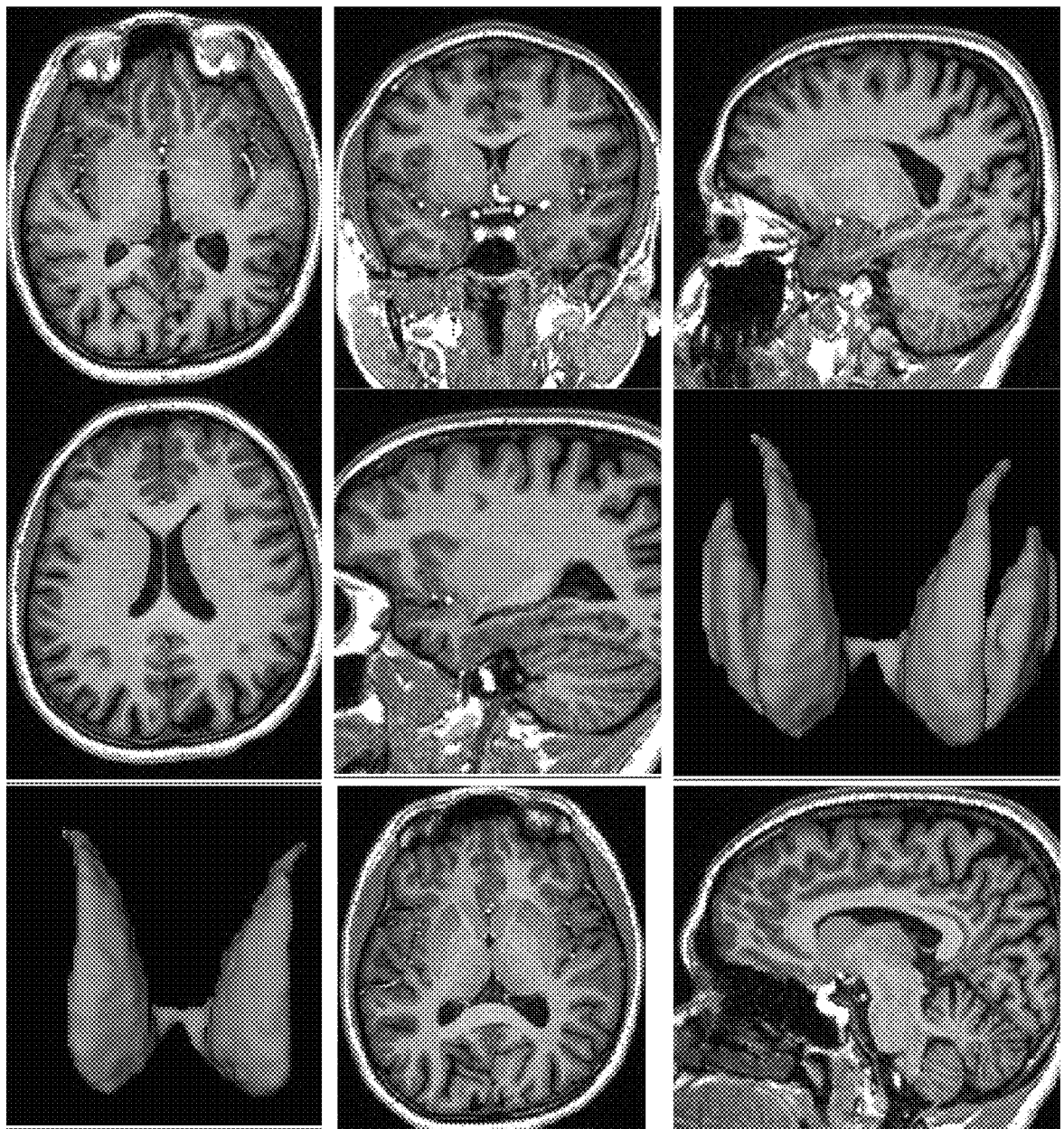

Once the segmentation and volume extraction of the right Basal Ganglia and left Basal Ganglia are complete, the server enables the user to save the one or more first images, the workspace, the mesh and the one or more segmented image with patient id name. The server enables the user to place the directory location for the image files in the patient ID folder. The server enables the user to capture screenshots of the segmented image at all anatomical planes in such a way that both the Left Basal Ganglia and Right Basal Ganglia are displayed well with labels. The server further allows the user to capture screenshots of the segmented image in a three-dimensional image format with both the left Basal Ganglia and right Basal Ganglia zoomed well. Boundaries of the right Basal Ganglia and the left Basal Ganglia are shown in FIG. 21g. The server further enables to segment the Caudate Nucleus by removing Putamen from the Basal Ganglia segmentation and adding bubbles to the Caudate Nucleus with its label. The RGB values are: R-104, G-176, B-138.

FIG. 21g illustrates the following. The Basal Ganglia comprises: the striatum; both dorsal striatum (Caudate Nucleus and Putamen) and Ventral Striatum (Nucleus Accumbens and Olfactory Tubercle), Globus Pallidus, Ventral Pallidum, Substantia Nigra and Subthalamic Nucleus. In this segmentation, only the Caudate Nucleus and the Putamen are included. The Subthalamic Nucleus and the Substantia Nigra are segmented separately. The Caudate Nucleus is a C-shaped structure that is associated with the lateral wall of Lateral Ventricle. Caudate is the largest at its anterior pole (the head), and its size diminishes posteriorly as it follows the course of the Lateral Ventricle (the body) all the way to the Temporal Lobe (the tail), where it terminates at the Amygdaloid Nuclei. The Putamen is separated from the Caudate Nucleus by the Anterior limb of the internal capsule. The Putamen is connected to the Caudate head by bridges of cells that cut across the Internal Capsule.

Figure 22A:
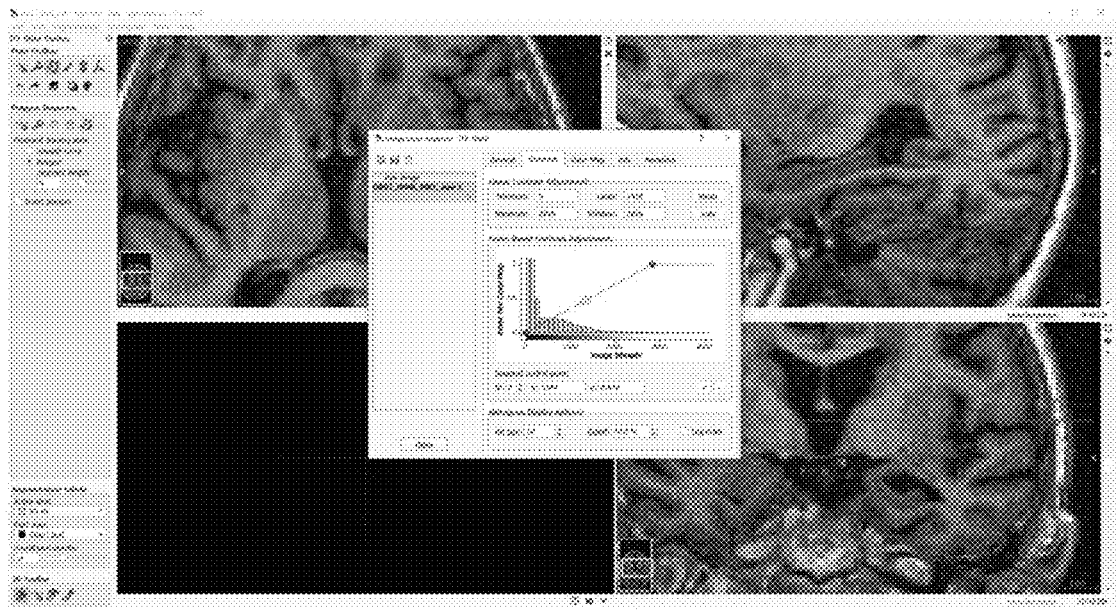

FIG. 22a-22f illustrate a process of segmentation of Thalamus, according to one or more embodiments. The process of segmentation of the Thalamus comprises the following technical steps. One or more first images of the region of interest (i.e., skull) are uploaded to an ITK snap layer of a server. An "active label" is selected as "Thalamus". Thalamus label file comprises predefined RGB values. In an embodiment, the predefined RGB values of the Thalamus are R-247, G222, B-130. A server enables a user to access a contrast inspector drop-down tool via a user interface to adjust the contrast so that grey matter (GM) and white matter (WM) differentiation is optimum as shown in FIG. 22a. The one or more first images comprising Thalamus are rendered in at least one anatomical plane (such as a sagittal plane, an axial plane, and a coronal plane). The one or more first images readily enable a user to visualize the Thalamus in the at least one anatomical plane and identify a location, a position and a shape of the Thalamus. The Thalamus comprises a right Thalamus and a left Thalamus.

Figure 22B:

Upon determining, when the one or more segmented images do not comprise optimized quality in terms of shape, boundary and volume of at least one structure, the segmented images can be further manually edited by performing manual segmentation. The server enables the user to move to an image slice using a sagittal plane when right Thalamus disappears and moves to the next visible image slice. The server provides a "polygon" tool on a main toolbar as shown in FIG. 22b. The "polygon" tool, as shown in FIG. 22b, upon selecting, enables the user to perform the manual segmentation by drawing and filling polygons in orthogonal image slices. In an embodiment, the manual segmentation can be done individually in the anatomical plane. The manual segmentation, via the polygon tool, enables the user to add points to the polygon and edit the completed polygon.

Figure 22C:
Figure 22D:
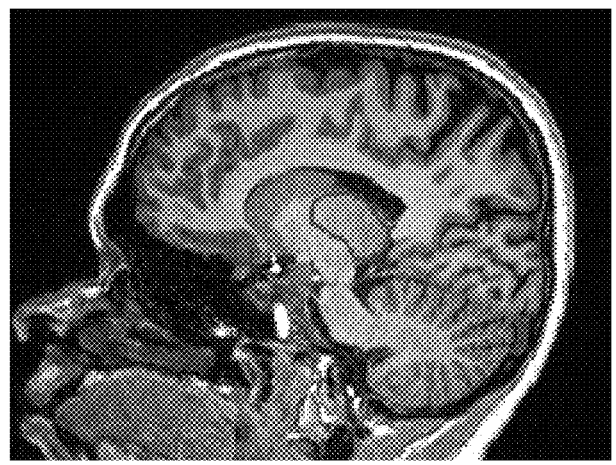

The "polygon" tool enables the user to zoom in and out (hold and drag) to view any specific portion of the Thalamus. The "polygon" tool further enables the user to place and move 3D cursor, scroll through image slices and scroll through image components to view, edit and correct the volume, shape and structure of the Thalamus. The server further provides an "active label" tool under "segmentation label". Under the "active label", the user is enabled to select an appropriate label (i.e., right Thalamus in this instance). The server further enables the user to select a "paint over" tool as all labels. The server rendered enables the user to choose opacity so as not to obscure/hide tissue boundaries. In an embodiment, the opacity ranges between 15-30. The server enables the user to outline the outermost border of the Thalamus using the image slice chosen as shown in FIGS. 22c and 22d. In an embodiment, a first color (e.g., pink) is used for active polygon and a second color (e.g., red) stands for completed polygon.

The server further enables the user to retrace borders of the Thalamus and detect any missing pixels or voxels by zooming in. The server further provides a "brush" tool. The "brush" tool further enables the user to edit and add the missing pixels by selecting an appropriate brush (e.g., round brush) and appropriate bush size. If the edits have been done more than the actual voxels (i.e., in case of over estimation), the server enables the user to select the "active label" as "clear label" and edit the voxels.

Figure 22E:
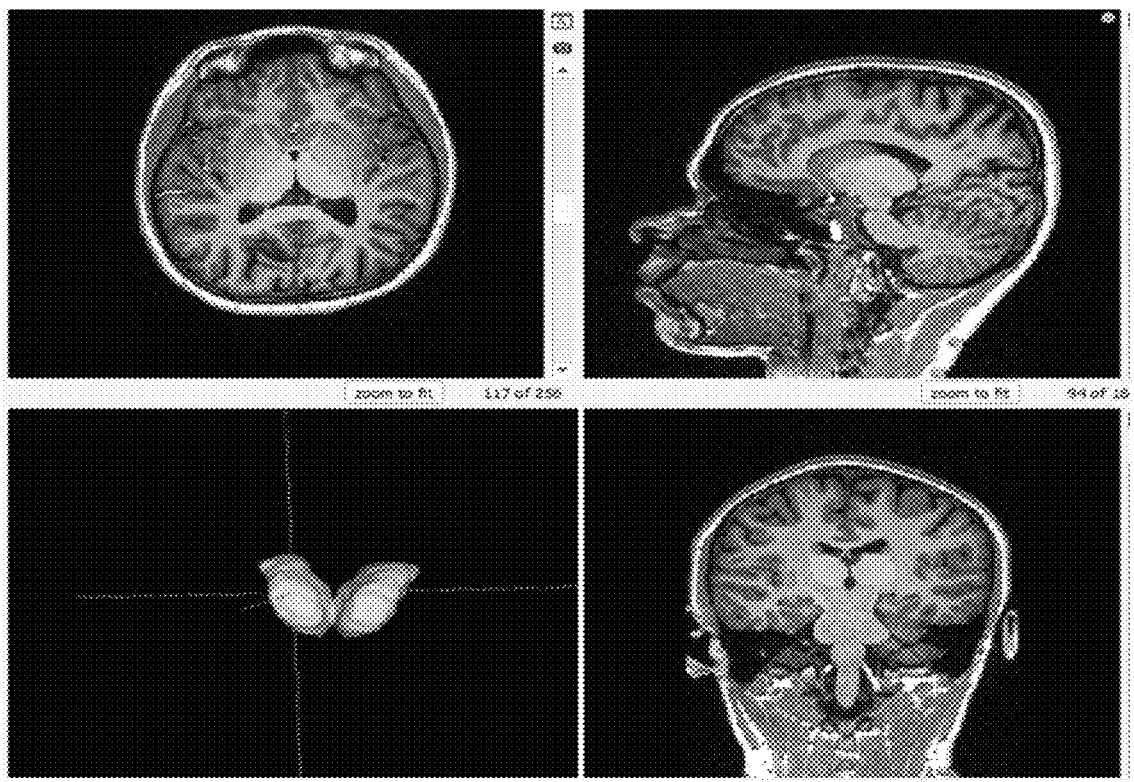

The server also enables the user to segment left Thalamus and extract volumes of the left Thalamus. Once the right Thalamus is completed repeat the above steps for the left Thalamus. To proceed with the left Thalamus, the user should change the "active label" as "left Thalamus" before starting left Thalamus. The segmented image and extracted volumes of both the left Thalamus and the right Thalamus are shown in FIG. 22e.

Once the segmentation and volume extraction of the right Thalamus and left Thalamus are complete, the server enables the user to save the one or more first images, the workspace, the mesh and the one or more segmented image with a patient id name. The server further enables the user to place the directory location for the image files in the patient ID folder. The server enables the user to capture screenshots of the segmented image at all anatomical planes in such a way that both the Left Thalamus and Right Thalamus are displayed well with labels. The server further allows the user to capture screenshots of the segmented image in a three-dimensional image format with both the left Thalamus and right Thalamus zoomed well. Boundaries of the right Thalamus and the left Thalamus are shown in FIG. 22f.

Figure 22F:
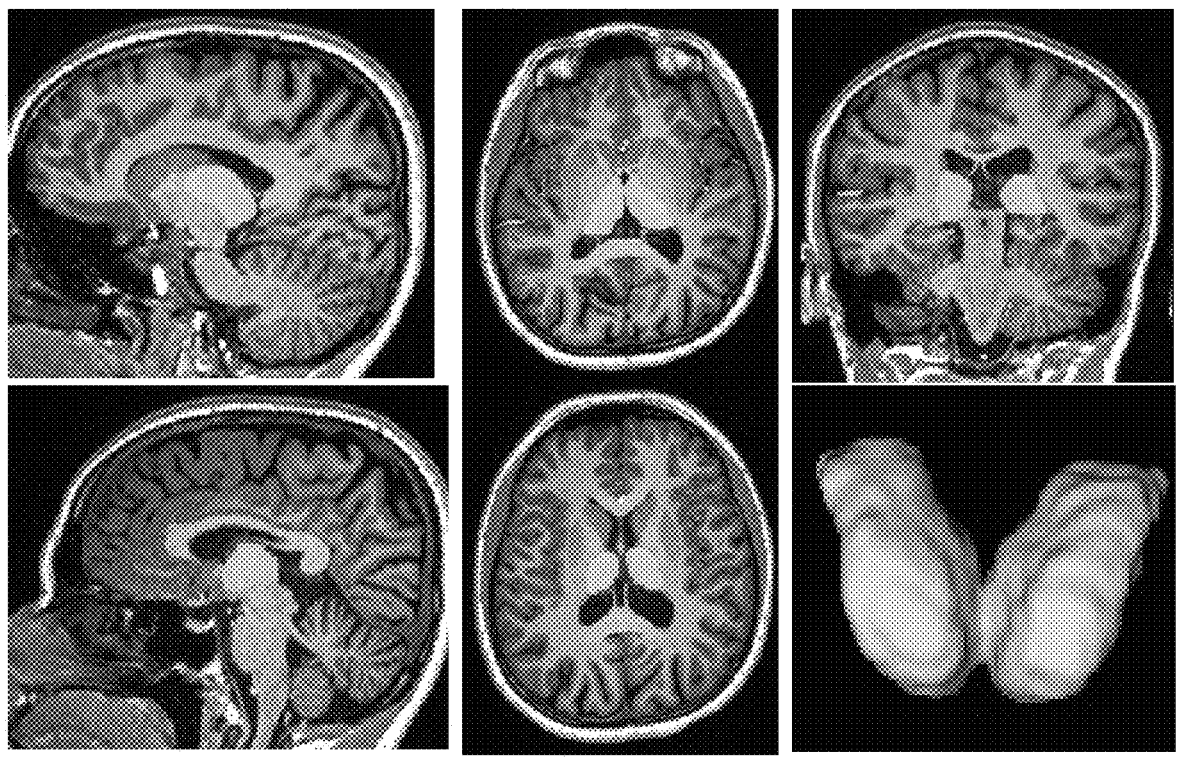

FIG. 22f illustrates the boundaries of the Thalamus. Anteriorly, the Thalamus is defined by the posterior boundary of Interventricular Foramen, a channel allowing the movement of Cerebrospinal Fluid from the lateral to the Third Ventricles. Posteriorly, it is defined by an expansion called the Pulvinar. Inferior border: The Tegmentum or floor of the Midbrain. Medially—lateral wall of the third Ventricle.

FIGS. 23a-23c illustrate a process of segmentation of Substantia Nigra, according to one or more embodiments. The process of segmentation of the Substantia Nigra comprises the following technical steps. One or more first images of the region of interest (i.e., skull) are uploaded to an ITK snap layer of a server. A label file is imported for the Substantia Nigra. Substantia Nigra label file comprises predefined RGB values. In an embodiment, the predefined RGB values of the Substantia Nigra assigned are R-255, G-187, B-188. A server enables a user to access a contrast inspector drop-down tool via a user interface to adjust the contrast so that grey matter (GM) and white matter (WM) differentiation is optimum as shown in FIG. 23a. The one or more first images comprising the Substantia Nigra are rendered in at least one anatomical plane such as a sagittal plane, an axial plane, and a coronal plane. The server readily enables a user to visualize the Substantia Nigra in the at least one anatomical plane and identify a location, a position, and a shape of the Substantia Nigra.

In an embodiment, upon determining, when the one or more segmented images do not comprise optimized quality in terms of shape, boundary and volume of at least one structure, the segmented images can be further manually edited by performing manual segmentation. The server provides a "polygon" tool on a main toolbar as shown in FIG. 23b. The "polygon" tool, upon selecting, enables the user to perform the manual segmentation by drawing and filling polygons in orthogonal image slices. In an embodiment, the manual segmentation can be done individually in the anatomical plane. The manual segmentation, via the polygon tool, enables the user to add points to the polygon and edit the completed polygon.

The "polygon" tool enables the user to zoom in and out (hold and drag) to view any specific portion of the Substantia Nigra. The "polygon" tool further enables the user to use a "cursor chase" tab and place and move 3D cursor, scroll through image slices and scroll through image components to view, edit and correct the volume, shape and structure of the Substantia Nigra. The server further provides an "active label" tool under "segmentation label". Under the "active label", the user is enabled to select an appropriate label (i.e., Substantia Nigra in this instance). The server further enables the user to select the "paint over" tool as all labels. The server, via the user interface rendered, enables the user to choose opacity so as not to obscure/hide tissue boundaries. In an embodiment, the opacity ranges between 15-30. The server enables the user to outline the outermost border of the Substantia Nigra using the image slice chosen. In an embodiment, a first color (e.g., pink) is used for active polygon and a second color (e.g., red) stands for completed polygon.

The server further enables the user to retrace borders of the Substantia Nigra and detect any missing pixels or voxels by zooming in. The server further provides a "brush" tool. The "brush" tool further enables the user to edit and add the missing pixels by selecting an appropriate brush (e.g., round brush) and appropriate bush size. If the edits have been done more than the actual voxels (i.e., in case of over estimation), the server enables the user to select the "active label" as "clear label" and edit the voxels.

Once the segmentation and volume extraction of the Substantia Nigra and the left Substantia Nigra are complete, the server renders the Substantia Nigra as shown in FIG. 23c and enables the user to save the one or more first images, the workspace, the mesh and the one or more segmented images with patient id name. The server enables the user to place the directory location for the image files in the patient ID folder. The server enables the user to capture screenshots of the segmented image at all anatomical planes in such a way that the Substantia Nigra is displayed well with labels. The server further allows the user to capture screenshots of the segmented image in a three-dimensional image format with the Substantia Nigra zoomed well.

Figure 24A:
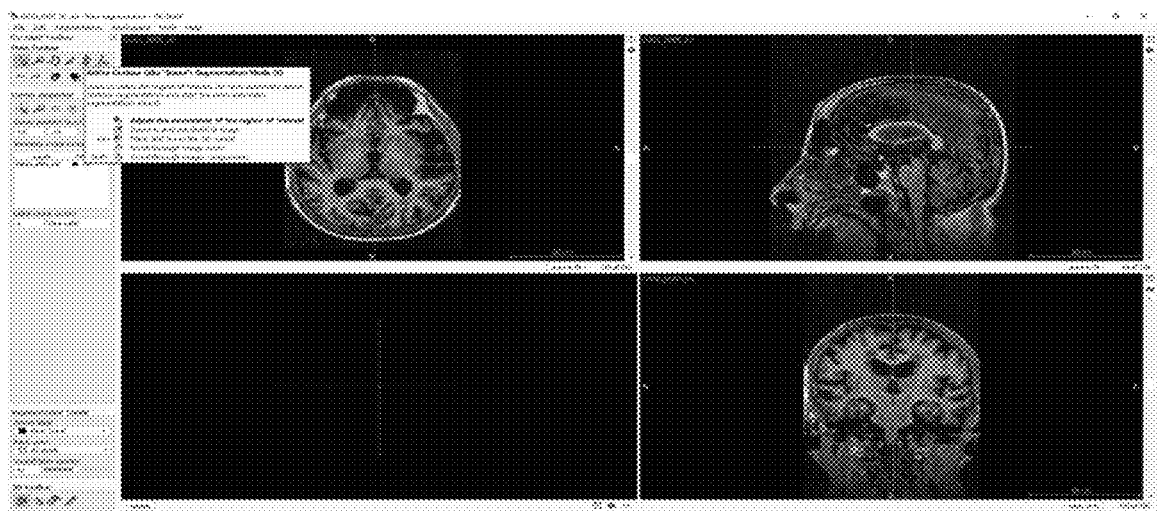

FIGS. 24*a*-24*j* illustrate a process of segmentation of Frontal Lobes, according to one or more embodiments. The process of segmentation of the Frontal Lobes comprises the following technical steps. While performing the segmentation, a server enables a user to select "active label" as "Frontal Lobes". In an embodiment, RGB Values assigned for the Frontal Lobes are: R-0, G-241, and B-193. The server further enables the user to select "Contour Segmentation mode" i.e., Semi-automatic segmentation. The contour segmentation allows the user to select semi-automatic active contour segmentation and start the semi-automatic segmentation as shown in FIG. 24*a*. The contour segmentation enables the user to adjust the boundaries of a region of interest covering the entire brain. The server enables a user to assign an "active label" as "Frontal Lobes". One or more first images comprising the Frontal Lobes are rendered in at least one anatomical plane and a three-dimensional format. The server enables the user to identify the Frontal Lobes in the at least one anatomical plane.

Figure 24B:
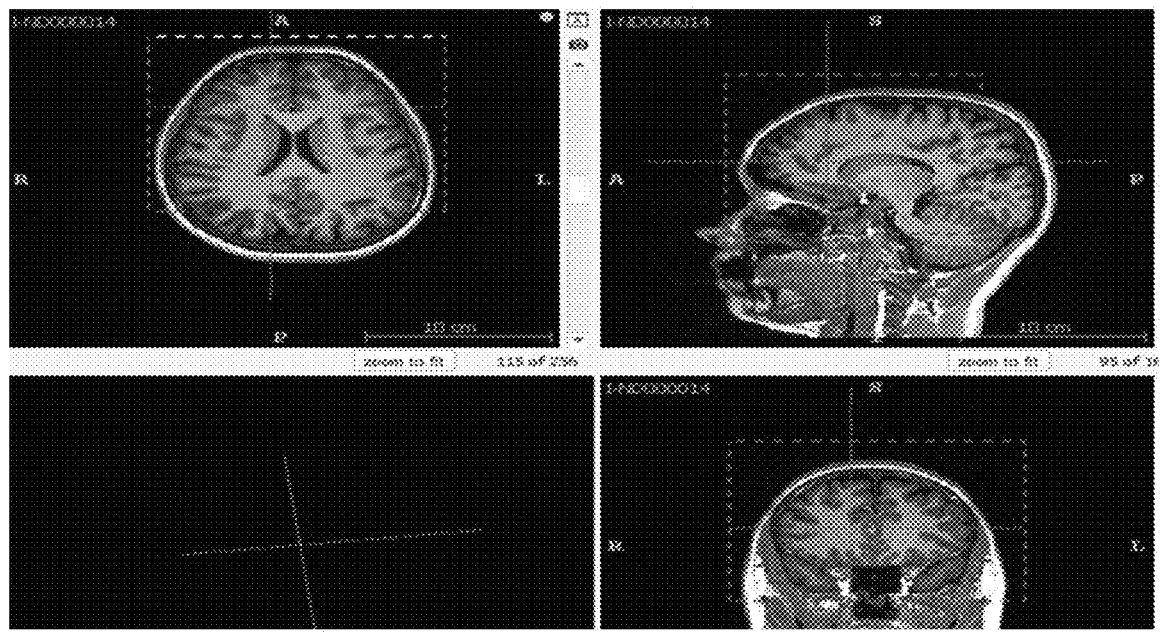

Once the Frontal Lobes is identified, the server enables the user to mark a region of interest covering the Frontal Lobes and check whether the Frontal Lobes is covered in the anatomical planes as shown in FIG. 24*b*. The server provides a "segment 3D" tool that allows the user to start semi-automatic segmentation. The user upon clicking the "segment 3D" tool, a toolbar appears. The toolbar provides a "pre-segmentation" tool. The "pre-segmentation" tool provides a "thresholding", "classification", "clustering", and "edge attraction". The user can select any of the four tools. For example, the "classification" tool is selected by the user.

Before starting the "classification" type segmentation, the server enables the user to choose a label indicating "Frontal Lobes" under the "Segmentation labels" tool. The "active label" under the "Segmentation label" tool is used to record and save information (e.g., volumes, boundaries, manual edits performed to the segmentation, etc.) obtained as a result of the segmentation performed on the at least one structure i.e., Frontal Lobes in this case. The server further provides a "brush" tool that allows the user to select appropriate brush (e.g., round brush) and appropriate brush size to mark the brain structures (e.g., GM, WM, frontal cortex). The Brain structure marked comprises brain structures (e.g., GM, WM, frontal cortex). The "classification" tool allows the user to classify between Frontal lobes and Intracranial Volume (ICV) by providing two labels "Frontal lobes" and "ICV". The "Frontal lobes" label is used to classify between white matter and grey matter. The "ICV" label is used to classify between dura, skull bone, ventricles or csf. In an embodiment, if there is an error, the "classification" tool further allows the user to add a third label as "Ventricles" to classify the Ventricles separately. The different tissue samples comprise white matter (WM) and grey matter (GM).

Figure 24C:
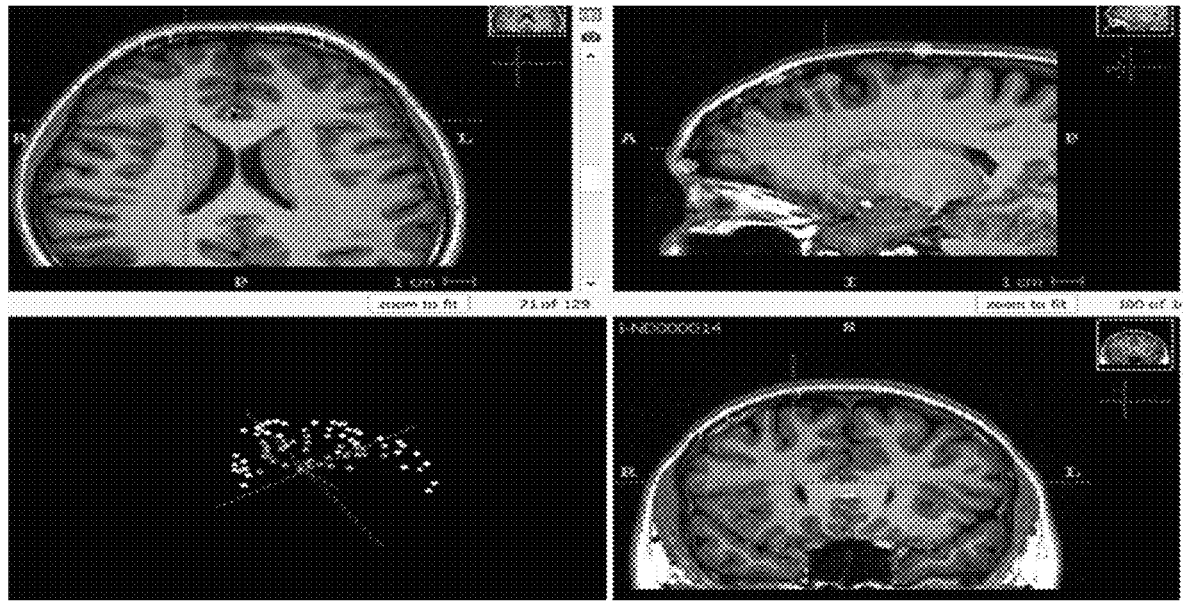

The server allows the user to mark tissue samples such as the WM and GM. The server further provides a "train classifier" tool that allows the user to train the classifier by clicking on the "train classifier" tool. The server further renders a speed image that shows the classification as shown in FIG. 24*c*. The "train classifier" assigns a first probability value to a voxel belonging to the "foreground" class and a second probability value to a voxel belonging to all other classes. Once the classifier is trained using the manual segmentation (i.e., marking and differentiating the tissue samples, Frontal Lobes, ICV, and the Ventricles) the classifier automatically segments at least one structure within the one or more first images of a different patient in future based on micro-ethnicity information, age and gender. The server provides a "Next" tab to complete the segmentation process.

Figure 24D:
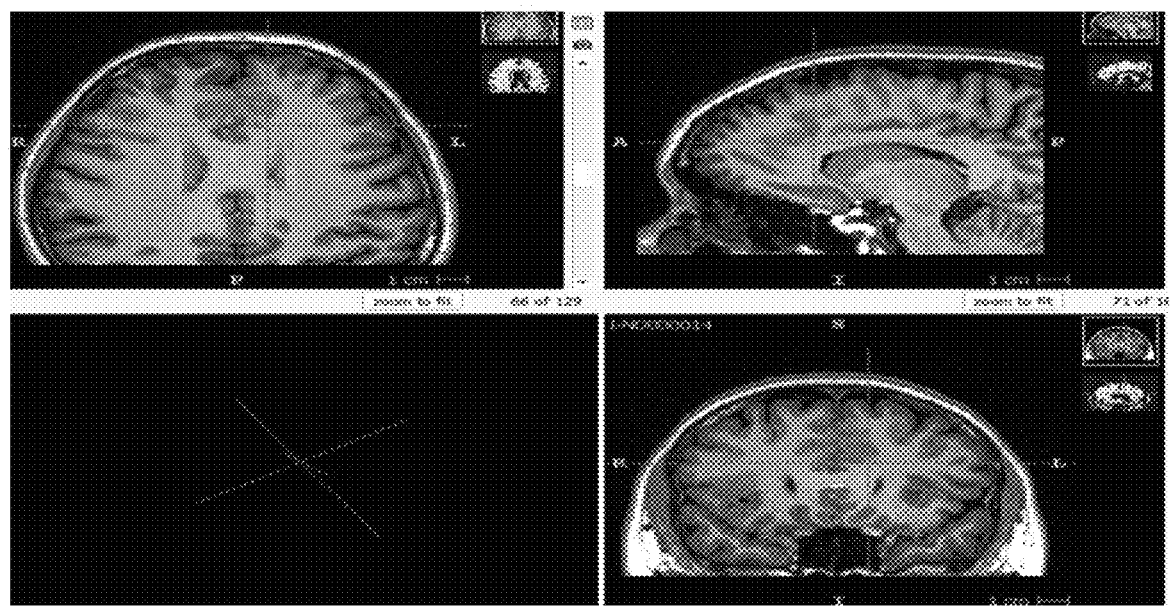

The server provides a "Add bubble at cursor" tool as shown in FIG. 24*d* that allows the user to populate bubbles of appropriate sizes exactly in the Frontal Lobes in at least three anatomical planes. Further the server provides a "Bubble radius" slider that allows the user to vary the size of the bubbles. The server further provides an "active bubble" drop down menu that shows the bubbles and its radius that are active. The server allows the user to add a sufficient number of bubbles in the Frontal Lobes. The server provides a "Next" tab to finalize the volume extraction.

Figure 24E:
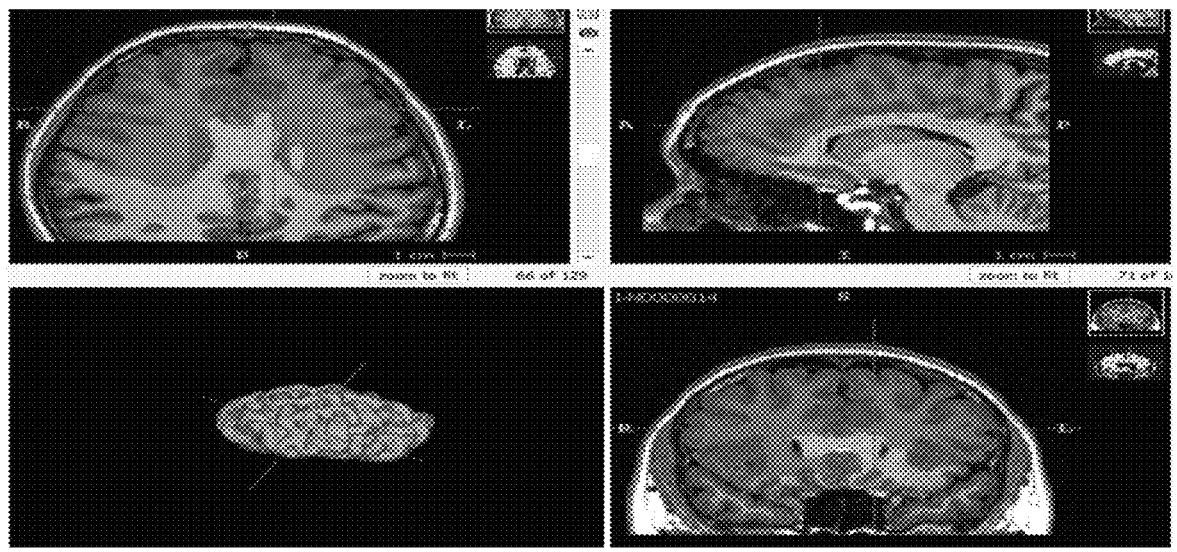

The server provides a "continuous update" tool in a three-dimensional window that enables to continuously update contour evolution. The server further provides a "play" tab that allows the user to play and pause Active Contour Evolution as shown in FIG. 24*e*. The server further provides a "finish" tab that allows the user to submit when the active contour evolution is done. In an embodiment, the server allows the user to change the "active label" to "clear label" and edit the voxels when the active contour evolution goes out of the boundaries of the Frontal Lobes. The server allows the user to edit the voxels by accessing the "brush" tool and selecting appropriate brush and appropriate brush size. In another embodiment, the server allows the user to change the "active label" to "Frontal Lobes" and edit/add the voxels when the active contour evolution has not reached any part of Frontal Cortex. The server allows the user to edit the voxels by accessing the "brush" tool and selecting appropriate brush and appropriate brush size.

The server may render and save the Frontal Lobes in at least one anatomical pane and in three-dimensional format under the "Active Label" as "Frontal Lobes". Once the segmentation and volume extraction of the Frontal Lobes are complete, the server enables the user to save the one or more first images, the workspace, the mesh and the one or more segmented image with patient id name. The server enables the user to place the directory location for the image files in the patient ID folder. The server enables the user to capture screenshots of the segmented image at all anatomical planes in such a way that Frontal Lobes are displayed well with labels. The server further allows the user to capture screenshots of the segmented image in a three-dimensional image format with the Frontal Lobes zoomed in and displayed well.

Figure 24F:
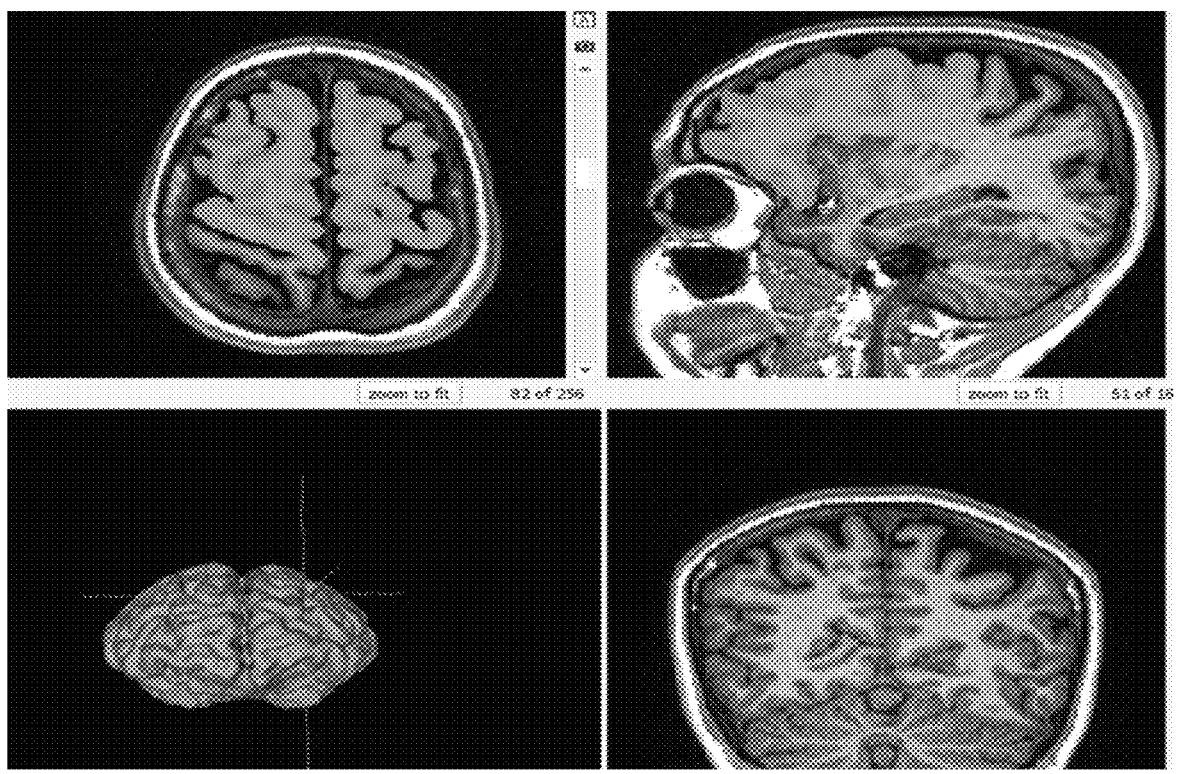
Figure 24G:
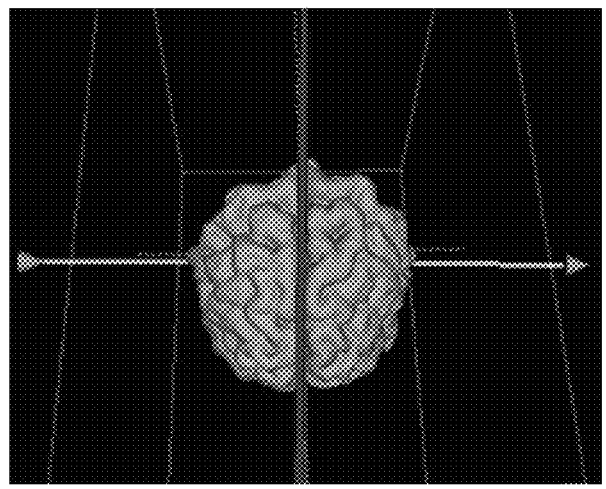
Figure 24H:
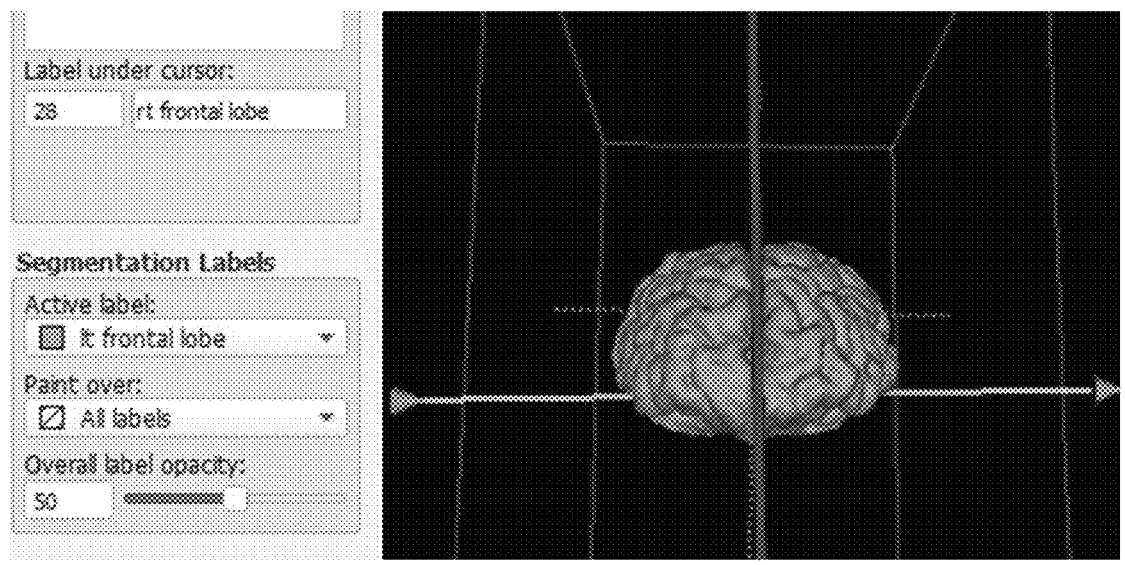
Figure 24I:
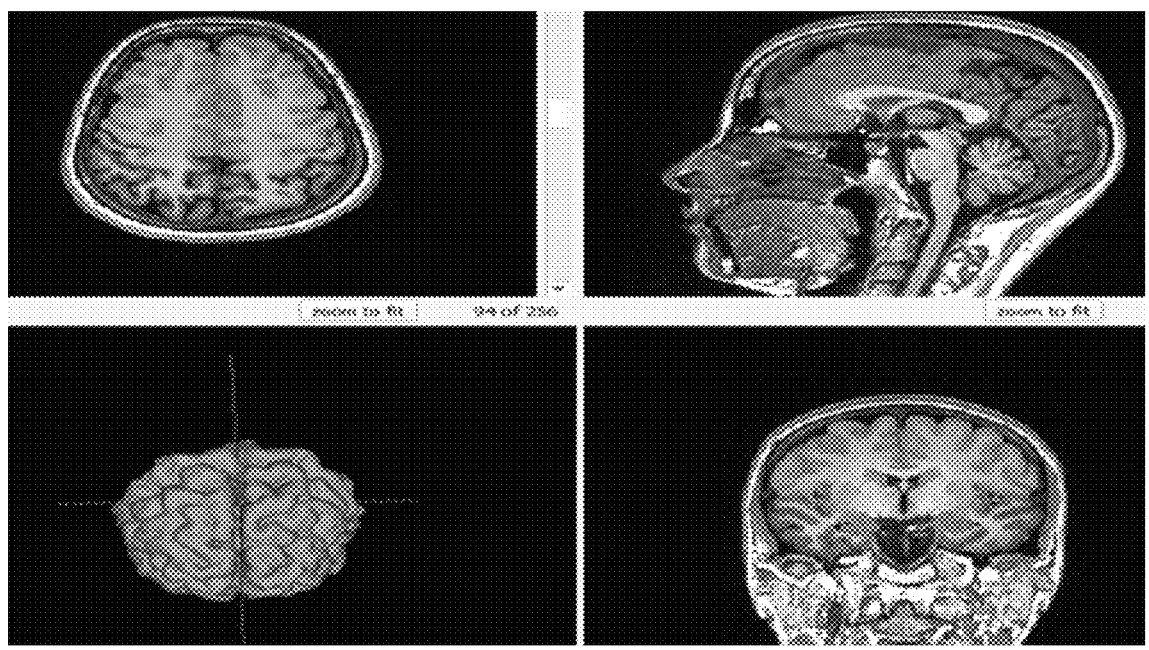

The server renders the Frontal lobes in a three-dimensional format as shown in FIG. 24*f* The server depicts the Frontal lobes with an arrow pointing at one of the left side, and right side as shown in FIG. 24*g*. The server allows the user to select the "active label" as "Left Frontal Lobes" when the arrow is pointing at the right side as shown in FIG. 24*h*. Similarly, the server allows the user to select the "active label" as "Right Frontal Lobes" when the arrow is pointing at the left side. The RGB values for the Left Frontal Lobes are: R-226, G-147, B-90. The server provides an "accept" tab that allows the user to accept and update the segmentation of 3D view format. The server further enables the user to check in an axial plane whether the Left Frontal Lobes has been labelled properly. The server provides a cursor and places it on a longitudinal fissure. The server provides a "split" tool that enables the user to place a line which traces the longitudinal fissure. The server further renders an arrow on the three-dimensional window. The server then renders the Frontal Lobes in at least one of three-dimensional format and at least one anatomical plane as shown in FIG. 24*i*.

Figure 24J:
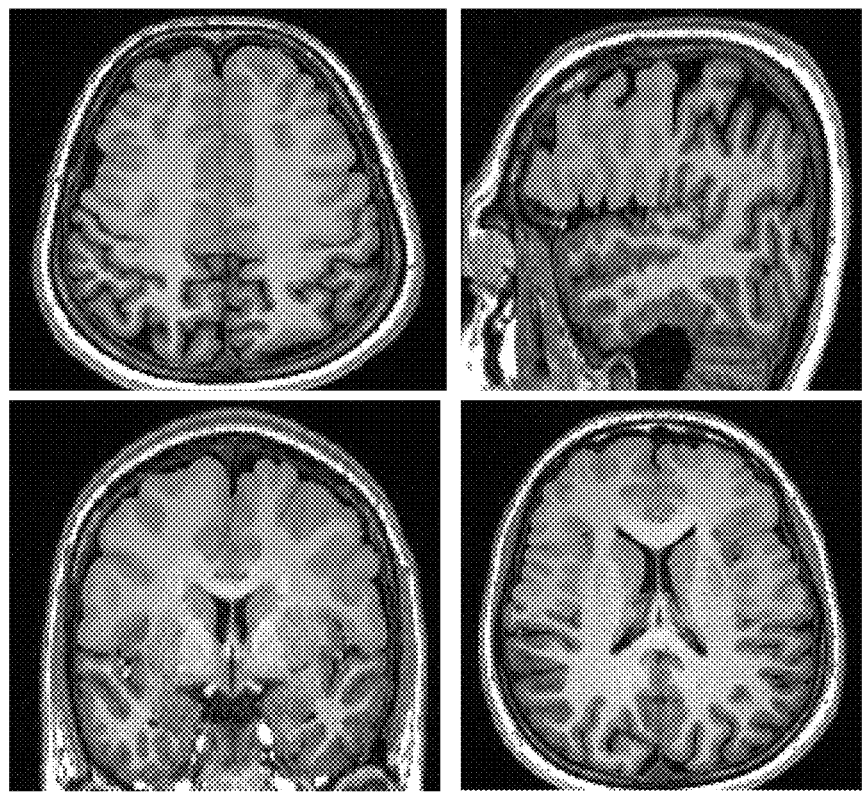

FIG. 24*j* comprise reference figures that illustrate the boundaries of the Frontal Lobes. Central Sulcus identifies the posterior border of the Frontal Lobe. The Sylvian Fissure demarcates the inferior border of the Frontal Lobe. The superior and middle Frontal Gyri are divided by the Superior Frontal Sulcus. The middle and inferior Frontal Gyri are divided by the Inferior Frontal Sulcus. Do not include the Corpus Callosum and the Basal Ganglia.

Figure 25A:
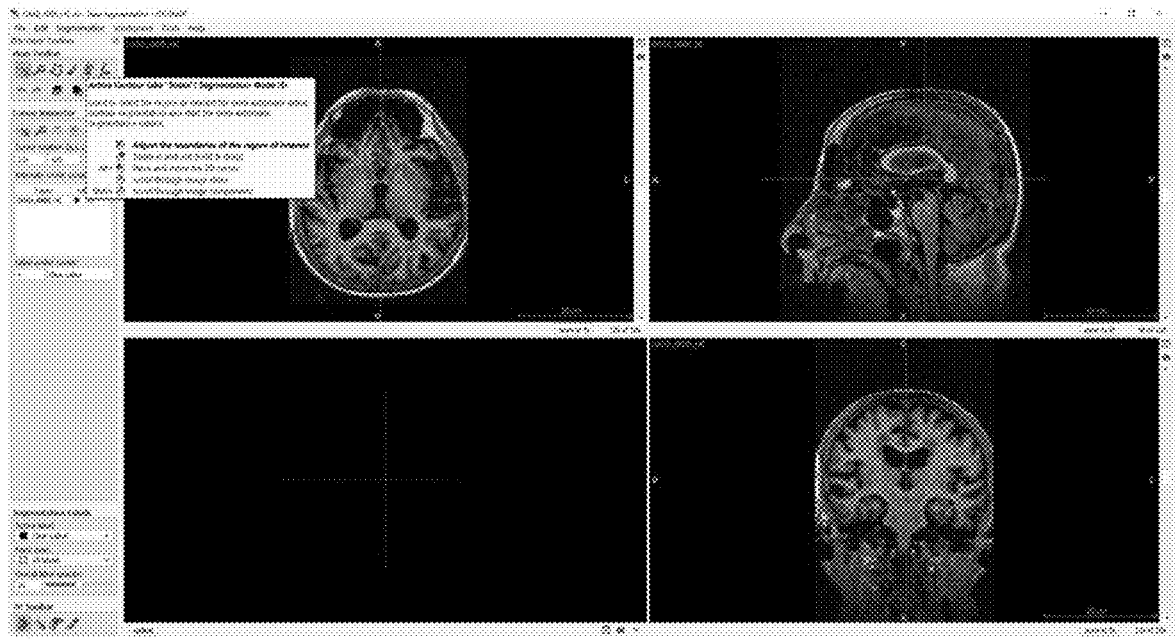

FIGS. 25a-25i illustrate a process of segmentation of Parietal Lobes, according to one or more embodiments. The process of segmentation of the Parietal Lobes comprises the following technical steps. While performing the segmentation, a server enables a user to select "active label" as "Parietal Lobes". In an embodiment, RGB Values assigned for the Ventricles are: R-194, G-255, and B-187. The server further enables the user to select "Contour Segmentation mode" i.e., Semi-automatic segmentation. The contour segmentation allows the user to select semi-automatic active contour segmentation and start the semi-automatic segmentation as shown in FIG. 25a. The contour segmentation enables the user to adjust the boundaries of the region of interest covering the Parietal Lobes. Once the 'active label' is assigned as "Parietal Lobes", one or more first images are rendered in at least one anatomical plane and a three-dimensional format. The server enables the user to identify the Parietal Lobes in the at least one anatomical plane.

Figure 25B:
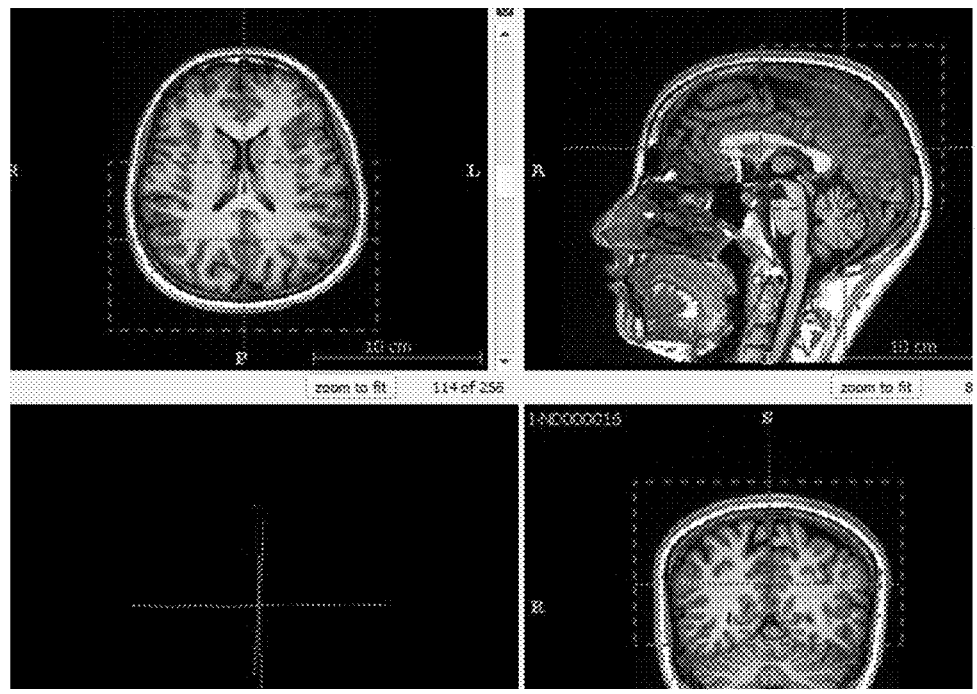

Once the Parietal Lobes is identified, the server enables the user to mark a region of interest covering the Parietal Lobes and check whether the Parietal Lobes is covered in the anatomical planes as shown in FIG. 25b. The server provides a "segment 3D" tool that allows the user to start semi-automatic segmentation. The user upon clicking the "segment 3D" tool a toolbar appears. The toolbar provides a "pre-segmentation" tool. The "pre-segmentation" tool provides a "thresholding", "classification", "clustering", and "edge attraction". The user can select any of the four tools. For example, the "classification" tool is selected by the user.

Figure 25C:
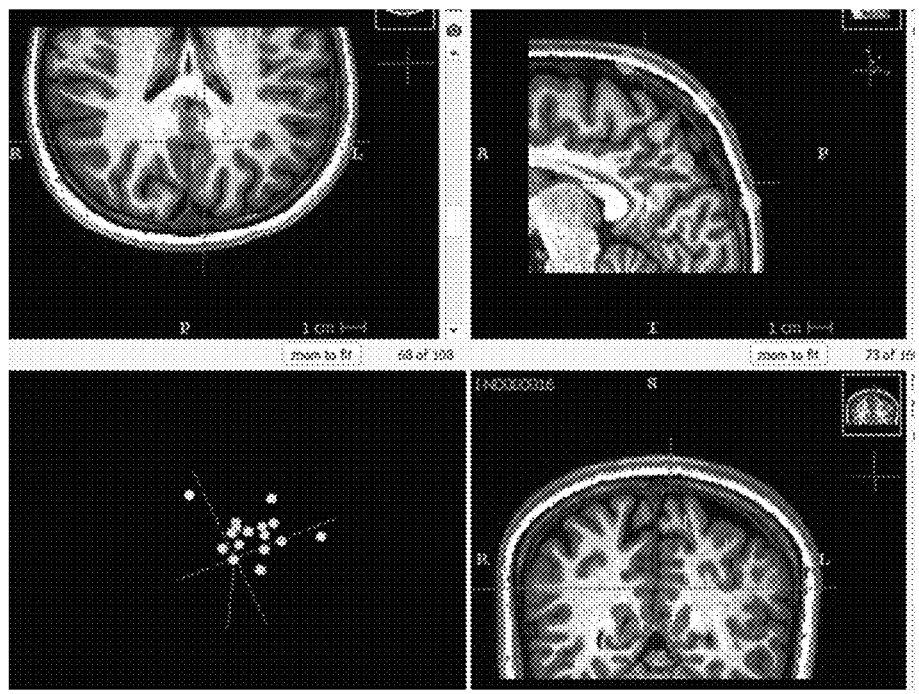

Before starting the "classification" type segmentation, the server enables the user to choose a label indicating "Parietal Lobes" under the "Segmentation labels" tool. The "Segmentation label" tool is used to record and save information (e.g., volumes, boundaries, manual edits performed to the segmentation, etc.) obtained as a result of the segmentation performed on the at least one structure i.e., Parietal Lobes in this case. The server further provides a "brush" tool that allows the user to select appropriate brush (e.g., round brush) and appropriate brush size to mark the brain structures (e.g., GM, WM, frontal cortex) as shown in FIG. 25c under the "Parietal Lobes" label of the "Segmentation labels". The Brain structure marked comprises brain structures (e.g., GM, WM, frontal cortex). The "classification" tool allows the user to classify between Parietal lobes and Intracranial Volume (ICV) by providing two labels "Parietal lobes" and "ICV". The "Right Parietal lobes" label is used to classify between white matter and grey matter. The "ICV" label is used to classify between dura, skull bone, ventricles or csf. In an embodiment, if there is an error, the "classification" tool further allows the user to add a third label as "Ventricles" to classify the Ventricles separately. The different tissue samples comprise white matter (WM) and grey matter (GM).

The server allows the user to mark tissue samples such as the WM and GM. The server further provides a "train classifier" tool that allows the user to train the classifier by clicking on the "train classifier" tool. The server further renders a speed image that shows the classification. The "train classifier" assigns a probability value to a voxel belonging to the "foreground" class vs. belonging to all other classes. Once the classifier is trained using the manual segmentation (i.e., marking and differentiating the tissue samples, Parietal Lobes, ICV, and the Ventricles) the classifier automatically segments at least one structure within the one or more first images of a different patient in future based on micro-ethnicity information, age and gender. The server provides a "Next" tab to complete the segmentation process.

Figure 25D:
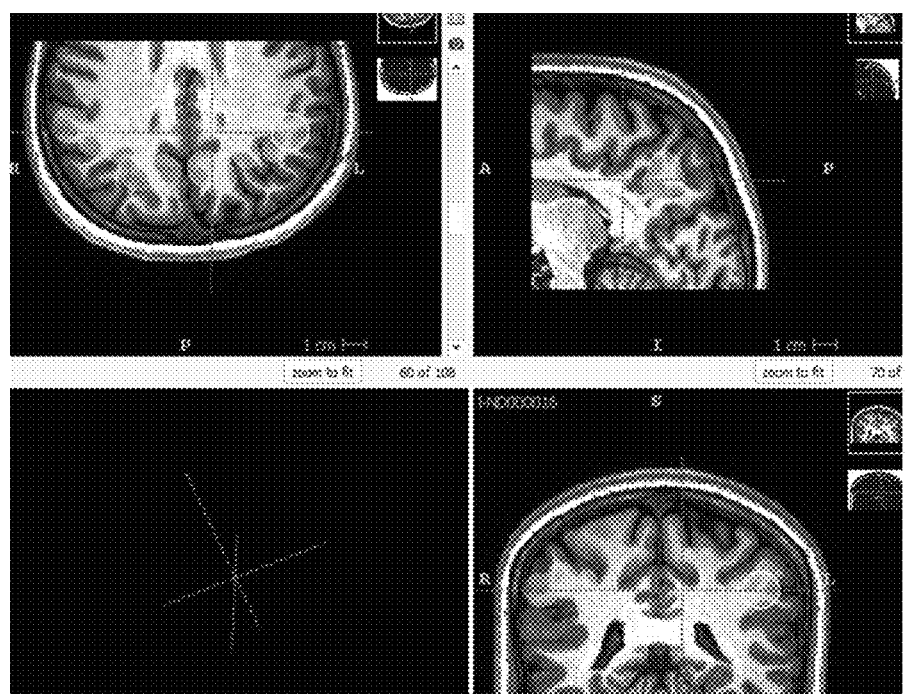
Figure 25E:
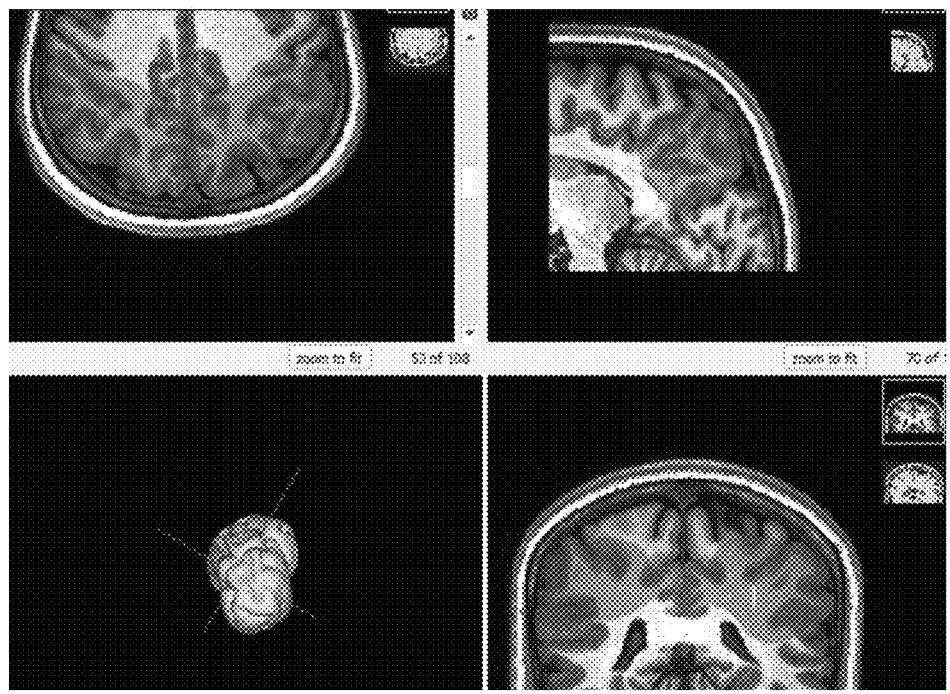

The server provides a "Add bubble at cursor" tool as shown in FIG. 25d that allows the user to populate bubbles of appropriate sizes exactly in the Parietal Lobes in at least three anatomical planes to exactly extract the volume of the Right Parietal Lobes as shown in FIG. 25e. Further the server provides a "Bubble radius" slider that allows the user to vary the size of the bubbles. The server further provides an "active bubbles" drop down menu that shows the bubbles and its radius that are active. The server allows the user to add a sufficient number of bubbles in the Parietal Lobes. The server provides a "Next" tab to finalize the volume extraction.

Figure 25F:
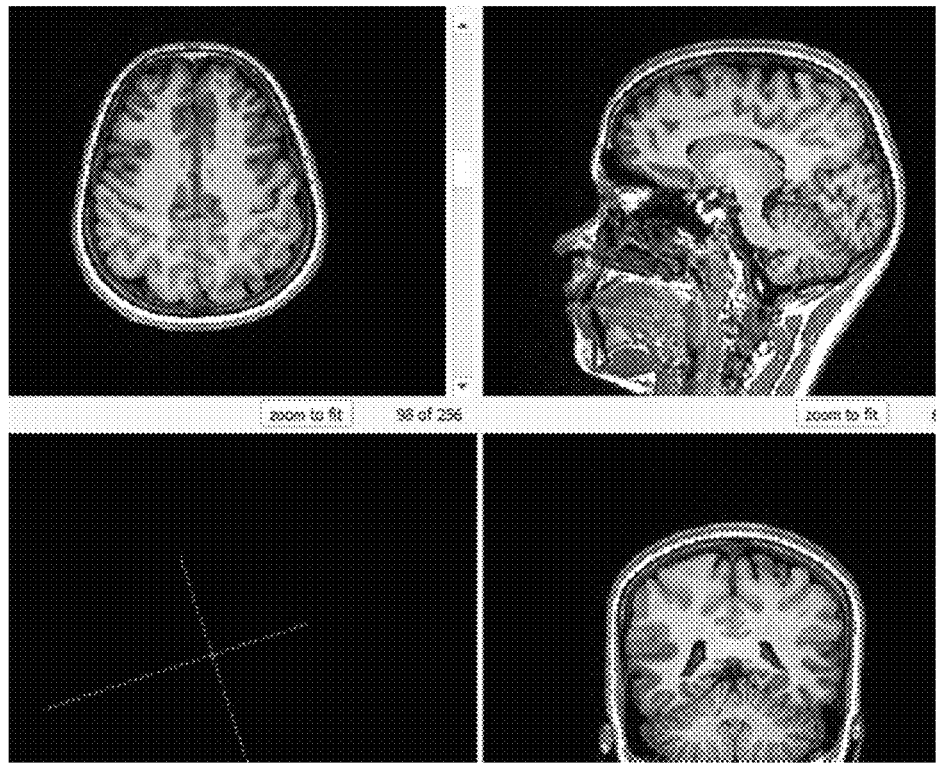

The server provides a "continuous update" that enables it to continuously update contour evolution. The server further provides a "play" tab that allows the user to run, play, and pause Active Contour Evolution as shown in FIG. 25f. The server further provides a "finish" tab that allows the user to submit when the active contour evolution is done. In an embodiment, the server allows the user to change the "active label" to "clear label" and edit the voxels when the active contour evolution goes out of the boundaries of the Parietal Lobes. The server allows the user to edit the voxels by accessing the "brush" tool and selecting appropriate brush and appropriate brush size. In another embodiment, the server allows the user to change the "active label" to "Parietal Lobes" and edit the voxels when the active contour evolution has not reached any part of the Right Parietal Lobes. The server allows the user to edit the voxels by accessing the "brush" tool and selecting appropriate brush and appropriate brush size.

The server may render and save the Parietal Lobes in at least one anatomical pane and in three-dimensional format under the "Active Label" as "Right Parietal Lobes". Once the segmentation and volume extraction of the Right Parietal Lobes are complete, the server enables a user to save the one or more first images, the workspace, the mesh and the one or more segmented image with patient id name. The server enables the user to place the directory location for the image files in the patient ID folder. The server enables the user to capture screenshots of the segmented image at all anatomical planes in such a way that Parietal Lobes are displayed well with labels. The server further allows the user to capture screenshots of the segmented image in a three-dimensional image format with the Parietal Lobes zoomed in and displayed well.

Figure 25G:
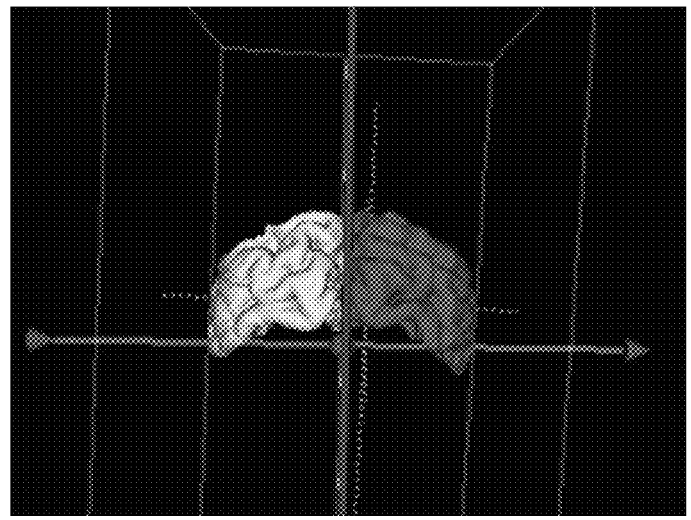
Figure 25H:
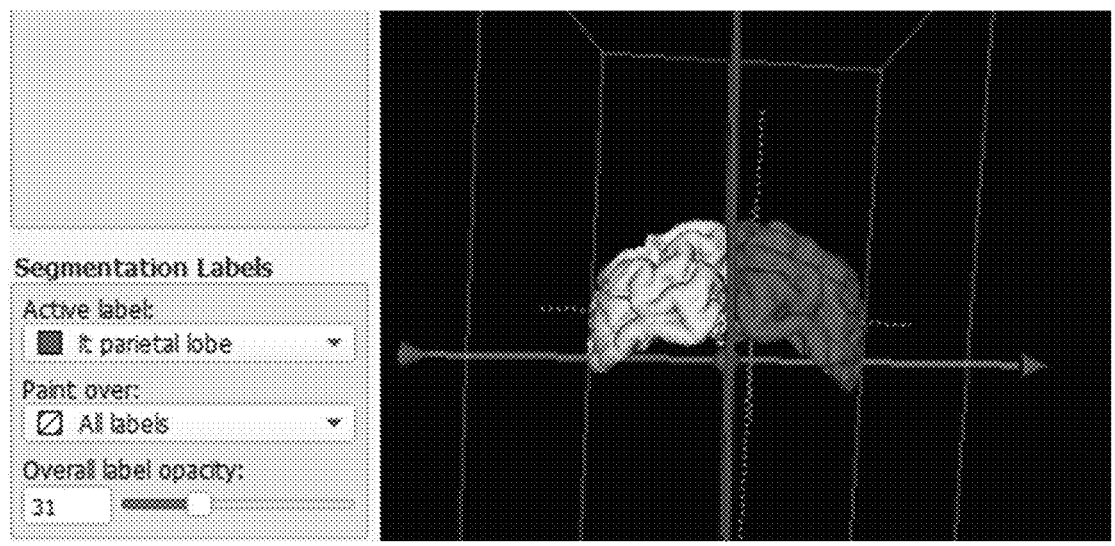

The server renders the Parietal lobes in a three-dimensional format. The server depicts the Parietal lobes with an arrow pointing at one of the left side, and right side as shown in FIG. 25g. The server provides a cursor and places it on a longitudinal fissure. The server provides a "split" tool that enables the user to place a line which traces the longitudinal fissure. The server further renders an arrow on the three-dimensional window. The server allows the user to select the "active label" as "Left Parietal Lobes" when the arrow is pointing at the right side as shown in FIG. 25h. The server allows the user to select the "active label" as "Right Parietal Lobes" when the arrow is pointing at the left side. The server allows the user to select the "active label" as "Right Parietal Lobes" when the arrow is pointing at the left side. The RGB values for the Left Parietal Lobes are: R-252, G-0, B-157.

The server provides an "accept" tab that allows the user to accept and update the segmentation of 3D view format. The server further enables the user to Check in the Axial plane whether the Left Parietal Lobes has been labelled properly.

Figure 25I:
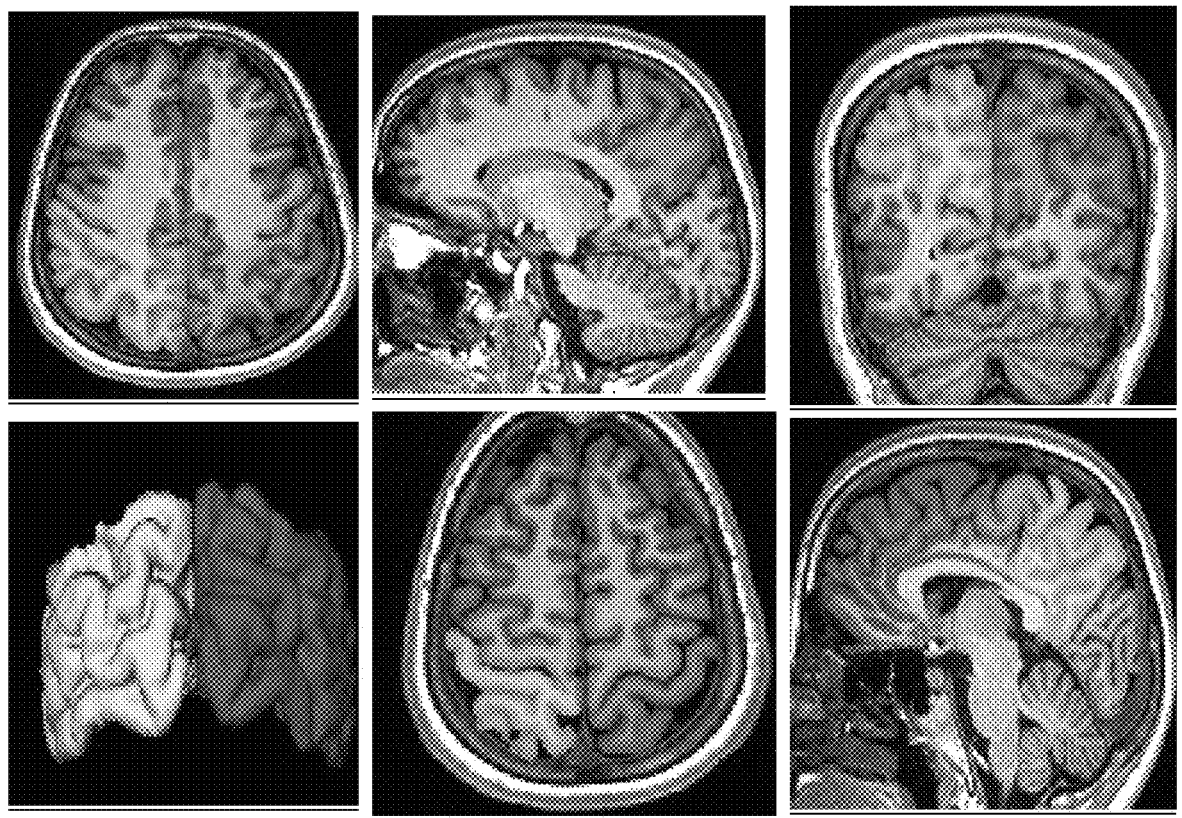

FIG. 25i are reference figures that illustrate the boundaries of the parietal Lobes. Central Sulcus separates the parietal lobe from the frontal lobe. Parieto-occipital sulcus separates the Parietal and Occipital lobes. Lateral Sulcus (Sylvian Fissure) is the most lateral boundary, separating it from the Temporal Lobe. The Longitudinal fissure divides the two hemispheres. The Parietal Lobes do not include Corpus Callosum.

Figure 26A:
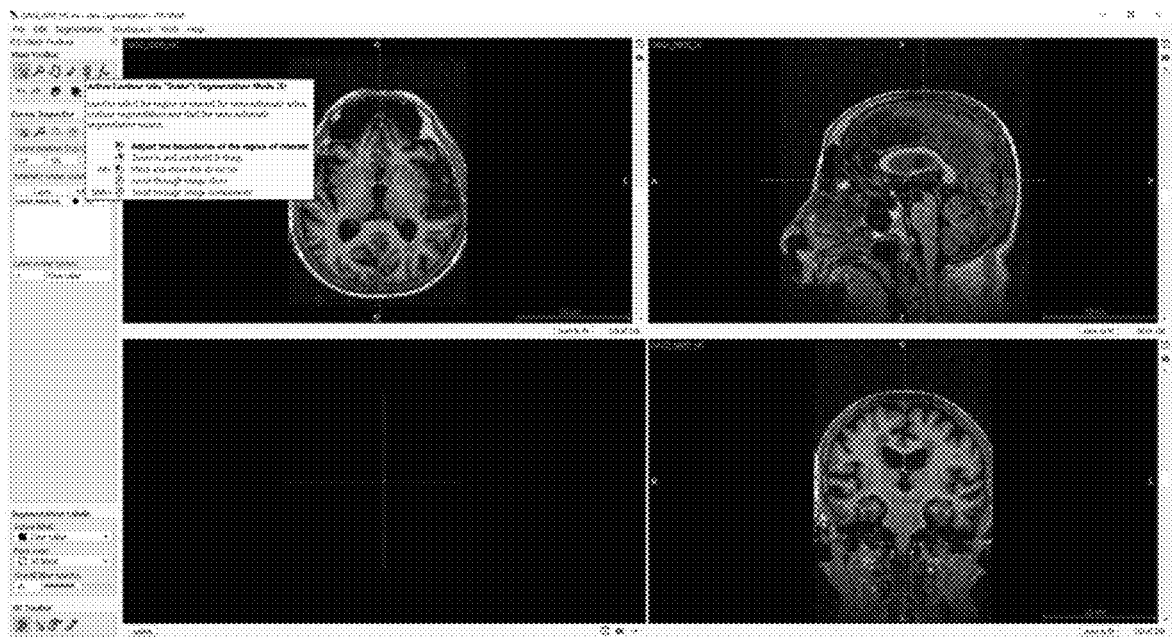

FIG. 26a-26h illustrate a process of segmentation of Occipital Lobes, according to one or more embodiments. The process of segmentation of the Occipital Lobes comprises the following technical steps. While performing the segmentation, a server enables a user to select "active label" as "Occipital Lobes". In an embodiment, RGB Values assigned for the Ventricles are: R-233, G-192, B-250. The server further enables the user to select "Contour Segmentation mode" i.e., Semi-automatic segmentation. The contour segmentation allows the user to select semi-automatic active contour segmentation and start the semi-automatic segmentation as shown in FIG. 26a. The contour segmentation enables the user to adjust the boundaries of the region of interest covering the Occipital Lobes. Once the 'active label' is assigned as "Occipital Lobes", one or more first images comprising the Occipital Lobes are rendered in at least one anatomical plane and a three-dimensional format. The server enables the user to identify the Occipital Lobes in the at least one anatomical plane.

Figure 26B:
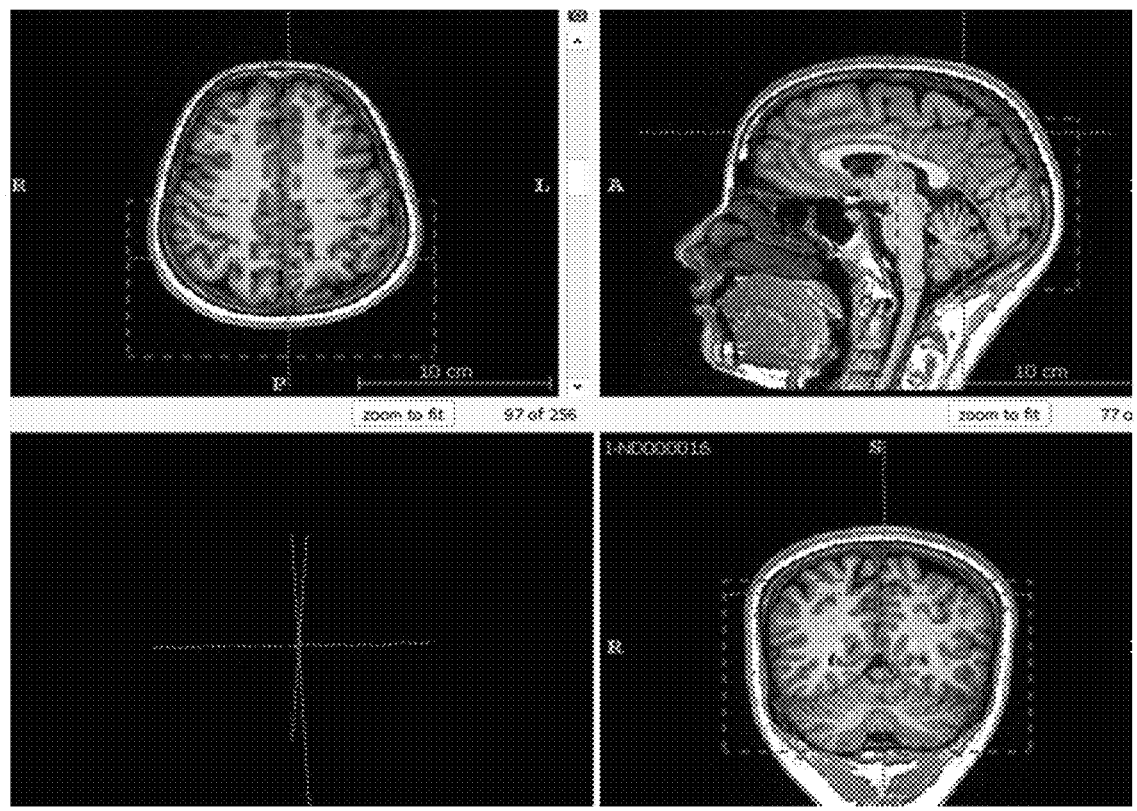

Once the Occipital Lobes is identified, the server enables the user to mark a region of interest covering the Occipital Lobes and check whether the Occipital Lobes is covered in the anatomical planes as shown in FIG. 26b. The server provides a "segment 3D" tool that allows the user to start semi-automatic segmentation. The user upon clicking the "segment 3D" tool a toolbar appears. The toolbar provides a "pre-segmentation" tool. The "pre-segmentation" tool provides a "thresholding", "classification", "clustering", and "edge attraction". The user can select any of the four tools. For example, the "classification" tool is selected by the user.

Figure 26C:
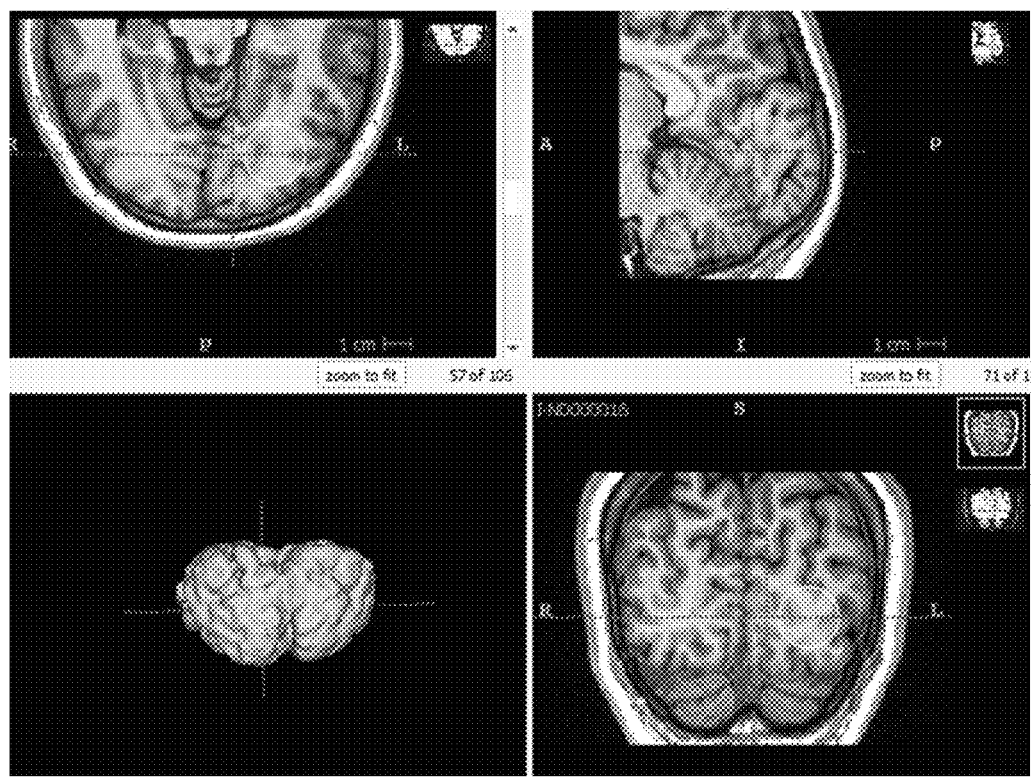

Before starting the "classification" type segmentation, the server enables the user to choose a label indicating "Occipital Lobes" under the "Segmentation labels" tool. The "active label" tool under "Segmentation label" tool is used to record and save information (e.g., volumes, boundaries, manual edits performed to the segmentation, etc.) obtained as a result of performing the segmentation performed on the at least one structure i.e., Occipital Lobes in this case. The server further provides a "brush" tool that allows the user to select appropriate brush (e.g., round brush) and appropriate brush size to mark the brain structures (e.g., GM, WM, frontal cortex) using the "Occipital Lobes" label of the "Segmentation labels" as shown in FIG. 26c. The Brain structure marked comprises brain structures (e.g., GM, WM, frontal cortex). The "classification" tool allows the user to classify between Occipital lobes and Intracranial Volume (ICV) by providing two labels "Occipital Lobes" and "ICV". The "Occipital lobes" label is used to classify between white matter and grey matter. The "ICV" label is used to classify between dura, skull bone, ventricles or csf. In an embodiment, if there is an error, the "classification" tool further allows the user to add a third label as "Ventricles" to classify the Ventricles separately. The different tissue samples comprise white matter (WM) and grey matter (GM).

The server allows the user to mark tissue samples such as the WM and GM. The server further provides a "train classifier" tool that allows the user to train the classifier by clicking on the "train classifier" tool. The server further renders a speed image that shows the classification. The "train classifier" assigns a probability value to a voxel belonging to the "foreground" class vs. belonging to all other classes. Once the classifier is trained using the manual segmentation (i.e., marking and differentiating the tissue samples, Occipital Lobes, ICV, and the Ventricles) the classifier automatically segments at least one structure within the one or more first images of a different patient in future based on micro-ethnicity information, age and gender. The server provides a "Next" tab to complete the process.

Figure 26D:
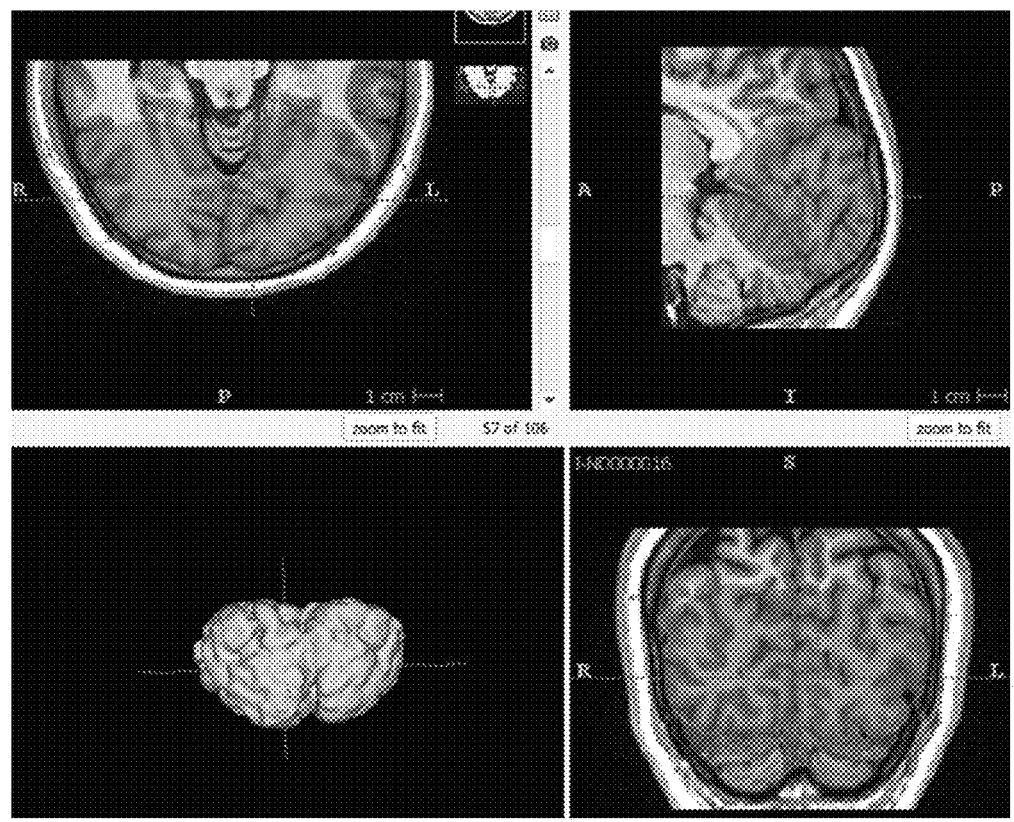
Figure 26E:
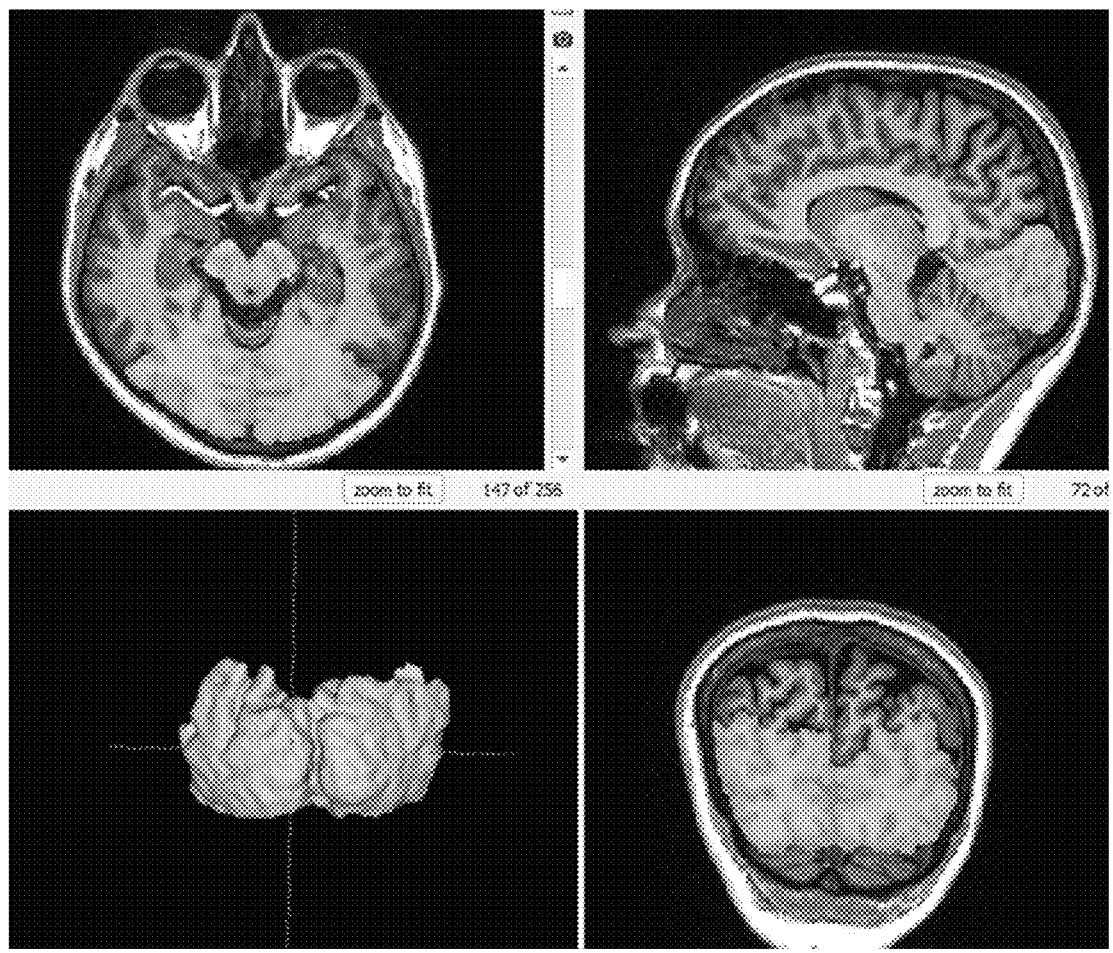

The server provides a "Add bubble at cursor" tool as shown in FIG. 26d that allows the user to populate bubbles of appropriate sizes exactly in the Occipital Lobes in at least three anatomical planes to exactly extract the volume of the Occipital Lobes as shown in FIG. 26e. Further the server provides a "Bubble radius" slider that allows the user to vary the size of the bubbles. The server further provides an "active bubbles" drop down menu that shows the bubbles and its radius that are active. The server allows the user to add a sufficient number of bubbles in the Occipital Lobes. The server provides a "Next" tab to finalize bubbles' evolution.

The server provides a "continuous update" in a three-dimensional window that enables to continuously update contour evolution. The server further provides a "play" tab that allows the user to run, play, and pause Active Contour Evolution. The server further provides a "finish" tab that allows the user to submit when the active contour evolution is done. In an embodiment, the server allows the user to change the "active label" to "clear label" and delete the voxels when the active contour evolution goes out of the boundaries of the Occipital Lobes. The server allows the user to edit the voxels by accessing the "brush" tool and selecting appropriate brush and appropriate brush size. In another embodiment, the server allows the user to change the "active label" to "Occipital Lobes" and add the voxels when the active contour evolution has not reached any part of the Occipital Lobes. The server allows the user to edit the voxels by accessing the "brush" tool and selecting appropriate brush and appropriate brush size.

The server may render and save the Right Occipital Lobes in at least one anatomical pane and in three-dimensional format under the "Active Label" as "Occipital Lobes". Once the segmentation and volume extraction of the Occipital Lobes are complete, the server enables the user to save the one or more first images, the workspace, the mesh and the one or more segmented image with a patient id name. The server enables the user to place the directory location for the image files in the patient ID folder. The server enables the user to capture screenshots of the segmented image at all anatomical planes in such a way that Occipital Lobes are displayed well with labels. The server further allows the user to capture screenshots of the segmented image in a three-dimensional image format with the Occipital Lobes zoomed in and displayed well.

Figure 26F:
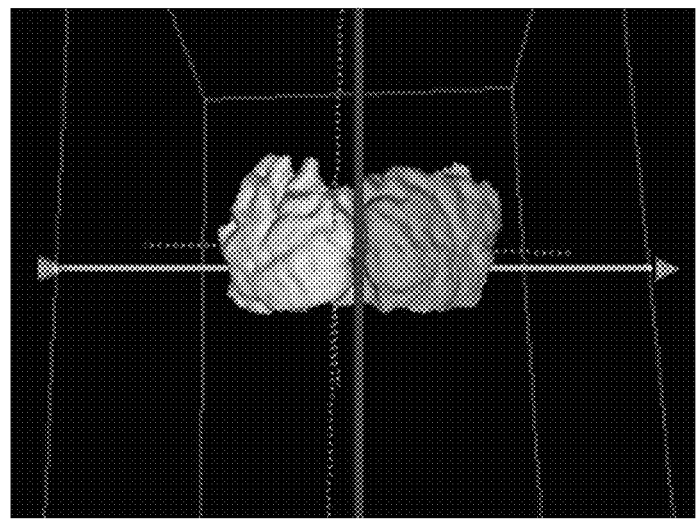
Figure 26G:
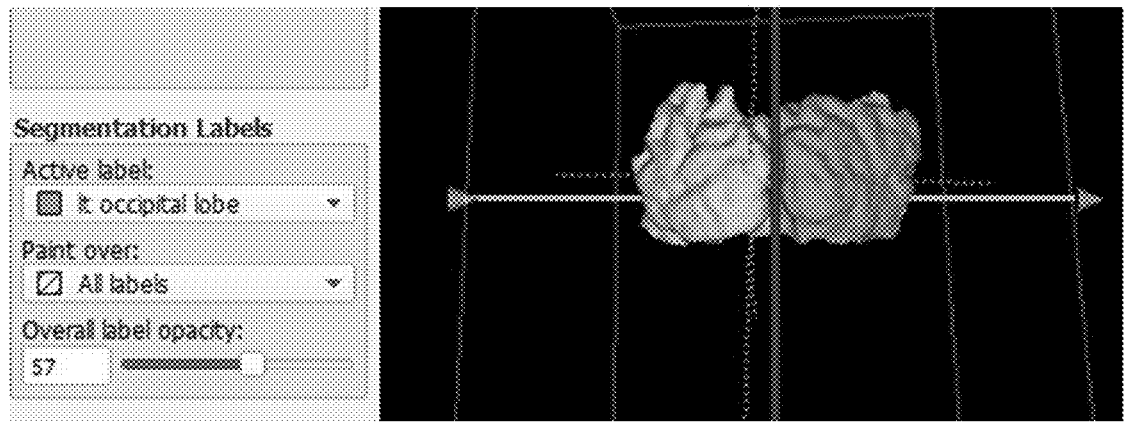

The server renders the Occipital lobes in a three-dimensional format. The server depicts the Occipital lobes with an arrow pointing at one of the left side and right side as shown in FIG. 26f. The server provides a cursor and places it on a longitudinal fissure. The server provides a "split" tool that enables the user to place a line which traces the longitudinal fissure. The server further renders an arrow on the three-dimensional window. The server allows the user to select the "active label" as "Left Occipital Lobes" when the arrow is pointing at the right side as shown in FIG. 26g. The server allows the user to select the "active label" as "Right Occipital Lobes" when the arrow is pointing at the left side. The RGB values for the Left Occipital Lobes are: R-169, G-176, B-136. Similarly, the server allows the user to select the "active label" as "right Occipital Lobes" when the arrow is pointing at the left side. The server provides an "accept" tab that allows the user to accept and update the segmentation of 3D view format. The server further enables the user to Check in the Axial plane whether the Left Occipital Lobes has been labelled properly.

Figure 26H:
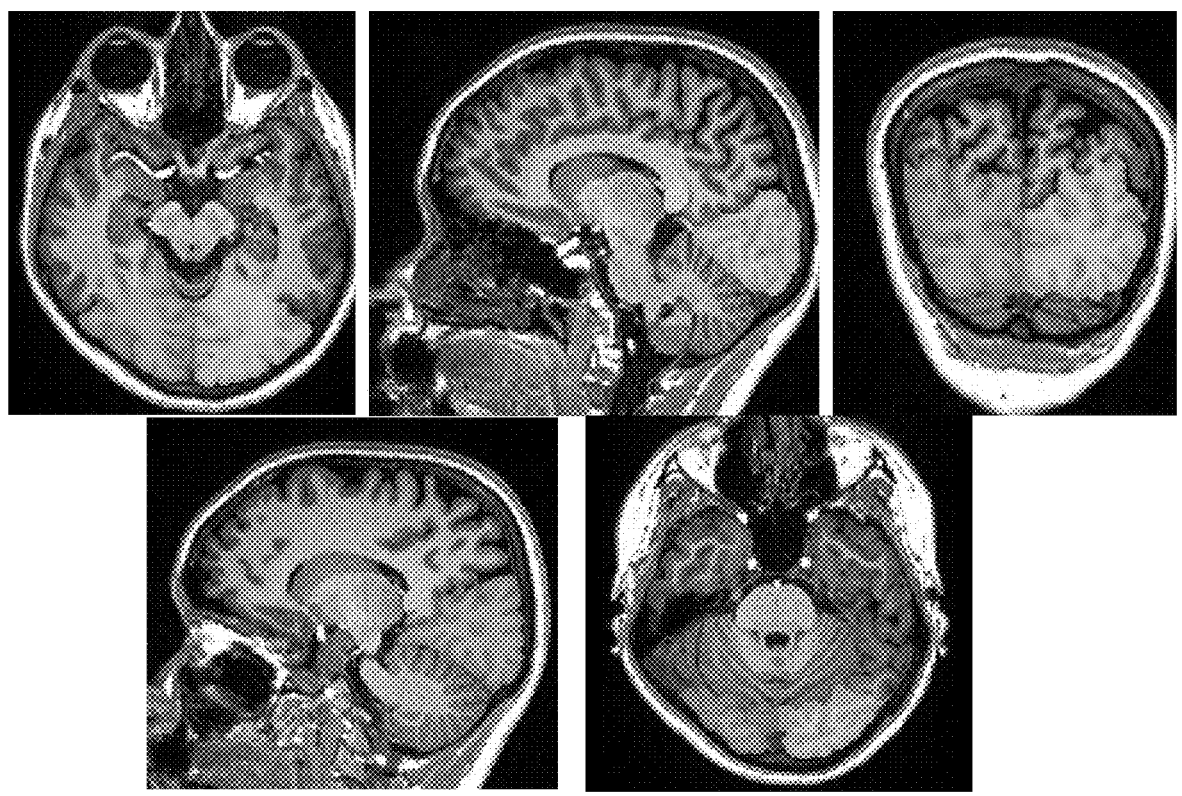

FIG. 26h are reference figures provided for the segmentation that illustrates the following. The lobes rest on the Tentorium Cerebelli, a process of dura mater that separates the Cerebrum from a Cerebellum. The lobes are structurally isolated in their respective Cerebral hemispheres by the separation of the Cerebral Fissure. The Parieto-Occipital Sulcus separates the Parietal and Occipital Lobes. The lateral side is differentiated by the Lateral Parietotemporal line.

Figure 27A:
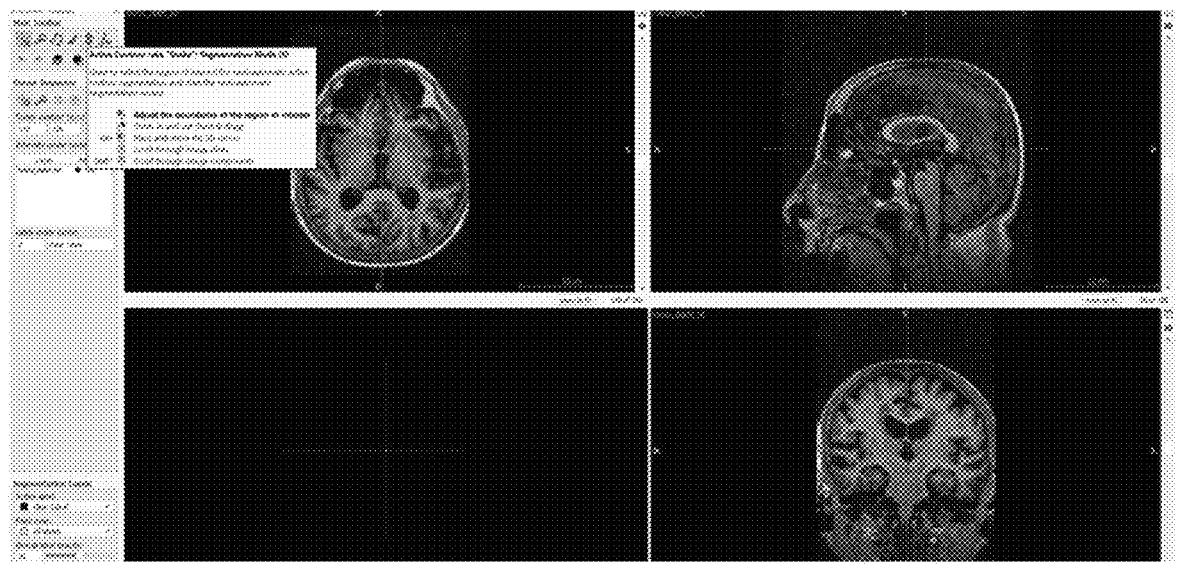

FIG. 27a-27g illustrate a process of segmentation of Temporal Lobes, according to one or more embodiments. The process of segmentation of the Temporal Lobes comprises the following technical steps. While performing the segmentation, a server enables a user to select "active label" as "Temporal Lobes". The server further enables the user to select "Contour Segmentation mode" i.e., Semi-automatic segmentation. The contour segmentation allows the user to select semi-automatic active contour segmentation and start the semi-automatic segmentation as shown in FIG. 27a. The contour segmentation tool enables a user to adjust the boundaries of a region of interest covering the Temporal Lobes. Once the 'active label' is assigned as "Temporal Lobes", one or more first images are rendered in at least one anatomical plane and a three-dimensional format. The server enables the user to identify the Temporal Lobes in the at least one anatomical plane.

Figure 27B:
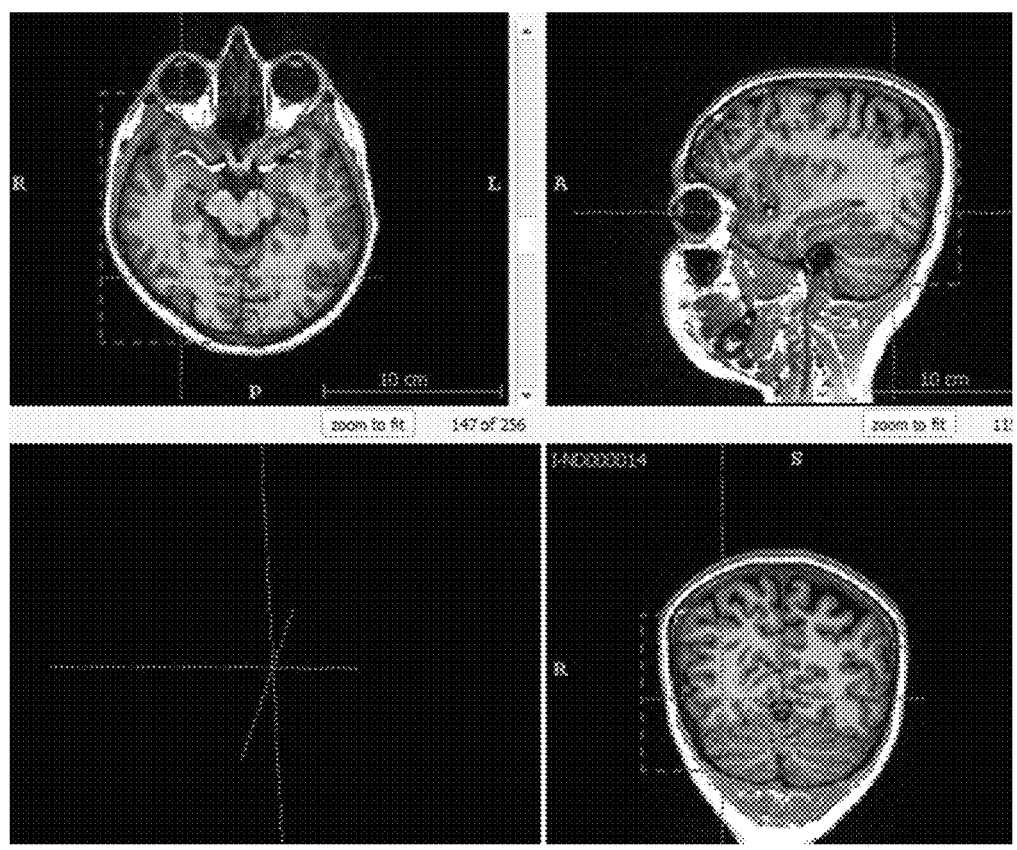

Once the Temporal Lobes is identified, the server enables the user to mark a region of interest covering the Temporal Lobes and check whether the Temporal Lobes is covered in the anatomical planes as shown in FIG. 27b. The server provides a "segment 3D" tool that allows the user to start semi-automatic segmentation. The user upon clicking the "segment 3D" tool a toolbar appears. The toolbar provides a "pre-segmentation" tool. The "pre-segmentation" tool provides a "thresholding", "classification", "clustering", and "edge attraction". The user can select any of the four tools. For example, the "classification" tool is selected by the user.

Before starting the "classification" type segmentation, the server enables the user to choose a label indicating "Right Temporal Lobes" under the "Segmentation labels" tool. The "Segmentation label" tool is used to record and save information (e.g., volumes, boundaries, manual edits performed to the segmentation, etc.) obtained as a result of the segmentation performed on the at least one structure i.e., Temporal Lobes in this case. The RGB values for the right temporal lobe are: R-102, G-205, B-130.

The server further provides a "brush" tool that allows the user to select appropriate brush (e.g., round brush) and appropriate brush size to mark the brain structures (e.g., GM, WM, frontal cortex) using the "Right Temporal Lobes" label of the "Segmentation labels". The Brain structure marked comprises brain structures (e.g., GM, WM, frontal cortex). The "classification" tool allows the user to classify between Right Temporal lobes and Intracranial Volume (ICV) by providing two labels "Right Temporal Lobes" and "ICV". The "Right Temporal lobes" label is used to classify between white matter and grey matter. The "ICV" label is used to classify between dura, skull bone, ventricles or csf. In an embodiment, if there is an error, the "classification" tool further allows the user to add a third label as "Ventricles" to classify the Ventricles separately. The different tissue samples comprise white matter (WM) and grey matter (GM).

Figure 27C:
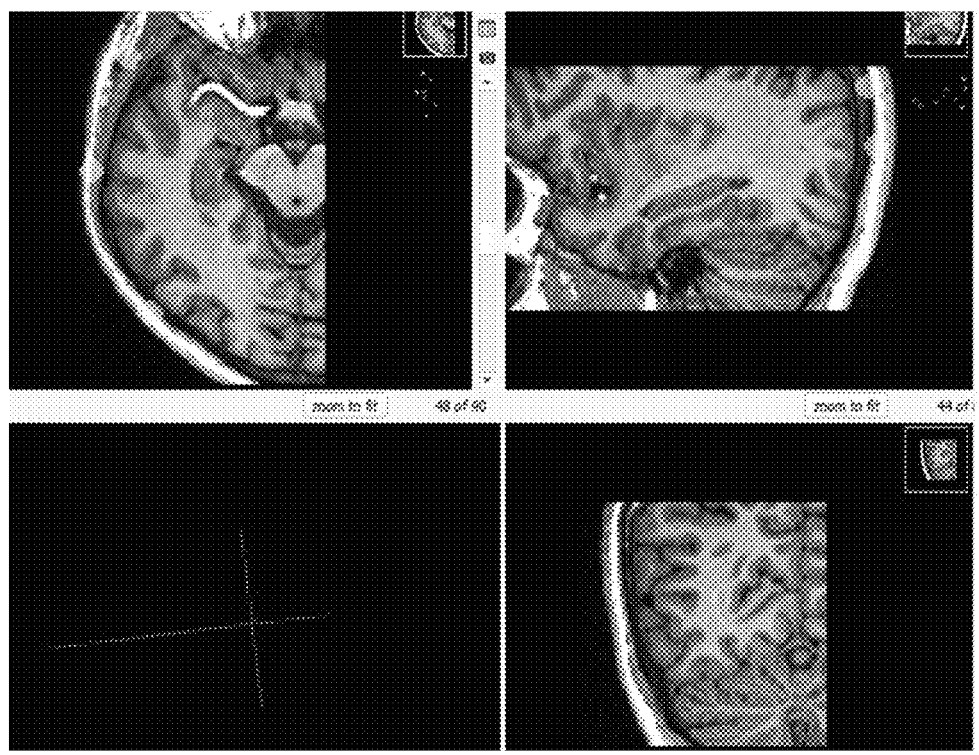

The server allows the user to mark tissue samples such as the WM and GM as shown in FIG. 27c. The server further provides a "train classifier" tool that allows the user to train the classifier by clicking on the "train classifier" tool. The server further renders a speed image that shows the classification. The "train classifier" tool assigns a probability value to a voxel belonging to the "foreground" class vs. belonging to all other classes. Once the classifier is trained using the manual segmentation (i.e., marking and differentiating the tissue samples, Right Temporal Lobes, ICV, and the Ventricles) the classifier automatically segments at least one structure within the one or more first images of a different patient in future based on micro-ethnicity information, age and gender and the like. The server provides a "Next" tab to complete the process.

Figure 27D:
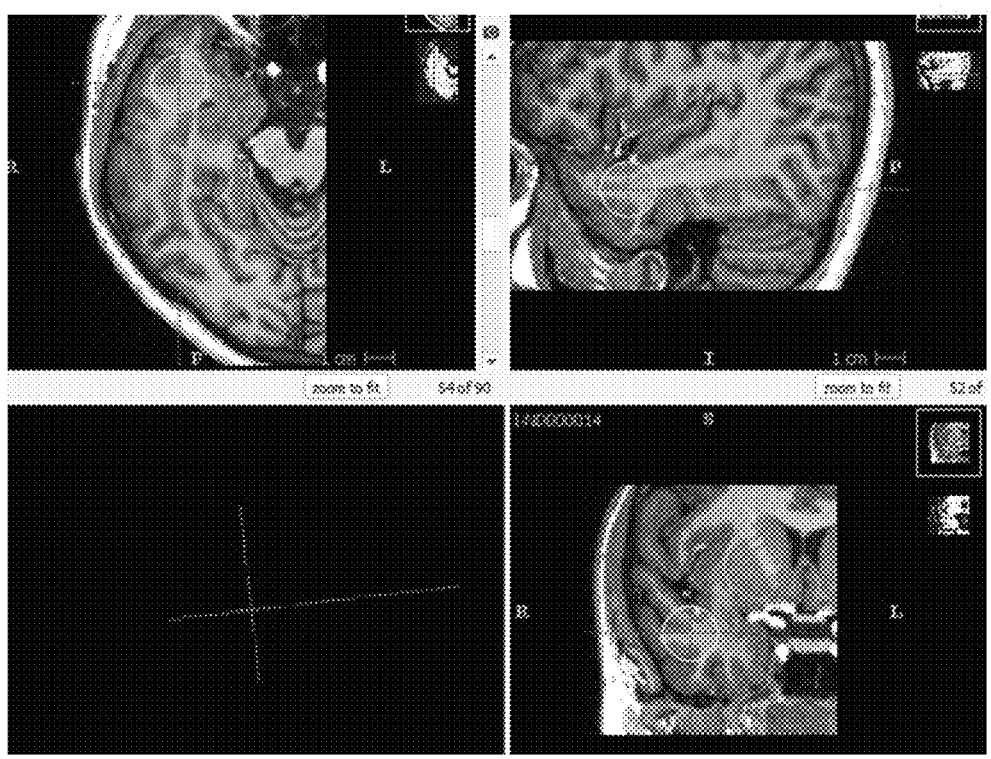
Figure 27E:
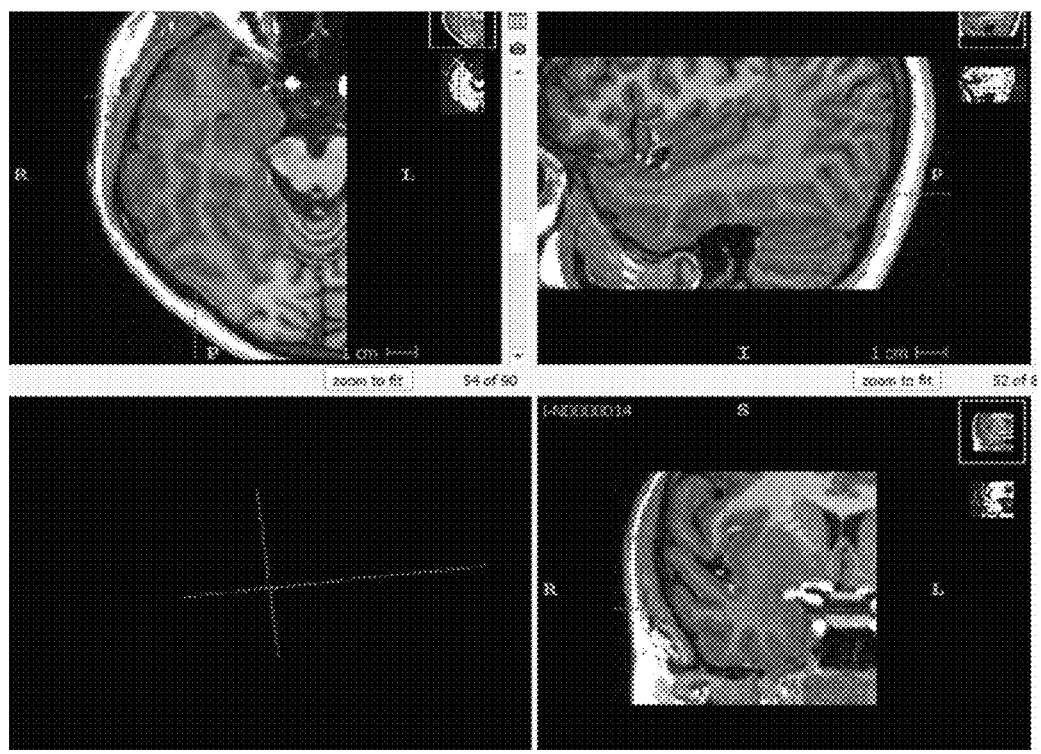

The server provides a "Add bubble at cursor" tool that allows the user to populate bubbles of appropriate sizes exactly in the Right Temporal Lobes, as shown in FIG. 27d, in at least three anatomical planes to exactly extract the volume of the Right Temporal Lobes. Further the server provides a "Bubble radius" slider that allows the user to vary the size of the bubbles. The server further provides an "active bubbles" drop down menu that shows the bubbles and its radius that are active. The server allows the user to add a sufficient number of bubbles in the Right Temporal Lobes as shown in FIG. 27e. The server provides a "Next" tab to finalize bubbles' evolution.

Figure 27F:
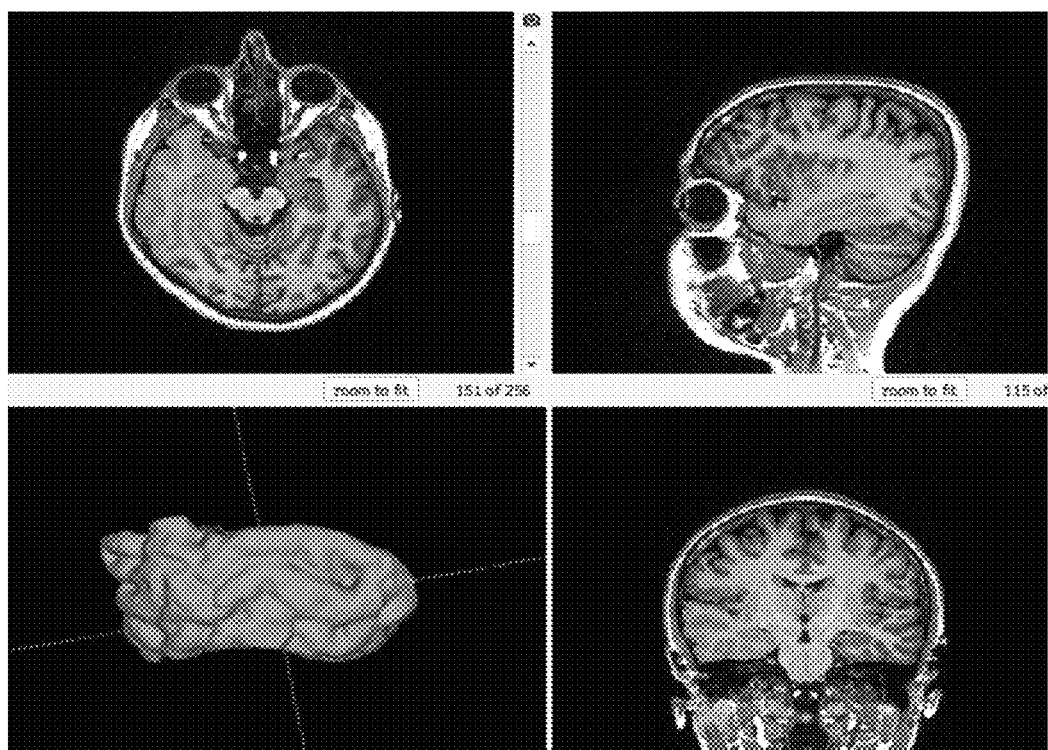

The server provides a "continuous update" that enables it to continuously update contour evolution. The server further provides a "play" tab that allows the user to run, play, and pause Active Contour Evolution as shown in FIG. 27f. The server further provides a "finish" tab that allows the user to submit when the active contour evolution is done. In an embodiment, the server allows the user to change the "active label" to "clear label" and delete the voxels when the active contour evolution goes out of the boundaries of the Right Temporal Lobes. The server allows the user to edit the voxels by accessing the "brush" tool and selecting appropriate brush and appropriate brush size. In another embodiment, the server allows the user to change the "active label" to "Right Temporal Lobes" and add the voxels when the active contour evolution has not reached any part of the Right Temporal Lobes. The server allows the user to edit the voxels by accessing the "brush" tool and selecting appropriate brush and appropriate brush size.

Figure 27G:
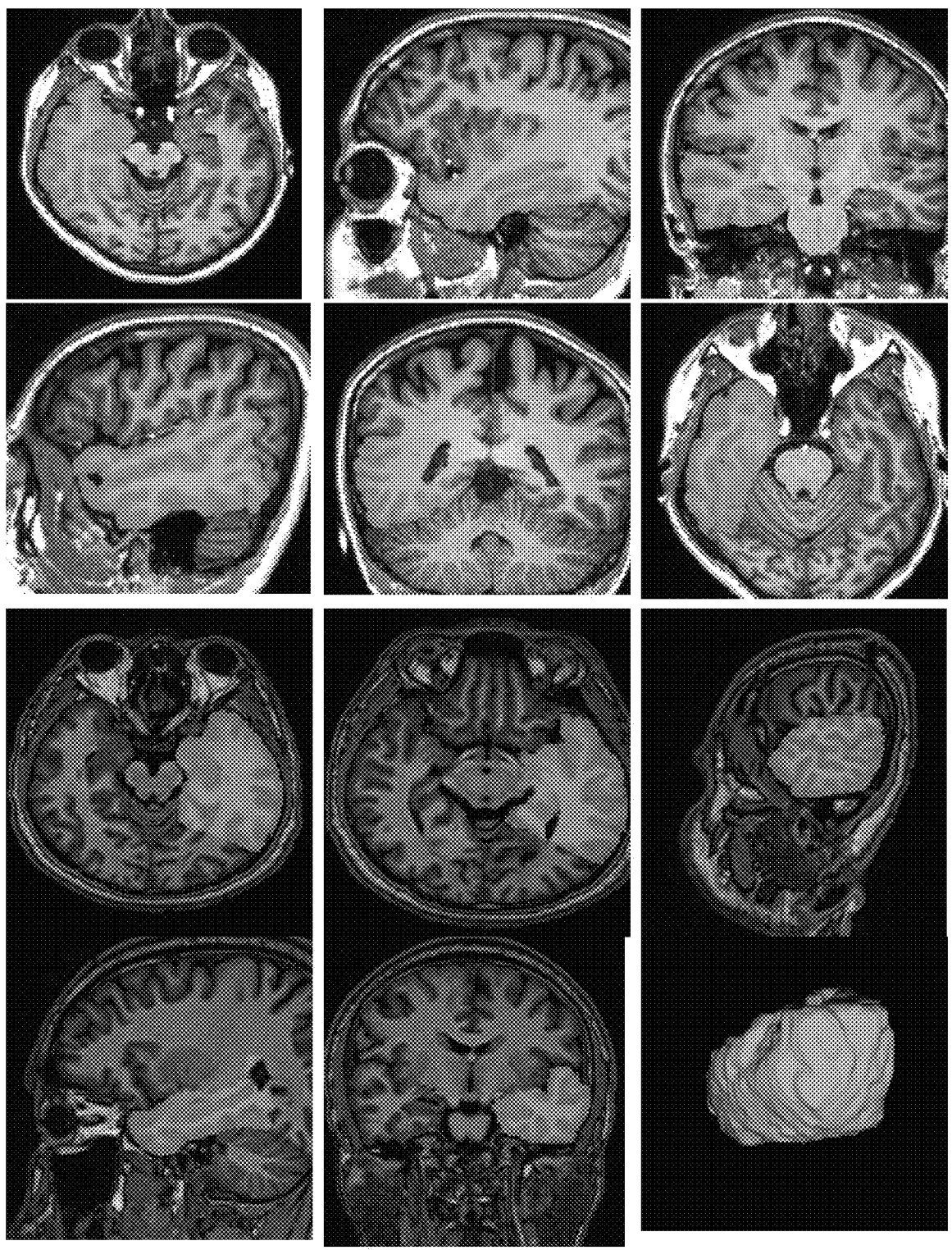

The server may render and save the Right Temporal Lobes in at least one anatomical pane and in three-dimensional format under the "Active Label" as "Right Temporal Lobes". Once the segmentation and volume extraction of the Right Temporal Lobes are complete, the server enables a user to save one or more first images, the workspace, the mesh and the one or more segmented image with a patient id name. The server enables a user to place the directory location for the image files in the patient ID folder. The server enables the user to capture screenshots of the segmented image at all anatomical planes in such a way that Right Temporal Lobes are displayed well with labels. The server further allows the user to capture screenshots of the segmented image in a three-dimensional image format with the Right Temporal Lobes zoomed in and displayed well. The server is configured to repeat the above steps for the Left Temporal Lobes. The RGB values for the Left Temporal Lobes are: R-210, G-140, B-206. The server provides an "accept" tab that allows the user to accept and update the segmentation of 3D view format. FIG. 27g illustrates the boundaries of the Temporal Lobes. The lobe extends superiorly to Sylvian fissure. Posteriorly, the lobe is differentiated by Lateral Parietotemporal line, which separates the Temporal Lobe from Inferior Parietal Lobule of the Parietal Lobe superiorly and the Occipital Lobe inferiorly.

FIGS. 28a and 28b illustrate a structure-based analysis report showing a structure-based analysis, according to one or more embodiments. The structure-based analysis report comprises a patient details section, a snippet section, a volumetric analysis section, a feature, and a volumetric derived analysis section. The feature comprises at least one of the one or more volumes of the region of interest (ROI), a cortical thickness, an atrophy percentage, an asymmetry index score, a subfield volumetry of the region of interest, annular volume changes, a progressive supranuclear palsy (psp) index score, a magnetic resonance perfusion imaging (MRPI) score, a frontal horn width to intercaudate distance ratio (FH/CC), a medial temporal lobe atrophy (MTA) score, a global cortical atrophy (GCA) scale, identification of Intracranial bleeds, hemorrhage, microbleeds and their volume analysis, a fracture detection, a midline shift identification, a measurement of the midline shift identification and the at least one structure with respect to the midline shift identification, identifying a pathology associated with the at least one structure, classifying the pathology identified, a tissue density identification, an infarct identification, a Penumbra-core-viable tissue identification, classification and volume calculation, diffusion-weighted imaging (DWI) maps and apparent diffusion coefficient (ADC) maps of the at least one structure, perfusion maps comprising resting state functional magnetic resonance imaging (rsfMRI), an alberta stroke programme early CT score (ASPECTS) calculation, a collateral detection, a mismatch ratio calculation, an angiography labeling and/or annotation, a large vessel occlusion (LVO) detection, an Hypoperfusion index calculation, Diffusion tensor imaging (DTI) fiber tracks, neural pathway connectivity maps, correlation between a signal input, an image input and the text input, classifying the signal input, identifying a normal signal, identifying an abnormal signal, identifying a pre-ictal signal, identifying an ictal signal, extracting symptoms, and grading of condition specific effects. The patient details section comprises information related to a patient such as an age, a gender, a site ID, a patient ID, a patient name, a patient contact, an exam date, and referring physician information (e.g., a referring physician ID, referring physician name, etc.). The snippet section may comprise quantitative volume such as whole brain volume, an intracranial volume (ICV), and a brief summary of output of the analysis report. The brief summary may comprise clinical information indicating volume loss and volume loss percentage, if any. The clinical information comprises symptoms, existing conditions, etc. The brief summary further indicates abnormalities in volumes of at least one structure. The brief summary may also indicate normality in volumes of at least one structure.

The volumetric analysis section shows volumes of at least one structure, volume as % ICV, and reference range of the at least one structure. The reference range is estimated between 25th and 95th percentile. The volumetric derived analysis section shows one or more derived analyzes that are derived from the one or more volumes extracted. The volumetric derived analysis shows the corresponding output and reference values. The volumetric derived analysis section may comprise age expected atrophy, total atrophy percentage, Whole Brain, Hippocampus. Hippocampus Asymmetry index, Lobar Asymmetry index, annual volume changes, etc.

The structure-based analysis report may also comprise a graphical representation of volumetric changes. The graphic representation of volumetric changes depicts a time series volumetric changes over time that aids physicians in their assessment of a patient's prognosis and diagnosis. The analysis report may also comprise a pictorial representation of volumes. The pictorial representation of volumes shows orientation, position, shape, and volumes of at least one structure within the segmented image. The pictorial representation of volumes depicts the segmented image in at least one of a three-dimensional format, and an anatomical plane.

FIG. 29a-29c illustrate an integrated analysis report showing an integrated analysis of an image input, a text input, and a signal input, according to one or more embodiments. The integrated analysis report depicts a cognitive test result prepared by performing the integrated analysis of the image input, the text input, and the signal input.

The integrated analysis report shows the one or more physiological signals comprising at least one spike that indicates if there are any abnormalities. The integrated analysis report may show the feature, and the one or more volumes in a three-dimensional format, and at least one anatomical plane that is rendered to the user to investigate, analyze, edit, and/or correct the one or more volumes. The integrated analysis report renders the one or more physiological signals comprising at least one spike and the one or more volumes, and the one or more quantitative volumes parallelly. This aids the user (e.g., physician) to perform predictive prognosis, diagnosis and predict atrophy changes. The integrated analysis report further aids the user to ensure that an analysis, determined via a first input (e.g., the image input), is correct by performing the analysis determined via a second input (e.g., the signal input). In other words, the analysis report enables the user to ensure the accuracy of the output by comparing the outputs of the patient in a first dimension (e.g., obtained via the image input), and a second dimension (e.g., obtained via the signal input).

The integrated analysis report comprises at least one of the feature, a patient details section, a snippet section, a volumetric analysis section, and a volumetric derived analysis section. The patient details section comprises information related to a patient such as an age, a gender, a site ID, a patient ID, a patient name, a patient contact, an exam date, and referring physician information (e.g., a referring physician ID, referring physician name, etc.). The snippet section may comprise clinical information. The clinical information comprises symptoms, existing conditions, additional info (applicable history/family history, etc.), and cognitive function test, etc. The integrated analysis report further renders cognitive test output. The analysis report further comprises the Mill volumetric analysis section. The MRI volumetric analysis section comprises pictorial representation of one or more volumes in at least one anatomical plane. The MRI volumetric analysis section further renders cortical image and at least one segmented image.

The integrated analysis report further comprises a cortical analysis section, and structural volumetric analysis section. The cortical analysis section comprises absolute volumes and relative volumes of the at least one structure such as cerebrospinal fluid, grey matter, white matter, and cortical thickness. The structural volumetric analysis section comprises quantitative volume (ml), volume as ICV % and reference range for at least one structure. The reference range may be the 25th percentile and the 95th percentile. The structural volumetric analysis section further comprises graphical representation illustrating the recorded volume with respect to age. The graphical representation clearly illustrates a plot of the recorded volume, the 25th percentile, the 95th percentile and the 50th percentile that aids the doctors in their assessment.

The integrated analysis report further comprises a volumetric derived analysis section. The volumetric derived analysis section indicates analysis, output and reference range. The integrated analysis report further comprises a time series volumetric changes section. The time series volumetric changes section depicts graphical representation that shows changes in volumetric measurement of the at least one structure over time. The time series volumetric changes section aids the physicians in performing their assessment. The integrated analysis report further comprises a Diffusion Tensor Imaging (DTI) and functional output section that indicates at least one of normality or abnormality in at least one organ. The DTI and functional output section comprise at least one structure in three-dimensional format and at least one anatomical plane. The DTI and functional output section indicate functional mapping of the at least one organ based on an imaging technique (e.g., Blood oxygenation level dependent (BOLD) imaging technique) to map different connectivity maps. The DTI and functional output section help in understanding disease affected areas and related cognitive/functional deficits for different functionalities such as executive and summary, motivation, decision-making, attention, orientation, etc.

The integrated analysis report further comprises a signal monitoring and recording section. The signal monitoring and recording section records at least one region of the one or more physiological signals that comprises spike indicating one of abnormality or normality in functioning of the at least one organ. The signal monitoring and recording section highlights and quantifies the region comprising at least one spike (for alpha, Beta and gamma waves) that is responsible for the abnormality or normality of the at least one organ with correlated temporal resolution. The analysis report further comprises a summary of findings. The summary of findings shows symptoms, at least one spike information, etc. from the at least one spike.

FIGS. 30a-30b illustrate an EEG detailed report, according to one or more embodiments. The EEG detailed report comprises a feature, an information/recording conditions section, a modulators/procedures section, a findings section, polygraphy channels section, a summary of findings section and a screenshot section. The information/recording conditions section comprises information pertinent to recording time, recording date, recording period, study ID, medical condition, alertness, etc. The modulators/procedures section comprises sensitivity information such as eye-closure sensitivity and other responses acquired from the patient. The modulators/procedures section may also comprise event related potential responses received from a patient. The findings section comprises background activity, sleep/drowsiness, Interictal findings, episodes, artifacts, if any. The background activity comprises information related to background such as amplitude, frequency, activity in response to the signal, etc. The sleep/drowsiness comprises sleep stages. The artifacts section comprises artifacts information such as low voltage, and lack of compliance. The polygraphy channels section comprise channel information acquired through one or more channels. The summary of findings section comprises symptoms, medical conditions, regions having at least one spike indicating abnormality, etc. and conclusion of the findings. The summary of findings section further comprises diagnostic significance, and clinical components. The clinical components section describes the diagnosis that is suitable for this patient based on the inference done. The screenshot section comprises screenshots of at least one physiological signal supporting the above findings and other inferences illustrated in the EEG detailed analysis report. The EEG detailed report further comprises graphical representation of EEG reports along with ICU monitoring of at least one spike and/or pre ictal detection. The EEG detailed report further comprises information comprising spectral analysis.

FIG. 31 illustrates monitoring of one or more physiological signals, according to one or more embodiments. A server is capable of receiving one or more physiological signals in real-time. The server may also receive the one or more physiological signals that are acquired and recorded previously. The server analyzes and monitors the one or more physiological signals for a predefined period of time. The server is pre-trained with the one or more physiological signals without any abnormal spikes and the one or more physiological signals having abnormal spikes. The server then analyzes the one or more physiological signals and detects at least one spike and/or pre-ictal that indicates abnormality, if any. The server upon finding the at least one spike, indicating abnormality, highlights a region, comprising the at least one spike using one or more identifiers with correlated temporal resolution, to the user to aid in their assessment. The server is also capable of performing spectral analysis and indicating amplitude, frequency and other related parameters that may impact the functioning of the at least one organ.

FIG. 32a illustrates a screenshot of a user interface that allows a user to upload patient details, according to one or more embodiments. A server, via a user interface depicted herein, allows the user to provide the inputs such as at least one of an image input, a text input, and a signal input. The server via the user interface allows the user to drag and drop and/or select one or more first images from an image source. The server, via the user interface, allows the user to enter the text input such as name, age, gender and select symptoms, micro-ethnicity, and medical conditions from a drop-down box. The server also allows the user to enter a referring physician's name. The server further provides a 'submit' tab that allows the user to submit the inputs and create a record once the inputs are provided.

FIG. 32b illustrates a screenshot of a user interface that allows a user to view patient details, according to one or more embodiments. The user herein may be a radiologist. The user interface view, depicted herein, provides a 'View patients' tab that allows the user to view patient details. The user interface shows a site ID, a patient age, a patient gender, a symptom, a medical condition, and an exam date when the user has accessed the 'View patients' tab. The site ID comprises information that helps to recognize a site from where the inputs are scanned, obtained and/or uploaded. The exam date refers to a date at which the patient is examined. The user interface depicts the patient details. However, identification information (e.g., facial information, name, locality, address, etc.) that are adapted to recognize an identity of the patient is anonymized i.e., not shown to the user.

The user interface further shows volumetric analysis of at least one structure or organ (e.g., cardiovascular organ, neural organ, orthopedic organ, etc.) of the patient. The volumetric analysis shows one or more quantitative volumes associated with the at least one structure or the organ. For example, when the inputs (e.g., the text input, the image input, and the signal input) related to brain is uploaded, the volumetric analysis shows the one or more quantitative volumes of the at least one structure associated with the brain such as intracranial volume (ICV), whole brain, ventricles, Lt. Hippocampus, Rt. Hippocampus, Lt. Temporal Lobe, Rt. Temporal Lobe, etc. The user interface further depicts the one or more quantitative volumes such as volumes in ml, volume as % ICV for the at least one structure and reference ranges for the at least one structure. The user interface also highlights the one or more quantitative volumes with a different color to readily identify and indicate that the values are out of the reference range.

FIG. 32c illustrates a screenshot of a user interface rendering a segmented image, according to one or more embodiments. The user interface shown in FIG. 32d renders the segmented image in a three-dimensional format and an anatomical plane. The server, via the user interface, allows the user to select and view a portion of the segmented image in an enhanced view. The enhanced view may be a zoomed view. The anatomical plane may comprise at least one of a parasagittal plane, a sagittal plane, a coronal plane, and an axial plane, etc. The server further allows the user to select the different anatomical plane and render the segmented image in the different anatomical plane. The server further allows the user to readily identify orientation, position, shape, and volumes of at least one structure within the segmented image and other information such as age, gender, ICV, and other micro-ethnicity information that may impact the volumes of the at least one structure.

FIG. 32d illustrates a screenshot of a user interface that allows a user to view patient details, according to one or more embodiments. The user herein may be a manager. The user interface, depicted herein, provides a 'View patients' tab that allows the user to view patient details. The user interface shows a site ID, a patient age, a patient gender, a symptom, a medical condition, and an exam date when the user has clicked the 'View patients' tab. The site ID comprises information to recognize a site from where the inputs are scanned, obtained and/or uploaded. The exam date refers to a date at which the patient is examined. The user interface renders the patient details. However, identification information (e.g., facial information, name, locality, address, etc.) that are adapted to recognize an identity of the patient, either digitally or manually, is anonymized i.e., not shown to the user.

The user interface further shows volumetric analysis of at least one structure or organ (e.g., cardiovascular organ, neural organ, orthopedic organ, etc.) of the patient. The volumetric analysis shows one or more quantitative volumes associated with the at least one structure or the organ. For example, when the inputs (e.g., the text input, the image input, and the signal input) related to brain is uploaded, the volumetric analysis shows the one or more quantitative volumes of the at least one structure associated with the brain such as intracranial volume (ICV), whole brain, ventricles, Lt. Hippocampus, Rt. Hippocampus, etc. The user interface further depicts the one or more quantitative volumes such as quantitative volumes (ml), volume as % ICV for the at least one structure, and reference ranges for the at least one structure. The user interface also highlights the one or more quantitative volumes with a different color to readily identify and indicate that the values are out of the reference range.

FIG. 33 illustrates processing of EEG signals, according to one or more embodiments. A server processing the EEG signal input comprises a) accepting data, b) pre-processing the data, c) data representation, d) post processing the data, e) EEG MRI overlay, f) report generation, g) cloud storage, h) building ERP pipeline for Dementia and neurodegeneration, and i) ICU monitoring. The server accepts the EEG signal from hardware itself where the server integrates with the hardware itself and accepts raw data in the form of EDF. In another embodiment, the EEG signal will be pushed to the server by the technician/doctor via a web application. The pre-processing of the raw data comprises sequential steps such as importing raw data, event markers, artifacts removal, interpolation, channel type selection/channel location, referencing/re-referencing, filtering, epoching, characteristics extraction and characteristics selection, classification/statistical manipulation and result evaluation. The data once pre-processed can be represented in several ways both in frequency domain and time domain. The most common format of data representation is in the form of a sinusoidal graph. The representation of the EEG signal in various formats assists in deeper understanding of the patient's condition. The formats comprise spectral analysis graphs, Fast Fourier Transform (FFT) analysis, amplitude graphs, asymmetry graphs, spatial representation of EEG data, etc.

The post processing comprises characteristic Extraction/Selection, that is to Identify statistically significant characteristics (e.g.—Spike in epilepsy) using at least one of Multivariate time series analysis, Wavelet transform (Time-frequency), Fourier transform (Frequency Domain), Principal component analysis (Time Domain), independent component analysis (ICA), etc. The post processing is continued by optimal parameter and characteristics set identification (e.g.,—characteristic shuffle analysis, ranking characteristics) and classification/statistical Manipulation of the signals applying various machine learning algorithms [e.g.,—Linear discriminant analysis (LDA), Multi-layer perceptron (MLP), Support vector machine (SVM), etc.]

The server further allows a user to overlay the EEG signal on the MRI Image as a Heat map for better visualization of the signal. The overlaying enables the user to better do surgical planning, because they better understand where the seizure is originating, and it helps them kind of understand the source of the seizure. The server stores all patient related data in the cloud and enables the user to access the data using a user ID. The server acquired event related potentials (ERP) from the patient and builds clinical endpoints in dementia and Mild cognitive impairment. The server then generates a report once the clinician has entered the patient history and has selected the at least one analysis. The server is further capable of performing intensive care unit (ICU) monitoring and detecting abnormalities. The server establishes a baseline of the normal EEG signal of the patient and points out any abnormalities in real time to alert the clinicians of any ongoing seizures.

FIG. 34 illustrates a data flow of a system, according to one or more embodiments. The data flow comprises sequential flow of data as described below. At step 3402, an upload page is rendered to a user by a server that allows the user to upload inputs upon logging into the server. At step 3404, the server allows the user to provide text inputs such as age, gender, symptom, medical condition, referring physicians, micro-ethnicity, etc. and DICOM format files. At step 3406, the server allows the user to submit DICOM files upon providing the details. The server further checks whether the DICOM format files have more than 1.5 Tesla and enables the user to check whether DICOM format files have predefined quality and quantity, at step 3408. The server also checks whether the DICOM format files are 3D gradient echo (GRE) ISO sequences, at step 3410. At step 3412, when the server detects upload error (i.e., not having pre-defined quality and quantity) or incorrect files, the server directs the user to the upload page again.

At step 3414, the server directs the uploaded DICOM format files to pre-processing, when the server detects that the uploaded DICOM files are optimum or good. At step 3416, the server converts the DICOM format files to NIfTI format files for data anonymization. At step 3418, the server performs denoising i.e., filtering noises from the inputs. At step 3420 and 3422, the server performs bias correction and matrix adjustments (reorient the image) respectively to make the uploaded files suitable for image segmentation. At step 3424, the server stores the files in S3 bucket. At step 3426, the server calls the uploaded files to the core application programming interface (API) for segmentation. At step 3428, the server performs image segmentation on the NIfTI format files. At step 3430, the server records the segmented files under a worklist of the corresponding user (e.g., physician, manager, admin etc.) as per privileges granted by the server. At step 3432, the server is enabled to extract image files from the S3 bucket and renders the image files for viewing, analysis and editing purposes. At step 3434, the server displays the image files (e.g., segmented images, analysis report, etc.) using a viewer configured (e.g., papaya viewer).

FIG. 35 illustrates a workflow diagram of a server, according to one or more embodiments. The workflow illustrates a sequential flow performed by the server. At step 3502, the server renders an upload page to a user upon login. At step 3504, the server receives the uploaded inputs and records case details online in a database to be accessed by the user. At step 3506, the server reorients the image. At step 3508, the server defaces the images to recognize the identity of the patient. At step 3510, the server then stores the inputs in S3 bucket for retrieval, editing, viewing, and future uses. At step 3512, the server calls core application programming interface (API) to process the case. At step 3514, the server downloads the case details from the S3 bucket. At step 3516, the server performs image segmentation. At step 3518, the server uploads the segmented images to S3 bucket. The uploaded segmented images may be utilized for study, analysis, investigation, volumetric extraction, volumetric analysis, atrophy, and predictive prognosis and diagnosis. In an embodiment, the server performs multimodal analysis and cross checks with other modes of analysis and ensures the accuracy of predictive prognosis, diagnosis and atrophy determination.

FIG. 36 further illustrates an architecture of a system, according to one or more embodiments. The architecture depicts that a user can communicate with a server through one of a product interface 3602, and a web interface 3604. The server may comprise a platform 3606 and core API 3608. The core API 3608 comprises segmentation API 3610 and core algorithm 3612. The core algorithm 3612 is configured to handle requests, coordinate functions, etc. The segmentation API 3610 is configured to perform image segmentation and other volumetric derived analysis. The platform 3606 comprises an upload API 3614, persistence script 3616, reorientation script 3618, and defacer script 3620. The upload API 3614 is configured to enable the user to upload the inputs such as image, text, and signal inputs. The persistence script 3616 enables the server to withstand optimum quality of the inputs. The reorientation script 3618 enables the server to reorient the images. The defacer script 3620 further enables the user to perform anonymization to break the link between data and a given participant so that the participant cannot be identified, directly or indirectly.

FIG. 37 illustrates an architecture of a system, according to one or more embodiments. The architecture shown comprises one or more computing units 3702 (A-N) communicating to a server via a communication network. The communication network may be a wireless communication network or a wired communication network. The computing unit communicates to the server using a product interface or a web interface though a secured internet gateway 3704. The server comprises a public subnet 3706 and private subnet 3708. The server, in an embodiment, comprises a graphical processing unit. The public subnet 3706 and the private subnet 3708 are secured. The private subnet 3708 comprises a core API 3710 and a platform API 3712. The platform API 3712 and the core API 3710 are already described in FIG. 36. The one or more computing units 3702 A-N communicate to the private subnets 3708 via the load balancers 3714 and 3716. The server stores the processed and raw inputs in an S3 bucket 3720. The public subnet may comprise a virtual private network (VPN) server 3718.

FIG. 38a-38e illustrate an analysis report generated based on condition specific analysis, according to one or more embodiments. A server receives input as at least one of an image input, a text input, and a signal input. Depending on the available data, the server performs the multimodal analysis. The server may extract the text input of relevant information using a natural language processing module from a text or documents stored on the Hospital Information System (HIS). The NLP module may extract relevant information such as symptoms, clinical history (e.g., vitamin deficiency, family history, genetic history, trauma, etc), and cognitive test analysis like Computerized Cognitive Testing in Epilepsy (CCTE), Montreal Score, Cambridge Neuropsychological Test Automated Battery (CANTAB), Mini Mental State Examination (MMSE), Mini-Cog, and the like.

The server may also receive the text input such as an electroencephalogram (EEG) signal. The server upon receipt of the EEG signal may monitor the signal input and detect abnormalities in the EEG signal with correlated temporal resolution either with Structural Magnetic Resonance Imaging (sMRI) or others. The server can acquire the EEG signal in real-time and monitoring abnormality of the EEG signal. The server is also capable of correlating the detected abnormality with other image input (such as scan images) to double-check/ensure the abnormality in the patient's health. The server receives the image input as at least one of sMRI, fMRI, CT, DTI, PET, etc.

The sMRI may be used to perform structural volumetric analysis based on 3D MRI correlated with normative population (specific to ethnicity) as well as condition specific population, cortical thickness analysis, subfield analysis, etc. The fMRI may be used to perform functional mapping of the brain based on 'BOLD' imaging technique to map different connectivity maps. The fMRI image input helps in understanding disease affected areas and related cognitive/functional deficits. The fMRI has poor temporal resolution and involves complex processing to understand which connectivity networks are involved & affected. The server can provide both fused images with structural MRI as well as automated connectivity maps where the problematic areas will be pointed out for physician's review. Upon receiving the CT input, the server provides structural as well as perfusion-based analysis of the CT images to derive a first look into the disease pattern.

The server receives the DTI and performs White matter tracts analysis. White matter tracts analysis has become the core of surgical planning in many conditions. The server provides automated DTI analysis highlighting the changes in the tracts. The server may receive the PET and perform functional analysis based on contrast uptake. As PET provides good spatial resolution with poor temporal information, the server help physicians understand temporal information by fusing PET with MRI and produce such overlays which can be visualized easily The server also provides a user interface to upload patient details in which users can enter a specific medical condition of a patient (e.g., epilepsy). The server upon receiving the medical condition enables it to perform a condition specific analysis. The condition specific analysis is performed by following steps. Consider the patient is having the medical condition as Epilepsy. The server then compares age, gender, ICV, micro-ethnicity information of the patient with a condition specific population i.e., (a population of individuals having the medical condition as epilepsy). In one embodiment, the server compares the information of the patient with the normative population (i.e., wide analysis). The server, in this embodiment, predicts a prognosis and analyzes the deterioration or improvement in volumetric changes, quantitative volume, abnormality of the patient.

In another embodiment, the server compares the information of the patient with a condition specific population (i.e., population of the individuals having the same medical condition as epilepsy) i.e., narrow down analysis. The server, in this embodiment, performs a prognosis, accurate diagnosis. The server, by performing a condition specific analysis, can perform a predictive prognosis over time, accurate diagnosis and comprehensive management of patient's health. The comprehensive management of the patient's health is performed by performing a predictive prognosis over time.

For instance, consider the server has predicted a first prognosis for a condition specific analysis for a first point of time. The first prognosis is predicted for the first point of time considering the medication information (e.g., medication that the patient has intake during the first point of time) of the patient and other relevant information. The first prognosis may be performed via a multimodal analysis. The server has also predicted a second prognosis for a condition specific analysis for a second point of time. The second prognosis is predicted for the second point of time considering the medication information (e.g., medication that the patient has intake during the second point of time) of the patient and other relevant information. The second prognosis may be performed via a multimodal analysis. The server is also capable of determining deterioration or improvement in at least one volumetric changes and quantitative volumes by comparing the first prognosis and the second prognosis. The server determines the deterioration or the improvement, in terms of percentage, between the first prognosis and the second prognosis. The server is then trained with different values of the deterioration or the improvement over time. The server is then capable of determining the deterioration or improvement in the volumetric changes and quantitative volumes for a third point of time (in future) based on the training provided. The server determines the deterioration or the improvement in quantitative values for the third point of time. The quantitative values of the deterioration or the improvement in the future enables and assists the physicians to treat/change the medication regime for the patient accordingly.

FIG. 38a-38e depicts the analysis report generated based on condition specific analysis. Once the medical condition (e.g., epilepsy) is specified, the server compares the information (age, gender, ICV, micro-ethnicity) of the patient with the condition specific population (i.e., individuals who are having epilepsy symptoms). The server then derives the 25th and the 95th percentile which are then used as the customized references in performing the predictive prognosis, accurate diagnosis and comprehensive management. The quantitative volumes, and the volumes of the patient which fall between the values of the 25th and the 95th percentile are considered to be healthy/normal. The quantitative volumes, and the volumes of the patient which falls beyond/outside the 25th and the 95th percentile are considered to be unhealthy/abnormal.

The analysis report shown in FIGS. 38a-38e is similar to FIGS. 28 and 29. The analysis report, shown in this embodiment, illustrates a condition specific integrated analysis of image, signal and text inputs. The analysis report comprises an output section which clearly describes a clinically analytical output obtained from an integrated and condition specific analysis. The output section points out an abnormality with respect to each input. The analysis report comprises a clinical information section which provides details about symptoms, existing conditions, and cognitive function test. An MRI volumetric analysis section renders an image of the region of interest which aids the physician to examine the volumes of the region of interest. The analysis report also renders segmented images.

The analysis report also comprises a cortical analysis section which comprises volume information of at least one of CSF, grey matter, white matter, and cortical thickness. The analysis report further comprises a structural volumetric analysis section which comprises volumes of the structures, volume as ICV %, and their reference ranges (i.e., 25th and 95th percentile). The analysis report further comprises a graph indicating condition specific population comparison with the recorded volumes of the patient. The analysis report further comprises a volumetric derived analysis section which indicates the differences in recorded volumes and the reference ranges. The volumetric derived analysis section also shows annual volume changes based on the derived analysis. The analysis report further shows a graph indicating time series volumetric changes at different points of time. The analysis report further renders a DTI and functional output which provides structural connectivity and functional connectivity information. The DTI and functional output also render connectivity mapping. The analysis report further comprises an EEG analysis section which indicates/highlights abnormal spikes. The abnormal spikes may be used to correlate with other temporal resolution either with sMRI or other inputs and perform an integrated analysis.

The foregoing disclosure provides illustration and description, but is not intended to be exhaustive or to limit the implementations to the precise form disclosed. Modifications and variations are possible in light of the above disclosure or may be acquired from practice of the implementations.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, etc. The invention may also be practiced in distributed system environments where local and remote computer systems, which are linked (either by hardwired data links, wireless data links, or by a combination of hardwired and wireless data links) through a network, both perform tasks. In a distributed system environment, program modules, units may be located in both local and remote memory storage devices.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Although the present embodiments have been described with reference to specific example embodiments, it will be evident that various modifications and changes may be made to these embodiments without departing from the broader spirit and scope of the various embodiments. For example, the various devices, units and modules described herein may be enabled and operated using hardware circuitry (e.g., CMOS based logic circuitry), firmware, software or any combination of hardware, firmware, and software (e.g., embodied in a non-transitory machine-readable medium). For example, the various electrical structures and methods may be embodied using transistors, logic gates, and electrical circuits (e.g., application specific integrated circuitry (ASIC) and/or Digital Signal Processor (DSP) circuitry).

In addition, it will be appreciated that the various operations, processes, and methods disclosed herein may be embodied in a non-transitory machine-readable medium and/or a system. Accordingly, the specification and drawings are to be regarded in an illustrative rather than a restrictive sense.

INCORPORATION BY REFERENCE

All patents, patent application publications, and non-patent literature mentioned in the application are incorporated by reference in their entirety.

G.B.D. Disease and Injury Incidence and Prevalence Collaborators, "Global, regional, and national incidence, prevalence, and years lived with disability for 328 diseases and injuries for 195 countries, 1990-2016: a systematic analysis for the global burden of disease study 2016," Lancet, vol. 390, pp. 1211-1259, 2017;

World Health Organization, Epilepsy: A Public Health Imperative, World Health Organization, Geneva, Switzerland, 2019;

M. Prince, A. Wimo, M. Guerchet, G. C. Ali, Y. T. Wu, and M. Prina, "The global impact of dementia. An analysis of prevalence, incidence, cost and trends," World Alzheimer Report 2015, Alzheimer's Disease International (ADI), London, U K, 2015;

H. A. Born, "Seizures in Alzheimer's disease," Neuroscience, vol. 286, pp. 251-263, 2015;

W. A. Hauser, M. L. Morris, L. L. Heston, and V. E. Anderson, "Seizures and myoclonus in patients with Alzheimer's disease," Neurology, vol. 36, no. 9, p. 1226, 1986;

N. Scarmeas, L. S. Honig, H. Choi et al., "Seizures in Alzheimer's disease: who, when, and how common?" Archives of Neurology, vol. 66, no. 8, pp. 992-997, 2009;

Y. Holler and E. Trinka, "What do temporal lobe epilepsy and progressive mild cognitive impairment have in common?" Frontiers in Systems Neuroscience, vol. 8, 2014;

P. Fischer, S. Jungwirth, S. Zehetmayer et al., "Conversion from subtypes of mild cognitive impairment to Alzheimer dementia," Neurology, vol. 68, no. 4, pp. 288-291, 2007;

C. B. Dodrill, "Neuropsychological effects of seizures," Epilepsy & Behavior, vol. 5, pp. 21-24, 2004;

Y. Holler and E. Trinka, "Is there a relation between EEG slow waves and memory dysfunction in epilepsy? a critical appraisal," Frontiers in Human Neuroscience, vol. 9, 2015;

M. D. Holmes, C. B. Dodrill, R. J. Wilkus, L. M. Ojemann, and G. A. Ojemann, "Is partial epilepsy progressive? ten-year follow-up of EEG and neuropsychological changes in adults with partial seizures," Epilepsia, vol. 39, no. 11, pp. 1189-1193, 1998;

H. Stefan and E. Pauli, "Progressive cognitive decline in epilepsy: an indication of ongoing plasticity," Progress in Brain Research, vol. 135, pp. 409-417, 2002;

G. L. Holmes, "What is more harmful, seizures or epileptic EEG abnormalities? is there any clinical data?" Epileptic Disorders, vol. 16, no. NS1, pp. 12-22, 2014;

B. Bondi, N. Philippi, O. Bousiges et al., "Do we know how to diagnose epilepsy early in Alzheimer's disease?" Revue Neurologique, vol. 173, no. 6, pp. 374-380, 2017;

K. A. Vossel, A. J. Beagle, G. D. Rabinovici et al., "Seizures and epileptiform activity in the early stages of Alzheimer disease," JAMA Neurology, vol. 70, no. 9, pp. 1158-1166, 2013;

D. Friedman, L. S. Honig, and N. Scarmeas, "Seizures and epilepsy in Alzheimer's disease," CNS Neuroscience & Therapeutics, vol. 18, no. 4, pp. 285-294, 2012;

A. Horváth, A. Szu}cs, G. Bares, J. L. Noebels, and A. Kamondi, "Epileptic seizures in Alzheimer disease," Alzheimer Disease & Associated Disorders, vol. 30, no. 2, pp. 186-192, 2016;

K. A. Vossel, K. G. Ranasinghe, A. J. Beagle et al., "Incidence and impact of subclinical epileptiform activity in Alzheimer's disease," Annals of Neurology, vol. 80, no. 6, pp. 858-870, 2016;

S. Shorvon and E. Trinka, "Nonconvulsive status epilepticus and the postictal state," Epilepsy & Behavior, vol. 19, no. 2, pp. 172-175, 2010;

E. Trinka, G. Krämer, and K. Werhahn, "Vascular precursor epilepsy—old wine in new skins?" Epilepsy & Behavior, vol. 48, pp. 103-104, 2015;

K. A. Vossel, M. C. Tartaglia, H. B. Nygaard, A. Z. Zeman, and B. L. Miller, "Epileptic activity in Alzheimer's disease: causes and clinical relevance," The Lancet Neurology, vol. 16, no. 4, pp. 311-322, 2017;

A. Bakker, G. L. Krauss, M. S. Albert et al., "Reduction of hippocampal hyperactivity improves cognition in amnestic mild cognitive impairment," Neuron, vol. 74, no. 3, pp. 467-474, 2012;

A. D. Lam, G. Deck, A. Goldman, E. N. Eskandar, J. Noebels, and A. J. Cole, "Silent hippocampal seizures and spikes identified by foramen ovale electrodes in Alzheimer's disease," Nature Medicine, vol. 23, no. 6, pp. 678-680, 2017;

H. Hampel, S. J. Teipel, and K. Bürger, "Neurobiologische fruhdiagnostik der alzheimer-krankheit," Der Nervenarzt, vol. 78, no. 11, pp. 1310-1318, 2007;

P. Suppa, H. Hampel, T. Kepp et al., "Performance of hippocampus volumetry with FSL-FIRST for prediction of Alzheimer's disease dementia in at risk subjects with amnestic mild cognitive impairment," Journal of Alzheimer's Disease, vol. 51, no. 3, pp. 867-873, 2016;

A. C. Burggren, B. Renner, M. Jones et al., "Thickness in entorhinal and subicular cortex predicts episodic memory decline in mild cognitive impairment," International Journal of Alzheimer's Disease, vol. 2011, Article ID 956053, 9 pages, 2011;

G. C. Chiang, P. S. Insel, D. Tosun et al., "Identifying cognitively healthy elderly individuals with subsequent memory decline by using automated MR temporoparietal volumes," Radiology, vol. 259, no. 3, pp. 844-851, 2011;

J. J. Gomar, M. T. Bobes-Bascaran, C. Conejero-Goldberg, P. Davies, and T. E. Goldberg, "Utility of combinations of biomarkers, cognitive markers, and risk factors to predict conversion from mild cognitive impairment to Alzheimer disease in patients in the Alzheimer's disease neuroimaging initiative," Archives of General Psychiatry, vol. 68, no. 9, pp. 961-969, 2011;

M. M. Mielke, O. C. Okonkwo, K. Oishi et al., "Fornix integrity and hippocampal volume predict memory decline and progression to Alzheimer's disease," Alzheimer's & Dementia, vol. 8, no. 2, pp. 105-113, 2012;

P. Vemuri, H. J. Wiste, S. D. Weigand et al., "MRI and CSF biomarkers in normal, MCI, and AD subjects: predicting future clinical change," Neurology, vol. 73, no. 4, pp. 294-301, 2009;

H. Wolf, M. Grunwald, G. M. Ecke et al., "The prognosis of mild cognitive impairment in the elderly," Alzheimer's Disease—From Basic Research to Clinical Applications, vol. 54, pp. 31-50, 1998;

J. L. Woodard, M. Seidenberg, K. A. Nielson et al., "Prediction of cognitive decline in healthy older adults using fMRI," Journal of Alzheimer's Disease, vol. 21, no. 3, pp. 871-885, 2010;

S. Kovacevic, M. S. Rafii, and J. B. Brewer, "High-throughput, fully automated volumetry for prediction of MMSE and CDR decline in mild cognitive impairment," Alzheimer Disease & Associated Disorders, vol. 23, no. 2, pp. 139-145, 2009;

S. Alam, G.-R. Kwon, J.-I. Kim, and C.-S. Park, "Twin SVM-based classification of Alzheimer's disease using complex dual-tree wavelet principal coefficients and LDA," Journal of Healthcare Engineering, vol. 2017, Article ID 8750506, 12 pages, 2017;

A. Ayaz, M. Z. Ahmad, K. Khurshid, and A. M. Kamboh, "MRI based automated diagnosis of alzheimer's: fusing 3D wavelet-features with clinical data," in Proceedings of the 2017 39th Annual International Conference of the IEEE Engineering in Medicine and Biology Society (EMBC), pp. 1210-12130, Seogwipo, South Korea, July 2017;

S. Wang, Y. Chen, Y. Zhang, E. Lee, Z. Dong, and P. Phillips, "3D-DWT improves prediction of AD and MCI," in Proceedings of the First International Conference on Information Science and Electronic Technology, ISET 2015, pp. 60-63, Wuhan, China, March 2015;

A. L. Dallora, S. Eivazzadeh, E. Mendes, J. Berglund, and P. Anderberg, "Machine learning and microsimulation techniques on the prognosis of dementia: a systematic literature review," PLoS One, vol. 12, no. 6, Article ID e0179804, 2017;

D. S. Goodin, "Electrophysiologic evaluation of dementia," Neurologic Clinics, vol. 3, no. 3, pp. 633-647, 1985;

E.-L. Helkala, V. Laulumaa, H. Soininen, J. Partanen, and P. J. Riekkinen, "Different patterns of cognitive decline related to normal or deteriorating EEG in a 3-year follow-up study of patients with Alzheimer's disease," Neurology, vol. 41, no. 4, p. 528, 1991;

H. Soininen, J. Partanen, V. Laulumaa, E.-L. Helkala, M. Laakso, and P. J. Riekkinen, "Longitudinal EEG spectral analysis in early stage of Alzheimer's disease," Electroencephalography and Clinical Neurophysiology, vol. 72, no. 4, pp. 290-297, 1989;

V. Jelic, S.-E. Johansson, O. Almkvist et al., "Quantitative electroencephalography in mild cognitive impairment: longitudinal changes and possible prediction of Alzheimer's disease," Neurobiology of Aging, vol. 21, no. 4, pp. 533-540, 2000;

A. Tsolaki, D. Kazis, I. Kompatsiaris, V. Kosmidou, and M. Tsolaki, "Electroencephalogram and Alzheimer's disease: clinical and research approaches," International Journal of Alzheimer's Disease, vol. 2014, Article ID 349249, 10 pages, 2014;

C. Babiloni, L. Benussi, G. Binetti et al., "Genotype (cystatin c) and EEG phenotype in Alzheimer disease and mild cognitive impairment: a multicentric study," NeuroImage, vol. 29, no. 3, pp. 948-964, 2006;

C. Babiloni, P. Bosco, R. Ghidoni et al., "Homocysteine and electroencephalographic rhythms in Alzheimer disease: a multicentric study," Neuroscience, vol. 145, no. 3, pp. 942-954, 2007;

K. Bennis, G. Rondouin, E. Benattar, A. Gabelle, and J. Touchon, "Can event-related potential predict the progression of mild cognitive impairment?" Journal of Clinical Neurophysiology, vol. 28, no. 6, pp. 625-632, 2011;

R. M. Chapman, J. W. McCrary, M. N. Gardner et al., "Brain ERP components predict which individuals progress to Alzheimer's disease and which do not," Neurobiology of Aging, vol. 32, no. 10, pp. 1742-1755, 2011;

C.-L. Lai, R.-T. Lin, L.-M. Liou, and C.-K. Liu, "The role of event-related potentials in cognitive decline in Alzheimer's disease," Clinical Neurophysiology, vol. 121, no. 2, pp. 194-199, 2010;

S. Jiang, C. Qu, F. Wang et al., "Using event-related potential P300 as an electrophysiological marker for differential diagnosis and to predict the progression of mild cognitive impairment: a meta-analysis," Neurological Sciences, vol. 36, no. 7, pp. 1105-1112, 2015;

P. Missonnier, M.-P. Deiber, G. Gold et al., "Working memory load-related electroencephalographic parameters can differentiate progressive from stable mild cognitive impairment," Neuroscience, vol. 150, no. 2, pp. 346-356, 2007;

P. Missonnier, G. Gold, L. Fazio-Costa et al., "Early event-related potential changes during working memory activation predict rapid decline in mild cognitive impairment," The Journals of Gerontology Series A: Biological Sciences and Medical Sciences, vol. 60, no. 5, pp. 660-666, 2005;

J. M. Olichney, J. R. Taylor, J. Gatherwright et al., "Patients with MCI and N400 or P600 abnormalities are at very high risk for conversion to dementia," Neurology, vol. 70, no. 19, pp. 1763-1770, 2008;

V. T. Papaliagkas, G. Anogianakis, M. N. Tsolaki, G. Koliakos, and V. K. Kimiskidis, "Combination of P300 and CSF β-amyloid (1-42) assays may provide a potential tool in the early diagnosis of Alzheimer's disease," Current Alzheimer Research, vol. 7, no. 4, pp. 295-299, 2010;

S. Elmstahl and I. Rosén, "Postural hypotension and EEG variables predict cognitive decline: results from a 5-year follow-up of healthy elderly women," Dementia and Geriatric Cognitive Disorders, vol. 8, no. 3, pp. 180-187, 1997;

A. A. Gouw, A. M. Alsema, B. M. Tijms et al., "EEG spectral analysis as a putative early prognostic biomarker in non-demented, amyloid positive subjects," Neurobiology of Aging, vol. 57, pp. 133-142, 2017;

C. Huang, L.-O. Wahlund, T. Dierks, P. Julin, B. Winblad, and V. Jelic, "Discrimination of alzheimer's disease and mild cognitive impairment by equivalent EEG sources: a cross-sectional and longitudinal study," Clinical Neurophysiology, vol. 111, no. 11, pp. 1961-1967, 2000;

C. Luckhaus, B. Grass-Kapanke, I. Blaeser et al., "Quantitative EEG in progressing vs stable mild cognitive impairment (MCI): results of a 1-year follow-up study," International Journal of Geriatric Psychiatry, vol. 23, no. 11, pp. 1148-1155, 2008;

P. Missonnier, G. Gold, F. R. Herrmann et al., "Decreased theta event-related synchronization during working memory activation is associated with progressive mild cognitive impairment," Dementia and Geriatric Cognitive Disorders, vol. 22, no. 3, pp. 250-259, 2006;

F. Nobili, F. Copello, P. Vitali et al., "Timing of disease progression by quantitative EEG in Alzheimer's patients," Journal of Clinical Neurophysiology, vol. 16, no. 6, pp. 566-573, 1999;

S.-S. Poil, W. de Haan, W. M. van der Flier, H. D. Mansvelder, P. Scheltens, and K. Linkenkaer-Hansen, "Integrative EEG biomarkers predict progression to Alzheimer's disease at the MCI stage," Frontiers in Aging Neuroscience, vol. 5, 2013;

G. Rodriguez, F. Nobili, A. Arrigo et al., "Prognostic significance of quantitative electroencephalography in Alzheimer patients: preliminary observations," Electroencephalography and Clinical Neurophysiology, vol. 99, no. 2, pp. 123-128, 1996;

H. Soininen, J. Partanen, V. Laulumaa, A. Pääkkönen, E.-L. Helkala, and P. J. Riekkinen, "Serial EEG in Alzheimer's disease: 3-year follow-up and clinical outcome," Electroencephalography and Clinical Neurophysiology, vol. 79, no. 5, pp. 342-348, 1991;

P. Giannakopoulos, P. Missonnier, E. Kövari, G. Gold, and A. Michon, "Electrophysiological markers of rapid cognitive decline in mild cognitive impairment," Dementia in Clinical Practice, vol. 24, pp. 39-46, 2009;

P. M. Rossini, C. Del Percio, P. Pasqualetti et al., "Conversion from mild cognitive impairment to Alzheimer's disease is predicted by sources and coherence of brain electroencephalography rhythms," Neuroscience, vol. 143, no. 3, pp. 793-803, 2006;

M. Buscema, E. Grossi, M. Capriotti, C. Babiloni, and P. Rossini, "The I.F.A.S.T. model allows the prediction of conversion to Alzheimer disease in patients with mild cognitive impairment with high degree of accuracy," Current Alzheimer Research, vol. 7, no. 2, pp. 173-187, 2010;

L. S. Prichep, E. R. John, S. H. Ferris et al., "Prediction of longitudinal cognitive decline in normal elderly with subjective complaints using electrophysiological imaging," Neurobiology of Aging, vol. 27, no. 3, pp. 471-481, 2006;

K. M. Baerresen, K. J. Miller, E. R. Hanson et al., "Neuropsychological tests for predicting cognitive decline in older adults," Neurodegenerative Disease Management, vol. 5, no. 3, pp. 191-201, 2015;

H. Brodaty, M. H. Connors, D. Ames, and M. Woodward, "Progression from mild cognitive impairment to dementia: a 3-year longitudinal study," Australian & New Zealand Journal of Psychiatry, vol. 48, no. 12, pp. 1137-1142, 2014;

L. R. Clark, D. M. Schiehser, G. H. Weissberger, D. P. Salmon, D. C. Delis, and M. W. Bondi, "Specific measures of executive function predict cognitive decline in older adults," Journal of the International Neuropsychological Society, vol. 18, no. 1, pp. 118-127, 2012;

P. Johnson, L. Vandewater, W. Wilson et al., "Genetic algorithm with logistic regression for prediction of progression to Alzheimer's disease," BMC Bioinformatics, vol. 15, no. 16, 2014;

T. Pereria, L. Lemos, S. Cardoso et al., "Predicting progression of mild cognitive impairment to dementia using neuropsychological data: a supervised learning approach using time windows," BMC Med Inform Decision Making, vol. 17, no. 1, 2017;

H. Wilhalme, N. Goukasian, F. De Leon et al., "A comparison of theoretical and statistically derived indices for predicting cognitive decline," Alzheimer's & Dementia: Diagnosis, Assessment & Disease Monitoring, vol. 6, no. 1, pp. 171-181, 2017;

C. Woolf, M. J. Slavin, B. Draper et al., "Can the clinical dementia rating scale identify mild cognitive impairment and predict cognitive and functional decline?" Dementia and Geriatric Cognitive Disorders, vol. 41, no. 5-6, pp. 292-302, 2016;

J. Chung, E. Plitman, S. Nakajima et al., "Depressive symptoms and small hippocampal volume accelerate the progression to dementia from mild cognitive impairment," Journal of Alzheimer's Disease: JAD, vol. 49, no. 3, pp. 743-754, 2015;

S. Van der Mussele, E. Fransen, H. Struyfs et al., "Depression in mild cognitive impairment is associated with progression to Alzheimer's disease: a longitudinal study," Journal of Alzheimer's Disease, vol. 42, no. 4, pp. 1239-1250, 2014;

A. G. Zippo and I. Castiglioni, "Integration of (18) FDG-PET metabolic and functional connectomes in the early diagnosis and prognosis of the Alzheimer's disease," Current Alzheimer Research, vol. 13, no. 5, pp. 487-497, 2016;

D. V. Moretti, G. B. Frisoni, C. Fracassi et al., "MCI patients' EEGs show group differences between those who progress and those who do not progress to AD," Neurobiology of Aging, vol. 32, no. 4, pp. 563-571, 2011;

R. C. Petersen, G. E. Smith, S. C. Waring, R. J. Ivnik, E. G. Tangalos, and E. Kokmen, "Mild cognitive impairment: clinical characterization and outcome," Archives of Neurology, vol. 56, no. 3, pp. 303-308, 1999;

S. Gauthier, B. Reisberg, M. Zaudig et al., "Mild cognitive impairment," The Lancet, vol. 367, no. 9518, pp. 1262-1270, 2006. B. Reisberg, S. Ferris, M. de Leon, and T. Crook, "The global deterioration scale for assessment of primary degenerative dementia," The American Journal of Psychiatry, vol. 139, no. 9, pp. 1136-1139, 1982;

B. Winblad, K. Palmer, M. Kivipelto et al., "Mild cognitive impairment-beyond controversies, towards a consensus: report of the international working group on mild cognitive impairment," Journal of Internal Medicine, vol. 256, no. 3, pp. 240-246, 2004;

A. Hammers, R. Allom, M. J. Koepp et al., "Three-dimensional maximum probability atlas of the human brain, with particular reference to the temporal lobe," Human Brain Mapping, vol. 19, no. 4, pp. 224-247, 2003;

G. Zhao and M. Pietikainen, "Dynamic texture recognition using local binary patterns with an application to facial expressions," IEEE Transactions on Pattern Analysis and Machine Intelligence, vol. 29, no. 6, pp. 1-14, 2007;

S. G. Mallat, "A theory for multiresolution signal decomposition: the wavelet representation," IEEE Transactions on Pattern Analysis and Machine Intelligence, vol. 11, no. 7, pp. 674-693, 1989;

M. J. Shensa, "The discrete wavelet transforms: wedding a trous and mallat algorithms," IEEE Transactions on Signal Processing, vol. 40, no. 10, pp. 2464-2482, 1992;

M. N. Do and M. Vetterli, "Wavelet-based texture retrieval using generalized Gaussian density and kullbackleibler distance," IEEE Transactions on Image Processing, vol. 11, no. 2, pp. 146-158, 2002;

M. von Aster, A. Neubauer, and R. Horn, "Wechsler intelligenztest für Erwachsene WIE," in Deutschsprachige Bearbeitung und Adaptation des WAIS-III von David Wechsler, Pearson Assessment, Frankfurt, Germany, 2nd edition, 2006;

C. Riekkinen and H. F. Durwen, "VLMT: verbaler lern-und merkfa higkeitstest. ein praktikables und differenziertes instrumentarium zur prüfung der verbalen gedächtnisleistungen," Schweiz Arch Neurol Psychiatr, vol. 141, pp. 21-30, 1990;

S. Weidlich and G. Lamberti, Diagnosticum für Cerebralsch Adigung: DCS; nach F. Hillers; Handbuch, Huber Verlag, Bern, Vienna, Austria, 1980;

A. Aschenbrenner, O. Tucha, and K. Lange, RWT Regensburger Wortflüssigkeits-Test. Handanweisung, Hogrefe Ver-lag, Göttingen, Germany, 2000;

P. Zimmermann and B. Fimm, A Test Battery for Attentional Performance, pp. 110-151, Psychology Press, London, U K, 2002;

M. Hautzinger, F. Keller, and C. Kühner, Beck Depressions Inventar: Revision (BDI-II), Harcourt Test Services, Frankfurt, Germany, 2006;

Z. S. Nasreddine, N. A. Phillips, V. BÃcdirian et al., "The montreal cognitive assessment, MoCA: a brief screening tool for mild cognitive impairment," Journal of the American Geriatrics Society, vol. 53, no. 4, pp. 695-699, 2005;

A. Schlogl and C. Brunner, "BioSig: a free and open-source software library for BCI research," Computer, vol. 41, no. 10, pp. 44-50, 2008;

S. Marple, Digital Spectral Analysis with Applications, Prentice Hall, Upper Saddle River, N.J., USA, 1987;

V. K. Murthy, "Estimation of the cross-spectrum," The Annals of Mathematical Statistics, vol. 34, no. 3, pp. 1012-1021, 1963;

M. Kaminski, M. Ding, W. A. Truccolo, and S. L. Bressler, "Evaluating causal relations in neural systems: granger causality, directed transfer function and statistical assessment of significance," Biological Cybernetics, vol. 85, no. 2, pp. 145-157, 2001;

M. Eichler, "On the evaluation of information flow in multivariate systems by the directed transfer function," Biological Cybernetics, vol. 94, no. 6, pp. 469-482, 2006;

G. Nolte, O. Bai, L. Wheaton, Z. Mari, S. Vorbach, and M. Hallett, "Identifying true brain interaction from EEG data using the imaginary part of coherency," Clinical Neurophysiology, vol. 115, no. 10, pp. 2292-2307, 2004;

W. Gersch and G. V. Goddard, "Epileptic focus location: spectral analysis method," Science, vol. 169, no. 3946, pp. 701-702, 1970;

L. A. Baccalá and K. Sameshima, "Partial directed coherence: a new concept in neural structure determination," Biological Cybernetics, vol. 84, no. 6, pp. 463-474, 2001;

L. Baccalá, D. Takahashi, and K. Sameshima, "Generalized partial directed coherence," in Proceedings of the 15th In-ternational Conference on Digital Signal Processing (DSP), S. Sanei, J. Chambers, J. McWhirter et al., Eds., pp. 162-166 pp. 162-, Wales, UK, July 2007;

M. J. Kaminski and K. J. Blinowska, "A new method of the description of the information flow in the brain structures," Biological Cybernetics, vol. 65, no. 3, pp. 203-210, 1991;

A. Korzeniewska, M. Mańczak, M. Kamiński, K. J. Blinowska, and S. Kasicki, "Determination of information flow direction among brain structures by a modified directed transfer function (dDTF) method," Journal of Neuroscience Methods, vol. 125, no. 1-2, pp. 195-207, 2003;

S. L. Bressler, C. G. Richter, Y. Chen, and M. Ding, "Cortical functional network organization from autoregressive modeling of local field potential oscillations," Statistics in Medicine, vol. 26, no. 21, pp. 3875-3885, 2007;

J. Geweke, "Measurement of linear dependence and feedback between multiple time series," Journal of the American Statistical Association, vol. 77, no. 378, pp. 304-313, 1982;

A. C. Bathke, S. Friedrich, M. Pauly et al., "Testing mean differences among groups: multivariate and repeated measures analysis with minimal assumptions," Multivariate Behavioral Research, vol. 53, no. 3, pp. 348-359, 2018;

S. Friedrich, F. Konietschke, and M. Pauly, "MANOVA.RM: a package for calculating test statistics and their resampling versions for heteroscedastic semi-parametric multivariate data or repeated measures designs," 2017;

C.-Y. Wee, P.-T. Yap, and D. Shen, "Prediction of Alzheimer's disease and mild cognitive impairment using cortical morphological patterns," Human Brain Mapping, vol. 34, no. 12, pp. 3411-3425, 2013;

Y. Cui, P. S. Sachdev, D. M. Lipnicki et al., "Predicting the development of mild cognitive impairment: a new use of pattern recognition," Neuroimage, vol. 60, no. 2, pp. 894-901, 2012;

X. Da, J. B. Toledo, J. Zee et al., "Integration and relative value of biomarkers for prediction of MCI to ad progression: spatial patterns of brain atrophy, cognitive scores, apoe genotype and CSF biomarkers," NeuroImage: Clinical, vol. 4, pp. 164-173, 2014;

C. Eckerström, E. Olsson, M. Bjerke et al., "A combination of neuropsychological, neuroimaging, and cerebrospinal fluid markers predicts conversion from mild cognitive impairment to dementia," Journal of Alzheimer's Disease, vol. 36, no. 3, pp. 421-431, 2013;

S. C. Egli, D. I. Hirni, K. I. Taylor et al., "Varying strength of cognitive markers and biomarkers to predict conversion and cognitive decline in an early-stage-enriched mild cognitive impairment sample," Journal of Alzheimer's Disease, vol. 44, no. 2, pp. 625-633, 2015;

S. J. Buchert, J. Kurth, B. Krause, and M. J. Grothe, "Alzheimer's disease neuroimaging initiative, 2015. The relative importance of imaging markers for the prediction of Alzheimer's disease dementia in mild cognitive impairment-beyond classical regression," NeuroImage: Clinical, vol. 8, pp. 583-593, 2015;

K. van der Hiele, E. L. E. M. Bollen, A. A. Vein et al., "EEG markers of future cognitive performance in the elderly," Journal of Clinical Neurophysiology, vol. 25, no. 2, pp. 83-89, 2008;

D. Ferrazzoli, M. Albanese, F. Sica et al., "Electroencephalography and dementia: a literature review and future perspectives," CNS & Neurological Disorders—Drug Targets, vol. 12, no. 4, pp. 512-519, 2013;

N. Hantke, K. A. Nielson, J. L. Woodard et al., "Comparison of semantic and episodic memory BOLD fMRI activation in predicting cognitive decline in older adults," Journal of the International Neuropsychological Society, vol. 19, no. 1, pp. 11-21, 2013;

N. A. Kochan, M. Breakspear, M. Valenzuela et al., "Cortical responses to a graded working memory challenge predict functional decline in mild cognitive impairment," Biological Psychiatry, vol. 70, no. 2, pp. 123-130, 2011;

S. L. Miller, E. Fenstermacher, J. Bates, D. Blacker, R. A. Sperling, and B. C. Dickerson, "Hippocampal activation in adults with mild cognitive impairment predicts subsequent cognitive decline," Journal of Neurology, Neurosurgery & Psychiatry, vol. 79, no. 6, pp. 630-635, 2007;

S. Haller, D. Nguyen, C. Rodriguez et al., "Individual prediction of cognitive decline in mild cognitive impairment using support vector machine-based analysis of diffusion tensor imaging data," Journal of Alzheimer's Disease, vol. 22, no. 1, pp. 315-327, 2010;

M. A. Lancaster, M. Seidenberg, J. C. Smith et al., "Diffusion tensor imaging predictors of episodic memory decline in healthy elders at genetic risk for Alzheimer's disease," Journal of the International Neuropsychological Society, vol. 22, no. 10, pp. 1005-1015, 2016;

S.-H. Jin and C. K. Chung, "Functional substrate for memory function differences between patients with left and right mesial temporal lobe epilepsy associated with hippocampal sclerosis," Epilepsy & Behavior, vol. 51, pp. 251-258, 2015. G. E. Doucet, X. He, M. Sperling, A. Sharan, and J. I. Tracy, "Gray matter abnormalities in temporal lobe epilepsy: relationships with resting-state functional connectivity and episodic memory performance," PLoS One, vol. 11, no. 5, Article ID e0154660, 2016;

V. Dinkelacker, R. Valabregue, L. Thivard et al., "Hippocampal-thalamic wiring in medial temporal lobe epilepsy: enhanced connectivity per hippocampal voxel," Epilepsia, vol. 56, no. 8, pp. 1217-1226, 2015;

A. J. Watrous, N. Tandon, C. R. Conner, T. Pieters, and A. D. Ekstrom, "Frequency-specific network connectivity increases underlie accurate spatiotemporal memory retrieval," Nature Neuroscience, vol. 16, no. 3, pp. 349-356, 2013;

D. W. Zaidel, M. M. Esiri, and J. M. Oxbury, "Regional differentiation of cell densities in the left and right hippocampi of epileptic patients," Journal of Neurology, vol. 240, no. 5, pp. 322-325, 1993;

E. Moradi, A. Pepe, C. Gaser, H. Huttunen, and J. Tohka, "Machine learning framework for early MRI-based Alzheimer's conversion prediction in MCI subjects," Neuro-image, vol. 104, pp. 398-412, 2015;

O. Hardt, K. Nader, and L. Nadel, "Decay happens: the role of active forgetting in memory," Trends in Cognitive Sciences, vol. 17, no. 3, pp. 111-120, 2013;

S. J. Wakefield, D. J. Blackburn, K. Harkness, A. Khan, M. Reuber, and A. Venneri, "Distinctive neuropsychological profiles differentiate patients with functional memory dis-order from patients with amnestic-mild cognitive impairment," Acta Neuropsychiatrica, vol. 30, no. 2, pp. 90-96, 2018;

M. Gschwandtner, Y. Holler, M. Liedlgruber, E. Trinka, and A. Uhl, "Assessing out-of-the-box software for automated hippocampus segmentation," in Bildverarbeitung für die Medizin 2016: Algorithmen—Systeme—Anwendungen, T. Tolxdorff, T. M. Deserno, H. Handels et al., Eds., Springer Berlin Heidelberg, Berlin, Germany, pp. 212-217, 2016;

M. A. Araque Cabellero, S. Klöppel, M. Dichgans, and M. Ewers, "Spatial patterns of longitudinal gray matter change as predictors of concurrent cognitive decline in amyloid positive healthy subjects," Journal of Alzheimer's Disease, vol. 55, no. 1, pp. 343-358, 2017;

R. A. Sarkis, B. C. Dickerson, A. J. Cole, and Z. N. Chemali, "Clinical and neurophysiologic characteristics of unprovoked seizures in patients diagnosed with dementia," The Journal of Neuropsychiatry and Clinical Neurosciences, vol. 28, no. 1, pp. 56-61, 2016;

Olaf Ronneberger, Philipp Fischer, and Thomas Brox, "U-Net: Convolutional Networks for Biomedical Image Segmentation", 18 May 2015;

Francois Lazeyras, PhD, Olaf Blanke, Steven Perrig, Ivan Zimine, Xavier Golay, Jacqueline Delavelle, Christoph M. Michel, Nicolas de Tribolet, Jean-Guy Villemure, and Margitta Seeck; "EEG-Triggered Functional MRI in Patients with Pharmacoresistant Epilepsy", 2000;

Diedre Carmo, Leticia Rittner, Roberto Lotufo, Bruna Silva, Clarissa Yasuda, "Extended 2D Consensus Hippocampus Segmentation", 2019;

Giuseppe Palma, Enrico Tedeschi, Pasquale Borrelli, Sirio Cocozza, Carmela Russo, Saifeng Liu, Yongquan Ye, Marco Comerci, Bruno Alfano, Marco Salvatore, E. Mark Haacke, Marcello Mancini, "A Novel Multiparametric Approach to 3D Quantitative MRI of the Brain;"

Susan M. Resnick, Dzung L. Pham, Michael A. Kraut, Alan B. Zonderman, and Christos Davatzikos, "Longitudinal Magnetic Resonance Imaging Studies of Older Adults: A Shrinking Brain"; Apr. 15, 2003;

Azar Zandifara, Vladimir Fonova, Pierrick Coupéc, Jens Pruessnerd, D. Louis Collinsa, "A comparison of accurate automatic hippocampal segmentation methods for the Alzheimer's Disease Neuroimaging Initiative;"

V. Calhoun, T. Adal, and J. Liu, "A feature-based approach to combine functional MRI, structural MRI and EEG brain imaging data", 2006;

Erik K. St. Louis, Lauren C. Frey, "An Introductory Text and Atlas of Normal and Abnormal Findings in Adults, Children, and Infants", N. White, S. Magda, C. Airriess2, J. Albright, "The New Personalized Segmentation Approach";

Kerry W. Kilborn, Zoe Tieges, Jessica Price, Susil Stephen, Bernard A. Conway, Delphine Duclap, Alan H. Hughes, Gillian McLean, "Source Localization of Event-Related Potential effects differentiates between vascular dementia and Alzheimer's disease;"

Saman Sargolzaei, Arman Sargolzaei, Mercedes Cabrerizo, Gang Chen, Mohammed Goryawala, Alberto Pinzon-Ardila, Sergio M. Gonzalez-Ariaa, Malek Adjouadi, "Estimating Intracranial Volume in Brain Research: an Evaluation of Methods;"

B. BRENT SIMMONS, and BRETT HARTMANN, "Evaluation of Suspected Dementia;"

DAVID R. FISH AND SUSAN S. SPENCER, "Clinical Correlations: MRI AND EEG;"

Emma R. Mulder, Remko A. de Jong, Dirk L. Knol, Ronald A. van Schijndel, Keith S. Cover, Pieter J. Visser, Frederik Barkhof, Hugo Vrenken, "Hippocampal volume change measurement: Quantitative assessment of the reproducibility of expert manual outlining and the automated methods for the Alzheimer's Disease Neuroimaging Initiative", 2014;

Dorothee Schoemaker, Claudia Buss, Kevin Head, Curt A. Sandman, Elysia P. Davis, M. Mallar Chakravarty, Serge Gauthier a, Jens C. Pruessner, "Hippocampus and amygdala volumes from magnetic resonance images in children: Assessing accuracy of FreeSurfer and FSL against manual segmentation;

Francois De Guio, Marco Duering, Franz Fazekas, Frank-Erik De Leeuw, Steve Greenberg, Leonardo Pantoni, Agne's Aghetti, Eric E Smith, Joanna Wardlaw, and Eric Jouvent, "Brain atrophy in cerebral small vessel diseases: Extent, consequences, technical limitations and perspectives: The HARNESS initiative;"

Charles W. Kanaly, Dale Ding, Ankit I. Mehta, Anthony F. Waller, Ian Crocker, Annick Desjardins, David A. Reardon, Allan H. Friedman, Darell D. Bigner, and John H. Sampson, "A Novel Method for Volumetric MRI Response Assessment of Enhancing Brain Tumors;"

Simon S. Keller, Jan-Christoph Schoene-Bake, Jan S. Gerdes, Bernd Weber, Michael Deppe, "Concomitant Fractional Anisotropy and Volumetric Abnormalities in Temporal Lobe Epilepsy: Cross-Sectional Evidence for Progressive Neurologic Injury;"

Tomas Kalincik, Manuela Vaneckova, Michaela Tyblova, Jan Krasensky, Zdenek Seidl, Eva Havrdova, Dana Horakova, "Volumetric MRI Markers and Predictors of Disease Activity in Early Multiple Sclerosis: A Longitudinal Cohort Study;"

Yu Zhang, Norbert Schuff, Monica Camacho, Linda L. Chao, Thomas P. Fletcher, Kristine Yaffe, Susan C. Woolley, Catherine Madison, Howard J. Rosen, Bruce L. Miller, Michael W. Weiner; "MRI Markers for Mild Cognitive Impairment: Comparisons between White Matter Integrity and Gray Matter Volume Measurements;"

Ricardo Saute, Kevin Dabbs, Jana E. Jones, Daren C. Jackson, Michael Seidenberg, Bruce P. Hermann, "Brain Morphology in Children with Epilepsy and ADHD;"

Margaret R. Lentz, Kristin L. Peterson, Wael G. Ibrahim, Dianne E. Lee, Joelle Sarlls, Martin J. Lizak, Dragan Maric, William C. Reid, Dima A. Hammoud, "Diffusion Tensor and Volumetric Magnetic Resonance Measures as Biomarkers of Brain Damage in a Small Animal Model of HIV;"

Sanaz Gabery, Nellie Georgiou-Karistianis, Sofia Hult Lundh, Rachel Y. Cheong, Andrew Churchyard, Phyllis Chua, Julie C. Stout, Gary F. Egan, Deniz Kirik, Åsa Petersen "Volumetric Analysis of the Hypothalamus in Huntington Disease Using 3T MRI: The IMAGE-HD Study;"

José Carlos Delgado-González, Francisco Mansilla-Legorburo, José Florensa-Vila, Ana María Insausti, Antonio Viñuela, Teresa Tuñón-Alvarez, Marcos Cruz, Alicia Mohedano-Moriano, Ricardo Insausti, Emilio Artacho-Pérula, "Quantitative Measurements in the Human Hippocampus and Related Areas: Correspondence between Ex-Vivo MRI and Histological Preparations;" Kashif Rajpoot, Atif Riaz, Waqas Majeed, Nasir Rajpoot, "Functional Connectivity Alterations in Epilepsy from Resting-State Functional MRI;"

Rene-Maxime Gracien, Alina Jurcoane, Marlies Wagner, Sarah C. Reitz, Christoph Mayer, Steffen Volz, Stephanie-Michelle Hof, Vinzenz Fleischer, Amgad Droby, Helmuth Steinmetz, Frauke Zipp, Elke Hattingen, Ralf Deichmann, Johannes C. Klein, "The Relationship between Gray Matter Quantitative MRI and Disability in Secondary Progressive Multiple Sclerosis;"

Meriem El Azami, Alexander Hammers, Julien Jung, Nicolas Costes, Romain Bouet, Carole Lartizien, "Detection of Lesions Underlying Intractable Epilepsy on T1-Weighted MRI as an Outlier Detection Problem;"

Oeslle Lucena, Roberto Souza, Letícia Rittner, Richard Frayne, Roberto Lotufo, "SILVER STANDARD MASKS FOR DATA AUGMENTATION APPLIED TO DEEP-LEARNING-BASED SKULL-STRIPPING", 2018;

William J. McGeown, Marco Cecchi, K C Fadem, "NEUROPSYCHOLOGICAL AND NEUROANATOMICAL CORRELATES OF EVENT-RELATED POTENTIALS IN PATIENTS WITH ALZHEIMER'S DISEASE;"

Nikdokht Farid, Holly M. Girard, Nobuko Kemmotsu, Michael E. Smith, Sebastian W. Magda, Wei Y. Lim, Roland R. Lee, Carrie R. McDonald, "Temporal Lobe Epilepsy: Quantitative MR Volumetry in Detection of Hippocampal Atrophy;"

Bahman Nasseroleslami, Stefan Dukic, Michael Broderick, Kieran Mohr, Christina Schuster, Brighid Gavin, Russell McLaughlin, Mark Heverin, Alice Vajda, Parameswaran M. Iyer, Niall Pender, Peter Bede, Edmund C. Lalor, and Orla Hardiman, "Characteristic Increases in EEG Connectivity Correlate with Changes of Structural MRI in Amyotrophic Lateral Sclerosis;"

D. Heister, J. B. Brewer, S. Magda, et al., "Predicting MCI outcome with clinically available MRI and CSF Biomarkers", 2011;

Trygve B. Leergaard, Nathan S. White, Alex de Crespigny, Ingeborg Bolstad, Helen D'Arceuil, Jan G. Bjaalie, Anders M. Dale, "Quantitative Histological Validation of Diffusion MRI Fiber Orientation Distributions in the Rat Brain;"

Riccardo Metere, Tobias Kober, Harald E. Moller, Andreas Schafer, "Simultaneous Quantitative MRI Mapping of T1, T2 and Magnetic Susceptibility with Multi-Echo MP2RAGE;"

Xin Xu, Jinshan Tang, Xiaolong Zhang, Xiaoming Liu, Hong Zhang, and Yimin Qiu, "Exploring Techniques for Vision Based Human Activity Recognition: Methods, Systems, and Evaluation", 2013;

Dr Subhash Kaul, "Stroke in India;"

Benjamin Thyreau, Kazunori Sato, Hiroshi Fukuda, Yasuyuki Taki, "Segmentation of the Hippocampus by Transferring Algorithmic Knowledge for large cohort processing;"

Woo Suk Tae, Sam Soo Kim, Kang Uk Lee, Eui-Cheol Nam, and Keun Woo Kim, "Validation of Hippocampal volumes measured using a manual method and two automated methods in chronic major depressive disorder;"

Junko Matsuzawa, Mie Matsui, Tohru Konishi, Kyo Noguchi, Ruben C. Gur, Warren Bilker and Toshio Miyawaki; "Age-related Volumetric Changes of Brain Gray and White Matter in Healthy Infants and Children;"

Michael Wagner, and Manfred Fuchs, "Integration of Functional MRI, Structural MRI, EEG, and MEG,"

Sven Haller, Enikö Kövari, François R Herrmann, Victor Cuvinciuc, Ann-Marie Tomm, Gilbert B Zulian, Karl-Olof Lovblad, Panteleimon Giannakopoulos, and Constantin Bouras, "Do brain T2/FLAIR white matter hyperintensities correspond to myelin loss in normal aging? A radiologic-neuropathologic correlation study;"

U.S. Pat. No. 7,283,652B2 entitled "Method and system for measuring disease relevant tissue changes;"

US20100266173 entitled "Computer-aided detection (cad) of a disease;"

U.S. Pat. No. 9,588,204 entitled "Magnetic resonance spectroscopic imaging volume of interest positioning;"

US20080249396 entitled "Method and Apparatus for Determining Indications Helping the Diagnosis of Orthopedical Diseases;"

US20190109830 entitled "Systems and Methods for Ensuring Data Security in the Treatment of Diseases and Disorders Using Digital Therapeutics;"

US20190139223 entitled "System and method for extracting a region of interest from volume data;"

U.S. Pat. No. 6,901,280 entitled "Evaluating disease progression using magnetic resonance imaging;"
CN101593345 entitled "Three-dimensional medical image display method based on the GPU acceleration;"
US20200315455 entitled "Medical image processing system and method for personalized brain disease diagnosis and status determination;"
U.S. Pat. No. 8,634,614B2 entitled "System and method for volumetric analysis of medical images;"
US20130267827 entitled "Method and magnetic resonance system for functional MR imaging of a predetermined volume segment of the brain of a living examination subject,"
US20100080432 entitled "Tools for aiding in the diagnosis of neurodegenerative diseases"; and
EP3714467 entitled "Content based image retrieval for lesion analysis;"
US20180220984A1 entitled "Medical Imaging Methods and Apparatus for Diagnosis and Monitoring of Diseases and Uses Therefor;"
U.S. Ser. No. 10/878,219B2 entitled "Method and system for artificial intelligence based medical image segmentation;"
JP5366356B2 entitled "Medical image processing apparatus and medical image processing method;"
US20040078238A1 entitled "Anonymizing tool for medical data;"
U.S. Ser. No. 10/198,832B2 entitled "Generalizable medical image analysis using segmentation and classification neural networks;"
US20180103917A1 entitled "Head-mounted display EEG device."

What is claimed is:

1. A method comprising:
obtaining one or more first images of a region of interest of an anatomy from an image source;
obtaining at least one of a text input, and one or more physiological signals of a patient, wherein the text input comprises information of at least one of micro-ethnicity information, an age, a race, a gender, a medical condition, a symptom, clinical history, a patient history, a medical test, medication information, and a cognitive analysis report;
automatically segmenting, through a neural network, one or more second images of at least one structure that resides within the one or more first images;
extracting one or more volumes of the at least one structure from the one or more first images of the region of interest;
determining a feature associated with the at least one structure based on the one or more volumes and one or more inputs;
rendering the feature in at least one of a two-dimensional (2D) format, a three-dimensional (3D) format, and at least one anatomical plane,
wherein the feature comprises at least one of the one or more volumes of the region of interest (ROI), a cortical thickness, an atrophy percentage, an asymmetry index score, a subfield volumetry of the region of interest, annular volume changes, a progressive supranuclear palsy (psp) index score, a magnetic resonance perfusion imaging (MRPI) score, a frontal horn width to intercaudate distance ratio (FH/CC), a medial temporal lobe atrophy (MTA) score, a global cortical atrophy (GCA) scale, identification of Intracranial bleeds, hemorrhage, microbleeds and their volume analysis, a fracture detection, a midline shift identification, a measurement of the midline shift identification and the at least one structure with respect to the midline shift identification, identifying a pathology associated with the at least one structure, classifying the pathology identified, a tissue density identification, an infarct identification, a Penumbra-core-viable tissue identification, classification and volume calculation, diffusion-weighted imaging (DWI) maps and apparent diffusion coefficient (ADC) maps of the at least one structure, perfusion maps comprising resting state functional magnetic resonance imaging (rsfMRI), an alberta stroke programme early CT score (ASPECTS) calculation, a collateral detection, a mismatch ratio calculation, an angiography labeling and/or annotation, a large vessel occlusion (LVO) detection, an Hypoperfusion index calculation, Diffusion tensor imaging (DTI) fiber tracks, neural pathway connectivity maps, correlation between a signal input, an image input and the text input, classifying the signal input, identifying a normal signal, identifying an abnormal signal, identifying a pre-ictal signal, identifying an ictal signal, extracting symptoms, and grading of condition specific effects;
transforming automatically the one or more physiological signals from a sinusoidal wave format to a quantitative format, wherein the quantitative format comprises a numerical representation of the one or more physiological signals;
predicting a prognosis based on correlation with the image input and integrated analysis of at least one spike detected, and the numerical representation of the one or more physiological signals; and
generating an analysis report based on the prognosis, wherein the analysis report comprising a snippet describing the prognosis, the one or more volumes of the at least one structure, one or more quantitative volumes, and a graphical representation of the prognosis.

2. The method of claim 1, wherein automatically segmenting, through the neural network, the one or more second images of the at least one structure that resides within the one or more first images comprise:
performing a second quality analysis manually on the one or more second images that are segmented; and
determining whether the one or more second images, that are segmented, passes the second quality analysis.

3. The method of claim 2, wherein determining whether the one or more second images, that are segmented, passes the second quality analysis comprises:
providing a user interface when the one or more second images that are segmented fails the second quality analysis;
manually editing and correcting at least one of boundaries and the one or more volumes of the at least one structure based on one or more inputs received; and
creating a mask for the at least one structure.

4. The method of claim 1, wherein automatically segmenting, through the neural network, the one or more second images of the at least one structure that resides within the one or more first images comprise:
training the neural network using at least one of (a) the one or more first images, (b) the information of at least one of the micro-ethnicity information, the age, the race, the gender, the medical condition, the symptom, the clinical history, the patient history, the medical test, the medication information, and the cognitive analysis report, (c) the one or more physiological signals, (d) the one or more volumes of the at least one structure, (e)

one or more reference volumes, and (f) one or more reference segmented second images.

5. The method of claim 3, wherein manually editing and correcting at least one of the boundaries and the one or more volumes of the at least one structure based on the one or more inputs received comprises:
creating a log for the mask using the one or more inputs received;
retraining the neural network based on the log created; and
automatically segmenting, through the neural network, the one or more second images of the at least one structure in future based on the retraining provided to the neural network.

6. The method of claim 1, wherein extracting the one or more volumes of the at least one structure from the one or more first images of the region of interest comprises:
assigning a voxel of a mask of the one or more second images, that are segmented, as a unit;
tabulating a plurality of units in the mask; and
estimating one or more quantitative volumes of the at least one structure from the plurality of units.

7. The method of claim 1, further comprising:
recording the one or more volumes of the at least one structure in a database; and
categorizing the one or more volumes of the at least one structure in the database with respect to one or more categories of at least one of the micro-ethnicity information, an intracranial volume (ICV), the age, the race, the gender, a family history, the clinical history, the patient history, the symptom, psych analysis information, brain dominance information, food habitat information, stress information, and the medical condition.

8. The method of claim 1, wherein extracting the one or more volumes of the at least one structure from the one or more first images of the region of interest:
extracting one or more boundaries of the at least one structure from the one or more first images; and
populating one or more voxels within the one or more boundaries of the at least one structure using one or more identifiers.

9. The method of claim 3, wherein manually editing and correcting at least one of the boundaries, and the one or more volumes of the at least one structure based on the one or more inputs received comprises:
performing at least one of adding, and deleting one or more voxels within the boundaries of the at least one structure based on the one or more inputs received.

10. The method of claim 1, further comprising:
detecting at least one spike within the one or more physiological signals that indicates abnormality; and
predicting the prognosis based on correlation and integrated analysis of the at least one spike detected, the text input, and the one or more volumes.

11. The method of claim 10, further comprising:
correlating with at least one of temporal resolution and spatial resolution of the image input and detecting an abnormal region, using the neural network, in the one or more volumes based on the at least one spike detected; and
indicating the abnormal region using a different identifier.

12. The method of claim 10, further comprising:
detecting an abnormal region, using the neural network, in the one or more physiological signals based on volumetric analysis; and
indicating the abnormal region, comprising the at least one spike, using a different identifier.

13. The method of claim 4, wherein the one or more reference volumes range between 25th and 95th percentile, wherein the 25th and the 95th percentile are calculated by matching at least one of the age, the gender, the micro-ethnicity information, and an intracranial volume (ICV) of the patient with a normative population of individuals and then deriving the 25th and the 95th percentile references.

14. The method of claim 13, wherein the 25th and the 95th percentile is calculated by matching the medical condition of the patient with a population of individuals having the medical condition and then deriving the 25th and the 95th percentile.

15. The method of claim 14, further comprising:
predicting a first prognosis state of the patient based at least one of the medical condition, and first medication information of the patient at a first point of time and generating a first analysis report; and
predicting a second prognosis state of the patient based on at least one of the medical condition, and second medication information of the patient at a second point of time and generating a second analysis report.

16. The method of claim 15, further comprising:
comparing the first prognosis state and the second prognosis state;
determining a percentage of one of a deterioration and an improvement in at least one of the one or more volumes, and one or more quantitative volumes based on comparison of the first prognosis state and the second prognosis state; and
training, the neural network, using at least one of medical condition, the first medication information, the second medication information, and the percentage of the deterioration or the improvement in at least one of the one or more volumes, and the one or more quantitative volumes at a plurality of different points of time.

17. The method of claim 16, further comprising:
detecting a diagnosis, via the neural network, at a third point of time by comparing the first prognosis state and the second prognosis state based on the training;
performing a predictive prognosis, via the neural network, and predicting a third prognosis state of the patient at the third point of time based on the training; and
generating a third analysis report comprising a clinical analytical outcome at the third point of time.

18. A system comprising:
a server comprising a memory, and a processor communicatively coupled to the memory, the processor operable to
obtain one or more first images of a region of interest of an anatomy from an image source;
obtain at least one of a text input, and one or more physiological signals of a patient, wherein the text input comprises information of at least one of micro-ethnicity information, an age, a race, a gender, a medical condition, a symptom, clinical history, a patient history, a medical test, medication information, and a cognitive analysis report;
automatically segment, through a neural network, one or more second images of at least one structure that resides within the one or more first images;
extract one or more volumes of the at least one structure from the one or more first images of the region of interest;
determine a feature associated with the at least one structure based on the one or more volumes and one or more inputs;

render the feature in at least one of a two-dimensional (2D) format, a three-dimensional (3D) format, and at least one anatomical plane,
wherein the feature comprises at least one of the one or more volumes of the region of interests (ROI), a cortical thickness, an atrophy percentage, an asymmetry index score, a subfield volumetry of the region of interest, annular volume changes, a progressive supranuclear palsy (psp) index score, a magnetic resonance perfusion imaging (MRPI) score, a frontal horn width to intercaudate distance ratio (FH/CC), a medial temporal lobe atrophy (MTA) score, a global cortical atrophy (GCA) scale, identification of Intracranial bleeds, hemorrhage, microbleeds and their volume analysis, a fracture detection, a midline shift identification, a measurement of the midline shift identification and the at least one structure with respect to the midline shift identification, identifying a pathology associated with the at least one structure, classifying the pathology identified, a tissue density identification, an infarct identification, a Penumbra-core-viable tissue identification, classification and volume calculation, diffusion-weighted imaging (DWI) maps and apparent diffusion coefficient (ADC) maps of the at least one structure, perfusion maps comprising resting state functional magnetic resonance imaging (rsfMRI), an alberta stroke programme early CT score (ASPECTS) calculation, a collateral detection, a mismatch ratio calculation, an angiography labeling and/or annotation, a large vessel occlusion (LVO) detection, an Hypoperfusion index calculation, Diffusion tensor imaging (DTI) fiber tracks, neural pathway connectivity maps, correlation between a signal input, an image input and the text input, classifying the signal input, identifying a normal signal, identifying an abnormal signal, identifying a pre-ictal signal, identifying an ictal signal, extracting symptoms, and grading of condition specific effects;
transform automatically the one or more physiological signals from a sinusoidal wave format to a quantitative format, wherein the quantitative format comprises a numerical representation of the one or more physiological signals;
predict a prognosis based on correlation with the image input and integrated analysis of at least one spike detected, and the numerical representation of the one or more physiological signals; and
generate an analysis report based on the prognosis, wherein the analysis report comprising a snippet describing the prognosis, the one or more volumes of the at least one structure, one or more quantitative volumes, and a graphical representation of the prognosis.

19. The system of claim 18, wherein the processor operable to detect at least one spike within the one or more physiological signals that indicates abnormality; and predict the prognosis based on correlation and integrated analysis of the at least one spike detected, the text input, and the one or more volumes.

20. A non-transitory computer storage medium storing a sequence of instructions, which when executed by a processor, causes:
obtaining one or more first images of a region of interest of an anatomy from an image source;
obtaining at least one of a text input, and one or more physiological signals of a patient, wherein the text input comprises information of at least one of micro-ethnicity information, an age, a race, a gender, a medical condition, a symptom, clinical history, a patient history, a medical test, medication information, and a cognitive analysis report;
automatically segmenting, through a neural network, one or more second images of at least one structure that resides within the one or more first images;
extracting one or more volumes of the at least one structure from the one or more first images of the region of interest;
determining a feature associated with the at least one structure based on the one or more volumes and one or more inputs;
rendering the feature in at least one of a two-dimensional (2D) format, a three-dimensional (3D) format, and at least one anatomical plane, wherein the feature comprises at least one of the one or more volumes of the region of interest (ROI), a cortical thickness, an atrophy percentage, an asymmetry index score, a subfield volumetry of the region of interest, annular volume changes, a progressive supranuclear palsy (psp) index score, a magnetic resonance perfusion imaging (MRPI) score, a frontal horn width to intercaudate distance ratio (FH/CC), a medial temporal lobe atrophy (MTA) score, a global cortical atrophy (GCA) scale, identification of Intracranial bleeds, hemorrhage, microbleeds and their volume analysis, a fracture detection, a midline shift identification, a measurement of the midline shift identification and the at least one structure with respect to the midline shift identification, identifying a pathology associated with the at least one structure, classifying the pathology identified, a tissue density identification, an infarct identification, a Penumbra-core-viable tissue identification, classification and volume calculation, diffusion-weighted imaging (DWI) maps and apparent diffusion coefficient (ADC) maps of the at least one structure, perfusion maps comprising resting state functional magnetic resonance imaging (rsfMRI), an alberta stroke programme early CT score (ASPECTS) calculation, a collateral detection, a mismatch ratio calculation, an angiography labeling and/or annotation, a large vessel occlusion (LVO) detection, an Hypoperfusion index calculation, Diffusion tensor imaging (DTI) fiber tracks, neural pathway connectivity maps, correlation between a signal input, an image input and the text input, classifying the signal input, identifying a normal signal, identifying an abnormal signal, identifying a pre-ictal signal, identifying an ictal signal, extracting symptoms, and grading of condition specific effects;
transforming automatically the one or more physiological signals from a sinusoidal wave format to a quantitative format, wherein the quantitative format comprises a numerical representation of the one or more physiological signals;
predicting a prognosis based on correlation with the image input and integrated analysis of at least one spike detected, and the numerical representation of the one or more physiological signals; and
generating an analysis report based on the prognosis, wherein the analysis report comprising a snippet describing the prognosis, the one or more volumes of the at least one structure, one or more quantitative volumes, and a graphical representation of the prognosis.

* * * * *